United States Patent
Barnthouse et al.

(10) Patent No.: US 12,129,292 B2
(45) Date of Patent: Oct. 29, 2024

(54) ANTI-TUMOR NECROSIS FACTOR (TNF) ANTIBODIES AND COMPOSITIONS THEREOF

(71) Applicant: Janssen Biotech, Inc., Horsham, PA (US)

(72) Inventors: Kristopher Barnthouse, Pottstown, PA (US); Subinay Ganguly, Newtown, PA (US); Maarten Groeneveld, Oegstgeest (NL); Manuel Lopez, Devon, PA (US); Michael Nedved, Downingtown, PA (US); Kevin D. Smith, Philadelphia, PA (US)

(73) Assignee: Janssen Biotech, Inc., Horsham, PA (US)

( * ) Notice: Subject to any disclaimer, the term of this patent is extended or adjusted under 35 U.S.C. 154(b) by 371 days.

(21) Appl. No.: 17/438,657

(22) PCT Filed: Feb. 26, 2020

(86) PCT No.: PCT/IB2020/051637
§ 371 (c)(1),
(2) Date: Sep. 13, 2021

(87) PCT Pub. No.: WO2020/183271
PCT Pub. Date: Sep. 17, 2020

(65) Prior Publication Data
US 2022/0153829 A1 May 19, 2022

Related U.S. Application Data

(60) Provisional application No. 62/818,305, filed on Mar. 14, 2019.

(51) Int. Cl.
*C07K 16/24* (2006.01)

(52) U.S. Cl.
CPC ........ *C07K 16/241* (2013.01); *C07K 2317/14* (2013.01); *C07K 2317/33* (2013.01); *C07K 2317/41* (2013.01); *C07K 2317/565* (2013.01); *C07K 2317/567* (2013.01); *C07K 2317/732* (2013.01); *C07K 2317/76* (2013.01); *C07K 2317/92* (2013.01)

(58) Field of Classification Search
CPC .............. C07K 16/241; C07K 2317/14; C07K 2317/33; C07K 2317/41; C07K 2317/565; C07K 2317/567; C07K 2317/732; C07K 2317/76; C07K 2317/92
See application file for complete search history.

(56) References Cited

U.S. PATENT DOCUMENTS

| | | |
|---|---|---|
| 3,773,919 A | 11/1973 | Boswell |
| 4,239,754 A | 12/1980 | Bertrand |
| 4,309,989 A | 1/1982 | Fahim |
| 4,399,216 A | 8/1983 | Axel |
| 4,634,665 A | 1/1987 | Axel |
| 4,656,134 A | 4/1987 | Ringold |
| 4,668,218 A | 5/1987 | Risto |
| 4,683,195 A | 7/1987 | Mullis |
| 4,683,202 A | 7/1987 | Mullis |
| 4,704,692 A | 11/1987 | Ladner |
| 4,766,067 A | 8/1988 | Biswas |
| 4,767,402 A | 8/1988 | Kost |
| 4,795,699 A | 1/1989 | Tabor |
| 4,800,159 A | 1/1989 | Mullis |
| 4,816,567 A | 3/1989 | Cabilly |
| 4,873,316 A | 10/1989 | Meade |
| 4,889,818 A | 12/1989 | Gelfand |
| 4,921,794 A | 5/1990 | Tabor |
| 4,925,673 A | 5/1990 | Steiner |
| 4,939,666 A | 7/1990 | Hardman |
| 4,946,778 A | 8/1990 | Ladner |
| 4,956,288 A | 9/1990 | Barsoum |
| 4,965,188 A | 10/1990 | Mullis |
| 4,994,370 A | 2/1991 | Silver |
| 5,066,584 A | 11/1991 | Gyllensten |
| 5,091,310 A | 2/1992 | Innis |
| 5,116,964 A | 5/1992 | Capon |
| 5,122,464 A | 6/1992 | Wilson |
| 5,130,238 A | 7/1992 | Malek |
| 5,142,033 A | 8/1992 | Innis |
| 5,149,636 A | 9/1992 | Axel |
| 5,168,062 A | 12/1992 | Stinski |
| 5,179,017 A | 1/1993 | Axel |
| 5,223,409 A | 6/1993 | Ladner |
| 5,225,538 A | 7/1993 | Capon |
| 5,225,539 A | 7/1993 | Winter |
| 5,231,024 A | 7/1993 | Moeller |

(Continued)

FOREIGN PATENT DOCUMENTS

| | | |
|---|---|---|
| CN | 1468308 | 1/2004 |
| CN | 105658799 | 6/2016 |

(Continued)

OTHER PUBLICATIONS

US 5,733,746 A, 03/1998, Treco (withdrawn)
Ladwig PM, et al. (May 2017) Clinical and Vaccine Immunology. 24(5). 17 pages (e00545-16).*
Alt, et al., "Selective Multiplication of Dihydrofolate Reductase Genes in Methotrexate-resistant Variants of Cultured Murine Cells", Journal of Biological Chemistry, vol. 253 (1978), pp. 1357-1370.
Anonymous, "Development issues: antibody stability, developability, immunogenicity, and comparability", "Therapeutic Antibody Engineering: Current and Future Advances Driving the Strongest Growth Area in the Pharmaceutical Industry (Woodhead Publishing Series in Biomedicine)", pp. 377-595, Jan. 1, 2012 (Jan. 1, 2012), Woodhead Publishing.

(Continued)

*Primary Examiner* — Robert S Landsman
(74) *Attorney, Agent, or Firm* — Riverside Law LLP

(57) ABSTRACT

Presented here are methods for producing a recombinant anti-TNF antibody having a heavy chain (HC) comprising SEQ ID NO:38 and a light chain (LC) comprising SEQ ID NO:37 and compositions comprising the recombinant anti-TNF antibody.

17 Claims, 29 Drawing Sheets

Specification includes a Sequence Listing.

(56) References Cited

U.S. PATENT DOCUMENTS

| | | |
|---|---|---|
| 5,260,203 A | 11/1993 | Ladner |
| 5,266,491 A | 11/1993 | Nagata |
| 5,304,489 A | 4/1994 | Rosen |
| 5,385,839 A | 1/1995 | Stinski |
| 5,403,484 A | 4/1995 | Ladner |
| 5,404,871 A | 4/1995 | Goodman |
| 5,427,908 A | 6/1995 | Dower |
| 5,447,851 A | 9/1995 | Beutler |
| 5,455,030 A | 10/1995 | Ladner |
| 5,458,135 A | 10/1995 | Patton |
| 5,514,670 A | 5/1996 | Friedman |
| 5,518,889 A | 5/1996 | Ladner |
| 5,530,101 A | 6/1996 | Queen |
| 5,534,621 A | 7/1996 | Ladner |
| 5,545,806 A | 8/1996 | Lonberg |
| 5,545,807 A | 8/1996 | Surani |
| 5,565,362 A | 10/1996 | Rosen |
| 5,569,825 A | 10/1996 | Lonberg |
| 5,571,698 A | 11/1996 | Ladner |
| 5,576,195 A | 11/1996 | Robinson |
| 5,580,717 A | 12/1996 | Dower |
| 5,580,734 A | 12/1996 | Treco |
| 5,585,089 A | 12/1996 | Queen |
| 5,595,898 A | 1/1997 | Robinson |
| 5,618,920 A | 4/1997 | Robinson |
| 5,625,126 A | 4/1997 | Lonberg |
| 5,625,825 A | 4/1997 | Rostoker |
| 5,627,052 A | 5/1997 | Schrader |
| 5,633,425 A | 5/1997 | Lonberg |
| 5,641,670 A | 6/1997 | Treco |
| 5,643,768 A | 7/1997 | Kawasaki |
| 5,656,730 A | 8/1997 | Lee |
| 5,658,754 A | 8/1997 | Kawasaki |
| 5,661,016 A | 8/1997 | Lonberg |
| 5,693,493 A | 12/1997 | Robinson |
| 5,693,762 A | 12/1997 | Queen |
| 5,698,417 A | 12/1997 | Robinson |
| 5,698,435 A | 12/1997 | Robinson |
| 5,714,352 A | 2/1998 | Aya |
| 5,723,323 A | 3/1998 | Kauffman |
| 5,733,761 A | 3/1998 | Treco |
| 5,750,373 A | 5/1998 | Garrard |
| 5,763,192 A | 6/1998 | Kauffman |
| 5,763,733 A | 6/1998 | Whitlow |
| 5,766,886 A | 6/1998 | Studnicka |
| 5,767,260 A | 6/1998 | Whitlow |
| 5,770,198 A | 6/1998 | Coller |
| 5,770,222 A | 6/1998 | Unger |
| 5,770,359 A | 6/1998 | Wilson |
| 5,770,428 A | 6/1998 | Boris-Lawrie |
| 5,789,650 A | 8/1998 | Lonberg |
| 5,814,476 A | 9/1998 | Kauffman |
| 5,814,599 A | 9/1998 | Mitragotri |
| 5,817,483 A | 10/1998 | Kauffman |
| 5,824,514 A | 10/1998 | Kauffman |
| 5,827,690 A | 10/1998 | Meade |
| 5,827,739 A | 10/1998 | Wilson |
| 5,837,500 A | 11/1998 | Ladner |
| 5,839,446 A | 11/1998 | Waner |
| 5,849,695 A | 12/1998 | Cohen |
| 5,849,992 A | 12/1998 | Meade |
| 5,851,198 A | 12/1998 | Castellano |
| 5,856,456 A | 1/1999 | Whitlow |
| 5,871,753 A | 2/1999 | Crabtree |
| 5,879,681 A | 3/1999 | Leone-Bay |
| 5,885,793 A | 3/1999 | Griffiths |
| 5,962,255 A | 10/1999 | Griffiths |
| 5,976,862 A | 11/1999 | Kauffman |
| 5,994,616 A | 11/1999 | Rosen |
| 6,171,825 B1 | 1/2001 | Chan |
| 6,180,370 B1 | 1/2001 | Queen |
| 6,204,023 B1 | 3/2001 | Robinson |
| 6,936,441 B2 | 8/2005 | Reiter |
| 7,250,165 B2 | 7/2007 | Heavner |
| 8,975,040 B2 | 3/2015 | Naso |
| 11,014,982 B2 | 5/2021 | Harrison |
| 11,041,020 B2 | 6/2021 | Harrison |
| 11,046,975 B2* | 6/2021 | Kim ................ C07K 16/22 |
| 2007/0212770 A1 | 9/2007 | Grillberger |
| 2008/0009040 A1 | 1/2008 | Grillberger |
| 2009/0074794 A1 | 3/2009 | Heavner |
| 2009/0182127 A1 | 7/2009 | Kristian |
| 2010/0015133 A1 | 1/2010 | Igawa |
| 2010/0028637 A1 | 2/2010 | Tavsanli |
| 2011/0123532 A1 | 5/2011 | Gurney |
| 2012/0149876 A1 | 6/2012 | Von Kreudenstein |
| 2013/0195849 A1 | 8/2013 | Spreter Von Kreudenstein |
| 2017/0247444 A1 | 8/2017 | Hedrick |

FOREIGN PATENT DOCUMENTS

| | | |
|---|---|---|
| CN | 106459185 | 2/2017 |
| CN | 109072303 | 12/2018 |
| EP | 229246 | 10/1986 |
| EP | 0218868 A2 | 4/1987 |
| EP | 0288088 | 10/1988 |
| EP | 368684 | 5/1990 |
| EP | 371998 | 6/1990 |
| EP | 0237507 B1 | 12/1991 |
| EP | 550400 | 7/1993 |
| EP | 0590689 A2 | 4/1994 |
| EP | 0229046 B1 | 5/1994 |
| EP | 0438474 B1 | 5/1996 |
| EP | 0710719 A1 | 5/1996 |
| EP | 0463151 B1 | 6/1996 |
| EP | 0814259 | 12/1997 |
| EP | 3059319 | 8/2016 |
| EP | 3323826 A1 | 5/2018 |
| GB | 2272440 A | 5/1994 |
| JP | 2016533769 | 11/2016 |
| JP | 2017528132 | 9/2017 |
| TW | 202100552 | 1/2021 |
| TW | 202100553 | 1/2021 |
| WO | 8605803 A1 | 10/1986 |
| WO | 8806630 A1 | 9/1988 |
| WO | 8906283 A1 | 7/1989 |
| WO | 9003809 A1 | 4/1990 |
| WO | 9004036 A1 | 4/1990 |
| WO | 1990005370 | 5/1990 |
| WO | 9014424 A1 | 11/1990 |
| WO | 9014430 A1 | 11/1990 |
| WO | 9014443 A1 | 11/1990 |
| WO | 9102078 A1 | 2/1991 |
| WO | 9117271 A1 | 11/1991 |
| WO | 9118980 A1 | 12/1991 |
| WO | 9119818 A1 | 12/1991 |
| WO | 1992001047 A1 | 1/1992 |
| WO | 1992003461 | 3/1992 |
| WO | 9205258 A1 | 4/1992 |
| WO | 9207076 A1 | 4/1992 |
| WO | 1992006204 | 4/1992 |
| WO | 1992011272 | 7/1992 |
| WO | 9214843 A1 | 9/1992 |
| WO | 9216221 A1 | 10/1992 |
| WO | 9218619 A1 | 10/1992 |
| WO | 1992020791 A1 | 11/1992 |
| WO | 9308278 A1 | 4/1993 |
| WO | 1993006213 A1 | 4/1993 |
| WO | 1993011236 A1 | 6/1993 |
| WO | 1993019172 A1 | 9/1993 |
| WO | 9406498 A1 | 3/1994 |
| WO | 9408552 A2 | 4/1994 |
| WO | 9416970 A1 | 8/1994 |
| WO | 1994018219 | 8/1994 |
| WO | 9425585 A1 | 11/1994 |
| WO | 1995001438 | 1/1995 |
| WO | 9516027 A1 | 6/1995 |
| WO | 1995015388 | 6/1995 |
| WO | 9607754 A1 | 3/1996 |
| WO | 9613583 A2 | 5/1996 |
| WO | 9619256 A1 | 6/1996 |
| WO | 9634096 A1 | 10/1996 |
| WO | 9708320 A1 | 3/1997 |
| WO | 9713852 A1 | 4/1997 |

(56) References Cited

FOREIGN PATENT DOCUMENTS

| WO | 9722376 A1 | 6/1997 | | |
|---|---|---|---|---|
| WO | 1997020032 | 6/1997 | | |
| WO | 9725086 | 7/1997 | | |
| WO | 1998001757 | 1/1998 | | |
| WO | 9824884 A1 | 6/1998 | | |
| WO | 9824893 A1 | 6/1998 | | |
| WO | 9835888 A1 | 8/1998 | | |
| WO | 9850433 A2 | 11/1998 | | |
| WO | 9853847 A1 | 12/1998 | | |
| WO | 1999006834 | 2/1999 | | |
| WO | 200212500 | 2/2002 | | |
| WO | 2006028936 A2 | 3/2006 | | |
| WO | 2007077217 | 7/2007 | | |
| WO | 2010136492 | 12/2010 | | |
| WO | 2011017294 | 2/2011 | | |
| WO | 2011078332 | 6/2011 | | |
| WO | 2011131746 A2 | 10/2011 | | |
| WO | 2012120500 | 9/2012 | | |
| WO | WO-2015053523 A1 * | 4/2015 | ............... | C07K 1/14 |
| WO | 2017186671 | 11/2017 | | |
| WO | 2018147915 | 8/2018 | | |

OTHER PUBLICATIONS

Ashkenazi et al., 1991, "Protection against endotoxic shock by a tumor necrosis factor receptor immunoadhesin," Proc. Natl. Acad. Sci. USA, 88(23): 10535-10539.

Babcook et al., "A novel strategy for generating monoclonal antibodies from single, isolated lymphocytes producing antibodies of defined specificities", Proc. Natl. Acad. Sci. USA , vol. 93 (1996), pp. 7843-7848.

Baker et al., "Control of established experimental allergic encephalomyelitis by inhibition of tumor necrosis factor (TNF) activity within the central nervous system using monoclonal antibodies and TNF receptor-immunoglobulin fusion proteins", European Journal of Immunology, vol. 24 (1994), pp. 2040-2048.

Bebbington, et al., "High-Level Expression of a Recombinant Antibody from Myeloma Cells Using a Glutamine Systhetase Gene as an Amplifiable Selectable Marker", Bio/Technology, vol. 10 (1992), pp. 169-175.

Beck et al., "Strategies and challenges for the next generation of therapeutic antibodies." Nature Reviews Immunology, vol. 10, No. 5 (2010), pp. 345-352.

Boshart, et al., "A Very Strong Enhancer Is Located Upstream of an Immediate Early Gene of Human Cytomegalovirus", Cell, vol. 41 (1985), pp. 521-530.

Bringman, Timothy S. and Aggarwal, Bharat B., "Monoclonal Antibodies to Human Tumor Necrosis Factors Alpha and Beta: Applications for Affinity Purification, Immunoassays, and as Structural Probes," Hybridoma, vol. 6, No. 5 (1987), pp. 489-507.

Butler et al., "TNF Receptor Fusion Proteins Are Effective Inhibitors of TNF-Mediated Cytotoxicity on Human KYM-1D4 Rhabdomyosarcoma Cells", Cytokine, vol. 6, No. 6 (1994), pp. 616-623.

Capellas, et al., "Enzymatic Condensation of Cholecystokinin CCK-8 (4-6) and CCK-8 (7-8) Peptide Fragments in Organic Media," Biotechnology and Bioengineering, vol. 56, No. 4 (1997), pp. 456-463.

Capon et al., "Designing CD4 immunoadhesins for AIDS therapy", Nature, vol. 337 (1989), pp. 525-531.

Carter et al., "Humanization of an anti-p185HER2 antibody for human cancer therapy", Proc. Natl. Acad. Sci. U.S. A., vol. 89 (1992), p. 4285.

Chothia, et al., "Canonical Structures for the Hypervariable Regions of Immunoglobulins", Journal of Molecular Biology, vol. 196 (1987), pp. 901-917.

Chung, C. H. et al., "Cetuximab-Induced Anaphylaxis and IgE Specific for Galactose-a-1,3-Galactose", N Eng J Med, vol. 358, No. 11 (2008), pp. 1109-1117.

Conrad et al., "Compartment-specific accumulation of recombinant immunoglobulins in plant cells: an essential tool for antibody production and immunomodulation of physiological functions and pathogen activity", Plant Molecular Biology, vol. 38 (1998), pp. 101-109.

Corcoran et al., "Characterization of ligand binding by the human p55 tumour-necrosis-factor receptor", European Journal of Biochemistry, vol. 223 (1994), pp. 831-840.

Cramer et al., "Transgenic Plants for Therapeutic Proteins: Linking Upstream and Downstream Strategies", Current Topics in Microbiology and Immunology, vol. 240 (1999), pp. 95-118.

Crowell et al., "Amino acid and manganese supplementation modulates the glycosylation state of erythropoietin in a CHO culture system" Biotechnology and Bioengineering, vol. 96, No. 3 (2007), pp. 538-549.

Cullen, et al., "Functional Analysis of the Transcription Control Region Located Within the Avian Retroviral Long Terminal Repeat", Molecular and Cellular Biology, vol. 5 (1985), pp. 438-447.

De Vos, et al., "Human Growth Hormone and Extracellular Domain of Its Receptor: Crystal Structure of the Complex", Science, vol. 255 (1992), pp. 306-312.

Dolinar, et al., "A Guide To Follow-On Biologics and Biosimilars With a Focus on Insulin." Endocrine Practice, vol. 24, No. 2, pp. 195-204, (Feb. 2018).

Elliott, M.J. et al., "A Repeated Therapy with Monoclonal Antibody to Tumour Necrosis Factor a (cA2) in Patients with Rheumatoid Arthritis", The Lancet, vol. 344 (1994), pp. 1125-1127.

Engelmann, Hartmut et al., "Two Tumor Necrosis Factor-binding Proteins Purified from Human Urine," Journal of Biological Chemistry, vol. 265, No. 3 (1990), pp. 1531-1536.

Eren et al. "Human monoclonal antibodies specific to hepatitis B virus generated in a human/mouse radiation chimera: the Trimera system", Immunology, vol. 93 (1998), pp. 154-161.

Fendly, Brian M. et al., "Murine Monoclonal Antibodies Defining Neutralizing Epitopes on Tumor Necrosis Factor," Hybridoma, vol. 6, No. 4 (1987), pp. 359-370.

Fisch et al., "Site-Specific Modification of a Fragment of a Chimeric Monoclonal Antibody Using Reverse Proteolysis", Bioconjugate Chemistry, vol. 3 (1992), pp. 147-153.

Fischer et al., "Towards molecular farming in the future: moving from diagnostic protein and antibody production in microbes to plants", Biotechnology and Applied Biochemistry, vol. 30 (1999), pp. 101-108.

Fishwild et al., "High-avidity human IgGk monoclonal antibodies from a novel strain of minilocus transgenic mice", Nature Biotechnology, vol. 14, No. 7 (1996), pp. 845-851.

Ghaderi et al., "Implications of the presence of N-glycolylneuraminic acid in recombinant therapeutic glycoproteins." Nature Biotechnology, vol. 28, No. 8 (2010), pp. 863-867.

Goetze et al., "High-mannose glycans on the Fc region of therapeutic IgG antibodies increase serum clearance in humans." Glycobiology, vol. 21, No. 7 (2011), pp. 949-959.

Gossen, and H. Bujard, "Tight control of gene expression in mammalian cells by tetracycline-responsive promotoers", Proc. Natl. Acad. Sci. USA, vol. 89 (1992), pp. 5547-5551.

Gray et al., "Secretion capture and report web: use of affinity derivatized agarose microdroplets for the selection of hybridoma cells", Journal of Immunological Methods, vol. 182 (1995), pp. 155-163.

Green et al., "Antigen-specific human monoclonal antibodies from mice engineered with human Ig heavy and light chain YACs", Nature Genetics, vol. 7 (1994), pp. 13-21.

Hanes et al. "Ribosome display efficiently selects and evolves high-affinity antibodies in vitro from immune libraries", Proc Natl. Aca. Sci USA, vol. 95 (1998), pp. 14130-14135.

Hanes et al., "In vitro selection and evolution of functional proteins by using ribosome display", Proc. Natl. Acad. Sci. USA, vol. 94 (1997), pp. 4937-4942.

Hirai, Makoto et al., "Production and characterization of monoclonal antibodies to human tumor necrosis factor," Journal of Immunological Methods, vol. 96 (1987), pp. 57-62.

(56) References Cited

OTHER PUBLICATIONS

Hodoniczky et al., "Control of recombinant monoclonal antibody effector functions by Fc N-glycan remodeling in vitro." Biotechnology Progress, vol. 21 (2005), pp. 1644-1652.
Hood et al., "Molecular Farming of Industrial Proteins from Transgenic Maize", Advances in Experimental Medicine and Biology, vol. 464 (1999), pp. 127-147.
Itoh et al., "Application of Inverse Substrates to Trypsin-Catalyzed Peptide Synthesis", Bioorganic Chemistry, vol. 24, No. 1 (1996), pp. 59-68.
J. L. Hamlin and C. Ma, "The mammalian dihydrofolate reductase locus", Biochimica et Biophysica Acta, vol. 1097 (1990), pp. 107-143.
Jayapal et al., "Recombinant protein therapeutics from CHO cells-20 years and counting", Chemical Engineering Progress, vol. 103 (2007), pp. 40-47.
Jones, et al., "Replacing the complementarity-determining regions in a human antibody with those from a mouse," Nature, vol. 321 (1986), pp. 522-525.
Katsube, Y., et al., "Analysis of k light chain contribution to anti-DNA antibody activity of a human VH4-21-encoded monoclonal antibody (NE-1) by antibody-phage display technique", International Journal of Molecular Medicine, vol. 1, No. 5 (1998), pp. 863-868.
Kenny et al., "Production of Monoclonal Antiboodies Using a Secretion Capture Report Web", Bio/Technology, vol. 13 (1995), pp. 787-790.
Kolls et al., "Prolonged and effective blockade of tumor necrosis factor activity through adeno virus-mediated gene transfer", Proc. Natl. Acad. Sci. USA, vol. 91 (1994), pp. 215-219.
Kumaran et al., "Conformationally driven protease-catalyzed splicing of peptide segments: V8 protease-mediated synthesis of fragments derived from thermolysin and ribonuclease A", Protein Science, vol. 6, No. 10 (1997), pp. 2233-2241.
Kunert et al. Advances in recombinant antibody manufacturing : Appl. Micorbiol. Biotechnol. 100:3451-3461, 2016.
Lee et al., "Glycosylation profile and biological activity of Remicade® compared with Flixabi® and Remsima®", MAbs, vol. 9, No. 6 (2017), pp. 968-977.
Lesslauer et al., "Recombinant soluble tumor necrosis factor receptor proteins protect mice from lipopolysaccharide-induced lethality", European Journal of Immunology, vol. 21 (1991), pp. 2883-2886.
Liang, Chi-Ming et al., "Production and Characterization of Monoclonal Antibodies Against Recombinant Human Tumor Necrosis Factor/Cachectin," Biochemistry & Biophysics Research Communication, vol. 137, No. 2 (1986), pp. 847-854.
Loetscher et al., "Molecular Cloning and Expression of the Human 55 kd Tumor Necrosis Factor Receptor", Cell, vol. 61 (1990), pp. 351-359.
Lonberg et al. "Antigen-specific human antibodies from mice comprising four distinct genetic modifications", Nature, vol. 368 (1994), pp. 856-859.
Lonberg et al., "Human Antibodies from Transgenic Mice", International Reviews of Immunology, vol. 13, No. 1 (1995), pp. 65-93.
M. J. Page and M. A. Sydenham, "High Level Expression of the Humanized Monoclonal Antibody Campath-1H in Chinese Hamster Ovary Cells", Biotechnology, vol. 9 (1991), pp. 64-68.
Ma et al., "Immunotherapeutic potential of antibodies produced in plants", Trends in Biotechnology, vol. 13 (1995), pp. 522-527.
Ma et al., "Plant Antibodies for Immunotherapy", Plant Physiology, vol. 109 (1995), pp. 341-346.
Marrack et al, "The Staphylococcal Enterotoxins and Their Relatives", Science, vol. 248 (1990), pp. 705-711.
Matsumiya et al., "Structural comparison of fucosylated and nonfucosylated Fc fragments of human immunoglobulin G1." Journal of Molecular Biology, vol. 368 (2007), pp. 767-779.
Meager, Anthony et al., "Preparation and Characterization of Monoclonal Antibodies Directed Against Antigenic Determinants of Recombinant Human Tumour Necrosis Factor (rTNF)," Hybridoma, vol. 6, No. 3 (1987), pp. 305-311.
Mendez, et al., "Functional transplant of megabase human immunoglobulin loci recapitulates human antibody response in mice," Nature Genetics, vol. 15, No. 2 (1997), pp. 146-156.
Milstein, et al., "Hybrid hybridomas and their Use in Immunohistochemistry," Nature, vol. 305 (1983), pp. 537-540.
Moller, Achim et al., "Monoclonal Antibodies to Human Tumor Necrosis Factor a: In Vitro and In Vivo Application," Cytokine, vol. 2, No. 3 (1990), pp. 162-169.
Murphy, et al., "Matrix metalloproteinase degradation of elastin, type IV collagen and proteoglycan", Biochem. J., vol. 277 (1991), pp. 277-279.
Neuberger, M., "Generating high-avidity human Mabs in mince", Nature Biotechnology, vol. 14 (1996), p. 826.
Nguyen et al., "Production of Human Monoclonal Antibodies in SCID Mouse", Microbiology and Immunology, vol. 41 (1997), pp. 901-907.
Onitsuka, M., et al., "Glycosylation analysis of an aggregated antibody produced by Chinese hamster ovary cells in bioreactor culture", Journal of Bioscience and Bioengineering, vol. 117, No. 5 (2014), pp. 639-644.
Ovchinnikov et al. "Role of framework mutations and antibody flexibility in the evolution of broadly neutralizing antibodies", eLife, vol. 7 (2018), Article e33038.
Park et al., "Expression and characterization of beta-1,4-galactosyltransferase from Neisseria meningitidis and Neisseria gonorrhoeae." Korean Society for Biochemistry and Molecular Biology, vol. 35, No. 3 (2002), pp. 330-336.
Peppel et al., "A Tumor Necrosis Factor (TNF) Receptor-IgG Heavy ChainChimeric Protein as a Bivalent Antagonist of TNF Activity", Journal of Experimental Medicine, vol. 174 (1991), pp. 1483-1489.
Powell et al., "Gel Microdroplets and Flow Cytometry: Rapid Determination of Antibody Secretion by Individual Cells Within a Cell Population", Biotechnology, vol. 8 (1990), pp. 333-337.
Presta, et al., "Humanization of an antibody y directed against IgE," Journal of Immunology, 151: 2623-2632 (1993).
Qasba et al., "Structure and function of beta-1,4-galactosyltransferase." Current Drug Targets, vol. 9, No. 4 (2008), pp. 292-309.
Qingrong Yan et al, "Structure Based Prediction of Asparagine Deamidation Propensity in Monoclonal Antibodies", MABS, vol. 10, No. 6 (2018), pp. 901-912.
Riechmann, et al., "Reshaping human antibodies for therapy," Nature, vol. 332 (1988), pp. 323-327.
Sandhu et al., "The Use of SCID Mice in Biotechnology and as a Model for Human Disease", Critical Reviews in Biotechnology, vol. 16 (1996), pp. 95-118.
Scallon, B. J., et al., "Higher levels of sialylated Fc glycans in immunoglobulin G molecules can adversly impact functionality", Mol Immunol, vol. 44, No. 7 (2007), pp. 1524-1534.
Scallon, et al., "Functional Comparisons of Different Tumour Necrosis Factor Receptor/IgG Fusion Proteins", Cytokine, vol. 7 (1995), pp. 759-770.
Schall, Thomas J. et al., "Molecular Cloning and Expression of a Receptor for Human Tumor Necrosis Factor," Cell, vol. 61 (1990), pp. 361-370.
Shade and Anthony, "Antibody Glycosylation and Inflammation." Antibodies, vol. 2, No. 3 (2013), pp. 392-414.
Siemiatkoski J, et al. Glycosylation of Therapeutic Proteins: Current Understanding of Structure-Function Relationships. BioProcess International, vol. 9, No. 6 (2011), pp. 48-53.
Sims et al., "A Humanized CD18 Antibody Can Block Function without Cell Destruction", Journal of Immunology, vol. 151 (1993), p. 2296.
Smith, et al., "Human Interleukin 4: The Solution Structure of a Four-helix Bundle Protein", Journal of Molecular Biology, vol. 224 (1992), pp. 899-904.
Sprague, et al., "Expression of a Recombinant DNA Gene Coding for the Vesiclar Stomatitis Virus Nucleocapsid Protein", Journal of Virology, vol. 45 (1983), pp. 773-781.

(56) References Cited

OTHER PUBLICATIONS

Steenbakkers et al., "Efficient generation of monoclonal antibodies from preselected antigen-specific B", Molecular Biology Reports, vol. 19 (1994), pp. 125-134.
Taylor et al., "A transgenic mouse that expresses a diversity of human sequence heavy and light chain immunoglobulins", Nucleic Acids Research, vol. 20, No. 23 (1992), pp. 6287-6295.
Taylor, et al., "Human immunoglobulin transgenes undergo rearrangement, somatic mutation and class switching in mice that lack endogenous IgM," International Immunology, vol. 6, No. 4 (1994), pp. 579-591.
Tuaillon et al., "Human immunoglobulin heavy-chain minilocus recombination in transgenic mice: Gene-segment use in u and y transcripts", Proc Natl Acad Sci USA, vol. 90, No. 8 (1993), pp. 3720-3724.
Verhoeyen et al., "Reshaping Human Antibodies: Grafting an Antilysozyme Activity", Science, vol. 239 (1988), p. 1534.
Voorter, C. E., et al. "Spontaneous peptide bond cleavage in aging alpha-crystallin through a succinimide intermediate." Journal of Biological Chemistry, vol. 263, No. 35 (1988), pp. 19020-19023.
Wen et al., "Limiting diluation assay for human B cells based on their activation by mutant EL4 thymoma cells:total and antimalaria responder B cell frequencies" Journal of Immunology, vol. 17 (1987), pp. 887-892.
Werlen et al., "Site-Specific Conjugation of an Enzyme and an Antibody Fragment", Bioconjugate Chemistry, vol. 5 (1994), pp. 411-417.
Whitelam, et al., "Antibody production in transgenic plants," Biochemical Society Transactions, Transgenic Plants and Plan Biochemistry, vol. 22 (1994), pp. 940-944.
Wood et al., "Staphylococcal enterotoxins and the immune system", FEMS Microbiology Immunology, vol. 76 (1991), pp. 121-134.
Yu, C., et al., "At least two Fc Neu5Gc residues of monoclonal antibodies are required for binding to anti-Neu5Gc antibody", Sci Rep., vol. 6 (2016), Article No. 20029.
Biotechnology & genetic engineering reviews. 2010. Stephenomenon E. Harding, Nottingham University Press, pp. 11-12.
Chen, Hongxia et al., "Development of a method for detection of serum neutralizing antibodies in cynomolgus monkeys undergoing repeated dose toxcity study of humanized anti-TNF-alpha monoclonal antibody WLB303", Chinese Journal of New Drugs. 2017. vol. 26, No. 20. pp. 2386-2395.
Endrenyi et al. 2017. "Biosimilar drug product development", CRC Publishing Group, Section 4.13-4.14.
Report on the deliberation results of "Golimumab (genetically modified)", Japan, Pharmaceuticals and Medical Devices Agency, May 9, 2011, (English translation of relevant sections appended) 18 pages.
Strohl W. et al., "Development issues: antibody stability, developability, immunogenicity, and comparability" Therapeutic Antibody Engineering, 2012, pp. 377-403, 459-595.

* cited by examiner

Fig. 2A

```
TNVs         ATGGGGTTTGGGCTGAGCTGGGTTTTCCTCGTTGCTCTTTTAAGA

Q   V   Q   L   V   E   S   G   G   G   V
germline                   CAGGTGCAGCTGGTGGAGTCTGGGGGAGGCGTG
TNVs         GGTGTCCAGTGT.................................
TNV148(B)    GGTGTCCAGTGT.....A...........................

V   Q   P   G   R   S   L   R   L   S   C   A   A   S   G
germline     GTCCAGCCTGGGAGGTCCCTGAGACTCTCCTGTGCAGCCTCTGGA
TNVs         .............................................

F   T   F   S   S   Y   A   M   H   W   V   R   Q   A   P
germline     TTCACCTTCAGTAGCTATGCTATGCACTGGGTCCGCCAGGCTCCA
TNV14,15     .............................................
TNV148(B)    ....T........................................
TNV196       ....................C........................

G   K   G   L   E   W   V   A   V   I   S   Y   D   G   S
germline     GGCAAGGGGCTGGAGTGGGTGGCAGTTATATCATATGATGGAAGC
TNV14        .........................A....C.T............T
TNV15        .............................T......T........T
TNV148(B)    .....C.......................T....G..........
TNV196       ..............................T..............

N   K   Y   Y   A   D   S   V   K   G   R   F   T   I   S     SEQ ID NO:7
germline     AATAAATACTACGCAGACTCCGTGAAGGGCCGATTCACCATCTCC              SEQ ID NO:34
TNV14        .GC...A.G.....G..................A...........
TNV15        ..C...A.G........................C...........
TNV148(B)    ......A.G.....................................
TNV196       ......A.G.C...........................G......
```

Fig. 2B

```
              R   D   N   S   K   N   T   L   Y   L   Q   M   N   S   L
germline      AGAGACAATTCCAAGAACACGCTGTATCTGCAAATGAACAGCCTG
TNV14         ............................................
TNV15         ....................G.......................
TNV148        .........C..................................
TNV148B       ............................................
TNV196        ..............................T.............

R   A   E   D   T   A   V   Y   Y   C   A   R
germline      AGAGCTGAGGACACGGCTGTGTATTACTGTGCGAGA
TNV14,15      ...................................GATCGAGGT
TNV148(B)     ...........................................A
TNV196        ........................T..................

Y   Y   Y   Y   Y   G   M   D   V   W
germline                  TACTACTACTACTACGGTATGGACGTCTGG
TNV14         ATATCAGCAGGTGGAA..............................
TNV15         G.C...........A.T..T..........................
TNV148(B)     ...G..........A...............................
TNV196        ..TGG.........A...............................

G   Q   G   T   T   V   T   V   S   S
germline      GGGCAAGGGACCACGGTCACCGTCTCCTCAG              SEQ ID NO:7
TNV14         ..C............................              SEQ ID NO:34
TNV15         ..C............................
TNV148(B)     ..C............................
TNV196        ..C..G.........................
```

Fig. 3

```
TNVs         ATGGAAGCCCCAGCTCAGCTTCTCTTCCTCCTGCTACTCTGGCTC

E  I  V  L  T  Q  S  P  A  T
germline     GAAATTGTGTTGACACAGTCTCCAGCCACC
TNVs         CCAGATACCACCGGA..............................

L  S  L  S  P  G  E  R  A  T  L  S  C  R  A
germline     CTGTCTTTGTCTCCAGGGGAAAGAGCCACCCTCTCCTGCAGGGCC
TNVs         .............................................

S  Q  S  V  S  S  Y  L  A  W  Y  Q  Q  K  P
germline     AGTCAGAGTGTTAGCAGCTACTTAGCCTGGTACCAACAGAAACCT
TNV14,15     .............................................
TNV148,196...............TA............................

G  Q  A  P  R  L  L  I  Y  D  A  S  N  R  A
germline     GGCCAGGCTCCCAGGCTCCTCATCTATGATGCATCCAACAGGGCC
TNVs         .............................................

T  G  I  P  A  R  F  S  G  S  G  S  G  T  D
germline     ACTGGCATCCCAGCCAGGTTCAGTGGCAGTGGGTCTGGGACAGAC
TNVs         .............................................

F  T  L  T  I  S  S  L  E  P  E  D  F  A  V
germline     TTCACTCTCACCATCAGCAGCCTAGAGCCTGAAGATTTTGCAGTT
TNVs         .............................................

Y  Y  C  Q  Q  R  S  N  W  P  P  F  T  F  G    SEQ ID NO:8
Germline     TATTACTGTCAGCAGCGTAGCAACTGGCCTCCATTCACTTTCGGC   SEQ ID NO:35
TNVs         ................................A............

P  G  T  K  V  D  I  K  R
germline     CCTGGGACCAAAGTGGATATCAAACGT
TNVs         ...........................
```

Fig. 4

```
germline    MGFGLSWVFLVALLRGVQC              signal   SEQ ID NO:32
TNVs        ..................

germline    QVQLVESGGGVVQPGRSLRLSCAASGFTFS    FR1     SEQ ID NO:7
TNVs        ..............................
TNV148(B)   .............................I..

germline    SYAMH                             CDR1    SEQ ID NO:1
TNVs        .....

germline    WVRQAPGKGLEWVA                    FR2     SEQ ID NO:7
TNVs        .............
TNV148(B)   .......N.....

germline    VISYDGSNKYYADSVKG                 CDR2    SEQ ID NO:2
TNV14       I.L.....S.K......D
TNV15       F.L......K.......
TNV148(B)   FM.......K.......
TNV196      F........KS......

germline    RFTISRDNSKNTLYLQMNSLRAEDTAVYYCAR  FR3     SEQ ID NO:7
TNV14       ...............................
TNV15       ..........A....................
TNV148      .......P.......................
TNV148B     ...............................
TNV196      ...V........F.............F....

germline    --------YYYYYGMDV
TNV14       DRGISAGGN........                 CDR3    SEQ ID NO:3
TNV15       ...V....N........
TNV148(B)   ....A...N........
TNV196      ....G...N........

germline    WGQGTTVTVSS                       J6      SEQ ID NO:7
TNVs        ...........
```

Fig. 5

```
TNVs         MEAPAQLLFLLLLWLPDTTG              signal SEQ ID NO:33 germline     EIVLTQSPATLSLSPGERATLSC           FR1  SEQ ID NO:8
TNVs         ......................

germline     RASQSVSSYLA                       CDR1 SEQ ID NO:4
TNV14        ..........
TNV15        ..........
TNV148(B)    ......Y...
TNV196       ......Y...

germline     WYQQKPGQAPRLLIY                   FR2  SEQ ID NO:8
TNVs         ...............

germline     DASNRAT                           CDR2 SEQ ID NO:5
TNVs         .......

germline     GIPARFSGSGSGTDFTLTISSLEPEDFAVYYC  FR3  SEQ ID NO:8
TNVs         ................................

germline     QQRSNWPPFT                        CDR3 SEQ ID NO:6
TNVs         ..........

germline     FGPGTKVDIK                        J3   SEQ ID NO:8
TNVs         ..........
```

Fig. 7
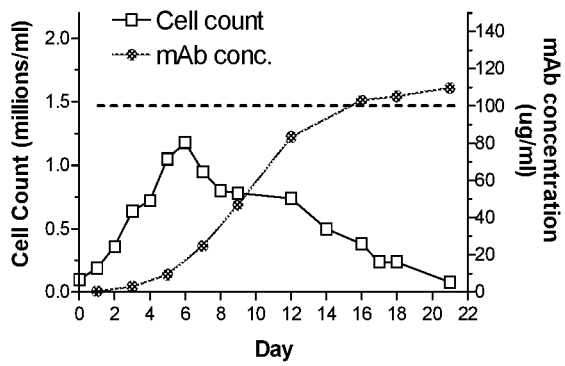
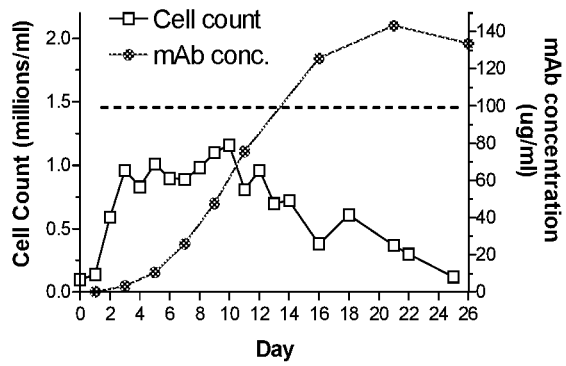
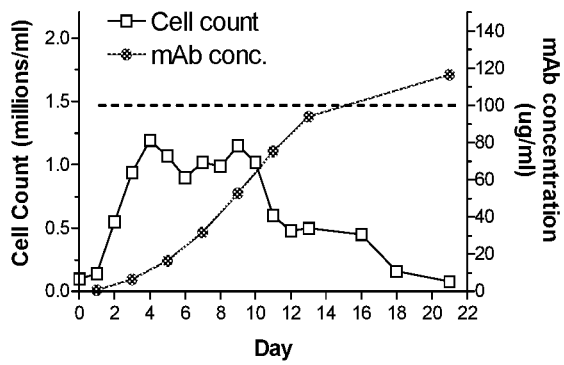
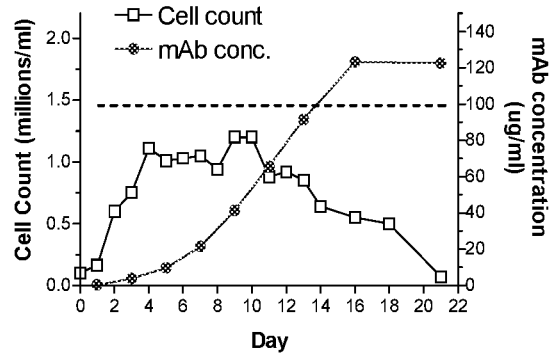
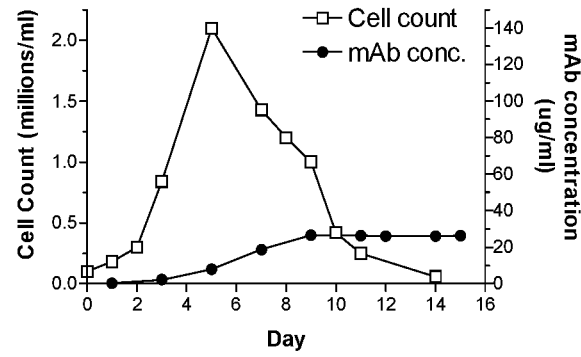

Fig. 9
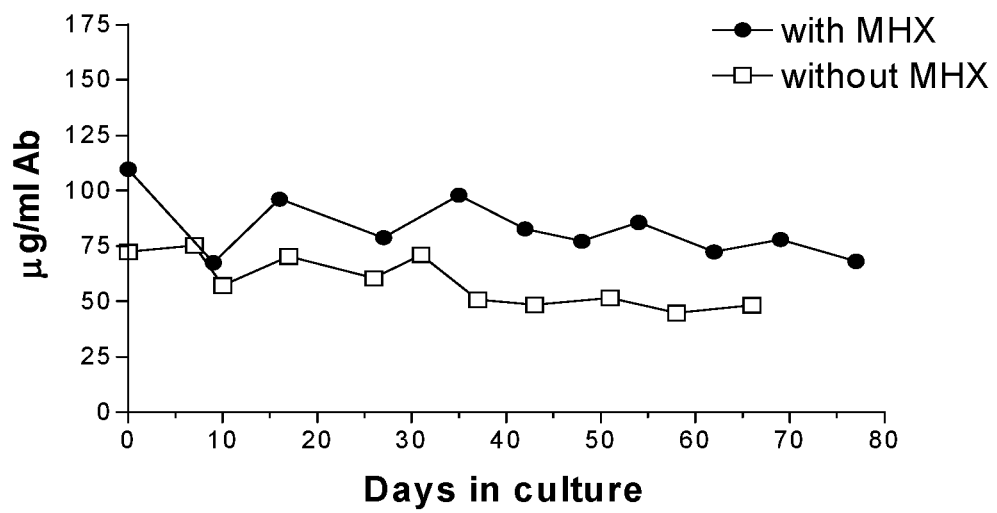
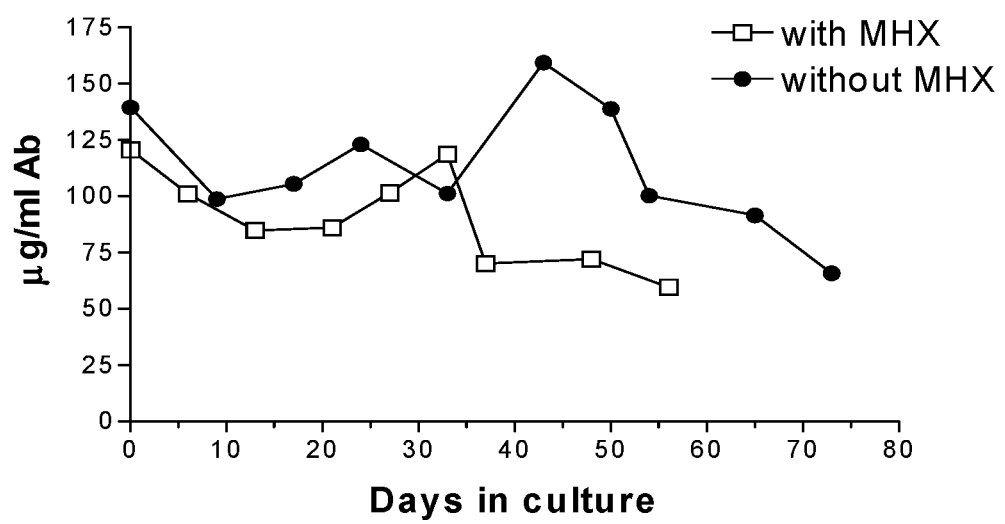

Fig. 11A
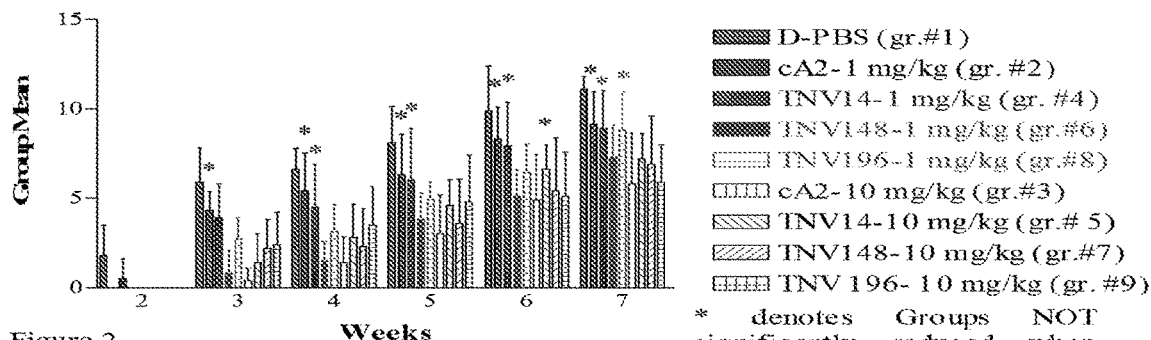
Figure 2
Fig. 11B
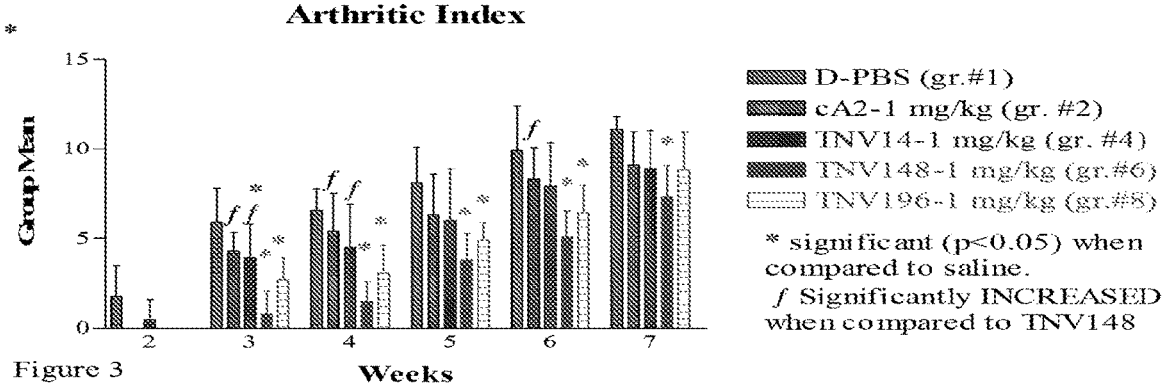
Figure 3
Fig. 11C
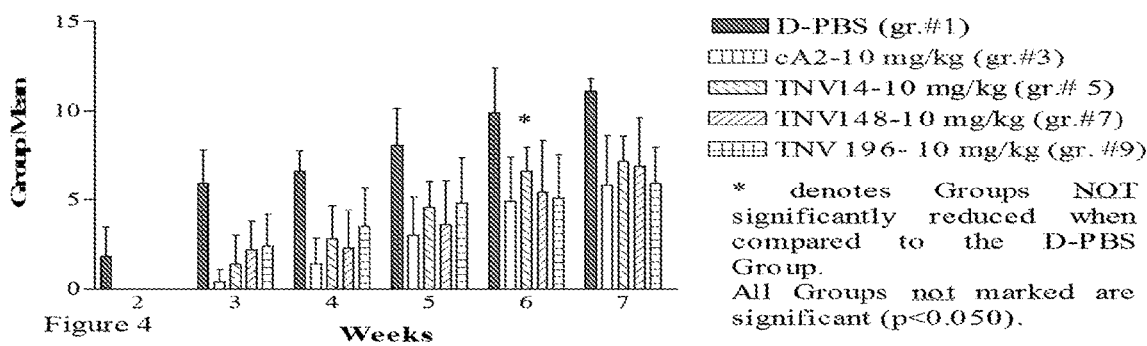
Figure 4

Stage 1 Process Flow Diagram for Preculture and Expansion of Cells

Stage 2 Process Flow Diagram

Diagram of primary N-linked oligosaccharide species
golimumab produced in Sp2/0 cells Representative HPLC chromatogram golimumab produced in Sp2/0 cells Representative Deconvoluted Mass Spectrum
for IRMA Analysis of Golimumab Produced in Sp2/0 Cells

Cyclic Imide Mediated Reactions for Asparagine in Proteins

Representative Lys C Peptide Map Chromatogram of Golimumab

Lys C peptide map chromatograms for forced deamidation of golimumab

Representative cIEF electropherogram profile golimumab produced in Sp2/0 cells

Correlation analysis of potency and % LC cycAsn93 for Golimumab

SEQUENCE LISTING

<160> NUMBER OF SEQ ID NOS: 38

<210> SEQ ID NO 1
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: Heavy Chain complementarity determining region
      1 (CDR1).

<400> SEQUENCE: 1

Ser Tyr Ala Met His
1               5

<210> SEQ ID NO 2
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: Heavy Chain complementarity determining region
      2 (CDR2).
<220> FEATURE:
<221> NAME/KEY: MISC_FEATURE
<222> LOCATION: (1)..(1)
<223> OTHER INFORMATION: Xaa at position 1 is selected from Ile, Phe or
      Val.
<220> FEATURE:
<221> NAME/KEY: MISC_FEATURE
<222> LOCATION: (2)..(2)
<223> OTHER INFORMATION: Xaa at position 2 is selected from Ile or Met.
<220> FEATURE:
<221> NAME/KEY: MISC_FEATURE
<222> LOCATION: (3)..(3)
<223> OTHER INFORMATION: Xaa at position 3 is selected from Ser or Leu.
<220> FEATURE:
<221> NAME/KEY: MISC_FEATURE
<222> LOCATION: (4)..(4)
<223> OTHER INFORMATION: Xaa at position 4 is selected from Tyr or Phe.
<220> FEATURE:
<221> NAME/KEY: MISC_FEATURE
<222> LOCATION: (10)..(10)
<223> OTHER INFORMATION: Xaa at position 10 is selected from Lys or Tyr.
<220> FEATURE:
<221> NAME/KEY: MISC_FEATURE
<222> LOCATION: (11)..(11)
<223> OTHER INFORMATION: Xaa at position 11 is selected from Ser or Tyr.
<220> FEATURE:
<221> NAME/KEY: MISC_FEATURE
<222> LOCATION: (17)..(17)
<223> OTHER INFORMATION: Xaa at position 17 is selected from Asp or Gly.

<400> SEQUENCE: 2

Xaa Xaa Xaa Xaa Asp Gly Ser Asn Lys Xaa Xaa Ala Asp Ser Val Lys
1               5                   10                  15

Xaa

<210> SEQ ID NO 3
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: Heavy Chain complementarity determining region
      3 (CDR3).
<220> FEATURE:
<221> NAME/KEY: MISC_FEATURE
<222> LOCATION: (4)..(4)
<223> OTHER INFORMATION: Xaa at position 4 is selected from Ile or Val.

```
<220> FEATURE:
<221> NAME/KEY: MISC_FEATURE
<222> LOCATION: (5)..(5)
<223> OTHER INFORMATION: Xaa at position 5 is selected from Ser, Ala or
      Gly.
<220> FEATURE:
<221> NAME/KEY: MISC_FEATURE
<222> LOCATION: (9)..(9)
<223> OTHER INFORMATION: Xaa at position 9 is selected from Asn or Tyr.

<400> SEQUENCE: 3

Asp Arg Gly Xaa Xaa Ala Gly Gly Xaa Tyr Tyr Tyr Tyr Gly Met Asp
1               5                   10                  15

Val

<210> SEQ ID NO 4
<211> LENGTH: 11
<212> TYPE: PRT
<213> ORGANISM: Homo sapiens
<220> FEATURE:
<221> NAME/KEY: MISC_FEATURE
<222> LOCATION: (1)..(11)
<223> OTHER INFORMATION: Light Chain complementarity determining region
      1 (CDR1).
<220> FEATURE:
<221> NAME/KEY: MISC_FEATURE
<222> LOCATION: (7)..(7)
<223> OTHER INFORMATION: Xaa at position 7 is selected from Ser or Tyr.

<400> SEQUENCE: 4

Arg Ala Ser Gln Ser Val Xaa Ser Tyr Leu Ala
1               5                   10

<210> SEQ ID NO 5
<211> LENGTH: 7
<212> TYPE: PRT
<213> ORGANISM: Homo sapiens
<220> FEATURE:
<221> NAME/KEY: MISC_FEATURE
<222> LOCATION: (1)..(7)
<223> OTHER INFORMATION: Light Chain complementarity determining region
      2 (CDR2).

<400> SEQUENCE: 5

Asp Ala Ser Asn Arg Ala Thr
1               5

<210> SEQ ID NO 6
<211> LENGTH: 10
<212> TYPE: PRT
<213> ORGANISM: Homo sapiens
<220> FEATURE:
<221> NAME/KEY: MISC_FEATURE
<222> LOCATION: (1)..(10)
<223> OTHER INFORMATION: Light Chain complementarity determining region
      3 (CDR3).

<400> SEQUENCE: 6

Gln Gln Arg Ser Asn Trp Pro Pro Phe Thr
1               5                   10

<210> SEQ ID NO 7
<211> LENGTH: 126
<212> TYPE: PRT
<213> ORGANISM: Homo sapiens
<220> FEATURE:
<221> NAME/KEY: MISC_FEATURE
<222> LOCATION: (1)..(126)
<223> OTHER INFORMATION: heavy chain variable region sequences as
      presented in original Figure 4
```

```
<220> FEATURE:
<221> NAME/KEY: MISC_FEATURE
<222> LOCATION: (1)..(30)
<223> OTHER INFORMATION: framework 1
<220> FEATURE:
<221> NAME/KEY: MISC_FEATURE
<222> LOCATION: (28)..(28)
<223> OTHER INFORMATION: Xaa at position 28 is selected from Ile or Thr.
<220> FEATURE:
<221> NAME/KEY: MISC_FEATURE
<222> LOCATION: (31)..(35)
<223> OTHER INFORMATION: complementarity determining region 1 (CDR1).
<220> FEATURE:
<221> NAME/KEY: MISC_FEATURE
<222> LOCATION: (36)..(49)
<223> OTHER INFORMATION: framework 2
<220> FEATURE:
<221> NAME/KEY: MISC_FEATURE
<222> LOCATION: (43)..(43)
<223> OTHER INFORMATION: Xaa at position 43 is selected from Lys or Asn.
<220> FEATURE:
<221> NAME/KEY: MISC_FEATURE
<222> LOCATION: (50)..(66)
<223> OTHER INFORMATION: complementarity determining region 2 (CDR2).
<220> FEATURE:
<221> NAME/KEY: MISC_FEATURE
<222> LOCATION: (50)..(50)
<223> OTHER INFORMATION: Xaa at position 50 is selected from Ile, Phe or
      Val.
<220> FEATURE:
<221> NAME/KEY: MISC_FEATURE
<222> LOCATION: (51)..(51)
<223> OTHER INFORMATION: Xaa at position 51 is selected from Ile or Met.
<220> FEATURE:
<221> NAME/KEY: MISC_FEATURE
<222> LOCATION: (52)..(52)
<223> OTHER INFORMATION: Xaa at position 52 is selected from Ser or Leu.
<220> FEATURE:
<221> NAME/KEY: MISC_FEATURE
<222> LOCATION: (53)..(53)
<223> OTHER INFORMATION: Xaa at position 53 is selected from Tyr or Phe.
<220> FEATURE:
<221> NAME/KEY: MISC_FEATURE
<222> LOCATION: (59)..(59)
<223> OTHER INFORMATION: Xaa at position 59 is selected from Lys or Tyr.
<220> FEATURE:
<221> NAME/KEY: MISC_FEATURE
<222> LOCATION: (60)..(60)
<223> OTHER INFORMATION: Xaa at position 60 is selected from Ser or Tyr.
<220> FEATURE:
<221> NAME/KEY: MISC_FEATURE
<222> LOCATION: (66)..(66)
<223> OTHER INFORMATION: Xaa at position 66 is selected from Asp or Gly.
<220> FEATURE:
<221> NAME/KEY: MISC_FEATURE
<222> LOCATION: (67)..(98)
<223> OTHER INFORMATION: framework 3
<220> FEATURE:
<221> NAME/KEY: MISC_FEATURE
<222> LOCATION: (70)..(70)
<223> OTHER INFORMATION: Xaa at position 70 is selected from Val or Ile.
<220> FEATURE:
<221> NAME/KEY: MISC_FEATURE
<222> LOCATION: (75)..(75)
<223> OTHER INFORMATION: Xaa at position 75 is selected from Ser or Pro.
<220> FEATURE:
<221> NAME/KEY: MISC_FEATURE
<222> LOCATION: (78)..(78)
<223> OTHER INFORMATION: Xaa at position 78 is selected from Thr or Ala.
<220> FEATURE:
<221> NAME/KEY: MISC_FEATURE
<222> LOCATION: (80)..(80)
<223> OTHER INFORMATION: Xaa at position 80 is selected from Tyr or Phe.
<220> FEATURE:
<221> NAME/KEY: MISC_FEATURE
<222> LOCATION: (94)..(94)
<223> OTHER INFORMATION: Xaa at position 94 is selected from Tyr or Phe.
<220> FEATURE:
<221> NAME/KEY: MISC_FEATURE
```

```
<222> LOCATION: (99)..(115)
<223> OTHER INFORMATION: complementarity determining region 3 (CDR3).
<220> FEATURE:
<221> NAME/KEY: MISC_FEATURE
<222> LOCATION: (102)..(102)
<223> OTHER INFORMATION: Xaa at position 102 is selected from Ile or
      Val.
<220> FEATURE:
<221> NAME/KEY: MISC_FEATURE
<222> LOCATION: (116)..(126)
<223> OTHER INFORMATION: J6 region

<400> SEQUENCE: 7

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Xaa Phe Ser Ser Tyr
            20                  25                  30

Ala Met His Trp Val Arg Gln Ala Pro Gly Xaa Gly Leu Glu Trp Val
        35                  40                  45

Ala Xaa Xaa Xaa Xaa Asp Gly Ser Asn Lys Xaa Xaa Ala Asp Ser Val
    50                  55                  60

Lys Xaa Arg Phe Thr Xaa Ser Arg Asp Asn Xaa Lys Asn Xaa Leu Xaa
65                  70                  75                  80

Leu Gln Met Asn Ser Leu Arg Ala Glu Asp Thr Ala Val Xaa Tyr Cys
                85                  90                  95

Ala Arg Asp Arg Gly Xaa Ala Ala Gly Gly Asn Tyr Tyr Tyr Tyr Gly
            100                 105                 110

Met Asp Val Trp Gly Gln Gly Thr Thr Val Thr Val Ser Ser
        115                 120                 125

<210> SEQ ID NO 8
<211> LENGTH: 108
<212> TYPE: PRT
<213> ORGANISM: Homo sapiens
<220> FEATURE:
<221> NAME/KEY: MISC_FEATURE
<222> LOCATION: (1)..(108)
<223> OTHER INFORMATION: light chain variable region sequences as
      presented in original Figure 5
<220> FEATURE:
<221> NAME/KEY: MISC_FEATURE
<222> LOCATION: (1)..(23)
<223> OTHER INFORMATION: framework 1
<220> FEATURE:
<221> NAME/KEY: MISC_FEATURE
<222> LOCATION: (24)..(34)
<223> OTHER INFORMATION: complementarity determining region 1 (CDR1).
<220> FEATURE:
<221> NAME/KEY: MISC_FEATURE
<222> LOCATION: (35)..(49)
<223> OTHER INFORMATION: framework 2
<220> FEATURE:
<221> NAME/KEY: MISC_FEATURE
<222> LOCATION: (50)..(56)
<223> OTHER INFORMATION: complementarity determining region 2 (CDR2).
<220> FEATURE:
<221> NAME/KEY: MISC_FEATURE
<222> LOCATION: (57)..(88)
<223> OTHER INFORMATION: framework 3
<220> FEATURE:
<221> NAME/KEY: MISC_FEATURE
<222> LOCATION: (89)..(98)
<223> OTHER INFORMATION: complementarity determining region 3 (CDR3).
<220> FEATURE:
<221> NAME/KEY: MISC_FEATURE
<222> LOCATION: (99)..(108)
<223> OTHER INFORMATION: J3 region

<400> SEQUENCE: 8
```

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65              70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys
            100                 105
```

```
<210> SEQ ID NO 9
<211> LENGTH: 157
<212> TYPE: PRT
<213> ORGANISM: Homo sapiens
<220> FEATURE:
<221> NAME/KEY: MISC_FEATURE
<222> LOCATION: (1)..(157)
<223> OTHER INFORMATION: human TNF alpha monomer sequence

<400> SEQUENCE: 9

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65              70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155
```

```
<210> SEQ ID NO 10
<211> LENGTH: 18
<212> TYPE: DNA
<213> ORGANISM: Homo sapiens

<400> SEQUENCE: 10
ttggtccagt cggactgg                                                 18

<210> SEQ ID NO 11
<211> LENGTH: 18
<212> TYPE: DNA
<213> ORGANISM: Homo sapiens
```

```
<400> SEQUENCE: 11
cacctgcact cggtgctt                                                18

<210> SEQ ID NO 12
<211> LENGTH: 30
<212> TYPE: DNA
<213> ORGANISM: Homo sapiens

<400> SEQUENCE: 12
cactgttttg agtgtgtacg ggcttaagtt                                   30

<210> SEQ ID NO 13
<211> LENGTH: 18
<212> TYPE: DNA
<213> ORGANISM: Homo sapiens

<400> SEQUENCE: 13
gccgcacgtg tggaaggg                                                18

<210> SEQ ID NO 14
<211> LENGTH: 25
<212> TYPE: DNA
<213> ORGANISM: Homo sapiens

<400> SEQUENCE: 14
agtcaaggtc ggactggctt aagtt                                        25

<210> SEQ ID NO 15
<211> LENGTH: 28
<212> TYPE: DNA
<213> ORGANISM: Homo sapiens

<400> SEQUENCE: 15
gttgtcccct ctcacaatct tcgaattt                                     28

<210> SEQ ID NO 16
<211> LENGTH: 18
<212> TYPE: DNA
<213> ORGANISM: Homo sapiens

<400> SEQUENCE: 16
ggcggtagac tactcgtc                                                18

<210> SEQ ID NO 17
<211> LENGTH: 7
<212> TYPE: PRT
<213> ORGANISM: Homo sapiens

<400> SEQUENCE: 17

Met Asp Trp Thr Trp Ser Ile
1               5

<210> SEQ ID NO 18
<211> LENGTH: 35
<212> TYPE: DNA
<213> ORGANISM: Homo sapiens

<400> SEQUENCE: 18
tttcgtacgc caccatggac tggacctgga gcatc                             35

<210> SEQ ID NO 19
<211> LENGTH: 34
<212> TYPE: DNA
```

```
<213> ORGANISM: Homo sapiens

<400> SEQUENCE: 19
tttcgtacgc caccatgggg tttgggctga gctg                                34

<210> SEQ ID NO 20
<211> LENGTH: 35
<212> TYPE: DNA
<213> ORGANISM: Homo sapiens

<400> SEQUENCE: 20
tttcgtacgc caccatggag tttgggctga gcatg                               35

<210> SEQ ID NO 21
<211> LENGTH: 35
<212> TYPE: DNA
<213> ORGANISM: Homo sapiens

<400> SEQUENCE: 21
tttcgtacgc caccatgaaa cacctgtggt tcttc                               35

<210> SEQ ID NO 22
<211> LENGTH: 35
<212> TYPE: DNA
<213> ORGANISM: Homo sapiens

<400> SEQUENCE: 22
tttcgtacgc caccatgggg tcaaccgcca tcctc                               35

<210> SEQ ID NO 23
<211> LENGTH: 6
<212> TYPE: PRT
<213> ORGANISM: Homo sapiens

<400> SEQUENCE: 23

Thr Val Thr Val Ser Ser
1               5

<210> SEQ ID NO 24
<211> LENGTH: 36
<212> TYPE: DNA
<213> ORGANISM: Homo sapiens

<400> SEQUENCE: 24
gtgccagtgg cagaggagtc cattcaagct taagtt                              36

<210> SEQ ID NO 25
<211> LENGTH: 5
<212> TYPE: PRT
<213> ORGANISM: Homo sapiens

<400> SEQUENCE: 25

Met Asp Met Arg Val
1               5

<210> SEQ ID NO 26
<211> LENGTH: 31
<212> TYPE: DNA
<213> ORGANISM: Homo sapiens

<400> SEQUENCE: 26
tttgtcgaca ccatggacat gagggtcctc c                                   31
```

```
<210> SEQ ID NO 27
<211> LENGTH: 28
<212> TYPE: DNA
<213> ORGANISM: Homo sapiens

<400> SEQUENCE: 27
tttgtcgaca ccatggaagc cccagctc                                      28

<210> SEQ ID NO 28
<211> LENGTH: 6
<212> TYPE: PRT
<213> ORGANISM: Homo sapiens

<400> SEQUENCE: 28

Thr Lys Val Asp Ile Lys
1               5

<210> SEQ ID NO 29
<211> LENGTH: 41
<212> TYPE: DNA
<213> ORGANISM: Homo sapiens

<400> SEQUENCE: 29
ctggtttcac ctatagtttg cattcagaat tcggcgcctt t                       41

<210> SEQ ID NO 30
<211> LENGTH: 35
<212> TYPE: DNA
<213> ORGANISM: Homo sapiens

<400> SEQUENCE: 30
catctccaga gacaattcca agaacacgct gtatc                              35

<210> SEQ ID NO 31
<211> LENGTH: 35
<212> TYPE: DNA
<213> ORGANISM: Homo sapiens

<400> SEQUENCE: 31
gtagaggtct ctgttaaggt tcttgtgcga catag                              35

<210> SEQ ID NO 32
<211> LENGTH: 19
<212> TYPE: PRT
<213> ORGANISM: Homo sapiens
<220> FEATURE:
<221> NAME/KEY: MISC_FEATURE
<222> LOCATION: (1)..(19)
<223> OTHER INFORMATION: Signal sequence for heavy chain variable region
      sequences as presented in original Figure 4

<400> SEQUENCE: 32

Met Gly Phe Gly Leu Ser Trp Val Phe Leu Val Ala Leu Leu Arg Gly
1               5                   10                  15

Val Gln Cys

<210> SEQ ID NO 33
<211> LENGTH: 20
<212> TYPE: PRT
<213> ORGANISM: Homo sapiens
<220> FEATURE:
<221> NAME/KEY: MISC_FEATURE
<222> LOCATION: (1)..(20)
<223> OTHER INFORMATION: Signal sequence for light chain variable region
      sequences as presented in original Figure 5
```

<400> SEQUENCE: 33

Met Glu Ala Pro Ala Gln Leu Leu Phe Leu Leu Leu Leu Trp Leu Pro
1               5                   10                  15

Asp Thr Thr Gly
            20

<210> SEQ ID NO 34
<211> LENGTH: 428
<212> TYPE: DNA
<213> ORGANISM: Homo sapiens

<400> SEQUENCE: 34

```
atggggtttg ggctgagctg ggttttcctc gttgctcttt taagaggtgt ccagtgtcag    60
gtgcagctgg tggagtctgg gggaggcgtg gtccagcctg gaggtccct gagactctcc    120
tgtgcagcct ctggttcacc ttcagtagct atgctatgca ctgggtccgc caggctccgg    180
caaggggctg agtgggtgg cagttatatc atatgatgga aaataaatac tacgcagact    240
ccgtgaaggg ccgattcacc atctagagac aattccaaga cacgctgta tctgcaaatg    300
aacagccaga gctgaggaca cggctgtgta ttactgtgcg agagatcgag gtatatcagc    360
aggtggaata ctactactac tacggtatgg acgtctgggg gcaagggacc acggtcaccg    420
tctcctca                                                             428
```

<210> SEQ ID NO 35
<211> LENGTH: 387
<212> TYPE: DNA
<213> ORGANISM: Homo sapiens

<400> SEQUENCE: 35

```
atggaagccc cagctcagct tctcttcctc ctgctactct ggctcccaga taccaccgga    60
gaaattgtgt tgacacagtc tccagccacc ctgtctttgt ctccagggga agagccacc    120
ctctcctgca gggccagtca gagtgttagc agctacttag cctggtacca acagaaacct    180
ggccaggctc ccaggctcct catctatgat gcatccaaca gggccactgg catcccagcc    240
aggttcagtg gcagtgggtc tgggacagac ttcactctca ccatcagcag cctagagcct    300
gaagattttg cagtttatta ctgtcagcag cgtagcaact ggcctccatt cactttcggc    360
cctgggacca agtggatat caaacgt                                         387
```

<210> SEQ ID NO 36
<211> LENGTH: 456
<212> TYPE: PRT
<213> ORGANISM: Homo sapiens
<220> FEATURE:
<221> NAME/KEY: MISC_FEATURE
<222> LOCATION: (1)..(456)
<223> OTHER INFORMATION: Golimumab Heavy Chain (HC)

<400> SEQUENCE: 36

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Ser Tyr
            20                  25                  30

Ala Met His Trp Val Arg Gln Ala Pro Gly Asn Gly Leu Glu Trp Val
        35                  40                  45

Ala Phe Met Ser Tyr Asp Gly Ser Asn Lys Lys Tyr Ala Asp Ser Val
    50                  55                  60

Lys Gly Arg Phe Thr Ile Ser Arg Asp Asn Ser Lys Asn Thr Leu Tyr

```
            65                  70                  75                  80
Leu Gln Met Asn Ser Leu Arg Ala Glu Asp Thr Ala Val Tyr Tyr Cys
                85                  90                  95

Ala Arg Asp Arg Gly Ile Ala Ala Gly Gly Asn Tyr Tyr Tyr Tyr Gly
                100                 105                 110

Met Asp Val Trp Gly Gln Gly Thr Thr Val Thr Val Ser Ser Ala Ser
                115                 120                 125

Thr Lys Gly Pro Ser Val Phe Pro Leu Ala Pro Ser Ser Lys Ser Thr
                130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
                180                 185                 190

Ser Val Val Thr Val Pro Ser Ser Ser Leu Gly Thr Gln Thr Tyr Ile
                195                 200                 205

Cys Asn Val Asn His Lys Pro Ser Asn Thr Lys Val Asp Lys Lys Val
210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
                260                 265                 270

Val Asp Val Ser His Glu Asp Pro Glu Val Lys Phe Asn Trp Tyr Val
                275                 280                 285

Asp Gly Val Glu Val His Asn Ala Lys Thr Lys Pro Arg Glu Glu Gln
                290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
                340                 345                 350

Arg Glu Pro Gln Val Tyr Thr Leu Pro Pro Ser Arg Asp Glu Leu Thr
                355                 360                 365

Lys Asn Gln Val Ser Leu Thr Cys Leu Val Lys Gly Phe Tyr Pro Ser
                370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
                420                 425                 430

Ser Cys Ser Val Met His Glu Ala Leu His Asn His Tyr Thr Gln Lys
                435                 440                 445

Ser Leu Ser Leu Ser Pro Gly Lys
                450                 455

<210> SEQ ID NO 37
<211> LENGTH: 215
<212> TYPE: PRT
<213> ORGANISM: Homo sapiens
```

```
<220> FEATURE:
<221> NAME/KEY: MISC_FEATURE
<222> LOCATION: (1)..(215)
<223> OTHER INFORMATION: Golimumab Light Chain (LC)

<400> SEQUENCE: 37
```

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
        210                 215

```
<210> SEQ ID NO 38
<211> LENGTH: 456
<212> TYPE: PRT
<213> ORGANISM: Artificial Sequence
<220> FEATURE:
<223> OTHER INFORMATION: HC N43D

<400> SEQUENCE: 38
```

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Ser Tyr
            20                  25                  30

Ala Met His Trp Val Arg Gln Ala Pro Gly Asp Gly Leu Glu Trp Val
        35                  40                  45

Ala Phe Met Ser Tyr Asp Gly Ser Asn Lys Lys Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Ile Ala Ala Gly Gly Asn Tyr Tyr Tyr Tyr Gly
            100                 105                 110

```
Met Asp Val Trp Gly Gln Gly Thr Thr Val Thr Val Ser Ser Ala Ser
        115                 120                 125
Thr Lys Gly Pro Ser Val Phe Pro Leu Ala Pro Ser Ser Lys Ser Thr
    130                 135                 140
Ser Gly Gly Thr Ala Ala Leu Gly Cys Leu Val Lys Asp Tyr Phe Pro
145                 150                 155                 160
Glu Pro Val Thr Val Ser Trp Asn Ser Gly Ala Leu Thr Ser Gly Val
                165                 170                 175
His Thr Phe Pro Ala Val Leu Gln Ser Ser Gly Leu Tyr Ser Leu Ser
            180                 185                 190
Ser Val Val Thr Val Pro Ser Ser Ser Leu Gly Thr Gln Thr Tyr Ile
        195                 200                 205
Cys Asn Val Asn His Lys Pro Ser Asn Thr Lys Val Asp Lys Lys Val
    210                 215                 220
Glu Pro Lys Ser Cys Asp Lys Thr His Thr Cys Pro Pro Cys Pro Ala
225                 230                 235                 240
Pro Glu Leu Leu Gly Gly Pro Ser Val Phe Leu Phe Pro Pro Lys Pro
                245                 250                 255
Lys Asp Thr Leu Met Ile Ser Arg Thr Pro Glu Val Thr Cys Val Val
            260                 265                 270
Val Asp Val Ser His Glu Asp Pro Glu Val Lys Phe Asn Trp Tyr Val
        275                 280                 285
Asp Gly Val Glu Val His Asn Ala Lys Thr Lys Pro Arg Glu Glu Gln
    290                 295                 300
Tyr Asn Ser Thr Tyr Arg Val Val Ser Val Leu Thr Val Leu His Gln
305                 310                 315                 320
Asp Trp Leu Asn Gly Lys Glu Tyr Lys Cys Lys Val Ser Asn Lys Ala
                325                 330                 335
Leu Pro Ala Pro Ile Glu Lys Thr Ile Ser Lys Ala Lys Gly Gln Pro
            340                 345                 350
Arg Glu Pro Gln Val Tyr Thr Leu Pro Pro Ser Arg Asp Glu Leu Thr
        355                 360                 365
Lys Asn Gln Val Ser Leu Thr Cys Leu Val Lys Gly Phe Tyr Pro Ser
    370                 375                 380
Asp Ile Ala Val Glu Trp Glu Ser Asn Gly Gln Pro Glu Asn Asn Tyr
385                 390                 395                 400
Lys Thr Thr Pro Pro Val Leu Asp Ser Asp Gly Ser Phe Phe Leu Tyr
                405                 410                 415
Ser Lys Leu Thr Val Asp Lys Ser Arg Trp Gln Gln Gly Asn Val Phe
            420                 425                 430
Ser Cys Ser Val Met His Glu Ala Leu His Asn His Tyr Thr Gln Lys
        435                 440                 445
Ser Leu Ser Leu Ser Pro Gly Lys
450                 455
```

ANTI-TUMOR NECROSIS FACTOR (TNF) ANTIBODIES AND COMPOSITIONS THEREOF

CROSS-REFERENCE TO RELATED APPLICATIONS

This application claims the benefit of International Application Number PCT/IB2020/051637, filed 26 Feb. 2020, which claims the benefit of U.S. Provisional Application No. 62/818,305, filed 14 Mar. 2019. The entire contents of each of the aforesaid applications are incorporated herein by reference in their entireties.

REFERENCE TO SEQUENCE LISTING SUBMITTED ELECTRONICALLY

This application contains a sequence listing, which is submitted electronically via EFS-Web as an ASCII formatted sequence listing with a file name "JBI6053USPSP1SEQLIST.TXT" creation date of Dec. 7, 2018 and having a size of 25,153 bytes. The sequence listing submitted via EFS-Web is part of the specification and is herein incorporated by reference in its entirety.

FIELD OF THE INVENTION

The present invention relates to methods for producing a recombinant anti-TNF antibody having a heavy chain (HC) comprising amino acid sequence SEQ ID NO:38 and a light chain (LC) comprising amino acid sequence SEQ ID NO:37 and compositions comprising the recombinant anti-TNF antibody.

BACKGROUND OF THE INVENTION

TNF alpha is a soluble homotrimer of 17 kD protein subunits. A membrane-bound 26 kD precursor form of TNF also exists.

Cells other than monocytes or macrophages also produce TNF alpha. For example, human non-monocytic tumor cell lines produce TNF alpha and CD4+ and CD8+ peripheral blood T lymphocytes and some cultured T and B cell lines also produce TNF alpha.

TNF alpha causes pro-inflammatory actions which result in tissue injury, such as degradation of cartilage and bone, induction of adhesion molecules, inducing procoagulant activity on vascular endothelial cells, increasing the adherence of neutrophils and lymphocytes, and stimulating the release of platelet activating factor from macrophages, neutrophils and vascular endothelial cells.

TNF alpha has been associated with infections, immune disorders, neoplastic pathologies, autoimmune pathologies and graft-versus-host pathologies. The association of TNF alpha with cancer and infectious pathologies is often related to the host's catabolic state. Cancer patients suffer from weight loss, usually associated with anorexia.

The extensive wasting which is associated with cancer, and other diseases, is known as "cachexia". Cachexia includes progressive weight loss, anorexia, and persistent erosion of lean body mass in response to a malignant growth. The cachectic state causes much cancer morbidity and mortality. There is evidence that TNF alpha is involved in cachexia in cancer, infectious pathology, and other catabolic states.

TNF alpha is believed to play a central role in gram-negative sepsis and endotoxic shock, including fever, malaise, anorexia, and cachexia. Endotoxin strongly activates monocyte/macrophage production and secretion of TNF alpha and other cytokines. TNF alpha and other monocyte-derived cytokines mediate the metabolic and neurohormonal responses to endotoxin. Endotoxin administration to human volunteers produces acute illness with flu-like symptoms including fever, tachycardia, increased metabolic rate and stress hormone release. Circulating TNF alpha increases in patients suffering from Gram-negative sepsis.

Thus, TNF alpha has been implicated in inflammatory diseases, autoimmune diseases, viral, bacterial and parasitic infections, malignancies, and/or neurodegenerative diseases and is a useful target for specific biological therapy in diseases, such as rheumatoid arthritis and Crohn's disease. Beneficial effects in open-label trials with monoclonal antibodies to TNF alpha have been reported with suppression of inflammation and with successful retreatment after relapse in rheumatoid arthritis and in Crohn's disease. Beneficial results in a randomized, double-blind, placebo-controlled trials have also been reported in rheumatoid arthritis with suppression of inflammation.

Neutralizing antisera or mAbs to TNF have been shown in mammals other than man to abrogate adverse physiological changes and prevent death after lethal challenge in experimental endotoxemia and bacteremia. This effect has been demonstrated, e.g., in rodent lethality assays and in primate pathology model systems.

Putative receptor binding loci of hTNF has been disclosed and the receptor binding loci of TNF alpha as consisting of amino acids 11-13, 37-42, 49-57 and 155-157 of TNF have been disclosed.

Non-human mammalian, chimeric, polyclonal (e.g., antisera) and/or monoclonal antibodies (Mabs) and fragments (e.g., proteolytic digestion or fusion protein products thereof) are potential therapeutic agents that are being investigated in some cases to attempt to treat certain diseases. However, such antibodies or fragments can elicit an immune response when administered to humans. Such an immune response can result in an immune complex-mediated clearance of the antibodies or fragments from the circulation, and make repeated administration unsuitable for therapy, thereby reducing the therapeutic benefit to the patient and limiting the administration of the antibody or fragment. For example, repeated administration of antibodies or fragments comprising non-human portions can lead to serum sickness and/or anaphylaxis. In order to avoid these and other problems, a number of approaches have been taken to reduce the immunogenicity of such antibodies and portions thereof, including chimerization and humanization, as well known in the art. These and other approaches, however, still can result in antibodies or fragments having some immunogenicity, low affinity, low avidity, or with problems in cell culture, scale up, production, and/or low yields. Thus, such antibodies or fragments can be less than ideally suited for manufacture or use as therapeutic proteins.

Accordingly, there is a need to provide anti-TNF antibodies or fragments thereof for use as therapeutics for treatment of diseases mediated by TNF alpha.

SUMMARY OF THE INVENTION

The embodiments of the invention are defined, respectively, by the independent and dependent claims appended hereto, which for the sake of brevity are incorporated by reference herein. Other embodiments, features, and advantages of the various aspects of the invention are apparent from the detailed description below taken in conjunction with the appended drawing figures.

In certain embodiments, the present invention provides anti-TNF antibodies comprising: (i) a heavy chain comprising an amino acid sequence of SEQ ID NO:38; and (ii) a light chain comprising an amino acid sequence of SEQ ID NO:37, wherein the anti-TNF antibodies are expressed in Chinese Hamster Ovary cells (CHO cells).

In certain embodiments, the present invention provides anti-TNF antibodies comprising: (i) a heavy chain comprising an amino acid sequence of SEQ ID NO:38; and (ii) a light chain comprising an amino acid sequence of SEQ ID NO:37, wherein the anti-TNF antibodies are expressed in Chinese Hamster Ovary cells (CHO cells), and wherein the oligosaccharide profile of the anti-TNF antibodies comprises total neutral oligosaccharide species>99.0% and total charged oligosaccharide species<1.0%.

In certain embodiments, the present invention provides anti-TNF antibodies comprising: (i) a heavy chain comprising an amino acid sequence of SEQ ID NO:38; and (ii) a light chain comprising an amino acid sequence of SEQ ID NO:37, wherein the anti-TNF antibodies are expressed in Chinese Hamster Ovary cells (CHO cells), and wherein the oligosaccharide profile of the anti-TNF antibodies further comprises individual neutral oligosaccharide species G0F>60.0%, G1F<20.0%, and G2F<5.0%.

In certain embodiments, the present invention provides anti-TNF antibodies comprising: (i) a heavy chain comprising an amino acid sequence of SEQ ID NO:38; and (ii) a light chain comprising an amino acid sequence of SEQ ID NO:37, wherein the anti-TNF antibodies are expressed in Chinese Hamster Ovary cells (CHO cells), and wherein the anti-TNF antibodies have no disialylated glycan species as determined by High Performance Liquid Chromatography (HPLC) or Reduced Mass Analysis (RMA).

In certain embodiments, the present invention provides anti-TNF antibodies comprising: (i) a heavy chain comprising an amino acid sequence of SEQ ID NO:38; and (ii) a light chain comprising an amino acid sequence of SEQ ID NO:37, wherein the anti-TNF antibodies are expressed in Chinese Hamster Ovary cells (CHO cells), and wherein the anti-TNF antibodies have a longer half-life or increased antibody-dependent cell-mediated cytotoxicity (ADCC) compared to anti-TNF antibodies expressed in Sp2/0 cells.

In certain embodiments, the present invention provides anti-TNF antibodies comprising: (i) a heavy chain comprising an amino acid sequence of SEQ ID NO:38; and (ii) a light chain comprising an amino acid sequence of SEQ ID NO:37, wherein the anti-TNF antibodies are expressed in Chinese Hamster Ovary cells (CHO cells), and wherein the anti-TNF antibodies are a follow-on biologic.

In certain embodiments, the present invention provides anti-TNF antibodies comprising: (i) a heavy chain comprising an amino acid sequence of SEQ ID NO:38; and (ii) a light chain comprising an amino acid sequence of SEQ ID NO:37, wherein the anti-TNF antibodies are expressed in Chinese Hamster Ovary cells (CHO cells), and wherein the anti-TNF antibodies have a longer half-life or increased antibody-dependent cell-mediated cytotoxicity (ADCC) compared to anti-TNF antibodies expressed in Sp2/0 cells.

In certain embodiments, the present invention provides anti-TNF antibodies comprising: (i) a heavy chain comprising an amino acid sequence of SEQ ID NO:38; and (ii) a light chain comprising an amino acid sequence of SEQ ID NO:37, wherein the anti-TNF antibodies are expressed in Chinese Hamster Ovary cells (CHO cells), and wherein the oligosaccharide profile of the anti-TNF antibodies comprises total neutral oligosaccharide species>99.0% and total charged oligosaccharide species<1.0%, and wherein the anti-TNF antibodies have a longer half-life or increased antibody-dependent cell-mediated cytotoxicity (ADCC) compared to anti-TNF antibodies expressed in Sp2/0 cells.

In certain embodiments, the present invention provides anti-TNF antibodies comprising: (i) a heavy chain comprising an amino acid sequence of SEQ ID NO:38; and (ii) a light chain comprising an amino acid sequence of SEQ ID NO:37, wherein the anti-TNF antibodies are expressed in Chinese Hamster Ovary cells (CHO cells), and wherein the oligosaccharide profile of the anti-TNF antibodies further comprises individual neutral oligosaccharide species G0F>60.0%, G1F<20.0%, and G2F<5.0%, and wherein the anti-TNF antibodies have a longer half-life or increased antibody-dependent cell-mediated cytotoxicity (ADCC) compared to anti-TNF antibodies expressed in Sp2/0 cells.

In certain embodiments, the present invention provides anti-TNF antibodies comprising: (i) a heavy chain comprising an amino acid sequence of SEQ ID NO:38; and (ii) a light chain comprising an amino acid sequence of SEQ ID NO:37, wherein the anti-TNF antibodies are expressed in Chinese Hamster Ovary cells (CHO cells), and wherein the anti-TNF antibodies have no disialylated glycan species as determined by High Performance Liquid Chromatography (HPLC) or Reduced Mass Analysis (RMA), and wherein the anti-TNF antibodies have a longer half-life or increased antibody-dependent cell-mediated cytotoxicity (ADCC) compared to anti-TNF antibodies expressed in Sp2/0 cells.

In certain embodiments, the present invention provides anti-TNF antibodies comprising: (i) a heavy chain comprising an amino acid sequence of SEQ ID NO:38; and (ii) a light chain comprising an amino acid sequence of SEQ ID NO:37, wherein the anti-TNF antibodies are expressed in Chinese Hamster Ovary cells (CHO cells), and wherein the anti-TNF antibodies have a longer half-life or increased antibody-dependent cell-mediated cytotoxicity (ADCC) compared to anti-TNF antibodies expressed in Sp2/0 cells.

In certain embodiments, the present invention provides anti-TNF antibodies comprising: (i) a heavy chain comprising an amino acid sequence of SEQ ID NO:38; and (ii) a light chain comprising an amino acid sequence of SEQ ID NO:37, wherein the anti-TNF antibodies are expressed in Chinese Hamster Ovary cells (CHO cells), and wherein the anti-TNF antibodies have a longer half-life or increased antibody-dependent cell-mediated cytotoxicity (ADCC) compared to anti-TNF antibodies expressed in Sp2/0 cells and the anti-TNF antibodies are a follow-on biologic.

In certain embodiments, the present invention provides anti-TNF antibodies comprising: (i) a heavy chain comprising an amino acid sequence of SEQ ID NO:38; and (ii) a light chain comprising an amino acid sequence of SEQ ID NO:37, wherein the anti-TNF antibodies are expressed in Chinese Hamster Ovary cells (CHO cells), and wherein the anti-TNF antibodies have a longer half-life or increased antibody-dependent cell-mediated cytotoxicity (ADCC) compared to anti-TNF antibodies expressed in Sp2/0 cells and the anti-TNF antibodies are a follow-on biologic.

In certain embodiments, the present invention provides anti-TNF antibodies comprising: (i) a heavy chain comprising an amino acid sequence of SEQ ID NO:38; and (ii) a light chain comprising an amino acid sequence of SEQ ID NO:37, wherein the anti-TNF antibodies are expressed in Chinese Hamster Ovary cells (CHO cells), and wherein the oligosaccharide profile of the anti-TNF antibodies comprises total neutral oligosaccharide species>99.0% and total charged oligosaccharide species<1.0%, and wherein the anti-TNF antibodies have a longer half-life or increased antibody-dependent cell-mediated cytotoxicity (ADCC) compared to anti-TNF antibodies expressed in Sp2/0 cells and the anti-TNF antibodies are a follow-on biologic.

In certain embodiments, the present invention provides anti-TNF antibodies comprising: (i) a heavy chain comprising an amino acid sequence of SEQ ID NO:38; and (ii) a light chain comprising an amino acid sequence of SEQ ID NO:37, wherein the anti-TNF antibodies are expressed in Chinese Hamster Ovary cells (CHO cells), and wherein the oligosaccharide profile of the anti-TNF antibodies further comprises individual neutral oligosaccharide species G0F>60.0%, G1F<20.0%, and G2F<5.0%, and wherein the anti-TNF antibodies have a longer half-life or increased antibody-dependent cell-mediated cytotoxicity (ADCC) compared to anti-TNF antibodies expressed in Sp2/0 cells and the anti-TNF antibodies are a follow-on biologic.

In certain embodiments, the present invention provides anti-TNF antibodies comprising: (i) a heavy chain comprising an amino acid sequence of SEQ ID NO:38; and (ii) a light chain comprising an amino acid sequence of SEQ ID NO:37, wherein the anti-TNF antibodies are expressed in Chinese Hamster Ovary cells (CHO cells), and wherein the anti-TNF antibodies have no disialylated glycan species as determined by High Performance Liquid Chromatography (HPLC) or Reduced Mass Analysis (RMA), and wherein the anti-TNF antibodies have a longer half-life or increased antibody-dependent cell-mediated cytotoxicity (ADCC) compared to anti-TNF antibodies expressed in Sp2/0 cells and the anti-TNF antibodies are a follow-on biologic.

In certain embodiments, the present invention provides anti-TNF antibodies comprising: (i) a heavy chain comprising an amino acid sequence of SEQ ID NO:38; and (ii) a light chain comprising an amino acid sequence of SEQ ID NO:37, wherein the anti-TNF antibodies are expressed in Chinese Hamster Ovary cells (CHO cells), and wherein the anti-TNF antibodies have a longer half-life or increased antibody-dependent cell-mediated cytotoxicity (ADCC) compared to anti-TNF antibodies expressed in Sp2/0 cells and the anti-TNF antibodies are a follow-on biologic.

In certain embodiments, the present invention provides a method of manufacture for producing anti-TNF antibodies comprising: (i) a heavy chain comprising an amino acid sequence of SEQ ID NO: 38; and (ii) a light chain comprising an amino acid sequence of SEQ ID NO:37, wherein the anti-TNF antibodies are produced by a method of manufacture comprising: a. culturing Chinese Hamster Ovary cells (CHO cells) with nucleotides encoding the anti-TNF antibodies; b. expressing the anti-TNF antibodies in the CHO cells; and, c. purifying the anti-TNF antibodies.

In certain embodiments, the present invention provides a method of manufacture for producing anti-TNF antibodies comprising: (i) a heavy chain comprising an amino acid sequence of SEQ ID NO:38; and (ii) a light chain comprising an amino acid sequence of SEQ ID NO:37, wherein the anti-TNF antibodies are produced by a method of manufacture comprising: a. culturing Chinese Hamster Ovary cells (CHO cells) with nucleotides encoding the anti-TNF antibodies; b. expressing the anti-TNF antibodies in the CHO cells; and, c. purifying the anti-TNF antibodies, wherein the oligosaccharide profile of the anti-TNF antibodies comprises total neutral oligosaccharide species>99.0% and total charged oligosaccharide species<1.0%, and In certain embodiments, the present invention provides a method of manufacture for producing anti-TNF antibodies comprising: (i) a heavy chain comprising an amino acid sequence of SEQ ID NO:38; and (ii) a light chain comprising an amino acid sequence of SEQ ID NO:37, wherein the anti-TNF antibodies are produced by a method of manufacture comprising: a. culturing Chinese Hamster Ovary cells (CHO cells) with nucleotides encoding the anti-TNF antibodies; b. expressing the anti-TNF antibodies in the CHO cells; and, c. purifying the anti-TNF antibodies, wherein the oligosaccharide profile of the anti-TNF antibodies further comprises individual neutral oligosaccharide species G0F>60.0%, G1F<20.0%, and G2F<5.0%.

In certain embodiments, the present invention provides a method of manufacture for producing anti-TNF antibodies comprising: (i) a heavy chain comprising an amino acid sequence of SEQ ID NO:38; and (ii) a light chain comprising an amino acid sequence of SEQ ID NO:37, wherein the anti-TNF antibodies are produced by a method of manufacture comprising: a. culturing Chinese Hamster Ovary cells (CHO cells) with nucleotides encoding the anti-TNF antibodies; b. expressing the anti-TNF antibodies in the CHO cells; and, c. purifying the anti-TNF antibodies, wherein the anti-TNF antibodies have no disialylated glycan species as determined by High Performance Liquid Chromatography (HPLC) or Reduced Mass Analysis (RMA).

In certain embodiments, the present invention provides a method of manufacture for producing anti-TNF antibodies comprising: (i) a heavy chain comprising an amino acid sequence of SEQ ID NO:38; and (ii) a light chain comprising an amino acid sequence of SEQ ID NO:37, wherein the anti-TNF antibodies are produced by a method of manufacture comprising: a. culturing Chinese Hamster Ovary cells (CHO cells) with 30 nucleotides encoding the anti-TNF antibodies; b. expressing the anti-TNF antibodies in the CHO cells; and, c. purifying the anti-TNF antibodies, wherein the anti-TNF antibodies have a longer half-life or increased antibody-dependent cell-mediated cytotoxicity (ADCC) compared to anti-TNF antibodies expressed in Sp2/0 cells. In certain embodiments, the present invention provides a method of manufacture for producing anti-TNF antibodies comprising: (i) a heavy chain comprising an amino acid sequence of SEQ ID NO:38; and (ii) a light chain comprising an amino acid sequence of SEQ ID NO:37, wherein the anti-TNF antibodies are produced by a method of manufacture comprising: a. culturing Chinese Hamster Ovary cells (CHO cells) with nucleotides encoding the anti-TNF antibodies; b. expressing the anti-TNF antibodies in the CHO cells; and, c. purifying the anti-TNF antibodies, wherein the anti-TNF antibodies are a follow-on biologic.

In certain embodiments, the present invention provides a method of manufacture for producing anti-TNF antibodies comprising: (i) a heavy chain comprising an amino acid sequence of SEQ ID NO:38; and (ii) a light chain comprising an amino acid sequence of SEQ ID NO:37, wherein the anti-TNF antibodies are produced by a method of manufacture comprising: a. culturing Chinese Hamster Ovary cells (CHO cells) with nucleotides encoding the anti-TNF antibodies; b. expressing the anti-TNF antibodies in the CHO cells; and, c. purifying the anti-TNF antibodies, wherein the oligosaccharide profile of the anti-TNF antibodies comprises total neutral oligosaccharide species>99.0% and total charged oligosaccharide species<1.0%, and wherein the anti-TNF antibodies have a longer half-life or increased antibody-dependent cell-mediated cytotoxicity (ADCC) compared to anti-TNF antibodies expressed in Sp2/0 cells.

In certain embodiments, the present invention provides a method of manufacture for producing anti-TNF antibodies comprising: (i) a heavy chain comprising an amino acid sequence of SEQ ID NO:38; and (ii) a light chain comprising an amino acid sequence of SEQ ID NO:37, wherein the anti-TNF antibodies are produced by a method of manufacture comprising: a. culturing Chinese Hamster Ovary cells (CHO cells) with 25 nucleotides encoding the anti-TNF antibodies; b. expressing the anti-TNF antibodies in the CHO cells; and, c. purifying the anti-TNF antibodies, wherein the oligosaccharide profile of the anti-TNF antibodies further comprises individual neutral oligosaccharide species G0F>60.0%, G1F<20.0%, and G2F<5.0%, and wherein the anti-TNF antibodies have a longer half-life or increased antibody-dependent cell-mediated cytotoxicity (ADCC) compared to anti-TNF antibodies expressed in Sp2/0 cells.

In certain embodiments, the present invention provides a method of manufacture for producing anti-TNF antibodies comprising: (i) a heavy chain comprising an amino acid sequence of SEQ ID NO:38; and (ii) a light chain comprising an amino acid sequence of SEQ ID NO:37, wherein the anti-TNF antibodies are produced by a method of manufacture comprising: a. culturing Chinese Hamster Ovary cells (CHO cells) with nucleotides encoding the anti-TNF antibodies; b. expressing the anti-TNF antibodies in the CHO cells; and, c. purifying the anti-TNF antibodies, wherein the anti-TNF antibodies have no disialylated glycan species as determined by High Performance Liquid Chromatography (HPLC) or Reduced Mass Analysis (RMA), and wherein the anti-TNF antibodies have a longer half-life or increased antibody-dependent cell-mediated cytotoxicity (ADCC) compared to anti-TNF antibodies expressed in Sp2/0 cells.

In certain embodiments, the present invention provides a method of manufacture for producing anti-TNF antibodies comprising: (i) a heavy chain comprising an amino acid sequence of SEQ ID NO:38; and (ii) a light chain comprising an amino acid sequence of SEQ ID NO:37, wherein the anti-TNF antibodies are produced by a method of manufacture comprising: a. culturing Chinese Hamster Ovary cells (CHO cells) with nucleotides encoding the anti-TNF antibodies; b. expressing the anti-TNF antibodies in the CHO cells; and, c. purifying the anti-TNF antibodies, wherein the anti-TNF antibodies have a longer half-life or increased antibody-dependent cell-mediated cytotoxicity (ADCC) compared to anti-TNF antibodies expressed in Sp2/0 cells.

In certain embodiments, the present invention provides a method of manufacture for producing anti-TNF antibodies comprising: (i) a heavy chain comprising an amino acid sequence of SEQ ID NO:38; and (ii) a light chain comprising an amino acid sequence of SEQ ID NO:37, wherein the anti-TNF antibodies are produced by a method of manufacture comprising: a. culturing Chinese Hamster Ovary cells (CHO cells) with nucleotides encoding the anti-TNF antibodies; b. expressing the anti-TNF antibodies in the CHO cells; and, c. purifying the anti-TNF antibodies, and wherein the anti-TNF antibodies have a longer half-life or increased antibody-dependent cell-mediated cytotoxicity (ADCC) compared to anti-TNF antibodies expressed in Sp2/0 cells the anti-TNF antibodies are a follow-on biologic.

In certain embodiments, the present invention provides a composition comprising anti-TNF antibodies: (i) a heavy chain comprising an amino acid sequence of SEQ ID NO:38; and (ii) a light chain comprising an amino acid sequence of SEQ ID NO:37, wherein the anti-TNF antibodies are expressed in Chinese Hamster Ovary cells (CHO cells).

In certain embodiments, the present invention provides a composition comprising anti-TNF antibodies: (i) a heavy chain comprising an amino acid sequence of SEQ ID NO:38; and (ii) a light chain comprising an amino acid sequence of SEQ ID NO:37, wherein the anti-TNF antibodies are expressed in Chinese Hamster Ovary cells (CHO cells), and wherein the oligosaccharide profile of the anti-TNF antibodies comprises total neutral oligosaccharide species>99.0% and total charged oligosaccharide species<1.0%.

In certain embodiments, the present invention provides a composition comprising anti-TNF antibodies: (i) a heavy chain comprising an amino acid sequence of SEQ ID NO:38; and (ii) a light chain comprising an amino acid sequence of SEQ ID NO:37, wherein the anti-TNF antibodies are expressed in Chinese Hamster Ovary cells (CHO cells), and wherein the oligosaccharide profile of the anti-TNF antibodies further comprises individual neutral oligosaccharide species G0F>60.0%, G1F<20.0%, and G2F<5.0%.

In certain embodiments, the present invention provides a composition comprising anti-TNF antibodies: (i) a heavy chain comprising an amino acid sequence of SEQ ID NO:38; and (ii) a light chain comprising an amino acid sequence of SEQ ID NO:37, wherein the anti-TNF antibodies are expressed in Chinese Hamster Ovary cells (CHO cells), and wherein the anti-TNF antibodies have no disialylated glycan species as determined by High Performance Liquid Chromatography (HPLC).

In certain embodiments, the present invention provides a composition comprising anti-TNF antibodies: (i) a heavy chain comprising an amino acid sequence of SEQ ID NO:38; and (ii) a light chain comprising an amino acid sequence of SEQ ID NO:37, wherein the anti-TNF antibodies are expressed in Chinese Hamster Ovary cells (CHO cells), and wherein the anti-TNF antibodies have a longer half-life or increased antibody-dependent cell-mediated cytotoxicity (ADCC) compared to anti-TNF antibodies expressed in Sp2/0 cells.

In certain embodiments, the present invention provides a composition comprising anti-TNF antibodies: (i) a heavy chain comprising an amino acid sequence of SEQ ID NO:38; and (ii) a light chain comprising an amino acid sequence of SEQ ID NO:37, wherein the anti-TNF antibodies are expressed in Chinese Hamster Ovary cells (CHO cells), and wherein the anti-TNF antibodies are a follow-on biologic.

In certain embodiments, the present invention provides a composition comprising anti-TNF antibodies: (i) a heavy chain comprising an amino acid sequence of SEQ ID NO:38; and (ii) a light chain comprising an amino acid sequence of SEQ ID NO:37, wherein the anti-TNF antibodies are expressed in Chinese Hamster Ovary cells (CHO cells), and wherein the oligosaccharide profile of the anti-TNF antibodies comprises total neutral oligosaccharide species>99.0% and total charged oligosaccharide species<1.0%, and wherein the anti-TNF antibodies have a longer half-life or increased antibody-dependent cell-mediated cytotoxicity (ADCC) compared to anti-TNF antibodies expressed in Sp2/0 cells.

In certain embodiments, the present invention provides a composition comprising anti-TNF antibodies: (i) a heavy chain comprising an amino acid sequence of SEQ ID NO:38; and (ii) a light chain comprising an amino acid sequence of SEQ ID NO:37, wherein the anti-TNF antibodies are expressed in Chinese Hamster Ovary cells (CHO cells), and wherein the oligosaccharide profile of the anti-TNF antibodies further comprises individual neutral oligosaccharide species G0F>60.0%, G1F<20.0%, and G2F<5.0%, and wherein the anti-TNF antibodies have a longer half-life or increased antibody-dependent cell-mediated cytotoxicity (ADCC) compared to anti-TNF antibodies expressed in Sp2/0 cells.

In certain embodiments, the present invention provides a composition comprising anti-TNF antibodies: (i) a heavy chain comprising an amino acid sequence of SEQ ID NO:38; and (ii) a light chain comprising an amino acid sequence of SEQ ID NO:37, wherein the anti-TNF antibodies are expressed in Chinese Hamster Ovary cells (CHO cells), and wherein the anti-TNF antibodies have no disialylated glycan species as determined by High Performance Liquid Chromatography (HPLC), and wherein the anti-TNF antibodies have a longer half-life or increased antibody-dependent cell-mediated cytotoxicity (ADCC) compared to anti-TNF antibodies expressed in Sp2/0 cells.

In certain embodiments, the present invention provides a composition comprising anti-TNF antibodies: (i) a heavy chain comprising an amino acid sequence of SEQ ID NO:38; and (ii) a light chain comprising an amino acid sequence of SEQ ID NO:37, wherein the anti-TNF antibodies are expressed in Chinese Hamster Ovary cells (CHO cells), and wherein the anti-TNF antibodies have a longer half-life or increased antibody-dependent cell-mediated cytotoxicity (ADCC) compared to anti-TNF antibodies expressed in Sp2/0 cells, and wherein the anti-TNF antibodies have a longer half-life or increased antibody-dependent cell-mediated cytotoxicity (ADCC) compared to anti-TNF antibodies expressed in Sp2/0 cells.

In certain embodiments, the present invention provides a composition comprising anti-TNF antibodies: (i) a heavy chain comprising an amino acid sequence of SEQ ID NO:38; and (ii) a light chain comprising an amino acid sequence of SEQ ID NO:37, wherein the anti-TNF antibodies are expressed in Chinese Hamster Ovary cells (CHO cells), and wherein the oligosaccharide profile of the anti-TNF antibodies comprises total neutral oligosaccharide species>99.0% and total charged oligosaccharide species<1.0%, and wherein the anti-TNF antibodies have a longer half-life or increased antibody-dependent cell-mediated cytotoxicity (ADCC) compared to anti-TNF antibodies expressed in Sp2/0 cells and the anti-TNF antibodies are a follow-on biologic.

In certain embodiments, the present invention provides a composition comprising anti-TNF antibodies: (i) a heavy chain comprising an amino acid sequence of SEQ ID NO:38; and (ii) a light chain comprising an amino acid sequence of SEQ ID NO:37, wherein the anti-TNF antibodies are expressed in Chinese Hamster Ovary cells (CHO cells), and wherein the oligosaccharide profile of the anti-TNF antibodies further comprises individual neutral oligosaccharide species G0F>60.0%, G1F<20.0%, and G2F<5.0%, and wherein the anti-TNF antibodies have a longer half-life or increased antibody-dependent cell-mediated cytotoxicity (ADCC) compared to anti-TNF antibodies expressed in Sp2/0 cells and the anti-TNF antibodies are a follow-on biologic.

In certain embodiments, the present invention provides a composition comprising anti-TNF antibodies: (i) a heavy chain comprising an amino acid sequence of SEQ ID NO:38; and (ii) a light chain comprising an amino acid sequence of SEQ ID NO:37, wherein the anti-TNF antibodies are expressed in Chinese Hamster Ovary cells (CHO cells), and wherein the anti-TNF antibodies have no disialylated glycan species as determined by High Performance Liquid Chromatography (HPLC), and wherein the anti-TNF antibodies have a longer half-life or increased antibody-dependent cell-mediated cytotoxicity (ADCC) compared to anti-TNF antibodies expressed in Sp2/0 cells and the anti-TNF antibodies are a follow-on biologic.

In certain embodiments, the present invention provides an isolated nucleic acid molecule encoding a recombinant anti-TNF antibody comprising a heavy chain (HC) comprising amino acid sequence SEQ ID NO:38 and a light chain (LC) comprising amino acid sequence SEQ ID NO:37.

In certain embodiments, the present invention provides a vector or recombinant eukaryotic host cell comprising a nucleic acid molecule encoding a recombinant anti-TNF antibody comprising a heavy chain (HC) comprising amino acid sequence SEQ ID NO:38 and a light chain (LC) comprising amino acid sequence SEQ ID NO:37.

In certain embodiments, the present invention provides a recombinant eukaryotic host cell comprising nucleic acid molecule encoding a recombinant anti-TNF antibody comprising a heavy chain (HC) comprising amino acid sequence SEQ ID NO:38 and a light chain (LC) comprising amino acid sequence SEQ ID NO:37, wherein the eukaryotic host cell is selected from the group consisting of: COS-1 cell, COS-7 cell, HEK293 cell, BHK21 cell, Chinese hamster ovary (CHO) cell, BSC-1 cell, Hep G2 cell, P3X63Ag8.653 (653) cell, Sp2/0 cell, HeLa cell, myeloma cell, and lymphoma cell.

In certain embodiments, the present invention provides a recombinant eukaryotic host cell comprising nucleic acid molecule encoding a recombinant anti-TNF antibody comprising a heavy chain (HC) comprising amino acid sequence SEQ ID NO:38 and a light chain (LC) comprising amino acid sequence SEQ ID NO:37, wherein the eukaryotic host cell is and Sp2/0 cell.

In certain embodiments, the present invention provides a method of producing a recombinant anti-TNF antibody comprising a heavy chain (HC) comprising amino acid sequence SEQ ID NO:38 and a light chain (LC) comprising amino acid sequence SEQ ID NO:37, the method comprising: a. culturing the recombinant eukaryotic host cell comprising a nucleic acid molecule encoding a recombinant anti-TNF antibody comprising a heavy chain (HC) comprising amino acid sequence SEQ ID NO:38 and a light chain (LC) comprising amino acid sequence SEQ ID NO:37 under conditions such that the anti-TNF antibody molecule is expressed; and, b. recovering the recombinant anti-TNF antibody.

In certain embodiments, the present invention provides a method of producing a recombinant anti-TNF antibody comprising a heavy chain (HC) comprising amino acid sequence SEQ ID NO:38 and a light chain (LC) comprising amino acid sequence SEQ ID NO:37, the method comprising: a. culturing the recombinant eukaryotic host cell comprising a nucleic acid molecule encoding a recombinant anti-TNF antibody comprising a heavy chain (HC) comprising amino acid sequence SEQ ID NO:38 and a light chain (LC) comprising amino acid sequence SEQ ID NO:37 under conditions such that the anti-TNF antibody molecule is expressed; and, b. recovering the recombinant anti-TNF antibody, wherein the eukaryotic host cell is selected from the group consisting of: COS-1 cell, COS-7 cell, HEK293 cell, BHK21 cell, Chinese hamster ovary (CHO) cell, BSC-1 cell, Hep G2 cell, P3X63Ag8.653 (653) cell, Sp2/0 cell, HeLa cell, myeloma cell, and lymphoma cell.

In certain embodiments, the present invention provides a method of producing a recombinant anti-TNF antibody comprising a heavy chain (HC) comprising amino acid sequence SEQ ID NO:38 and a light chain (LC) comprising amino acid sequence SEQ ID NO:37, the method comprising: a. culturing the recombinant eukaryotic host cell comprising a nucleic acid molecule encoding a recombinant anti-TNF antibody comprising a heavy chain (HC) comprising amino acid sequence SEQ ID NO:38 and a light chain (LC) comprising amino acid sequence SEQ ID NO:37 under conditions such that the anti-TNF antibody molecule is expressed; and, b. recovering the recombinant anti-TNF antibody, wherein the eukaryotic host cell is an Sp2/0 cell.

In certain embodiments, the present invention provides a recombinant anti-TNF antibody comprising a heavy chain (HC) comprising amino acid sequence SEQ ID NO:38 and a light chain (LC) comprising amino acid sequence SEQ ID NO:37, wherein the recombinant anti-TNF antibody is produced by a method comprising: a. culturing the recombinant eukaryotic host cell comprising a nucleic acid molecule encoding a recombinant anti-TNF antibody comprising a heavy chain (HC) comprising amino acid sequence SEQ ID NO:38 and a light chain (LC) comprising amino acid sequence SEQ ID NO:37 under conditions such that the anti-TNF antibody molecule is expressed; and, b. recovering the recombinant anti-TNF antibody.

In certain embodiments, the present invention provides a recombinant anti-TNF antibody comprising a heavy chain (HC) comprising amino acid sequence SEQ ID NO:38 and a light chain (LC) comprising amino acid sequence SEQ ID NO:37, wherein the recombinant anti-TNF antibody is produced by a method comprising: a. culturing the recombinant eukaryotic host cell comprising a nucleic acid molecule encoding a recombinant anti-TNF antibody comprising a heavy chain (HC) comprising amino acid sequence SEQ ID NO:38 and a light chain (LC) comprising amino acid sequence SEQ ID NO:37 under conditions such that the anti-TNF antibody molecule is expressed; and, b. recovering the recombinant anti-TNF antibody, and wherein the anti-TNF antibody inhibits the activity of TNF alpha (TNFα).

In certain embodiments, the present invention provides a recombinant anti-TNF antibody comprising a heavy chain (HC) comprising amino acid sequence SEQ ID NO:38 and a light chain (LC) comprising amino acid sequence SEQ ID NO:37, wherein the recombinant anti-TNF antibody is produced by a method comprising: a. culturing the recombinant eukaryotic host cell comprising a nucleic acid molecule encoding a recombinant anti-TNF antibody comprising a heavy chain (HC) comprising amino acid sequence SEQ ID NO:38 and a light chain (LC) comprising amino acid sequence SEQ ID NO:37 under conditions such that the anti-TNF antibody molecule is expressed; and, b. recovering the recombinant anti-TNF antibody, and wherein the eukaryotic host cell is selected from the group consisting of COS-1 cell, COS-7 cell, HEK293 cell, BHK21 cell, Chinese hamster ovary (CHO) cell, BSC-1 cell, Hep G2 cell, P3X63Ag8.653 (653) cell, Sp2/0 cell, HeLa cell, myeloma cell, and lymphoma cell.

In certain embodiments, the present invention provides a recombinant anti-TNF antibody comprising a heavy chain (HC) comprising amino acid sequence SEQ ID NO:38 and a light chain (LC) comprising amino acid sequence SEQ ID NO:37, wherein the recombinant anti-TNF antibody is produced by a method comprising: a. culturing the recombinant eukaryotic host cell comprising a nucleic acid molecule encoding a recombinant anti-TNF antibody comprising a heavy chain (HC) comprising amino acid sequence SEQ ID NO:38 and a light chain (LC) comprising amino acid sequence SEQ ID NO:37 under conditions such that the anti-TNF antibody molecule is expressed; and, b. recovering the recombinant anti-TNF antibody, and wherein the eukaryotic host cell is an Sp2/0 cell.

In certain embodiments, the present invention provides a pharmaceutical composition comprising a recombinant anti-TNF antibody comprising a heavy chain (HC) comprising amino acid sequence SEQ ID NO:38 and a light chain (LC) comprising amino acid sequence SEQ ID NO:37, wherein the recombinant anti-TNF antibody is produced by a method comprising: a. culturing the recombinant eukaryotic host cell comprising a nucleic acid molecule encoding a recombinant anti-TNF antibody comprising a heavy chain (HC) comprising amino acid sequence SEQ ID NO:38 and a light chain (LC) comprising amino acid sequence SEQ ID NO:37 under conditions such that the anti-TNF antibody molecule is expressed; and, b. recovering the recombinant anti-TNF antibody.

In certain embodiments, the present invention provides a pharmaceutical composition comprising a recombinant anti-TNF antibody comprising a heavy chain (HC) comprising amino acid sequence SEQ ID NO:38 and a light chain (LC) comprising amino acid sequence SEQ ID NO:37, wherein the recombinant anti-TNF antibody is produced by a method comprising: a. culturing the recombinant eukaryotic host cell comprising a nucleic acid molecule encoding a recombinant anti-TNF antibody comprising a heavy chain (HC) comprising amino acid sequence SEQ ID NO:38 and a light chain (LC) comprising amino acid sequence SEQ ID NO:37 under conditions such that the anti-TNF antibody molecule is expressed; and, b. recovering the recombinant anti-TNF antibody, and wherein the anti-TNF antibody inhibits the activity of TNF alpha (TNFα).

In certain embodiments, the present invention provides a pharmaceutical composition comprising a recombinant anti-TNF antibody comprising a heavy chain (HC) comprising amino acid sequence SEQ ID NO:38 and a light chain (LC) comprising amino acid sequence SEQ ID NO:37, wherein the recombinant anti-TNF antibody is produced by a method comprising: a. culturing the recombinant eukaryotic host cell comprising a nucleic acid molecule encoding a recombinant anti-TNF antibody comprising a heavy chain (HC) comprising amino acid sequence SEQ ID NO:38 and a light chain (LC) comprising amino acid sequence SEQ ID NO:37 under conditions such that the anti-TNF antibody molecule is expressed; and, b. recovering the recombinant anti-TNF antibody, and wherein the eukaryotic host cell is selected from the group consisting of: COS-1 cell, COS-7 cell, HEK293 cell, BHK21 cell, Chinese hamster ovary (CHO) cell, BSC-1 cell, Hep G2 cell, P3X63Ag8.653 (653) cell, Sp2/0 cell, HeLa cell, myeloma cell, and lymphoma cell.

In certain embodiments, the present invention provides a pharmaceutical composition comprising a recombinant anti-TNF antibody comprising a heavy chain (HC) comprising amino acid sequence SEQ ID NO:38 and a light chain (LC) comprising amino acid sequence SEQ ID NO:37, wherein the recombinant anti-TNF antibody is produced by a method comprising: a. culturing the recombinant eukaryotic host cell comprising a nucleic acid molecule encoding a recombinant anti-TNF antibody comprising a heavy chain (HC) comprising amino acid sequence SEQ ID NO:38 and a light chain (LC) comprising amino acid sequence SEQ ID NO:37 under conditions such that the anti-TNF antibody molecule is expressed; and, b. recovering the recombinant anti-TNF antibody, and wherein the eukaryotic host cell is an Sp2/0 cell.

FIG. 2A-B shows DNA sequences of the TNV mAb heavy chain variable regions. The germline gene shown is the DP-46 gene. 'TNVs' indicates that the sequence shown is the sequence of TNV14, TNV15, TNV148, and TNV196. The first three nucleotides in the TNV sequence define the translation initiation Met codon. Dots in the TNV mAb gene sequences indicate the nucleotide is the same as in the germline sequence. The first 19 nucleotides (underlined) of the TNV sequences correspond to the oligonucleotide used to PCR-amplify the variable region. An amino acid translation (single letter abbreviations) starting with the mature mAb is shown only for the germline gene. The three CDR domains in the germline amino acid translation are marked in bold and underlined. Lines labeled TNV148(B) indicate that the sequence shown pertains to both TNV148 and TNV148B. Gaps in the germline DNA sequence (CDR3) are due to the sequence not being known or not existing in the germline gene. The TNV mAb heavy chains use the J6 joining region.

FIG. 3 shows DNA sequences of the TNV mAb light chain variable regions. The germline gene shown is a representative member of the Vg/38K family of human kappa germline variable region genes. Dots in the TNV mAb gene sequences indicate the nucleotide is the same as in the germline sequence. The first 16 nucleotides (underlined) of the TNV sequences correspond to the oligonucleotide used to PCR-amplify the variable region. An amino acid translation of the mature mAb (single letter abbreviations) is shown only for the germline gene. The three CDR domains in the germline amino acid translation are marked in bold and underlined. Lines labeled TNV148(B) indicate that the sequence shown pertains to both TNV148 and TNV148B. Gaps in the germline DNA sequence (CDR3) are due to the sequence not being known or not existing in the germline gene. The TNV mAb light chains use the J3 joining sequence.

FIG. 4 shows deduced amino acid sequences of the TNV mAb heavy chain variable regions. The amino acid sequences shown (single letter abbreviations) were deduced from DNA sequence determined from both uncloned PCR products and cloned PCR products. The amino sequences are shown partitioned into the secretory signal sequence (signal), framework (FW), and complementarity determining region (CDR) domains. The amino acid sequence for the DP-46 germline gene is shown on the top line for each domain. Dots indicate that the amino acid in the TNV mAb is identical to the germline gene. TNV148(B) indicates that the sequence shown pertains to both TNV148 and TNV148B. 'TNVs' indicates that the sequence shown pertains to all TNV mAbs unless a different sequence is shown. Dashes in the germline sequence (CDR3) indicate that the sequences are not known or do not exist in the germline gene.

FIG. 5 shows deduced amino acid sequences of the TNV mAb light chain variable regions. The amino acid sequences shown (single letter abbreviations) were deduced from DNA sequence determined from both uncloned PCR products and cloned PCR products. The amino sequences are shown partitioned into the secretory signal sequence (signal), framework (FW), and complementarity determining region (CDR) domains. The amino acid sequence for the Vg/38K-type light chain germline gene is shown on the top line for each domain. Dots indicate that the amino acid in the TNV mAb is identical to the germline gene. TNV148 (B) indicates that the sequence shown pertains to both TNV148 and TNV148B. 'All' indicates that the sequence shown pertains to TNV14, TNV15, TNV148, TNV148B, and TNV186.

FIG. 6 shows schematic illustrations of the heavy and light chain expression plasmids used to make the rTNV148B-expressing C466 cells. p1783 is the heavy chain plasmid and p1776 is the light chain plasmid. The rTNV148B variable and constant region coding domains are shown as black boxes. The immunoglobulin enhancers in the J-C introns are shown as gray boxes. Relevant restriction sites are shown. The plasmids are shown oriented such that transcription of the Ab genes proceeds in a clockwise direction. Plasmid p1783 is 19.53 kb in length and plasmid p1776 is 15.06 kb in length.

The complete nucleotide sequences of both plasmids are known. The variable region coding sequence in p1783 can be easily replaced with another heavy chain variable region sequence by replacing the BsiWI/BstBI restriction fragment. The variable region coding sequence in p1776 can be replaced with another variable region sequence by replacing the SalI/AflII restriction fragment.

FIG. 7 shows graphical representation of growth curve analyses of five rTNV148B-producing cell lines. Cultures were initiated on day 0 by seeding cells into T75 flasks in I5Q+MHX media to have a viable cell density of $1.0\times10^5$ cells/ml in a 30 ml volume. The cell cultures used for these studies had been in continuous culture since transfections and subclonings were performed. On subsequent days, cells in the T flasks were thoroughly resuspended and a 0.3 ml aliquot of the culture was removed. The growth curve studies were terminated when cell counts dropped below $1.5\times10^5$ cells/ml. The number of live cells in the aliquot was determined by trypan blue exclusion and the remainder of the aliquot stored for later mAb concentration determination. An ELISA for human IgG was performed on all sample aliquots at the same time.

FIG. 8 shows a graphical representation of the comparison of cell growth rates in the presence of varying concentrations of MHX selection. Cell subclones C466A and C466B were thawed into MHX-free media (IMDM, 5% FBS, 2 mM glutamine) and cultured for two additional days. Both cell cultures were then divided into three cultures that contained either no MHX, 0.2×MHX, or 1×MHX. One day later, fresh T75 flasks were seeded with the cultures at a starting density of $1\times10^5$ cells/ml and cells counted at 24 hour intervals for one week. Doubling times during the first 5 days were calculated using the formula in SOP PD32.025 and are shown above the bars.

FIG. 9 shows graphical representations of the stability of mAb production over time from two rTNV148B-producing cell lines. Cell subclones that had been in continuous culture since performing transfections and subclonings were used to start long-term serial cultures in 24-well culture dishes.

Cells were cultured in I5Q media with and without MHX selection. Cells were continually passaged by splitting the cultures every 4 to 6 days to maintain new viable cultures while previous cultures were allowed to go spent. Aliquots of spent cell supernatant were collected shortly after cultures were spent and stored until the mAb concentrations were determined. An ELISA for human IgG was performed on all sample aliquots at the same time.

Figure 10:
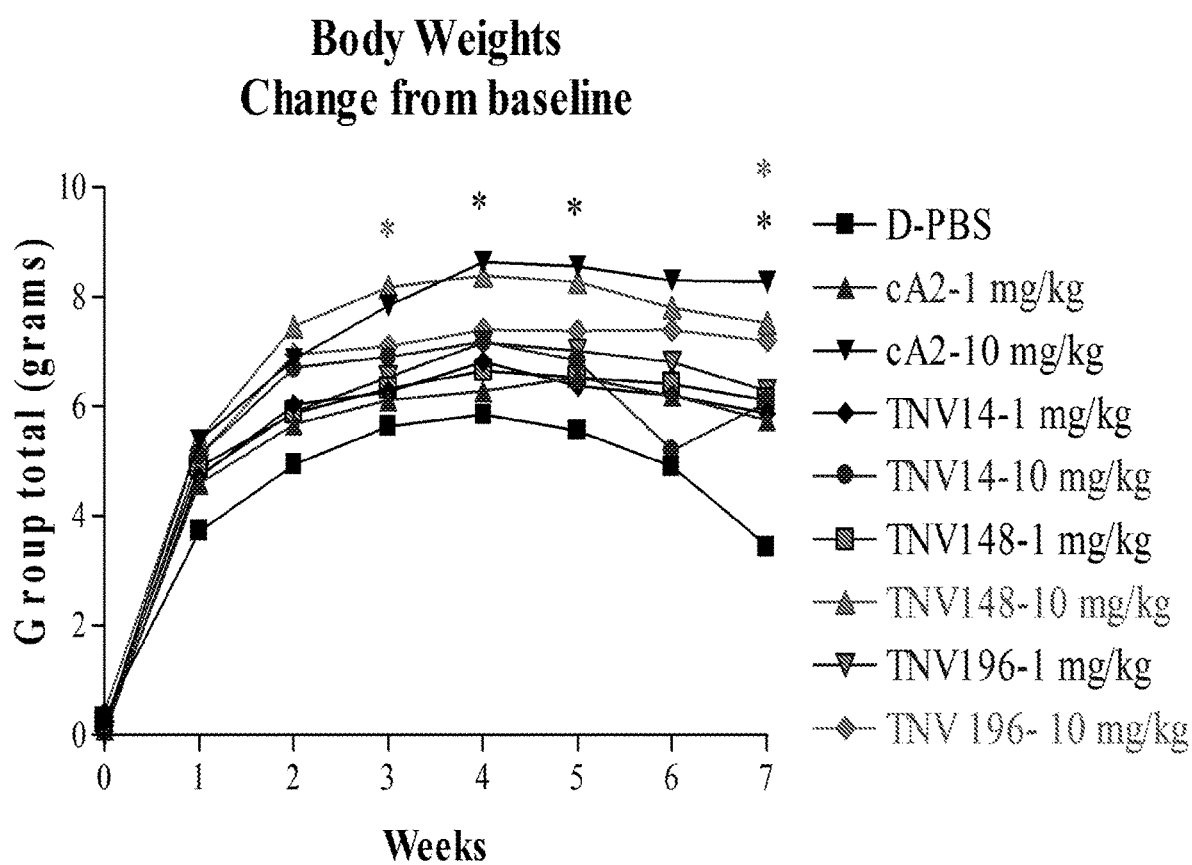

FIG. 10 shows arthritis mouse model mice Tg 197 weight changes in response to anti-TNF antibodies of the present invention as compared to controls in Example 4. At approximately 4 weeks of age the Tg197 study mice were assigned, based on gender and body weight, to one of 9 treatment groups and treated with a single intraperitoneal bolus dose of Dulbecco's PBS (D-PBS) or an anti-TNF antibody of the present invention (TNV14, TNV148 or TNV196) at either 1 mg/kg or 10 mg/kg. When the weights were analyzed as a change from pre-dose, the animals treated with 10 mg/kg cA2 showed consistently higher weight gain than the D-PBS-treated animals throughout the study. This weight gain was significant at weeks 3-7. The animals treated with 10 mg/kg TNV148 also achieved significant weight gain at week 7 of the study.

FIG. 11A-C represent the progression of disease severity based on the arthritic index as presented in Example 4. The 10 mg/kg cA2-treated group's arthritic index was lower than the D-PBS control group starting at week 3 and continuing throughout the remainder of the study (week 7). The animals treated with 1 mg/kg TNV14 and the animals treated with 1 mg/kg cA2 failed to show significant reduction in AI after week 3 when compared to the D-PBS-treated Group. There were no significant differences between the 10 mg/kg treatment groups when each was compared to the others of similar dose (10 mg/kg cA2 compared to 10 mg/kg TNV14, 148 and 196). When the 1 mg/kg treatment groups were compared, the 1 mg/kg TNV148 showed a significantly lower AI than 1 mg/kg cA2 at 3, 4 and 7 weeks. The 1 mg/kg TNV148 was also significantly lower than the 1 mg/kg TNV14-treated Group at 3 and 4 weeks. Although TNV196 showed significant reduction in AI up to week 6 of the study (when compared to the D-PBS-treated Group), TNV148 was the only 1 mg/kg treatment that remained significant at the conclusion of the study.

Figure 12:
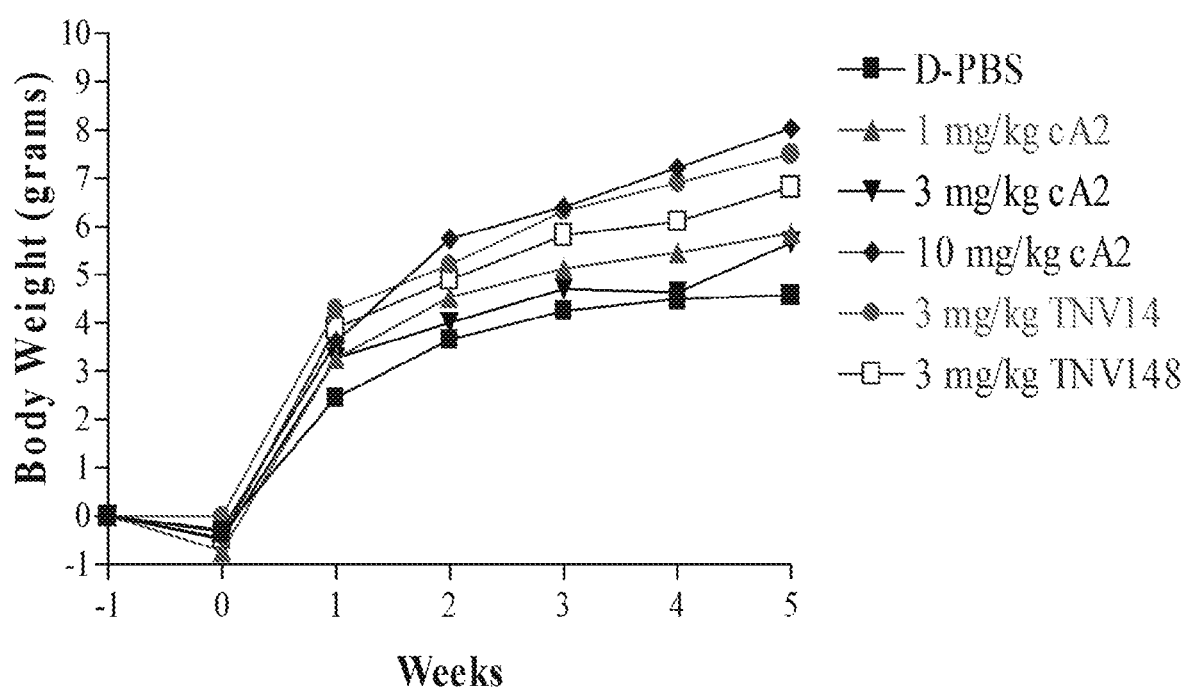

FIG. 12 shows arthritis mouse model mice Tg 197 weight changes in response to anti-TNF antibodies of the present invention as compared to controls in Example 5. At approximately 4 weeks of age the Tg197 study mice were assigned, based on body weight, to one of 8 treatment groups and treated with a intraperitoneal bolus dose of control article (D-PBS) or antibody (TNV14, TNV148) at 3 mg/kg (week 0). Injections were repeated in all animals at weeks 1, 2, 3, and 4. Groups 1-6 were evaluated for test article efficacy. Serum samples, obtained from animals in Groups 7 and 8 were evaluated for immune response induction and pharmacokinetic clearance of TNV14 or TNV148 at weeks 2, 3 and 4.

Figure 13A:
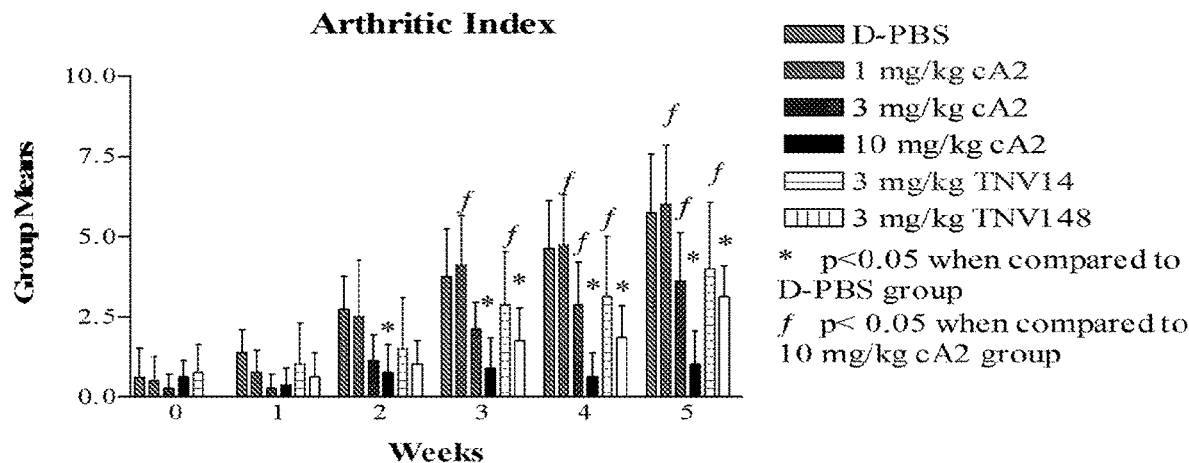
Figure 13B:
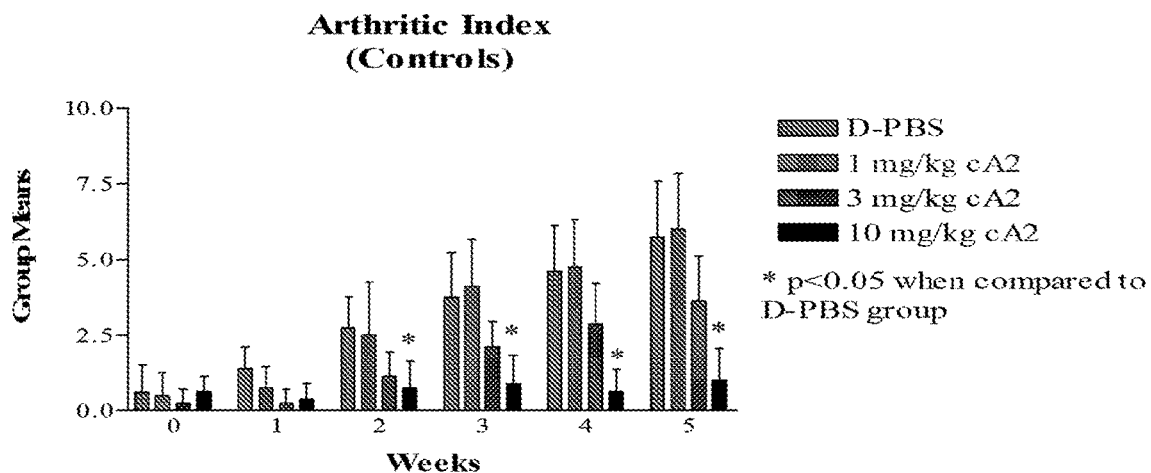
Figure 13C:
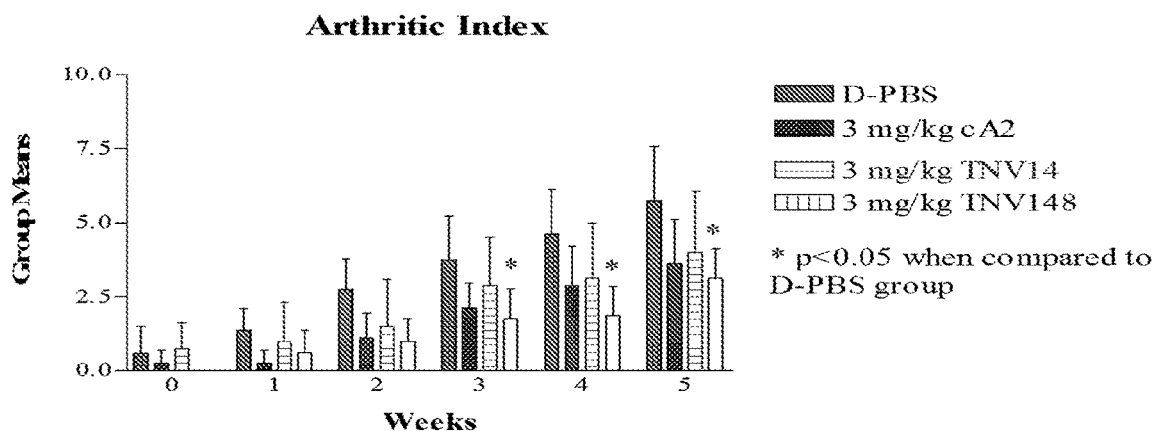

FIG. 13A-C are graphs representing the progression of disease severity in Example 5 based on the arthritic index. The 10 mg/kg cA2-treated group's arthritic index was significantly lower than the D-PBS control group starting at week 2 and continuing throughout the remainder of the study (week 5). The animals treated with 1 mg/kg or 3 mg/kg of cA2 and the animals treated with 3 mg/kg TNV14 failed to achieve any significant reduction in AI at any time throughout the study when compared to the d-PBS control group. The animals treated with 3 mg/kg TNV148 showed a significant reduction when compared to the d-PBS-treated group starting at week 3 and continuing through week 5. The 10 mg/kg cA2-treated animals showed a significant reduction in AI when compared to both the lower doses (1 mg/kg and 3 mg/kg) of cA2 at weeks 4 and 5 of the study and was also significantly lower than the TNV14-treated animals at weeks 3-5. Although there appeared to be no significant differences between any of the 3 mg/kg treatment groups, the AI for the animals treated with 3 mg/kg TNV14 were significantly higher at some time points than the 10 mg/kg whereas the animals treated with TNV148 were not significantly different from the animals treated with 10 mg/kg of cA2.

Figure 14:
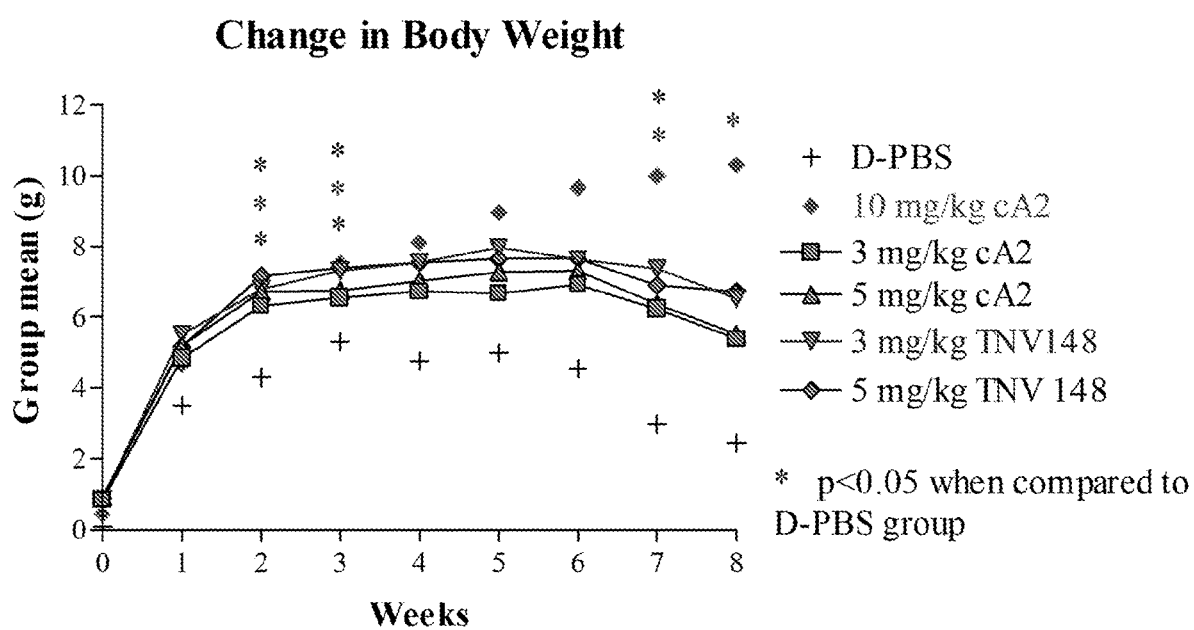

FIG. 14 shows arthritis mouse model mice Tg 197 weight changes in response to anti-TNF antibodies of the present invention as compared to controls in Example 6. At approximately 4 weeks of age the Tg197 study mice were assigned, based on gender and body weight, to one of 6 treatment groups and treated with a single intraperitoneal bolus dose of antibody (cA2, or TNV148) at either 3 mg/kg or 5 mg/kg. This study utilized the D-PBS and 10 mg/kg cA2 control Groups.

Figure 15:
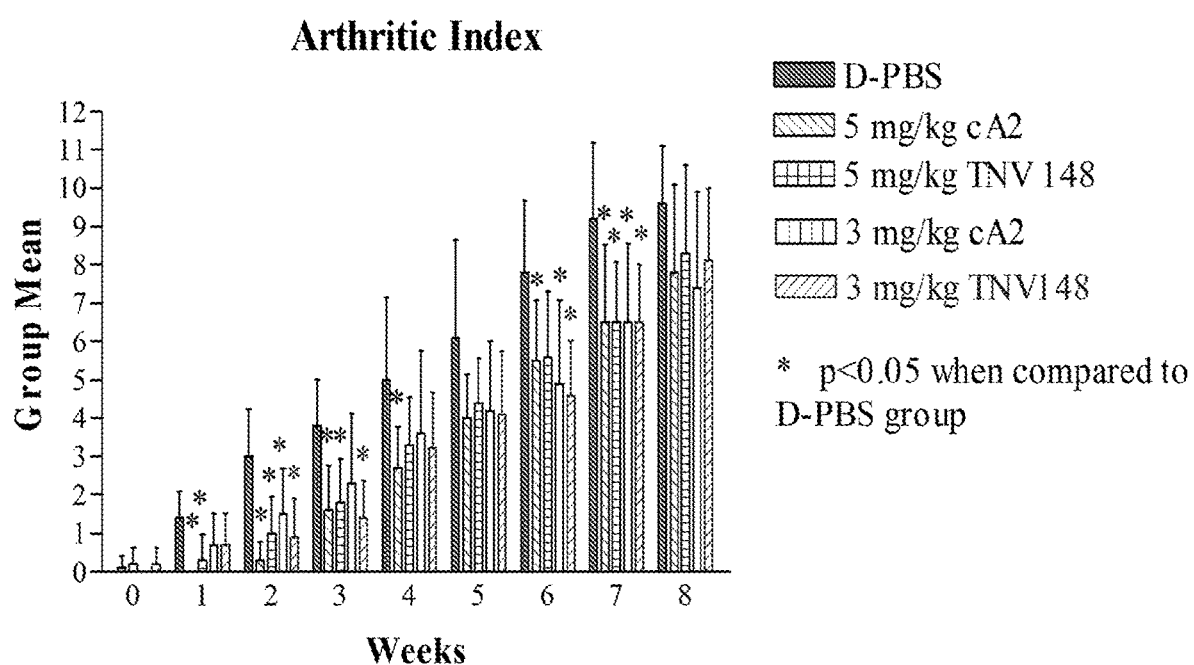

FIG. 15 represents the progression of disease severity based on the arthritic index as presented in Example 6. All treatment groups showed some protection at the earlier time points, with the 5 mg/kg cA2 and the 5 mg/kg TNV148 showing significant reductions in AI at weeks 1-3 and all treatment groups showing a significant reduction at week 2. Later in the study the animals treated with 5 mg/kg cA2 showed some protection, with significant reductions at weeks 4, 6 and 7. The low dose (3 mg/kg) of both the cA2 and the TNV148 showed significant reductions at 6 and all treatment groups showed significant reductions at week 7. None of the treatment groups were able to maintain a significant reduction at the conclusion of the study (week 8). There were no significant differences between any of the treatment groups (excluding the saline control group) at any time point.

Figure 16:
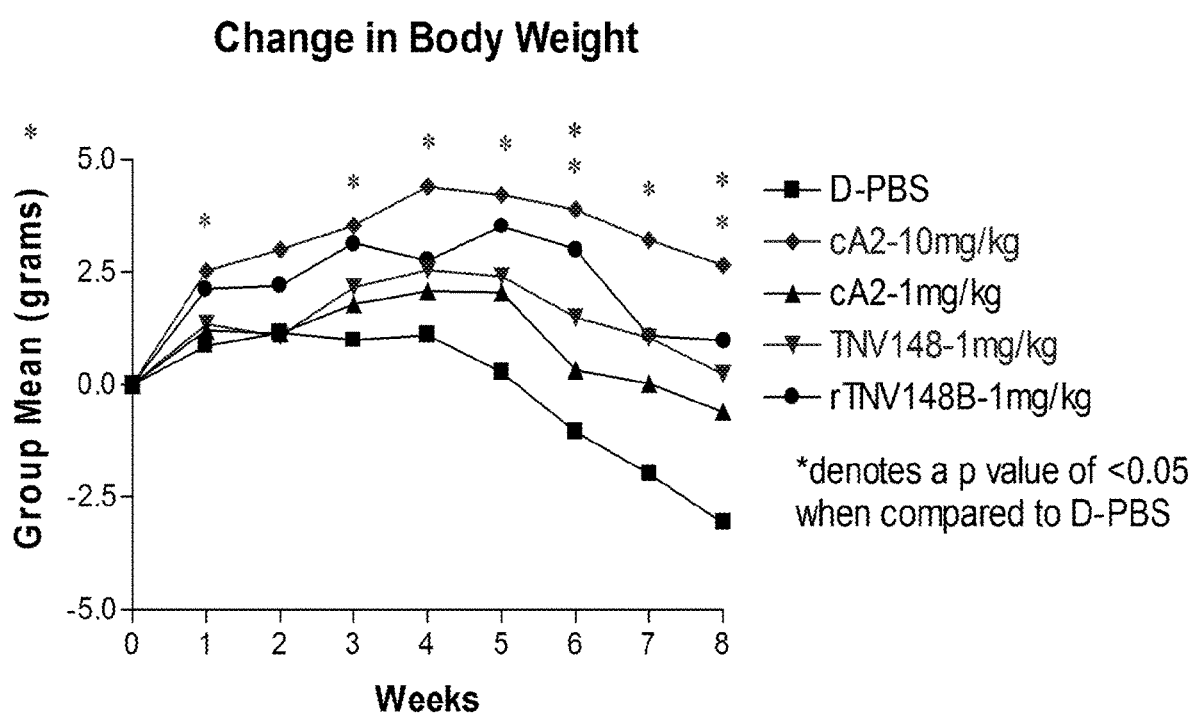

FIG. 16 shows arthritis mouse model mice Tg 197 weight changes in response to anti-TNF antibodies of the present invention as compared to controls in Example 7. To compare the efficacy of a single intraperitoneal dose of TNV148 (derived from hybridoma cells) and rTNV148B (derived from transfected cells). At approximately 4 weeks of age the Tg197 study mice were assigned, based on gender and body weight, to one of 9 treatment groups and treated with a single intraperitoneal bolus dose of Dulbecco's PBS (D-PBS) or antibody (TNV148, rTNV148B) at 1 mg/kg.

Figure 17:
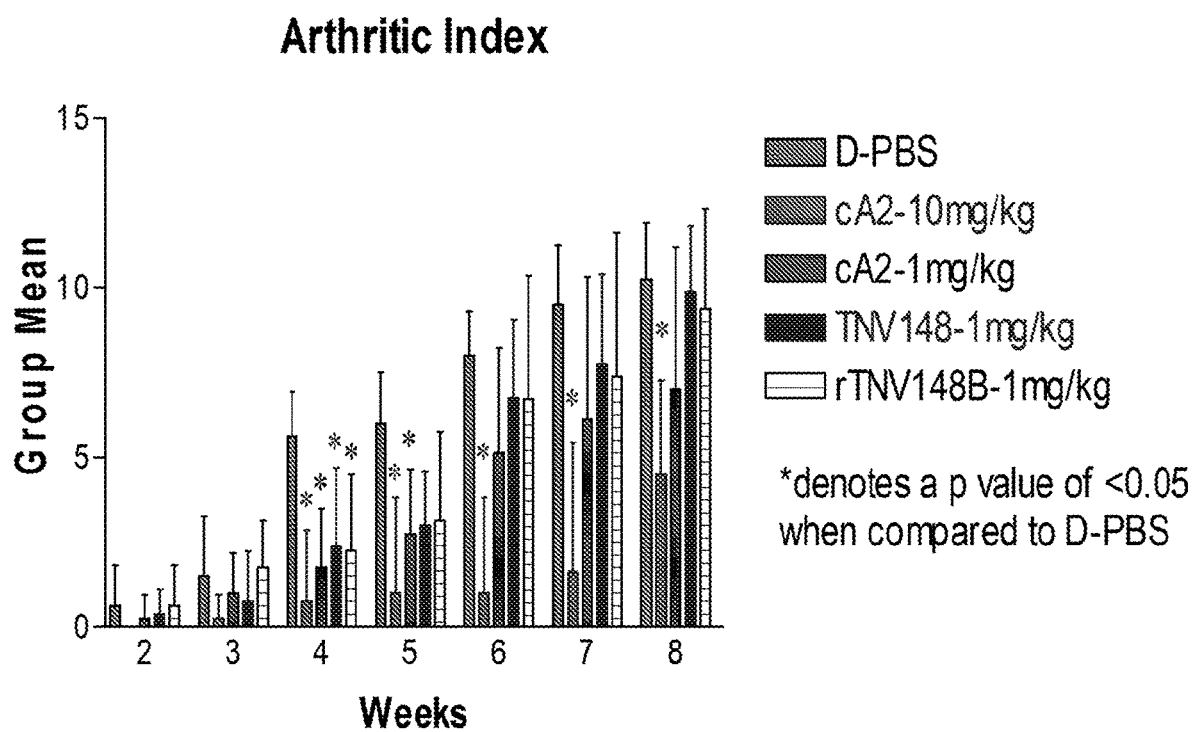

FIG. 17 represents the progression of disease severity based on the arthritic index as presented in Example 7. The 10 mg/kg cA2-treated group's arthritic index was lower than the D-PBS control group starting at week 4 and continuing throughout the remainder of the study (week 8). Both of the TNV148-treated Groups and the 1 mg/kg cA2-treated Group showed a significant reduction in AI at week 4. Although a previous study (P-099-017) showed that TNV148 was slightly more effective at reducing the Arthritic Index following a single 1 mg/kg intraperitoneal bolus, this study showed that the AI from both versions of the TNV antibody-treated groups was slightly higher. Although (with the exception of week 6) the 1 mg/kg cA2-treated Group was not significantly increased when compared to the 10 mg/kg cA2 group and the TNV148-treated Groups were significantly higher at weeks 7 and 8, there were no significant differences in AI between the 1 mg/kg cA2, 1 mg/kg TNV148 and 1 mg/kg TNV148B at any point in the study.

Figure 18:
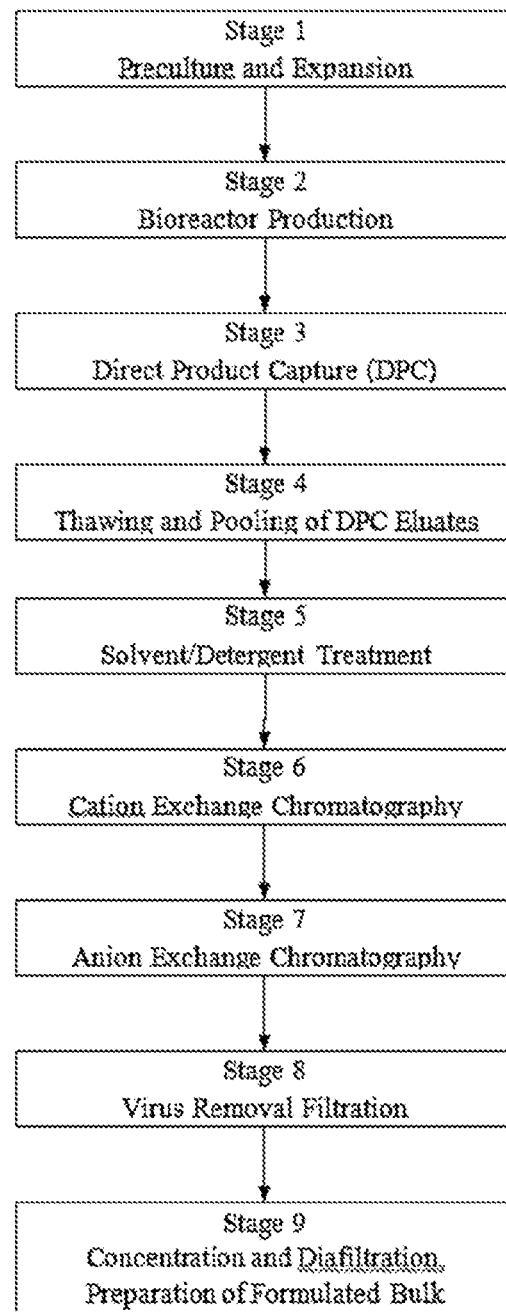

FIG. 18 shows an overview of the 9 stages of the golimumab manufacturing process.

Figure 19:
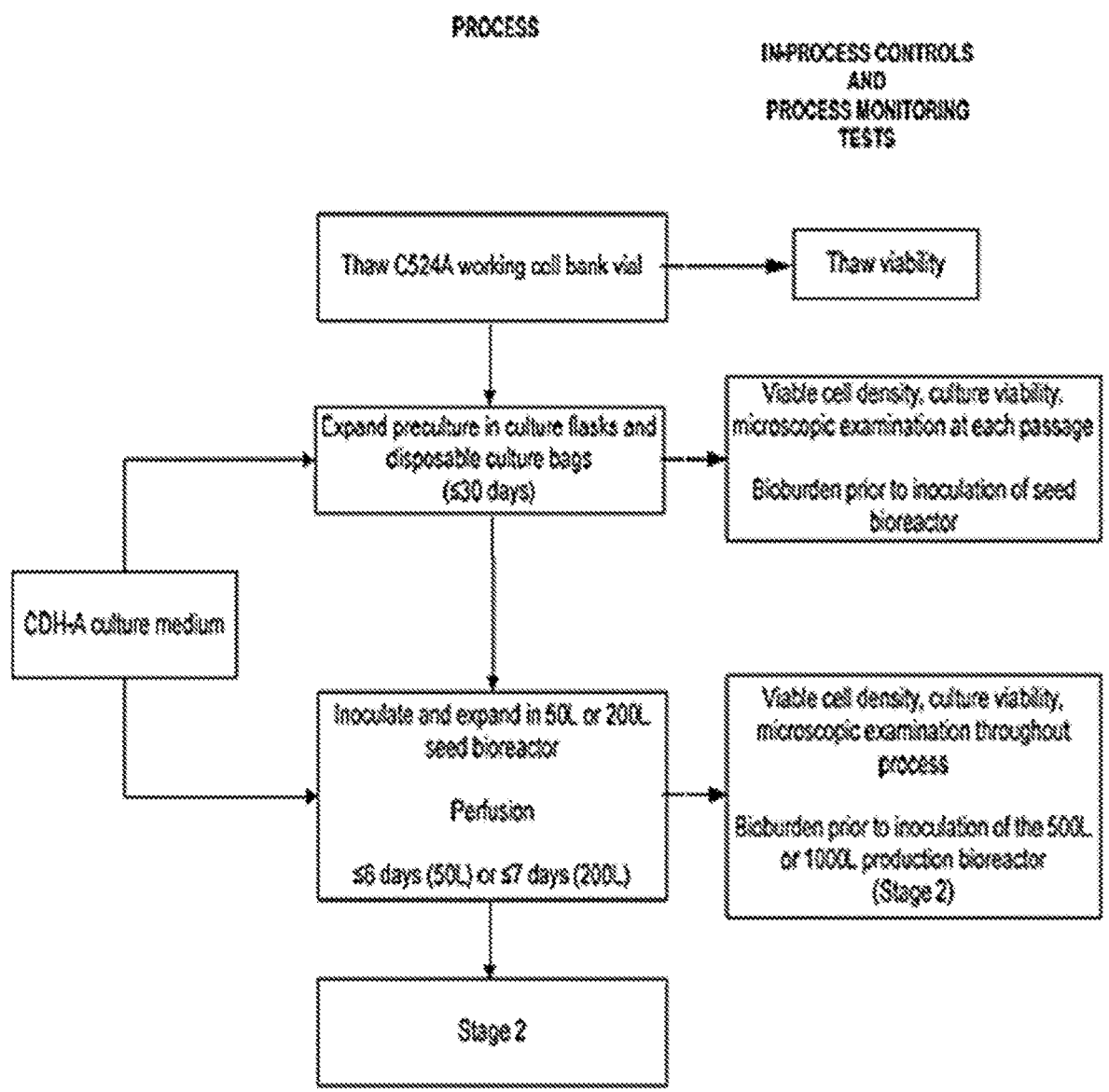

FIG. 19 shows a flow diagram of Stage 1 manufacturing process for the preculture and expansion steps, including the in-process controls and process monitoring tests.

Figure 20:
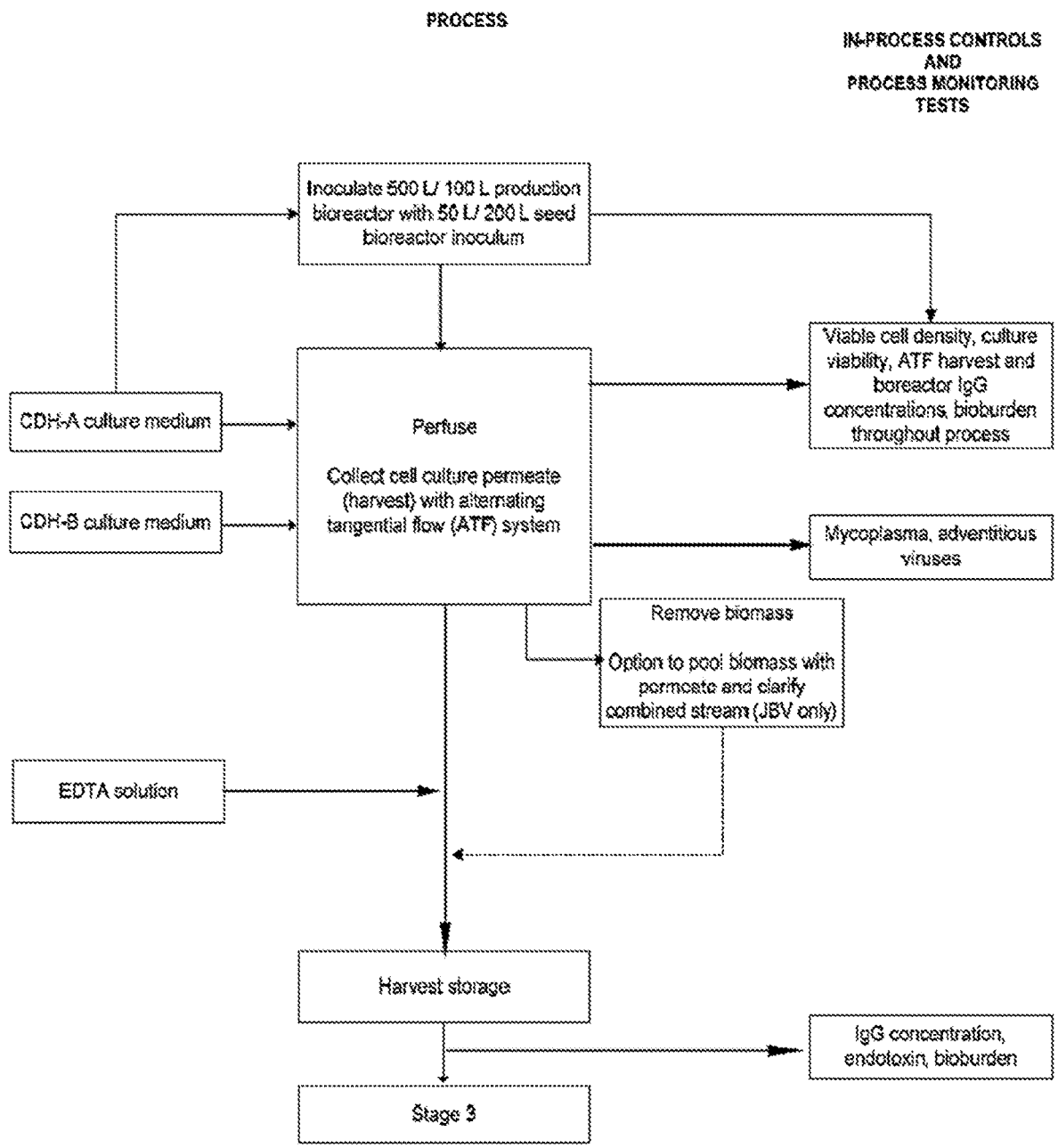

FIG. 20 shows a flow diagram of Stage 2 manufacturing process steps, including the in-process controls and process monitoring tests.

Figure 21:
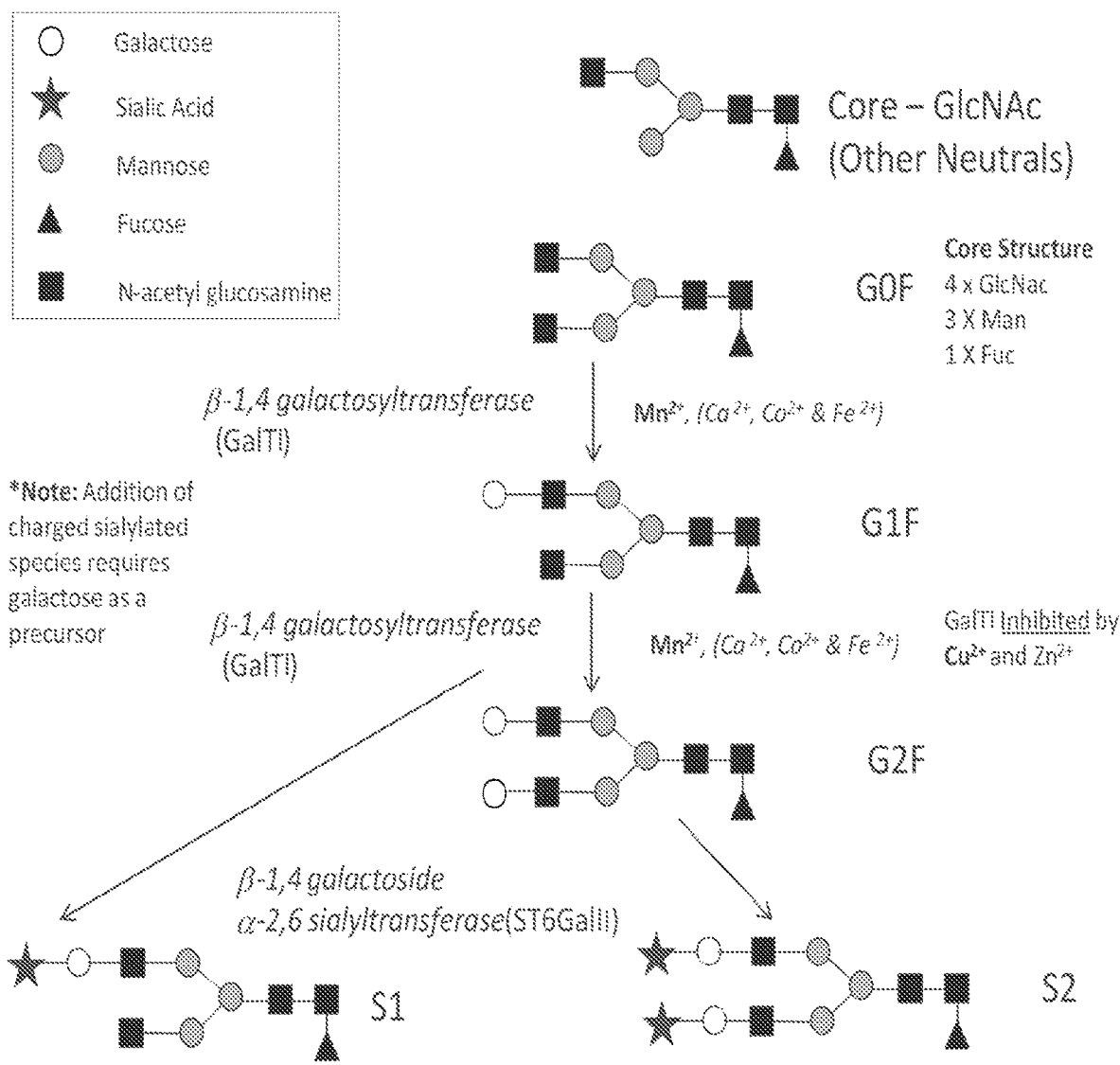

FIG. 21 shows a diagrammatic overview of some of the primary N-linked oligosaccharide species in golimumab IgG. The role of some of the enzymes in the glycosylation maturation process and role of some divalent cations (e.g. $Mn^{2+}$ as a co-factor and $Cu^{2+}$ as an inhibitor of GalTI) are also shown (see, e.g., *Biotechnol Bioeng.* 2007 Feb. 15; 96(3):538-49; *Curr Drug Targets.* 2008 April; 9(4):292-309; *J Biochem Mol Biol.* 2002 May 31; 35(3):330-6). Note that species with terminal sialic acid (S1 and S2) are charged species and species lacking the terminal sialic acid (G0F, G1F, and G2F) are neutral species, but generation of charged species depends on the presence of the galactose in G1F and G2F added by the GalT1 enzyme.

Figure 22:
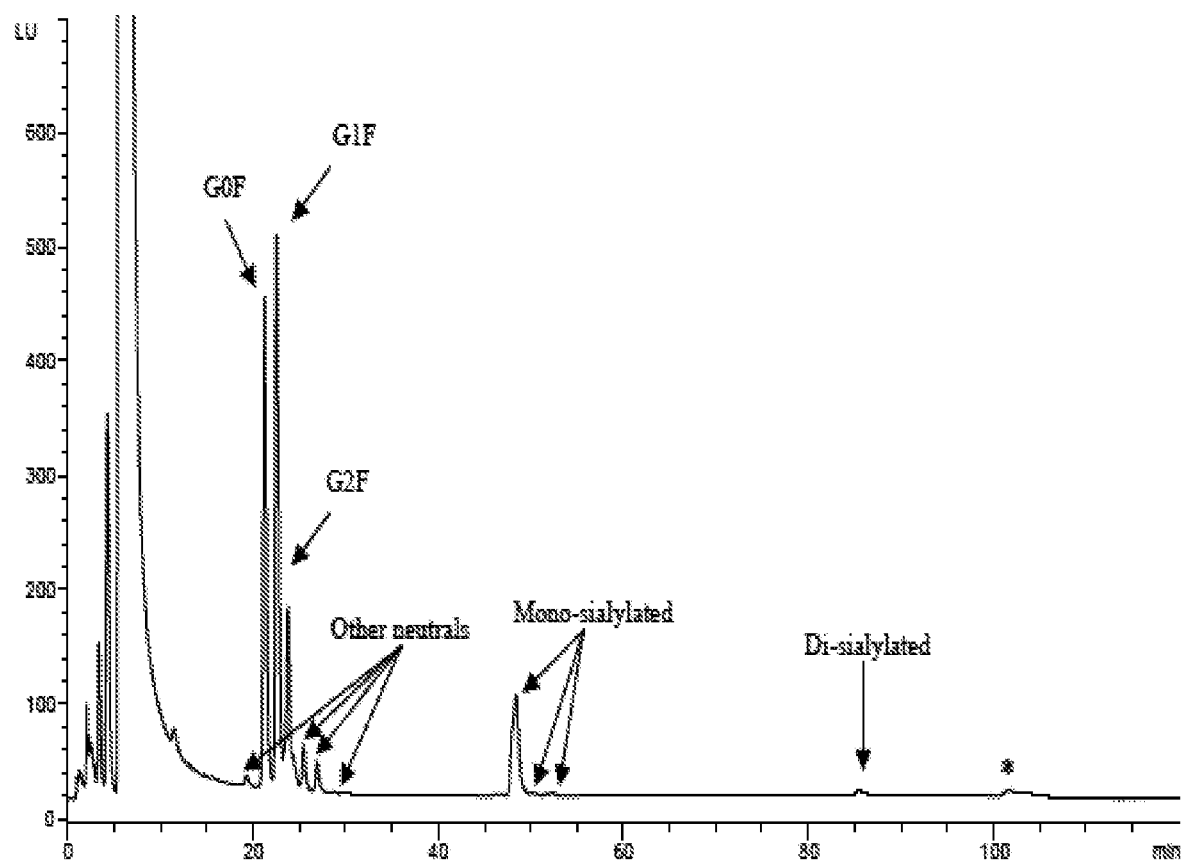

FIG. 22 shows a representative HPLC chromatogram for oligosaccharide analysis of a golimumab reference standard using HPLC with fluorescence detection. Peaks associated with different species are labeled. The * indicates a system peak that is not associated with golimumab.

Figure 23:
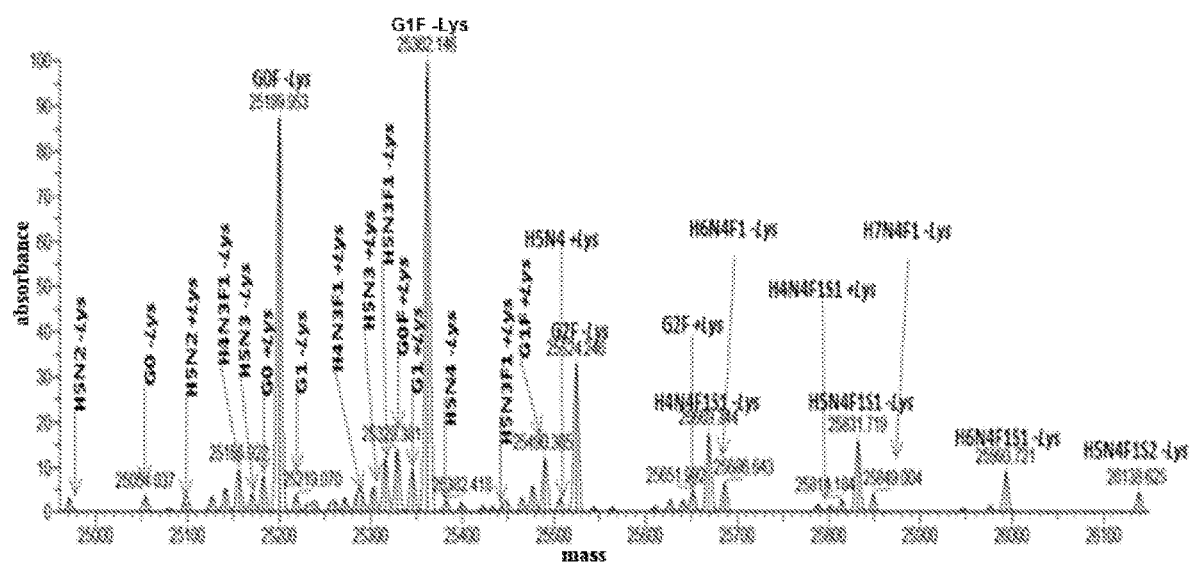

FIG. 23 shows a representative deconvoluted mass spectrum for IRMA analysis of golimumab produced in Sp2/0 cells.

Figure 24:
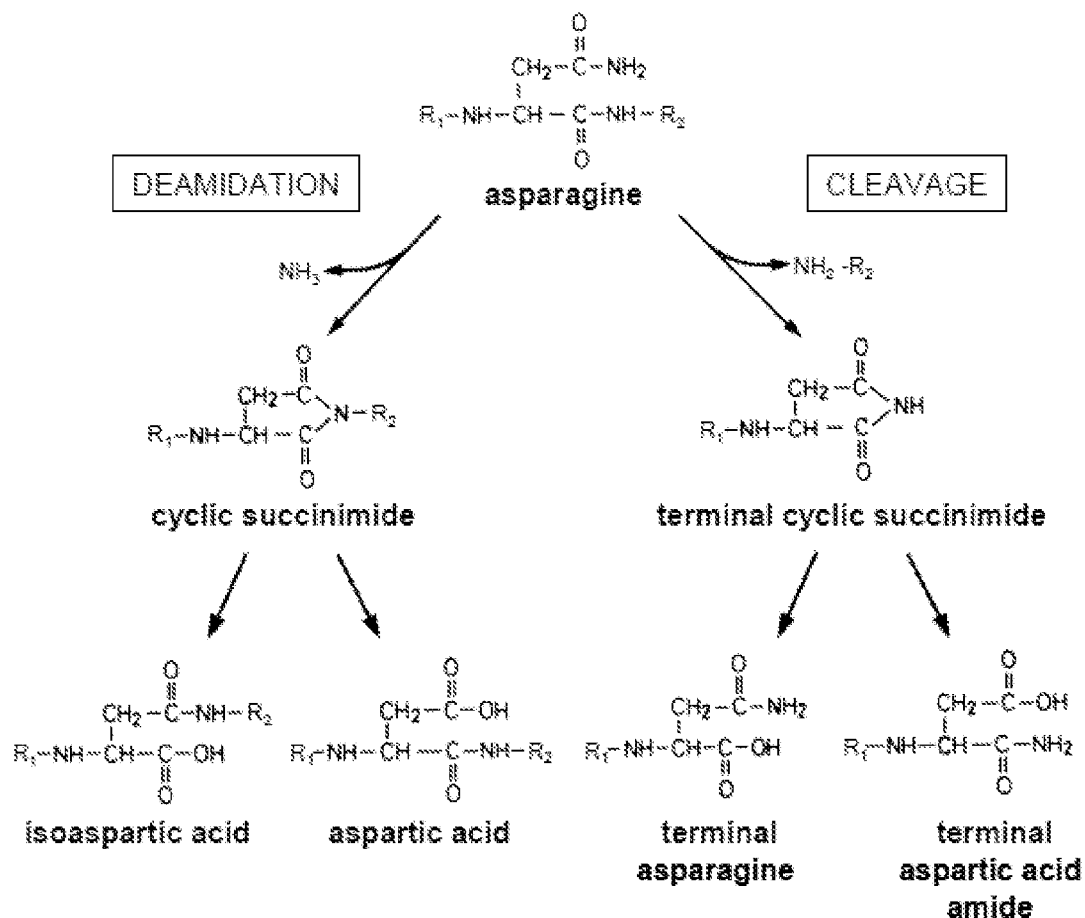

FIG. 24 shows cyclic imide mediated reactions for asparagine in proteins; figure was modified from (Voorter, C. E., et al. (1988). "Spontaneous peptide bond cleavage in aging alpha-crystallin through a succinimide intermediate." *J Biol Chem* 263(35): 19020-19023).

Figure 25:
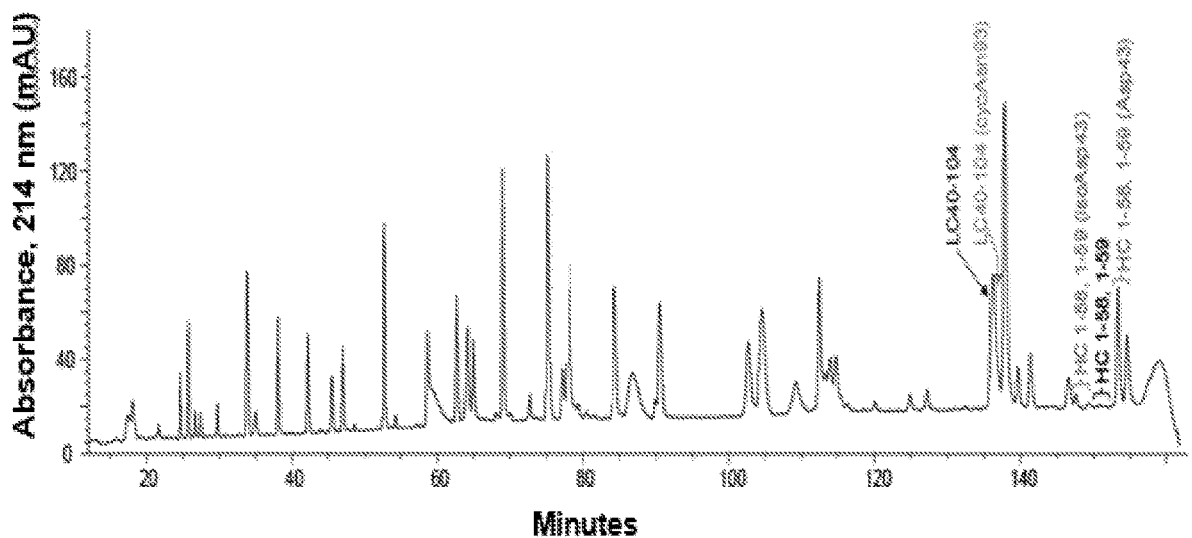

FIG. 25 shows a representative Lys C peptide map chromatogram (214 nm) of golimumab. Modified (in grey) and parent (in black) peptides of interest are labeled. The peak at approximately 34 min is not related to golimumab.

Figure 26:
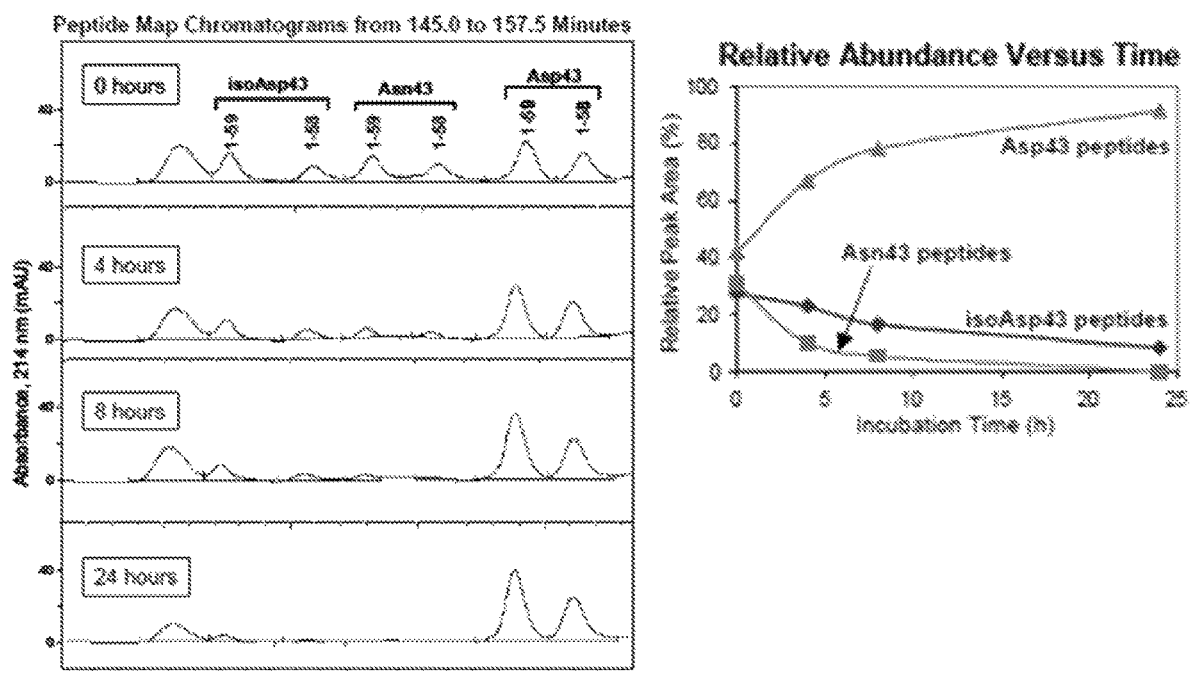

FIG. 26 shows a peptide map analysis of golimumab after 0, 4, 8, and 24 hours under forced deamidation conditions showing a change in levels of peptides 1-58 and 1-59 (left panel). The change resulted from deamidation of Asn43 to Asp43 and isoAsp43, and from isomerization of isoAsp43 to Asp43 (upper right panel; relative peak areas of Asn, Asp, and isoAsp forms of peptides 1-58 and 1-59 were employed to calculate abundance). The Asn43, Asp43, and isoAsp43 forms of peptides 1-58 and 1-59 were identified by mass spectrometry (MS) (lower right panel) and by retention time comparison to a synthetic Asp43 peptide 1-58 (not shown).

Figure 27:
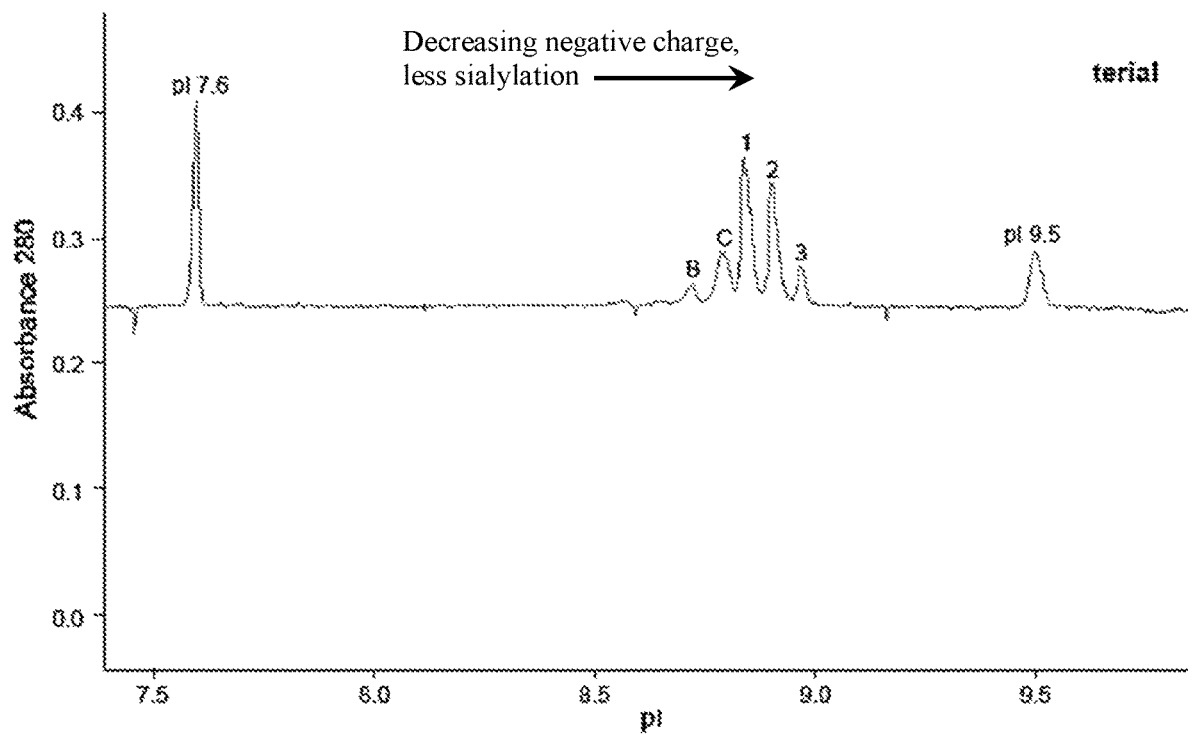

FIG. 27 shows a representative cIEF electropherogram profile of golimumab with the four major peaks labeled as C, 1, 2, and 3 and one minor peak labeled B. Internal standards of pI 7.6 and 9.5 are also labeled.

Figure 28:
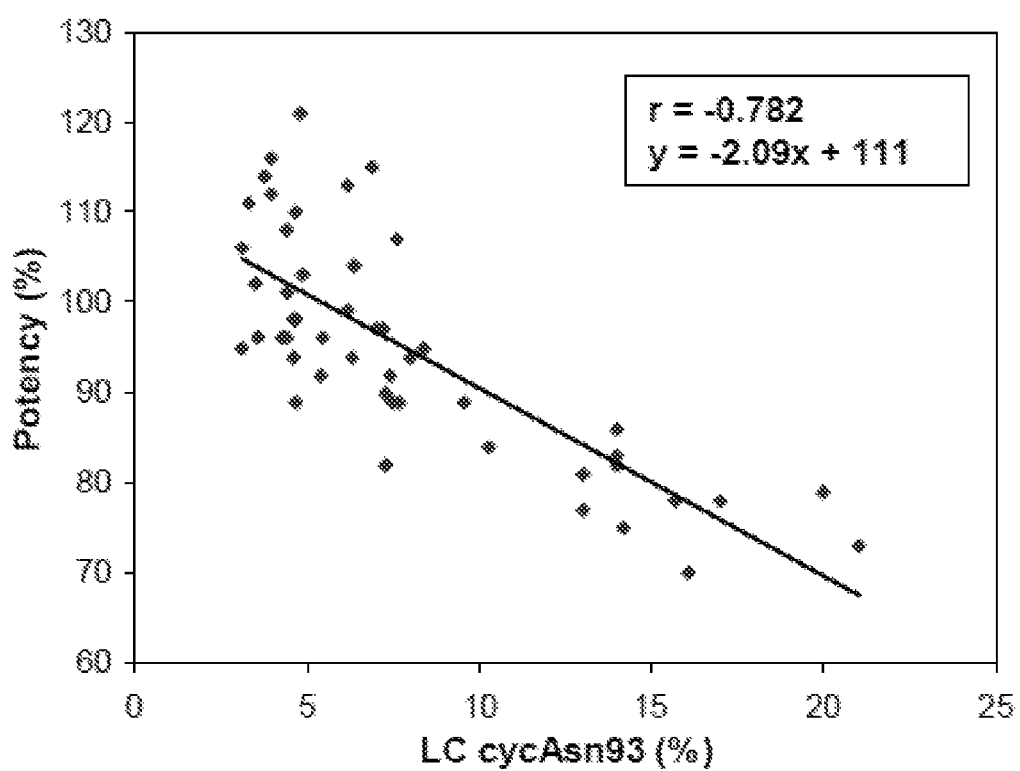

FIG. 28 shows correlation analysis of potency and % LC cycAsn93 for golimumab. LC cycAsn93 percentage was determined using the deamidation assay. Results are shown for 49 time points taken from different batches with varying amounts of LC cycAsn93. Statistical analysis was performed with commercial software; r is Pearson's correlation coefficient.

DESCRIPTION OF THE INVENTION

The present invention provides compositions comprising anti-TNF antibodies having a heavy chain (HC) comprising SEQ ID NO:38 and a light chain (LC) comprising SEQ ID NO:37 and methods for producing such anti-TNF antibodies.

As used herein, an "anti-tumor necrosis factor alpha antibody," "anti-TNF antibody," "anti-TNF antibody portion," or "anti-TNF antibody fragment" and/or "anti-TNF antibody variant" and the like include any protein or peptide containing molecule that comprises at least a portion of an immunoglobulin molecule, such as but not limited to at least one complementarity determining region (CDR) of a heavy or light chain or a ligand binding portion thereof, a heavy chain or light chain variable region, a heavy chain or light chain constant region, a framework region, or any portion thereof, or at least one portion of an TNF receptor or binding protein, which can be incorporated into an antibody of the present invention. Such antibody optionally further affects a specific ligand, such as but not limited to where such antibody modulates, decreases, increases, antagonizes, agonizes, mitigates, alleviates, blocks, inhibits, abrogates and/or interferes with at least one TNF activity or binding, or with TNF receptor activity or binding, in vitro, in situ and/or in vivo. As a non-limiting example, a suitable anti-TNF antibody, specified portion or variant of the present invention can bind at least one TNF, or specified portions, variants or domains thereof. A suitable anti-TNF antibody, specified portion, or variant can also optionally affect at least one of TNF activity or function, such as but not limited to, RNA, DNA or protein synthesis, TNF release, TNF receptor signaling, membrane TNF cleavage, TNF activity, TNF production and/or synthesis. The term "antibody" is further intended to encompass antibodies, digestion fragments, specified portions and variants thereof, including antibody mimetics or comprising portions of antibodies that mimic the structure and/or function of an antibody or specified fragment or portion thereof, including single chain antibodies and fragments thereof. Functional fragments include antigen-binding fragments that bind to a mammalian TNF. For example, antibody fragments capable of binding to TNF or portions thereof, including, but not limited to Fab (e.g., by papain digestion), Fab' (e.g., by pepsin digestion and partial reduction) and F(ab')$_2$ (e.g., by pepsin digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments, are encompassed by the invention (see, e.g., Colligan, Immunology, supra).

Such fragments can be produced by enzymatic cleavage, synthetic or recombinant techniques, as known in the art and/or as described herein. antibodies can also be produced in a variety of truncated forms using antibody genes in which one or more stop codons have been introduced upstream of the natural stop site. For example, a combination gene encoding a F(ab')$_2$ heavy chain portion can be designed to include DNA sequences encoding the $C_{H1}$ domain and/or hinge region of the heavy chain. The various portions of antibodies can be joined together chemically by conventional techniques or can be prepared as a contiguous protein using genetic engineering techniques.

As used herein, the term "human antibody" refers to an antibody in which substantially every part of the protein (e.g., CDR, framework, $C_L$, $C_H$ domains (e.g., $C_H1$, $C_H2$, and $C_H3$), hinge, ($V_L$, $V_H$)) is substantially non-immunogenic in humans, with only minor sequence changes or variations. Similarly, antibodies designated primate (monkey, baboon, chimpanzee, etc.), rodent (mouse, rat, rabbit, guinea pig, hamster, and the like) and other mammals designate such species, sub-genus, genus, sub-family, family specific antibodies. Further, chimeric antibodies include any combination of the above. Such changes or variations optionally and preferably retain or reduce the immunogenicity in humans or other species relative to non-modified antibodies. Thus, a human antibody is distinct from a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

Bispecific, (e.g., DuoBody®), heterospecific, heteroconjugate or similar antibodies can also be used that are monoclonal, preferably human or humanized, antibodies that have binding specificities for at least two different antigens. In the present case, one of the binding specificities is for at least one TNF protein, the other one is for any other antigen. Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, Nature 305:537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, can be cumbersome with low product yields and different strategies have been developed to facilitate bispecific antibody production.

Full length bispecific antibodies can be generated for example using Fab arm exchange (or half molecule exchange) between two monospecific bivalent antibodies by introducing substitutions at the heavy chain CH3 interface in each half molecule to favor heterodimer formation of two antibody half molecules having distinct specificity either in vitro in cell-free environment or using co-expression. The Fab arm exchange reaction is the result of a disulfide-bond isomerization reaction and dissociation-association of CH3 domains. The heavy-chain disulfide bonds in the hinge regions of the parent monospecific antibodies are reduced. The resulting free cysteines of one of the parent monospecific antibodies form an inter heavy-chain disulfide bond with cysteine residues of a second parent monospecific antibody molecule and simultaneously CH3 domains of the parent antibodies release and reform by dissociation-association. The CH3 domains of the Fab arms may be engineered to favor heterodimerization over homodimerization. The resulting product is a bispecific antibody having two Fab arms or half molecules which each can bind a distinct epitope.

"Homodimerization" as used herein refers to an interaction of two heavy chains having identical CH3 amino acid sequences. "Homodimer" as used herein refers to an antibody having two heavy chains with identical CH3 amino acid sequences.

"Heterodimerization" as used herein refers to an interaction of two heavy chains having non-identical CH3 amino acid sequences. "Heterodimer" as used herein refers to an antibody having two heavy chains with non-identical CH3 amino acid sequences.

The "knob-in-hole" strategy (see, e.g., PCT Intl. Publ. No. WO 2006/028936) can be used to generate full length bispecific antibodies. Briefly, selected amino acids forming the interface of the CH3 domains in human IgG can be mutated at positions affecting CH3 domain interactions to promote heterodimer formation. An amino acid with a small side chain (hole) is introduced into a heavy chain of an antibody specifically binding a first antigen and an amino acid with a large side chain (knob) is introduced into a heavy chain of an antibody specifically binding a second antigen. After co-expression of the two antibodies, a heterodimer is formed as a result of the preferential interaction of the heavy chain with a "hole" with the heavy chain with a "knob". Exemplary CH3 substitution pairs forming a knob and a hole are (expressed as modified position in the first CH3 domain of the first heavy chain/modified position in the second CH3 domain of the second heavy chain): T366Y/F405A, T366W/F405W, F405W/Y407A, T394W/Y407T, T394S/Y407A, T366W/T394S, F405W/T394S and T366W/T366S_L368A_Y407V.

Other strategies such as promoting heavy chain heterodimerization using electrostatic interactions by substituting positively charged residues at one CH3 surface and negatively charged residues at a second CH3 surface may be used, as described in US Pat. Publ. No. US2010/0015133; US Pat. Publ. No. US2009/0182127; US Pat. Publ. No. US2010/028637 or US Pat. Publ. No. US2011/0123532. In other strategies, heterodimerization may be promoted by following substitutions (expressed as modified position in the first CH3 domain of the first heavy chain/modified position in the second CH3 domain of the second heavy chain): L351Y_F405A_Y407V/T394W, T366I_K392M_T394W/F405A_Y407V, T366L_K392M_T394W/F405A_Y407V, L351Y_Y407A/T366A_K409F, L351Y_Y407A/T366V_K409F, Y407A/T366A_K409F, or T350V_L351Y_F405A_Y407V/T350V_T366L_K392L_T394W as described in U.S. Pat. Publ. No. US2012/0149876 or U.S. Pat. Publ. No. US2013/0195849.

In addition to methods described above, bispecific antibodies can be generated in vitro in a cell-free environment by introducing asymmetrical mutations in the CH3 regions of two monospecific homodimeric antibodies and forming the bispecific heterodimeric antibody from two parental monospecific homodimeric antibodies in reducing conditions to allow disulfide bond isomerization according to methods described in Intl. Pat. Publ. No. WO2011/131746. In the methods, the first monospecific bivalent antibody and the second monospecific bivalent antibody are engineered to have certain substitutions at the CH3 domain that promoter heterodimer stability; the antibodies are incubated together under reducing conditions sufficient to allow the cysteines in the hinge region to undergo disulfide bond isomerization; thereby generating the bispecific antibody by Fab arm exchange. The incubation conditions may optimally be restored to non-reducing. Exemplary reducing agents that may be used are 2-mercaptoethylamine (2-MEA), dithiothreitol (DTT), dithioerythritol (DTE), glutathione, tris(2-carboxyethyl) phosphine (TCEP), L-cysteine and beta-mercaptoethanol, preferably a reducing agent selected from the group consisting of: 2-mercaptoethylamine, dithiothreitol and tris(2-carboxyethyl)phosphine. For example, incubation for at least 90 min at a temperature of at least 20° C. in the presence of at least 25 mM 2-MEA or in the presence of at least 0.5 mM dithiothreitol at a pH of from 5-8, for example at pH of 7.0 or at pH of 7.4 may be used.

Anti-TNF antibodies (also termed TNF antibodies) useful in the methods and compositions of the present invention can optionally be characterized by high affinity binding to TNF and optionally and preferably having low toxicity. In particular, an antibody, specified fragment or variant of the invention, where the individual components, such as the variable region, constant region and framework, individually and/or collectively, optionally and preferably possess low immunogenicity, is useful in the present invention. The antibodies that can be used in the invention are optionally characterized by their ability to treat patients for extended periods with measurable alleviation of symptoms and low and/or acceptable toxicity. Low or acceptable immunogenicity and/or high affinity, as well as other suitable properties, can contribute to the therapeutic results achieved. "Low immunogenicity" is defined herein as raising significant HAHA, HACA or HAMA responses in less than about 75%, or preferably less than about 50% of the patients treated and/or raising low titres in the patient treated (less than about 300, preferably less than about 100 measured with a double antigen enzyme immunoassay) (Elliott et al., Lancet 344: 1125-1127 (1994), entirely incorporated herein by reference).

Utility: The isolated nucleic acids of the present invention can be used for 30 production of at least one anti-TNF antibody or specified variant thereof, which can be used to measure or effect in an cell, tissue, organ or animal (including mammals and humans), to diagnose, monitor, modulate, treat, alleviate, help prevent the incidence of, or reduce the symptoms of, at least one TNF condition, selected from, but not limited to, at least one of an immune disorder or disease, a cardiovascular disorder or disease, an infectious, malignant, and/or neurologic disorder or disease.

Such a method can comprise administering an effective amount of a composition or a pharmaceutical composition comprising at least one anti-TNF antibody to a cell, tissue, organ, animal or patient in need of such modulation, treatment, alleviation, prevention, or reduction in symptoms, effects or mechanisms. The effective amount can comprise an amount of about 0.001 to 500 mg/kg per single (e.g., bolus), multiple or continuous administration, or to achieve a serum concentration of 0.01-5000 μg/ml serum concentration per single, multiple, or continuous administration, or any effective range or value therein, as done and determined using known methods, as described herein or known in the relevant arts. Citations. All publications or patents cited herein are entirely incorporated herein by reference as they show the state of the art at the time of the present invention and/or to provide description and enablement of the present invention. Publications refer to any scientific or patent publications, or any other information available in any media format, including all recorded, electronic or printed formats. The following references are entirely incorporated herein by reference: Ausubel, et al., ed., Current Protocols in Molecular Biology, John Wiley & Sons, Inc., NY, NY (1987-2001); Sambrook, et al., Molecular Cloning: A Laboratory Manual, $2^{nd}$ Edition, Cold Spring Harbor, N Y (1989); Harlow and Lane, antibodies, a Laboratory Manual, Cold Spring Harbor, N Y (1989); Colligan, et al., eds., Current Protocols in Immunology, John Wiley & Sons, Inc., NY (1994-2001); Colligan et al., Current Protocols in Protein Science, John Wiley & Sons, NY, NY, (1997-2001).

Antibodies of the Present Invention: At least one anti-TNF antibody of the present invention comprising all of the heavy chain variable CDR regions of SEQ ID NOS:1, 2 and 3 and/or all of the light chain variable CDR regions of SEQ ID NOS:4, 5 and 6 can be optionally produced by a cell line, a mixed cell line, an immortalized cell or clonal population of immortalized cells, as well known in the art. See, e.g., Ausubel, et al., ed., Current Protocols in Molecular Biology, John Wiley & Sons, Inc., NY, NY (1987-2001); Sambrook, et al., Molecular Cloning: A Laboratory Manual, $2^{nd}$ Edition, Cold Spring Harbor, N Y (1989); Harlow and Lane, antibodies, a Laboratory Manual, Cold Spring Harbor, N Y (1989); Colligan, et al., eds., Current Protocols in Immunology, John Wiley & Sons, Inc., NY (1994-2001); Colligan et al., Current Protocols in Protein Science, John Wiley & Sons, NY, NY, (1997-2001), each entirely incorporated herein by reference.

Human antibodies that are specific for human TNF proteins or fragments thereof can be raised against an appropriate immunogenic antigen, such as isolated and/or TNF protein or a portion thereof (including synthetic molecules, such as synthetic peptides). Other specific or general mammalian antibodies can be similarly raised. Preparation of immunogenic antigens, and monoclonal antibody production can be performed using any suitable technique.

In one approach, a hybridoma is produced by fusing a suitable immortal cell line (e.g., a myeloma cell line such as, but not limited to, Sp2/0, Sp2/0-AG14, NSO, NS1, NS2, AE-1, L.5, >243, P3X63Ag8.653, Sp2 SA3, Sp2 MAI, Sp2 SS1, Sp2 SA5, U937, MLA 144, ACT IV, MOLT4, DA-1, JURKAT, WEHI, K-562, COS, RAJI, NIH 3T3, HL-60, MLA 144, NAMAIWA, NEURO 2A, or the like, or heteromylomas, fusion products thereof, or any cell or fusion cell derived therefrom, or any other suitable cell line as known in the art. See, e.g., www.atcc.org, www.lifetech.com, and the like, with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. See, e.g., Ausubel, supra, and Colligan, Immunology, supra, chapter 2, entirely incorporated herein by reference.

Antibody producing cells can also be obtained from the peripheral blood or, preferably the spleen or lymph nodes, of humans or other suitable animals that have been immunized with the antigen of interest. Any other suitable host cell can also be used for expressing heterologous or endogenous nucleic acid encoding an antibody, specified fragment or variant thereof, of the present invention. The fused cells (hybridomas) or recombinant cells can be isolated using selective culture conditions or other suitable known methods, and cloned by limiting dilution or cell sorting, or other known methods. Cells which produce antibodies with the desired specificity can be selected by a suitable assay (e.g., ELISA).

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, or the like, display library; e.g., as available from Cambridge antibody Technologies, Cambridgeshire, UK; MorphoSys, Martinsreid/Planegg, DE; Biovation, Aberdeen, Scotland, UK; BioInvent, Lund, Sweden; Dyax Corp., Enzon, Affymax/Biosite; Xoma, Berkeley, CA; Ixsys. See, e.g., EP 368,684, PCT/GB91/01134; PCT/GB92/01755; PCT/GB92/002240; PCT/GB92/00883; PCT/GB93/00605; U.S. Ser. No. 08/350,260(May 12, 1994); PCT/GB94/01422; PCT/

GB94/02662; PCT/GB97/01835; (CAT/MRC); WO90/14443; WO90/14424; WO90/14430; PCT/US94/1234; WO92/18619; WO96/07754; (Scripps); EP 614 989 (MorphoSys); WO95/16027 (BioInvent); WO88/06630; WO90/3809 (Dyax); U.S. Pat. No. 4,704,692 (Enzon); PCT/US91/02989 (Affymax); WO89/06283; EP 371 998; EP 550 400; (Xoma); EP 229 046; PCT/US91/07149 (Ixsys); or stochastically generated peptides or proteins—U.S. Pat. Nos. 5,723,323, 5,763,192, 5,814,476, 5,817,483, 5,824,514, 5,976,862, WO 86/05803, EP 590 689 (Ixsys, now Applied Molecular Evolution (AME), each entirely incorporated herein by reference) or that rely upon immunization of transgenic animals (e.g., SCID mice, Nguyen et al., Microbiol. Immunol. 41:901-907 (1997); Sandhu et al., Crit. Rev. Biotechnol. 16:95-118 (1996); Eren et al., Immunol. 93:154-161 (1998), each entirely incorporated by reference as well as related patents and applications) that are capable of producing a repertoire of human antibodies, as known in the art and/or as described herein. Such techniques, include, but are not limited to, ribosome display (Hanes et al., Proc. Natl. Acad. Sci. USA, 94:4937-4942 (May 1997); Hanes et al., Proc. Natl. Acad. Sci. USA, 95:14130-14135 (November 1998)); single cell antibody producing technologies (e.g., selected lymphocyte antibody method ("SLAM") (U.S. Pat. No. 5,627,052, Wen et al., J. Immunol. 17:887-892 (1987); Babcook et al., Proc. Natl. Acad. Sci. USA 93:7843-7848 (1996)); gel microdroplet and flow cytometry (Powell et al., Biotechnol. 8:333-337 (1990); One Cell Systems, Cambridge, MA; Gray et al., J. Imm. Meth. 182:155-163 (1995); Kenny et al., Bio/Technol. 13:787-790 (1995)); B-cell selection (Steenbakkers et al., Molec. Biol. Reports 19:125-134 (1994); Jonak et al., Progress Biotech, Vol. 5, In Vitro Immunization in Hybridoma Technology, Borrebaeck, ed., Elsevier Science Publishers B.V., Amsterdam, Netherlands (1988)).

Methods for engineering or humanizing non-human or human antibodies can also be used and are well known in the art. Generally, a humanized or engineered antibody has one or more amino acid residues from a source which is non-human, e.g., but not limited to mouse, rat, rabbit, non-human primate or another mammal. These human amino acid residues are often referred to as "import" residues, which are typically taken from an "import" variable, constant or other domain of a known human sequence.

Known human Ig sequences are disclosed in numerous publications and websites, for example:
www.ncbi.nlm.nih.gov/entrez/query.fcgi;
www.atcc.org/phage/hdb.html;
www.sciquest.com/;
www.abcam.com/;
www.antibodyresource.com/onlinecomp.html;
www.public.iastate.edu/~pedro/research_tools.html;
www.mgen.uni-heidelberg.de/SD/IT/IT.html;
www.whfreeman.com/immunology/CH05/kubyO5.htm;
www.library.thinkquest.org/12429/Immune/Antibody.html;
www.hhmi.org/grants/lectures/1996/vlab/;
www.path.cam.ac.uk/~mrc7/mikeimages.html;
www.antibodyresource.com/;
www.mcb.harvard.edu/BioLinks/Immunology.html.
www.immunologylink.com/;
www.pathbox.wustl.edu/~hcenter/index.html;
www.biotech.ufl.edu/~hcl/;
www.pebio.com/pa/340913/340913.html;
www.nal.usda.gov/awic/pubs/antibody/;
www.m.ehime-u.ac.jp/~yasuhito/Elisa.html;
www.biodesign.com/table.asp;
www.icnet.uk/axp/facs/davies/links.html;
www.biotech.ufl.edu/~fccl/protocol.html;
www.isac-net.org/sites_geo.html;
www.aximt1.imt.uni-marburg.de/~rek/AEPStart.html;
www.baserv.uci.kun.nl/~jraats/links1.html;
www.recab.uni-hd.de/immuno.bme.nwu.edu/;
www.mrc-cpe.cam.ac.uk/imt-doc/public/INTRO.html;
www.ibt.unam.mx/vir/V_mice.html; imgt.cnusc.fr:8104/;
www.biochem.ucl.ac.uk/~martin/abs/index.html;
www.antibody.bath.ac.uk/; abgen.cvm.tamu.edu/lab/wwwabgen.html;
www.unizh.ch/~honegger/AHOseminar/Slide01.html;
www.cryst.bbk.ac.uk/~ubcg07s/;
www.nimr.mrc.ac.uk/CC/ccaewg/ccaewg.htm;
www.path.cam.ac.uk/~mrc7/humanisation/TAHHP.html;
www.ibt.unam.mx/vir/structure/stat_aim.html;
www.biosci.missouri.edu/smithgp/index.html;
www.cryst.bioc.cam.ac.uk/~fmolina/Web-pages/Pept/spottech.html;
www.jerini.de/fr_products.htm;
www.patents.ibm.com/ibm.html.Kabat et al.,
Sequences of Proteins of Immunological Interest, U.S. Dept. Health (1983), each entirely incorporated herein by reference.

Such imported sequences can be used to reduce immunogenicity or reduce, enhance or modify binding, affinity, on-rate, off-rate, avidity, specificity, half-life, or any other suitable characteristic, as known in the art. Generally, part or all of the non-human or human CDR sequences are maintained while the non-human sequences of the variable and constant regions are replaced with human or other amino acids. antibodies can also optionally be humanized with retention of high affinity for the antigen and other favorable biological properties. To achieve this goal, humanized antibodies can be optionally prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Humanization or engineering of antibodies of the present invention can be performed using any known method, such as but not limited to those described in, Winter (Jones et al., Nature 321:522 (1986); Riechmann et al., Nature 332:323 (1988); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,723,323, 5,976,862, 5,824,514, 5,817,483, 5,814,476, 5,763,192, 5,723,323, 5,766,886, 5714352, 6204023, 6180370, 5693762, 5530101, 5585089, 5225539; 4816567, PCT/: US98/16280, US96/18978, US91/09630, US91/05939, US94/1234, GB89/01334, GB91/01134, GB92/01755; WO90/14443, WO90/14424, WO90/14430, EP 229246, each entirely incorporated herein by reference, included references cited therein.

The anti-TNF antibody can also be optionally generated by immunization of a transgenic animal (e.g., mouse, rat, hamster, non-human primate, and the like) capable of producing a repertoire of human antibodies, as described herein and/or as known in the art. Cells that produce a human anti-TNF antibody can be isolated from such animals and immortalized using suitable methods, such as the methods described herein.

Transgenic mice that can produce a repertoire of human antibodies that bind to human antigens can be produced by known methods (e.g., but not limited to, U.S. Pat. Nos. 5,770,428, 5,569,825, 5,545,806, 5,625,126, 5,625,825, 5,633,425, 5,661,016 and 5,789,650 issued to Lonberg et al.; Jakobovits et al. WO 98/50433, Jakobovits et al. WO 98/24893, Lonberg et al. WO 98/24884, Lonberg et al. WO 97/13852, Lonberg et al. WO 94/25585, Kucherlapate et al. WO 96/34096, Kucherlapate et al. EP 0463 151 B1, Kucherlapate et al. EP 0710 719 A1, Surani et al. U.S. Pat. No. 5,545,807, Bruggemann et al. WO 90/04036, Bruggemann et al. EP 0438 474 B1, Lonberg et al. EP 0814 259 A2, Lonberg et al. GB 2 272 440 A, Lonberg et al. *Nature* 368:856-859 (1994), Taylor et al., *Int. Immunol.* 6(4)579-591 (1994), Green et al, *Nature Genetics* 7:13-21 (1994), Mendez et al., *Nature Genetics* 15:146-156 (1997), Taylor et al., *Nucleic Acids Research* 20(23):6287-6295 (1992), Tuaillon et al., *Proc Natl Acad Sci USA* 90(8)3720-3724 (1993), Lonberg et al., *Int Rev Immunol* 13(1):65-93 (1995) and Fishwald et al., *Nat Biotechnol* 14(7):845-851 (1996), which are each entirely incorporated herein by reference). Generally, these mice comprise at least one transgene comprising DNA from at least one human immunoglobulin locus that is functionally rearranged, or which can undergo functional rearrangement. The endogenous immunoglobulin loci in such mice can be disrupted or deleted to eliminate the capacity of the animal to produce antibodies encoded by endogenous genes.

Screening antibodies for specific binding to similar proteins or fragments can be conveniently achieved using peptide display libraries. This method involves the screening of large collections of peptides for individual members having the desired function or structure. antibody screening of peptide display libraries is well known in the art. The displayed peptide sequences can be from 3 to 5000 or more amino acids in length, frequently from 5-100 amino acids long, and often from about 8 to 25 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT Patent Publication Nos. 91/17271, 91/18980, 91/19818, and 93/08278. Other systems for generating libraries of peptides have aspects of both in vitro chemical synthesis and recombinant methods. See, PCT Patent Publication Nos. 92/05258, 92/14843, and 96/19256. See also, U.S. Pat. Nos. 5,658,754; and 5,643,768. Peptide display libraries, vector, and screening kits are commercially available from such suppliers as Invitrogen (Carlsbad, CA), and Cambridge antibody Technologies (Cambridgeshire, UK). See, e.g., U.S. Pat. Nos. 4,704,692, 4,939,666, 4,946,778, 5,260,203, 5,455,030, 5,518,889, 5,534,621, 5,656,730, 5,763,733, 5,767,260, 5,856,456, assigned to Enzon; U.S. Pat. Nos. 5,223,409, 5,403,484, 5,571,698, 5,837,500, assigned to Dyax, 5427908, 5580717, assigned to Affymax; 5885793, assigned to Cambridge antibody Technologies; 5750373, assigned to Genentech, 5618920, 5595898, 5576195, 5698435, 5693493, 5698417, assigned to Xoma, Colligan, supra; Ausubel, supra; or Sambrook, supra, each of the above patents and publications entirely incorporated herein by reference.

Antibodies of the present invention can also be prepared using at least one anti-TNF antibody encoding nucleic acid to provide transgenic animals or mammals, such as goats, cows, horses, sheep, and the like, that produce such antibodies in their milk. Such animals can be provided using known methods. See, e.g., but not limited to, U.S. Pat. Nos. 5,827,690; 5,849,992; 4,873,316; 5,849,992; 5,994,616; 5,565,362; 5,304,489, and the like, each of which is entirely incorporated herein by reference.

Antibodies of the present invention can additionally be prepared using at least one anti-TNF antibody encoding nucleic acid to provide transgenic plants and cultured plant cells (e.g., but not limited to tobacco and maize) that produce such antibodies, specified portions or variants in the plant parts or in cells cultured therefrom. As a non-limiting example, transgenic tobacco leaves expressing recombinant proteins have been successfully used to provide large amounts of recombinant proteins, e.g., using an inducible promoter. See, e.g., Cramer et al., Curr. Top. Microbol. Immunol. 240:95-118 (1999) and references cited therein. Also, transgenic maize plants have been used to express mammalian proteins at commercial production levels, with biological activities equivalent to those produced in other recombinant systems or purified from natural sources. See, e.g., Hood et al., Adv. Exp. Med. Biol. 464:127-147 (1999) and references cited therein. antibodies have also been produced in large amounts from transgenic plant seeds including antibody fragments, such as single chain antibodies (scFv's), including tobacco seeds and potato tubers. See, e.g., Conrad et al., Plant Mol. Biol. 38:101-109 (1998) and reference cited therein. Thus, antibodies of the present invention can also be produced using transgenic plants, according to know methods. See also, e.g., Fischer et al., Biotechnol. Appl. Biochem. 30:99-108 (October, 1999), Ma et al., Trends Biotechnol. 13:522-7 (1995); Ma et al., Plant Physiol. 109:341-6 (1995); Whitelam et al., Biochem. Soc. Trans. 22:940-944 (1994); and references cited therein. Each of the above references is entirely incorporated herein by reference.

The antibodies of the invention can bind human TNF with a wide range of affinities ($K_D$). In a preferred embodiment, at least one human mAb of the present invention can optionally bind human TNF with high affinity. For example, a human mAb can bind human TNF with a $K_D$ equal to or less than about $10^{-7}$ M, such as but not limited to, 0.1-9.9 (or any range or value therein)$\times 10^{-7}$, $10^{-8}$, $10^{-9}$, $10^{-10}$, $10^{-11}$, $10^{-12}$, $10^{-13}$ or any range or value therein.

The affinity or avidity of an antibody for an antigen can be determined experimentally using any suitable method. (See, for example, Berzofsky, et al., "Antibody-Antigen Interactions," In *Fundamental Immunology*, Paul, W. E., Ed., Raven Press: New York, NY (1984); Kuby, Janis *Immunology*, W.H. Freeman and Company: New York, NY (1992); and methods described herein). The measured affinity of a particular antibody-antigen interaction can vary if measured under different conditions (e.g., salt concentration, pH). Thus, measurements of affinity and other antigen-binding parameters (e.g., $K_D$, $K_a$, $K_d$) are preferably made with standardized solutions of antibody and antigen, and a standardized buffer, such as the buffer described herein.

Nucleic Acid Molecules. Using the information provided herein, such as the nucleotide sequences encoding at least 70-100% of the contiguous amino acids of at least one of SEQ ID NOS:1, 2, 3, 4, 5, 6, 7, 8, specified fragments, variants or consensus sequences thereof, or a deposited vector comprising at least one of these sequences, a nucleic acid molecule of the present invention encoding at least one anti-TNF antibody comprising all of the heavy chain variable CDR regions of SEQ ID NOS:1, 2 and 3 and/or all of the light chain variable CDR regions of SEQ ID NOS:4, 5 and 6 can be obtained using methods described herein or as known in the art.

Nucleic acid molecules of the present invention can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

Isolated nucleic acid molecules of the present invention can include nucleic acid molecules comprising an open reading frame (ORF), optionally with one or more introns, e.g., but not limited to, at least one specified portion of at least one CDR, as CDR1, CDR2 and/or CDR3 of at least one heavy chain (e.g., SEQ ID NOS:1-3) or light chain (e.g., SEQ ID NOS: 4-6); nucleic acid molecules comprising the coding sequence for an anti-TNF antibody or variable region (e.g., SEQ ID NOS:7,8); and nucleic acid molecules which comprise a nucleotide sequence substantially different from those described above but which, due to the degeneracy of the genetic code, still encode at least one anti-TNF antibody as described herein and/or as known in the art. Of course, the genetic code is well known in the art. Thus, it would be routine for one skilled in the art to generate such degenerate nucleic acid variants that code for specific anti-TNF antibodies of the present invention. See, e.g., Ausubel, et al., supra, and such nucleic acid variants are included in the present invention. Non-limiting examples of isolated nucleic acid molecules of the present invention include SEQ ID NOS:10, 11, 12, 13, 14, 15, corresponding to non-limiting examples of a nucleic acid encoding, respectively, HC CDR1, HC CDR2, HC CDR3, LC CDR1, LC CDR2, LC CDR3, HC variable region and LC variable region.

As indicated herein, nucleic acid molecules of the present invention which comprise a nucleic acid encoding an anti-TNF antibody can include, but are not limited to, those encoding the amino acid sequence of an antibody fragment, by itself; the coding sequence for the entire antibody or a portion thereof; the coding sequence for an antibody, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example—ribosome binding and stability of mRNA); an additional coding sequence that codes for additional amino acids, such as those that provide additional functionalities. Thus, the sequence encoding an antibody can be fused to a marker sequence, such as a sequence encoding a peptide that facilitates purification of the fused antibody comprising an antibody fragment or portion.

Polynucleotides Which Selectively Hybridize to a Polynucleotide as Described Herein. The present invention provides isolated nucleic acids that hybridize under selective hybridization conditions to a polynucleotide disclosed herein. Thus, the polynucleotides of this embodiment can be used for isolating, detecting, and/or quantifying nucleic acids comprising such polynucleotides. For example, polynucleotides of the present invention can be used to identify, isolate, or amplify partial or full-length clones in a deposited library. In some embodiments, the polynucleotides are genomic, or cDNA sequences isolated, or otherwise complementary to, a cDNA from a human or mammalian nucleic acid library.

Preferably, the cDNA library comprises at least 80% full-length sequences, preferably at least 85% or 90% full-length sequences, and more preferably at least 95% full-length sequences. The cDNA libraries can be normalized to increase the representation of rare sequences. Low or moderate stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

Optionally, polynucleotides of this invention will encode at least a portion of an antibody encoded by the polynucleotides described herein. The polynucleotides of this invention embrace nucleic acid sequences that can be employed for selective hybridization to a polynucleotide encoding an antibody of the present invention. See, e.g., Ausubel, supra; Colligan, supra, each entirely incorporated herein by reference.

Construction of Nucleic Acids. The isolated nucleic acids of the present invention can be made using (a) recombinant methods, (b) synthetic techniques, (c) purification techniques, or combinations thereof, as well-known in the art.

The nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the present invention. For example, a hexa-histidine marker sequence provides a convenient means to purify the proteins of the present invention. The nucleic acid of the present invention—excluding the coding sequence—is optionally a vector, adapter, or linker for cloning and/or expression of a polynucleotide of the present invention.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra).

Recombinant Methods for Constructing Nucleic Acids. The isolated nucleic acid compositions of this invention, such as RNA, cDNA, genomic DNA, or any combination thereof, can be obtained from biological sources using any number of cloning methodologies known to those of skill in the art. In some embodiments, oligonucleotide probes that selectively hybridize, under stringent conditions, to the polynucleotides of the present invention are used to identify the desired sequence in a cDNA or genomic DNA library.

The isolation of RNA, and construction of cDNA and genomic libraries, is well known to those of ordinary skill in the art. (See, e.g., Ausubel, supra; or Sambrook, supra).

Nucleic Acid Screening and Isolation Methods. A cDNA or genomic library can be screened using a probe based upon the sequence of a polynucleotide of the present invention, such as those disclosed herein. Probes can be used to hybridize with genomic DNA or cDNA sequences to isolate homologous genes in the same or different organisms. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by one or more of temperature, ionic strength, pH and the presence of a partially denaturing solvent such as formamide. For example, the stringency of hybridization is conveniently varied by changing the polarity of the reactant solution through, for example, manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100%, or 70-100%, or any range or value therein. However, it should be understood that minor sequence variations in the probes and primers can be compensated for by reducing the stringency of the hybridization and/or wash medium.

Methods of amplification of RNA or DNA are well known in the art and can be used according to the present invention without undue experimentation, based on the teaching and guidance presented herein.

Known methods of DNA or RNA amplification include, but are not limited to, polymerase chain reaction (PCR) and related amplification processes (see, e.g., U.S. Pat. Nos. 4,683,195, 4,683,202, 4,800,159, 4,965,188, to Mullis, et al.; 4,795,699 and 4,921,794 to Tabor, et al; U.S. Pat. No. 5,142,033 to Innis; U.S. Pat. No. 5,122,464 to Wilson, et al.; U.S. Pat. No. 5,091,310 to Innis; U.S. Pat. No. 5,066,584 to Gyllensten, et al; U.S. Pat. No. 4,889,818 to Gelfand, et al; U.S. Pat. No. 4,994,370 to Silver, et al; U.S. Pat. No. 4,766,067 to Biswas; U.S. Pat. No. 4,656,134 to Ringold) and RNA mediated amplification that uses anti-sense RNA to the target sequence as a template for double-stranded DNA synthesis (U.S. Pat. No. 5,130,238 to Malek, et al, with the trade name NASBA), the entire contents of which references are incorporated herein by reference. (See, e.g., Ausubel, supra; or Sambrook, supra.)

For instance, polymerase chain reaction (PCR) technology can be used to amplify the sequences of polynucleotides of the present invention and related genes directly from genomic DNA or cDNA libraries. PCR and other in vitro amplification methods can also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, supra, Sambrook, supra, and Ausubel, supra, as well as Mullis, et al., U.S. Pat. No. 4,683,202 (1987); and Innis, et al., PCR Protocols A Guide to Methods and Applications, Eds., Academic Press Inc., San Diego, CA (1990). Commercially available kits for genomic PCR amplification are known in the art. See, e.g., Advantage-GC Genomic PCR Kit (Clontech). Additionally, e.g., the T4 gene 32 protein (Boehringer Mannheim) can be used to improve yield of long PCR products.

Synthetic Methods for Constructing Nucleic Acids. The isolated nucleic acids of the present invention can also be prepared by direct chemical synthesis by known methods (see, e.g., Ausubel, et al., supra). Chemical synthesis generally produces a single-stranded oligonucleotide, which can be converted into double-stranded DNA by hybridization with a complementary sequence, or by polymerization with a DNA polymerase using the single strand as a template. One of skill in the art will recognize that while chemical synthesis of DNA can be limited to sequences of about 100 or more bases, longer sequences can be obtained by the ligation of shorter sequences.

Recombinant Expression Cassettes. The present invention further provides recombinant expression cassettes comprising a nucleic acid of the present invention. A nucleic acid sequence of the present invention, for example a cDNA or a genomic sequence encoding an antibody of the present invention, can be used to construct a recombinant expression cassette that can be introduced into at least one desired host cell. A recombinant expression cassette will typically comprise a polynucleotide of the present invention operably linked to transcriptional initiation regulatory sequences that will direct the transcription of the polynucleotide in the intended host cell. Both heterologous and non-heterologous (i.e., endogenous) promoters can be employed to direct expression of the nucleic acids of the present invention.

In some embodiments, isolated nucleic acids that serve as promoter, enhancer, or other elements can be introduced in the appropriate position (upstream, downstream or in intron) of a non-heterologous form of a polynucleotide of the present invention so as to up or down regulate expression of a polynucleotide of the present invention. For example, endogenous promoters can be altered in vivo or in vitro by mutation, deletion and/or substitution.

Vectors and Host Cells. The present invention also relates to vectors that include isolated nucleic acid molecules of the present invention, host cells that are genetically engineered with the recombinant vectors, and the production of at least one anti-TNF antibody by recombinant techniques, as is well known in the art. See, e.g., Sambrook, et al., supra; Ausubel, et al., supra, each entirely incorporated herein by reference.

The polynucleotides can optionally be joined to a vector containing a selectable marker for propagation in a host. Generally, a plasmid vector is introduced in a precipitate, such as a calcium phosphate precipitate, or in a complex with a charged lipid. If the vector is a virus, it can be packaged in vitro using an appropriate packaging cell line and then transduced into host cells.

The DNA insert should be operatively linked to an appropriate promoter. The expression constructs will further contain sites for transcription initiation, termination and, in the transcribed region, a ribosome binding site for translation. The coding portion of the mature transcripts expressed by the constructs will preferably include a translation initiating site at the beginning and a termination codon (e.g., UAA, UGA or UAG) appropriately positioned at the end of the mRNA to be translated, with UAA and UAG preferred for mammalian or eukaryotic cell expression.

Expression vectors will preferably but optionally include at least one selectable marker. Such markers include, e.g., but not limited to, methotrexate (MTX), dihydrofolate reductase (DHFR, U.S. Pat. Nos. 4,399,216; 4,634,665; 4,656,134; 4,956,288; 5,149,636; 5,179,017, ampicillin, neomycin (G418), mycophenolic acid, or glutamine synthetase (GS, U.S. Pat. Nos. 5,122,464; 5,770,359; 5,827,739) resistance for eukaryotic cell culture, and tetracycline or ampicillin resistance genes for culturing in *E. coli* and other bacteria or prokaryotics (the above patents are entirely incorporated hereby by reference). Appropriate culture mediums and conditions for the above-described host cells are known in the art. Suitable vectors will be readily apparent to the skilled artisan. Introduction of a vector construct into a host cell can be affected by calcium phosphate transfection, DEAE-dextran mediated transfection, cationic lipid-mediated transfection, electroporation, transduction, infection or other known methods. Such methods are described in the art, such as Sambrook, supra, Chapters 1-4 and 16-18; Ausubel, supra, Chapters 1, 9, 13, 15, 16.

At least one antibody of the present invention can be expressed in a modified form, such as a fusion protein, and can include not only secretion signals, but also additional heterologous functional regions. For instance, a region of additional amino acids, particularly charged amino acids, can be added to the N-terminus of an antibody to improve stability and persistence in the host cell, during purification, or during subsequent handling and storage. Also, peptide moieties can be added to an antibody of the present invention to facilitate purification. Such regions can be removed prior to final preparation of an antibody or at least one fragment thereof. Such methods are described in many standard laboratory manuals, such as Sambrook, supra, Chapters 17.29-17.42 and 18.1-18.74; Ausubel, supra, Chapters 16, 17 and 18.

Those of ordinary skill in the art are knowledgeable in the numerous expression systems available for expression of a nucleic acid encoding a protein of the present invention.

Alternatively, nucleic acids of the present invention can be expressed in a host cell by turning on (by manipulation) in a host cell that contains endogenous DNA encoding an antibody of the present invention. Such methods are well known in the art, e.g., as described in U.S. Pat. Nos. 5,580,734, 5,641,670, 5,733,746, and 5,733,761, entirely incorporated herein by reference.

Cells useful for the production of the antibodies, specified portions or variants thereof, are mammalian cells. Mammalian cell systems often will be in the form of monolayers of cells although mammalian cell suspensions or bioreactors can also be used. A number of suitable host cell lines capable of expressing intact glycosylated proteins have been developed in the art, and include the COS-1 (e.g., ATCC® CRL-1650), COS-7 (e.g., ATCC® CRL-1651), HEK293, BHK21 (e.g., ATCC® CCL-10), and BSC-1 (e.g., ATCC® CCL-26) cell lines, Cos-7 cells, CHO cells, Hep G2 cells, P3X63Ag8.653, Sp2/0-Ag14, 293 cells, HeLa cells and the like, which are readily available from, for example, American Type Culture Collection, Manassas, Va (www.atcc.org). In certain embodiments, host cells include cells of lymphoid origin such as myeloma and lymphoma cells, e.g., P3X63Ag8.653 cells (ATCC® CRL-1580) and Sp2/0-Ag14 cells (ATCC® CRL-1581).

CHO Cell Lines

Despite the availability of several other mammalian cell lines, a majority of recombinant therapeutic proteins produced today are made in Chinese hamster ovary (CHO) cells (Jayapal K P, et al. Recombinant protein therapeutics from CHO cells-20 years and counting. *Chem Eng Prog.* 2007; 103:40-47; Kunert R, Reinhart D. Advances in recombinant antibody manufacturing. *Appl Microbiol Biotechnol.* 2016; 100(8):3451-61). Their strengths include, e.g., robust growth as adherent cells or in suspension, adaptability to serum-free and chemically defined media, high productivity, and an established history of regulatory approval for therapeutic recombinant protein production.

They are also very amenable to genetic modifications and the methods for cell transfection, recombinant protein expression, and clone selection are all well characterized. CHO cells can also provide human-compatible post-translational modifications. As used herein, "CHO cells" include, but are not limited to, e.g., CHO-DG44, CHO-Kl, CHO-M, CHO-S, CHO GS knockout, and modifications and derivatives thereof.

Expression vectors for these cells can include one or more of the following expression control sequences, such as, but not limited to an origin of replication; a promoter (e.g., late or early SV40 promoters, the CMV promoter (U.S. Pat. Nos. 5,168,062; 5,385,839), an HSV tk promoter, a pgk (phosphoglycerate kinase) promoter, an EF-1 alpha promoter (U.S. Pat. No. 5,266,491), at least one human immunoglobulin promoter; an enhancer, and/or processing information sites, such as ribosome binding sites, RNA splice sites, polyadenylation sites (e.g., an SV40 large T Ag poly A addition site), and transcriptional terminator sequences. See, e.g., Ausubel et al., supra; Sambrook, et al., supra. Other cells useful for production of nucleic acids or proteins of the present invention are known and/or available, for instance, from the American Type Culture Collection Catalogue of Cell Lines and Hybridomas (www.atcc.org) or other known or commercial sources.

When eukaryotic host cells are employed, polyadenlyation or transcription terminator sequences are typically incorporated into the vector. An example of a terminator sequence is the polyadenlyation sequence from the bovine growth hormone gene. Sequences for accurate splicing of the transcript can also be included. An example of a splicing sequence is the VP1 intron from SV40 (Sprague, et al., J. Virol. 45:773-781 (1983)). Additionally, gene sequences to control replication in the host cell can be incorporated into the vector, as known in the art.

Purification of an Antibody. An anti-TNF antibody can be recovered and purified from recombinant cell cultures by well-known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, NY, (1997-2001), e.g., Chapters 1, 4, 6, 8, 9, 10, each entirely incorporated herein by reference.

Antibodies of the present invention include naturally purified products, products of chemical synthetic procedures, and products produced by recombinant techniques from a eukaryotic host, including, for example, yeast, higher plant, insect and mammalian cells. Depending upon the host employed in a recombinant production procedure, the antibody of the present invention can be glycosylated or can be non-glycosylated, with glycosylated preferred. Such methods are described in many standard laboratory manuals, such as Sambrook, supra, Sections 17.37-17.42; Ausubel, supra, Chapters 10, 12, 13, 16, 18 and 20, Colligan, Protein Science, supra, Chapters 12-14, all entirely incorporated herein by reference.

Anti-TNF Antibodies.

The isolated antibodies of the present invention, comprising all of the heavy chain variable CDR regions of SEQ ID NOS:1, 2 and 3 and/or all of the light chain variable CDR regions of SEQ ID NOS:4, 5 and 6, comprise antibody amino acid sequences disclosed herein encoded by any suitable polynucleotide, or any isolated or prepared antibody. Preferably, the human antibody or antigen-binding fragment binds human TNF and, thereby partially or substantially neutralizes at least one biological activity of the protein. An antibody, or specified portion or variant thereof, that partially or preferably substantially neutralizes at least one biological activity of at least one TNF protein or fragment can bind the protein or fragment and thereby inhibit activities mediated through the binding of TNF to the TNF receptor or through other TNF-dependent or mediated mechanisms. As used herein, the term "neutralizing antibody" refers to an antibody that can inhibit an TNF-dependent activity by about 20-120%, preferably by at least about 10, 20, 30, 40, 50, 55, 60, 65, 70, 75, 80, 85, 90, 91, 92, 93, 94, 95, 96, 97, 98, 99, 100% or more depending on the assay. The capacity of an anti-TNF antibody to inhibit an TNF-dependent activity is preferably assessed by at least one suitable TNF protein or receptor assay, as described herein and/or as known in the art. A human antibody of the invention can be of any class (IgG, IgA, IgM, IgE, IgD, etc.) or isotype and can comprise a kappa or lambda light chain. In one embodiment, the human antibody comprises an IgG heavy chain or defined fragment, for example, at least one of isotypes, IgG1, IgG2, IgG3 or IgG4. Antibodies of this type can be prepared by employing a transgenic mouse or other transgenic non-human mammal comprising at least one human light chain (e.g., IgG, IgA) and IgM (e.g., γ1, γ2, γ3, γ4) transgenes as 5 described herein and/or as known in the art. In another embodiment, the anti-human TNF human antibody comprises an IgG1 heavy chain and a IgG1 light chain.

As used herein, the terms "antibody" or "antibodies", include biosimilar antibody molecules approved under the Biologics Price Competition and Innovation Act of 2009 (BPCI Act) and similar laws and regulations globally. Under the BPCI Act, an antibody may be demonstrated to be biosimilar if data show that it is "highly similar" to the reference product notwithstanding minor differences in clinically inactive components and are "expected" to produce the same clinical result as the reference product in terms of safety, purity and potency (*Endocrine Practice*: February 2018, Vol. 24, No. 2, pp. 195-204). These biosimilar antibody molecules are provided an abbreviated approval pathway, whereby the applicant relies upon the innovator reference product's clinical data to secure regulatory approval. Compared to the original innovator reference antibody that was FDA approved based on successful clinical trials, a biosimilar antibody molecule is referred to herein as a "follow-on biologic". As presented herein, SIMPONI® (golimumab) is the original innovator reference anti-TNF antibody that was FDA approved based on successful clinical trials. Golimumab has been on sale in the United States since 2009.

At least one antibody of the invention binds at least one specified epitope specific to at least one TNF protein, subunit, fragment, portion or any combination thereof. The at least one epitope can comprise at least one antibody binding region that comprises at least one portion of said protein, which epitope is preferably comprised of at least one extracellular, soluble, hydrophilic, external or cytoplasmic portion of said protein. The at least one specified epitope can comprise any combination of at least one amino acid sequence of at least 1-3 amino acids to the entire specified portion of contiguous amino acids of the SEQ ID NO:9.

Generally, the human antibody or antigen-binding fragment of the present invention will comprise an antigen-binding region that comprises at least one human complementarity determining region (CDR1, CDR2 and CDR3) or variant of at least one heavy chain variable region and at least one human complementarity determining region (CDR1, CDR2 and CDR3) or variant of at least one light chain variable region. As a non-limiting example, the antibody or antigen-binding portion or variant can comprise at least one of the heavy chain CDR3 having the amino acid sequence of SEQ ID NO:3, and/or a light chain CDR3 having the amino acid sequence of SEQ ID NO:6. In a particular embodiment, the antibody or antigen-binding fragment can have an antigen-binding region that comprises at least a portion of at least one heavy chain CDR (i.e., CDR1, CDR2 and/or CDR3) having the amino acid sequence of the corresponding CDRs 1, 2 and/or 3 (e.g., SEQ ID NOS:1, 2, and/or 3). In another particular embodiment, the antibody or antigen-binding portion or variant can have an antigen-binding region that comprises at least a portion of at least one light chain CDR (i.e., CDR1, CDR2 and/or CDR3) having the amino acid sequence of the corresponding CDRs 1, 2 and/or 3 (e.g., SEQ ID NOS: 4, 5, and/or 6). In a preferred embodiment the three heavy chain CDRs and the three light chain CDRs of the antibody or antigen-binding fragment have the amino acid sequence of the corresponding CDR of at least one of mAb TNV148, TNV14, TNV15, TNV196, TNV118, TNV32, TNV86, as described herein. Such antibodies can be prepared by chemically joining together the various portions (e.g., CDRs, framework) of the antibody using conventional techniques, by preparing and expressing a (i.e., one or more) nucleic acid molecule that encodes the antibody using conventional techniques of recombinant DNA technology or by using any other suitable method.

The anti-TNF antibody can comprise at least one of a heavy or light chain variable region having a defined amino acid sequence. For example, in a preferred embodiment, the anti-TNF antibody comprises at least one of heavy chain variable region, optionally having the amino acid sequence of SEQ ID NO:7 and/or at least one light chain variable region, optionally having the amino acid sequence of SEQ ID NO:8. antibodies that bind to human TNF and that comprise a defined heavy or light chain variable region can be prepared using suitable methods, such as phage display (Katsube, Y., et al., *Int J Mol. Med,* 1(5):863-868 (1998)) or methods that employ transgenic animals, as known in the art and/or as described herein. For example, a transgenic mouse, comprising a functionally rearranged human immunoglobulin heavy chain transgene and a transgene comprising DNA from a human immunoglobulin light chain locus that can undergo functional rearrangement, can be immunized with human TNF or a fragment thereof to elicit the production of antibodies. If desired, the antibody producing cells can be isolated and hybridomas or other immortalized antibody-producing cells can be prepared as described herein and/or as known in the art. Alternatively, the antibody, specified portion or variant can be expressed using the encoding nucleic acid or portion thereof in a suitable host cell.

The invention also relates to antibodies, antigen-binding fragments, immunoglobulin chains and CDRs comprising amino acids in a sequence that is substantially the same as an amino acid sequence described herein. Preferably, such antibodies or antigen-binding fragments and antibodies comprising such chains or CDRs can bind human TNF with high affinity (e.g., $K_D$ less than or equal to about $10^{-9}$ M). Amino acid sequences that are substantially the same as the sequences described herein include sequences comprising conservative amino acid substitutions, as well as amino acid deletions and/or insertions. A conservative amino acid substitution refers to the replacement of a first amino acid by a second amino acid that has chemical and/or physical properties (e.g., charge, structure, polarity, hydrophobicity/hydrophilicity) that are similar to those of the first amino acid. Conservative substitutions include replacement of one amino acid by another within the following groups: lysine (K), arginine (R) and histidine (H); aspartate (D) and glutamate (E); asparagine (N), glutamine (Q), serine (S), threonine (T), tyrosine (Y), K, R, H, D and E; alanine (A), valine (V), leucine (L), isoleucine (I), proline (P), phenylalanine (F), tryptophan (W), methionine (M), cysteine (C) and glycine (G); F, W and Y; C, S and T.

Amino Acid Codes. The amino acids that make up anti-TNF antibodies of the present invention are often abbreviated. The amino acid designations can be indicated by designating the amino acid by its single letter code, its three letter code, name, or three nucleotide codon(s) as is well understood in the art (see Alberts, B., et al., Molecular Biology of The Cell, Third Ed., Garland Publishing, Inc., New York, 1994):

| SINGLE LETTER CODE | THREE LETTER CODE | NAME | THREE NUCLEOTIDE CODON(S) |
|---|---|---|---|
| A | Ala | Alanine | GCA, GCC, GCG, GCU |
| C | Cys | Cysteine | UGC, UGU |
| D | Asp | Aspartic acid | GAC, GAU |
| E | Glu | Glutamic acid | GAA, GAG |
| F | Phe | Phenylanine | UUC, UUU |
| G | Gly | Glycine | GGA, GGC, GGG, GGU |
| H | His | Histidine | CAC, CAU |
| I | Ile | Isoleucine | AUA, AUC, AUU |
| K | Lys | Lysine | AAA, AAG |
| L | Leu | Leucine | UUA, UUG, CUA, CUC, CUG, CUU |
| M | Met | Methionine | AUG |
| N | Asn | Asparagine | AAC, AAU |
| P | Pro | Proline | CCA, CCC, CCG, CCU |
| Q | Gln | Glutamine | CAA, CAG |
| R | Arg | Arginine | AGA, AGG, CGA, CGC, CGG, CGU |
| S | Ser | Serine | AGC, AGU, UCA, UCC, UCG, UCU |
| T | Thr | Threonine | ACA, ACC, ACG, ACU |
| V | Val | Valine | GUA, GUC, GUG, GUU |
| W | Trp | Tryptophan | UGG |
| Y | Tyr | Tyrosine | UAC, UAU |

An anti-TNF antibody of the present invention can include one or more amino acid substitutions, deletions or additions, either from natural mutations or human manipulation, as specified herein.

Of course, the number of amino acid substitutions a skilled artisan would make depends on many factors, including those described above. Generally speaking, the number of amino acid substitutions, insertions or deletions for any given anti-TNF antibody, fragment or variant will not be more than 40, 30, 20, 19, 18, 17, 16, 15, 14, 13, 12, 11, 10, 9, 8, 7, 6, 5, 4, 3, 2, 1, such as 1-30 or any range or value therein, as specified herein.

Amino acids in an anti-TNF antibody of the present invention that are essential for function can be identified by methods known in the art, such as site-directed mutagenesis or alanine-scanning mutagenesis (e.g., Ausubel, supra, Chapters 8, 15; Cunningham and Wells, Science 244:1081-1085 (1989)). The latter procedure introduces single alanine mutations at every residue in the molecule. The resulting mutant molecules are then tested for biological activity, such as, but not limited to at least one TNF neutralizing activity. Sites that are critical for antibody binding can also be identified by structural analysis such as crystallization, nuclear magnetic resonance or photoaffinity labeling (Smith, et al., J. Mol. Biol. 224:899-904 (1992) and de Vos, et al., Science 255:306-312 (1992)).

Anti-TNF antibodies of the present invention can include, but are not limited to, at least one portion, sequence or combination selected from 1 to all of the contiguous amino acids of at least one of SEQ ID NOS:1, 2, 3, 4, 5, 6.

A(n) anti-TNF antibody can further optionally comprise a polypeptide of at least one of 70-100% of the contiguous amino acids of at least one of SEQ ID NOS:7, 8.

In one embodiment, the amino acid sequence of an immunoglobulin chain, or portion thereof (e.g., variable region, CDR) has about 70-100% identity (e.g., 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or any range or value therein) to the amino acid sequence of the corresponding chain of at least one of SEQ ID NOS:7, 8. For example, the amino acid sequence of a light chain variable region can be compared with the sequence of SEQ ID NO:8, or the amino acid sequence of a heavy chain CDR3 can be compared with SEQ ID NO:7. Preferably, 70-100% amino acid identity (i.e., 90, 91, 92, 93, 94, 95, 96, 97, 98, 99, 100 or any range or value therein) is determined using a suitable computer algorithm, as known in the art.

Exemplary heavy chain and light chain variable regions sequences are provided in SEQ ID NOS: 7, 8. The antibodies of the present invention, or specified variants thereof, can comprise any number of contiguous amino acid residues from an antibody of the present invention, wherein that number is selected from the group of integers consisting of from 10-100% of the number of contiguous residues in an anti-TNF antibody. Optionally, this subsequence of contiguous amino acids is at least about 10, 20, 30, 40, 50, 60, 70, 80, 90, 100, 110, 120, 130, 140, 150, 160, 170, 180, 190, 200, 210, 220, 230, 240, 250 or more amino acids in length, or any range or value therein. Further, the number of such subsequences can be any integer selected from the group consisting of from 1 to 20, such as at least 2, 3, 4, or 5.

As those of skill will appreciate, the present invention includes at least one biologically active antibody of the present invention. Biologically active antibodies have a specific activity at least 20%, 30%, or 40%, and preferably at least 50%, 60%, or 70%, and most preferably at least 80%, 90%, or 95%-1000% of that of the native (non-synthetic), endogenous or related and known antibody. Methods of assaying and quantifying measures of enzymatic activity and substrate specificity, are well known to those of skill in the art.

In another aspect, the invention relates to human antibodies and antigen-binding fragments, as described herein, which are modified by the covalent attachment of an organic moiety. Such modification can produce an antibody or antigen-binding fragment with improved pharmacokinetic properties (e.g., increased in vivo serum half-life). The organic moiety can be a linear or branched hydrophilic polymeric group, fatty acid group, or fatty acid ester group.

In particular embodiments, the hydrophilic polymeric group can have a molecular weight of about 800 to about 120,000 Daltons and can be a polyalkane glycol (e.g., polyethylene glycol (PEG), polypropylene glycol (PPG)), carbohydrate polymer, amino acid polymer or polyvinyl pyrolidone, and the fatty acid or fatty acid ester group can comprise from about eight to about forty carbon atoms.

The modified antibodies and antigen-binding fragments of the invention can comprise one or more organic moieties that are covalently bonded, directly or indirectly, to the antibody. Each organic moiety that is bonded to an antibody or antigen-binding fragment of the invention can independently be a hydrophilic polymeric group, a fatty acid group or a fatty acid ester group. As used herein, the term "fatty acid" encompasses mono-carboxylic acids and di-carboxylic acids. A "hydrophilic polymeric group," as the term is used herein, refers to an organic polymer that is more soluble in water than in octane. For example, polylysine is more soluble in water than in octane. Thus, an antibody modified by the covalent attachment of polylysine is encompassed by the invention. Hydrophilic polymers suitable for modifying antibodies of the invention can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. Preferably, the hydrophilic polymer that modifies the antibody of the invention has a molecular weight of about 800 to about 150,000 Daltons as a separate molecular entity. For example, $PEG_{5000}$ and $PEG_{20,000}$, wherein the subscript is the average molecular weight of the polymer in Daltons, can be used. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N, N-carbonyl diimidazole) on a fatty acid or fatty acid ester can be coupled to a hydroxyl group on a polymer.

Fatty acids and fatty acid esters suitable for modifying antibodies of the invention can be saturated or can contain one or more units of unsaturation. Fatty acids that are suitable for modifying antibodies of the invention include, for example, n-dodecanoate ($C_{12}$, laurate), n-tetradecanoate ($C_{14}$, myristate), n-octadecanoate (Cis, stearate), n-eicosanoate ($C_{20}$, arachidate), n-docosanoate ($C_{22}$, behenate), n-triacontanoate ($C_3M$), n-tetracontanoate ($C_{40}$), cis-Δ9-octadecanoate (Cis, oleate), all cis-Δ5,8,11,14-eicosatetraenoate ($C_{20}$, arachidonate), octanedioic acid, tetradecanedioic acid, octadecanedioic acid, docosanedioic acid, and the like. Suitable fatty acid esters include mono-esters of dicarboxylic acids that comprise a linear or branched lower alkyl group. The lower alkyl group can comprise from one to about twelve, preferably one to about six, carbon atoms.

The modified human antibodies and antigen-binding fragments can be prepared using suitable methods, such as by reaction with one or more modifying agents. A "modifying agent" as the term is used herein, refers to a suitable organic group (e.g., hydrophilic polymer, a fatty acid, a fatty acid ester) that comprises an activating group. An "activating group" is a chemical moiety or functional group that can, under appropriate conditions, react with a second chemical group thereby forming a covalent bond between the modifying agent and the second chemical group. For example, amine-reactive activating groups include electrophilic groups such as tosylate, mesylate, halo (chloro, bromo, fluoro, iodo), N-hydroxysuccinimidyl esters (NHS), and the like. Activating groups that can react with thiols include, for example, maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, Hermanson, G. T., *Bioconjugate Techniques*, Academic Press: San Diego, CA (1996)). An activating group can be bonded directly to the organic group (e.g., hydrophilic polymer, fatty acid, fatty acid ester), or through a linker moiety, for example a divalent $C_1$-$C_{12}$ group wherein one or more carbon atoms can be replaced by a heteroatom such as oxygen, nitrogen or sulfur. Suitable linker moieties include, for example, tetraethylene glycol, —(CH$_2$)$_3$—, —NH—(CH$_2$)$_6$—NH—, —(CH$_2$)$_2$—NH— and —CH$_2$—O—CH$_2$—CH$_2$—O—CH$_2$—CH$_2$—O—CH—NH—. Modifying agents that comprise a linker moiety can be produced, for example, by reacting a mono-Boc-alkyldiamine (e.g., mono-Boc-ethylenediamine, mono-Boc-diaminohexane) with a fatty acid in the presence of 1-ethyl-3-(3-dimethylaminopropyl) carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate as described or can be reacted with maleic anhydride and the resulting product cyclized to produce an activated maleimido derivative of the fatty acid. (See, for example, Thompson, et al., WO 92/16221 the entire teachings of which are incorporated herein by reference.)

The modified antibodies of the invention can be produced by reacting a human antibody or antigen-binding fragment with a modifying agent. For example, the organic moieties can be bonded to the antibody in a non-site specific manner by employing an amine-reactive modifying agent, for example, an NHS ester of PEG. Modified human antibodies or antigen-binding fragments can also be prepared by reducing disulfide bonds (e.g., intra-chain disulfide bonds) of an antibody or antigen-binding fragment. The reduced antibody or antigen-binding fragment can then be reacted with a thiol-reactive modifying agent to produce the modified antibody of the invention. Modified human antibodies and antigen-binding fragments comprising an organic moiety that is bonded to specific sites of an antibody of the present invention can be prepared using suitable methods, such as reverse proteolysis (Fisch et al., *Bioconjugate Chem.*, 3:147-153 (1992); Werlen et al., *Bioconjugate Chem.*, 5:411-417 (1994); Kumaran et al., *Protein Sci.* 6(10):2233-2241 (1997); Itoh et al., *Bioorg. Chem.*, 24(1): 59-68 (1996); Capellas et al., *Biotechnol. Bioeng.*, 56(4):456-463 (1997)), and the methods described in Hermanson, G. T., *Bioconjugate Techniques*, Academic Press: San Diego, CA (1996).

Anti-Idiotype Antibodies to Anti-TNF Antibody Compositions. In addition to monoclonal or chimeric anti-TNF antibodies, the present invention is also directed to an anti-idiotypic (anti-Id) antibody specific for such antibodies of the invention. An anti-Id antibody is an antibody which recognizes unique determinants generally associated with the antigen-binding region of another antibody. The anti-Id can be prepared by immunizing an animal of the same species and genetic type (e.g. mouse strain) as the source of the Id antibody with the antibody or a CDR containing region thereof. The immunized animal will recognize and respond to the idiotypic determinants of the immunizing antibody and produce an anti-Id antibody. The anti-Id antibody may also be used as an "immunogen" to induce an immune response in yet another animal, producing a so-called anti-anti-Id antibody.

Anti-TNF Antibody Compositions. The present invention also provides at least one anti-TNF antibody composition comprising at least one, at least two, at least three, at least four, at least five, at least six or more anti-TNF antibodies thereof, as described herein and/or as known in the art that are provided in a non-naturally occurring composition, mixture or form. Such compositions comprise non-naturally occurring compositions comprising at least one or two full length, C- and/or N-terminally deleted variants, domains, fragments, or specified variants, of the anti-TNF antibody amino acid sequence selected from the group consisting of 70-100% of the contiguous amino acids of SEQ ID NOS:1, 2, 3, 4, 5, 6, 7, 8, or specified fragments, domains or variants thereof. Preferred anti-TNF antibody compositions include at least one or two full length, fragments, domains or variants as at least one CDR or LBR containing portions of the anti-TNF antibody sequence of 70-100% of SEQ ID NOS:1, 2, 3, 4, 5, 6, or specified fragments, domains or variants thereof. Further preferred compositions comprise 40-99% of at least one of 70-100% of SEQ ID NOS:1, 2, 3, 4, 5, 6, or specified fragments, domains or variants thereof. Such composition percentages are by weight, volume, concentration, molarity, or molality as liquid or dry solutions, mixtures, suspension, emulsions or colloids, as known in the art or as described herein.

Anti-TNF antibody compositions of the present invention can further comprise at least one of any suitable and effective amount of a composition or pharmaceutical composition comprising at least one anti-TNF antibody to a cell, tissue, organ, animal or patient in need of such modulation, treatment or therapy, optionally further comprising at least one selected from at least one TNF antagonist (e.g., but not limited to a TNF antibody or fragment, a soluble TNF receptor or fragment, fusion proteins thereof, or a small molecule TNF antagonist), an antirheumatic (e.g., methotrexate, auranofin, aurothioglucose, azathioprine, etanercept, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anethetic, a neuromuscular blocker, an antimicrobial (e.g., aminoglycoside, an antifungal, an antiparasitic, an antiviral, a carbapenem, cephalosporin, a flurorquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropieitin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine or a cytokine antagonist. Non-limiting examples of such cytokines include, but are not limited to, any of IL-1 to IL-23. Suitable dosages are well known in the art. See, e.g., Wells et al., eds., Pharmacotherapy Handbook, 2$^{nd}$ Edition, Appleton and Lange, Stamford, C T (2000); PDR Pharmacopoeia, Tarascon Pocket Pharmacopoeia 2000, Deluxe Edition, Tarascon Publishing, Loma Linda, CA (2000), each of which references are entirely incorporated herein by reference.

Such anti-cancer or anti-infectives can also include toxin molecules that are associated, bound, co-formulated or co-administered with at least one antibody of the present invention. The toxin can optionally act to selectively kill the pathologic cell or tissue. The pathologic cell can be a cancer or other cell. Such toxins can be, but are not limited to, purified or recombinant toxin or toxin fragment comprising at least one functional cytotoxic domain of toxin, e.g., selected from at least one of ricin, diphtheria toxin, a venom toxin, or a bacterial toxin. The term toxin also includes both endotoxins and exotoxins produced by any naturally occurring, mutant or recombinant bacteria or viruses which may cause any pathological condition in humans and other mammals, including toxin shock, which can result in death. Such toxins may include, but are not limited to, enterotoxigenic *E. coli* heat-labile enterotoxin (LT), heat-stable enterotoxin (ST), *Shigella* cytotoxin, *Aeromonas* enterotoxins, toxic shock syndrome toxin-1 (TSST-1), Staphylococcal enterotoxin A (SEA), B (SEB), or C (SEC), Streptococcal enterotoxins and the like. Such bacteria include, but are not limited to, strains of a species of enterotoxigenic *E. coli* (ETEC), enterohemorrhagic *E. coli* (e.g., strains of serotype O157:H7), *Staphylococcus* species (e.g., *Staphylococcus aureus, Staphylococcus pyogenes*), *Shigella* species (e.g., *Shigella dysenteriae, Shigella flexneri, Shigella boydii,* and *Shigella sonnei*), *Salmonella* species (e.g., *Salmonella typhi, Salmonella* cholera-suis, *Salmonella enteritidis*), *Clostridium* species (e.g., *Clostridium perfringens, Clostridium dificile, Clostridium botulinum*), *Campylobacter* species (e.g., *Campylobacter jejuni, Campylobacter fetus*), *Helicobacter* species, (e.g., *Helicobacter pylori*), *Aeromonas* species (e.g., *Aeromonas sobria, Aeromonas hydrophila, Aeromonas caviae*), *Plesiomonas shigelloides, Yersinia enterocolitica, Vibrio* species (e.g., *Vibrio cholerae, Vibrio parahemolyticus*), *Klebsiella* species, *Pseudomonas aeruginosa,* and Streptococci. See, e.g., Stein, ed., INTERNAL MEDICINE, 3rd ed., pp 1-13, Little, Brown and Co., Boston, (1990); Evans et al., eds., Bacterial Infections of Humans: Epidemiology and Control, 2d. Ed., pp 239-254, Plenum Medical Book Co., New York (1991); Mandell et al, Principles and Practice of Infectious Diseases, 3d. Ed., Churchill Livingstone, New York (1990); Berkow et al, eds., *The Merck Manual,* 16th edition, Merck and Co., Rahway, N.J., 1992; Wood et al, FEMS Microbiology Immunology, 76:121-134 (1991); Marrack et al, Science, 248:705-711 (1990), the contents of which references are incorporated entirely herein by reference.

Anti-TNF antibody compounds, compositions or combinations of the present invention can further comprise at least one of any suitable auxiliary, such as, but not limited to, diluent, binder, stabilizer, buffers, salts, lipophilic solvents, preservative, adjuvant or the like. Pharmaceutically acceptable auxiliaries are preferred. Non-limiting examples of, and methods of preparing such sterile solutions are well known in the art, such as, but limited to, Gennaro, Ed., *Remington's Pharmaceutical Sciences,* 18$^{th}$ Edition, Mack Publishing Co. (Easton, PA) 1990. Pharmaceutically acceptable carriers can be routinely selected that are suitable for the mode of administration, solubility and/or stability of the anti-TNF antibody, fragment or variant composition as well known in the art or as described herein.

Pharmaceutical excipients and additives useful in the present composition include but are not limited to proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. One preferred amino acid is glycine.

Carbohydrate excipients suitable for use in the invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. Preferred carbohydrate excipients for use in the present invention are mannitol, trehalose, and raffinose.

Anti-TNF antibody compositions can also include a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. Preferred buffers for use in the present compositions are organic acid salts such as citrate.

Additionally, anti-TNF antibody compositions of the invention can include polymeric excipients/additives such as polyvinylpyrrolidones, ficolls (a polymeric sugar), dextrates (e.g., cyclodextrins, such as 2-hydroxypropyl-β-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents (e.g., EDTA). These and additional known pharmaceutical excipients and/or additives suitable for use in the anti-TNF antibody, portion or variant compositions according to the invention are known in the art, e.g., as listed in "Remington: The Science & Practice of Pharmacy", $19^{th}$ ed., Williams & Williams, (1995), and in the "Physician's Desk Reference", $52^{nd}$ ed., Medical Economics, Montvale, NJ (1998), the disclosures of which are entirely incorporated herein by reference. Preferred carrier or excipient materials are carbohydrates (e.g., saccharides and alditols) and buffers (e.g., citrate) or polymeric agents.

Formulations. As noted above, the invention provides for stable formulations, which is preferably a phosphate buffer with saline or a chosen salt, as well as preserved solutions and formulations containing a preservative as well as multiuse preserved formulations suitable for pharmaceutical or veterinary use, comprising at least one anti-TNF antibody in a pharmaceutically acceptable formulation. Preserved formulations contain at least one known preservative or optionally selected from the group consisting of at least one phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1-2% m-cresol (e.g., 0.2, 0.3. 0.4, 0.5, 0.9, 1.0%), 0.1-3% benzyl alcohol (e.g., 0.5, 0.9, 1.1, 1.5, 1.9, 2.0, 2.5%), 0.001-0.5% thimerosal (e.g., 0.005, 0.01), 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, 1.0%), and the like.

As noted above, the invention provides an article of manufacture, comprising packaging material and at least one vial comprising a solution of at least one anti-TNF antibody with the prescribed buffers and/or preservatives, optionally in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater. The invention further comprises an article of manufacture, comprising packaging material, a first vial comprising lyophilized at least one anti-TNF antibody, and a second vial comprising an aqueous diluent of prescribed buffer or preservative, wherein said packaging material comprises a label that instructs a patient to reconstitute the at least one anti-TNF antibody in the aqueous diluent to form a solution that can be held over a period of twenty-four hours or greater.

The at least one anti-TNF antibody used in accordance with the present invention can be produced by recombinant means, including from mammalian cell or transgenic preparations, or can be purified from other biological sources, as described herein or as known in the art.

The range of at least one anti-TNF antibody in the product of the present invention includes amounts yielding upon reconstitution, if in a wet/dry system, concentrations from about 1.0 μg/ml to about 1000 mg/ml, although lower and higher concentrations are operable and are dependent on the intended delivery vehicle, e.g., solution formulations will differ from transdermal patch, pulmonary, transmucosal, or osmotic or micro pump methods.

Preferably, the aqueous diluent optionally further comprises a pharmaceutically acceptable preservative. Preferred preservatives include those selected from the group consisting of phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof. The concentration of preservative used in the formulation is a concentration sufficient to yield an antimicrobial effect. Such concentrations are dependent on the preservative selected and are readily determined by the skilled artisan.

Other excipients, e.g. isotonicity agents, buffers, antioxidants, preservative enhancers, can be optionally and preferably added to the diluent. An isotonicity agent, such as glycerin, is commonly used at known concentrations. A physiologically tolerated buffer is preferably added to provide improved pH control. The formulations can cover a wide range of pHs, such as from about pH 4 to about pH 10, and preferred ranges from about pH 5 to about pH 9, and a most preferred range of about 6.0 to about 8.0. Preferably the formulations of the present invention have pH between about 6.8 and about 7.8. Preferred buffers include phosphate buffers, most preferably sodium phosphate, particularly phosphate buffered saline (PBS).

Other additives, such as a pharmaceutically acceptable solubilizers like Tween 20 (polyoxyethylene (20) sorbitan monolaurate), Tween 40 (polyoxyethylene (20) sorbitan monopalmitate), Tween 80 (polyoxyethylene (20) sorbitan monooleate), Pluronic F68 (polyoxyethylene polyoxypropylene block copolymers), and PEG (polyethylene glycol) or non-ionic surfactants such as polysorbate 20 or 80 or poloxamer 184 or 188, Pluronic® polyols, other block co-polymers, and chelators such as EDTA and EGTA can optionally be added to the formulations or compositions to reduce aggregation. These additives are particularly useful if a pump or plastic container is used to administer the formulation. The presence of pharmaceutically acceptable surfactant mitigates the propensity for the protein to aggregate.

The formulations of the present invention can be prepared by a process which comprises mixing at least one anti-TNF antibody and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing the at least one anti-TNF antibody and preservative in an aqueous diluent is carried out using conventional dissolution and mixing procedures. To prepare a suitable formulation, for example, a measured amount of at least one anti-TNF antibody in buffered solution is combined with the desired preservative in a buffered solution in quantities sufficient to provide the protein and preservative at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed formulations can be provided to patients as clear solutions or as dual vials comprising a vial of lyophilized at least one anti-TNF antibody that is reconstituted with a second vial containing water, preservatives and/or excipients, preferably a phosphate buffer and/or saline and a chosen salt, in an aqueous diluent. Either a single solution vial or dual vial requiring reconstitution can be reused multiple times and can suffice for a single or multiple cycles of patient treatment and thus can provide a more convenient treatment regimen than currently available.

The present claimed articles of manufacture are useful for administration over a period of immediately to twenty-four hours or greater. Accordingly, the presently claimed articles of manufacture offer significant advantages to the patient. Formulations of the invention can optionally be safely stored at temperatures of from about 2 to about 40° C. and retain the biologically activity of the protein for extended periods of time, thus, allowing a package label indicating that the solution can be held and/or used over a period of 6, 12, 18, 24, 36, 48, 72, or 96 hours or greater. If preserved diluent is used, such label can include use up to 1-12 months, one-half, one and a half, and/or two years.

The solutions of at least one anti-TNF antibody in the invention can be prepared by a process that comprises mixing at least one antibody in an aqueous diluent. Mixing is carried out using conventional dissolution and mixing procedures. To prepare a suitable diluent, for example, a measured amount of at least one antibody in water or buffer is combined in quantities sufficient to provide the protein and optionally a preservative or buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed products can be provided to patients as clear solutions or as dual vials comprising a vial of lyophilized at least one anti-TNF antibody that is reconstituted with a second vial containing the aqueous diluent. Either a single solution vial or dual vial requiring reconstitution can be reused multiple times and can suffice for a single or multiple cycles of patient treatment and thus provides a more convenient treatment regimen than currently available.

The claimed products can be provided indirectly to patients by providing to pharmacies, clinics, or other such institutions and facilities, clear solutions or dual vials comprising a vial of lyophilized at least one anti-TNF antibody that is reconstituted with a second vial containing the aqueous diluent. The clear solution in this case can be up to one liter or even larger in size, providing a large reservoir from which smaller portions of the at least one antibody solution can be retrieved one or multiple times for transfer into smaller vials and provided by the pharmacy or clinic to their customers and/or patients.

Recognized devices comprising these single vial systems include those pen-injector devices for delivery of a solution such as BD Pens, BD Autojector®, Humaject®, NovoPen®, B-D©Pen, AutoPen®, and OptiPen®, GenotropinPen®, Genotronorm Pen®, Humatro Pen®, Reco-Pen®, Roferon Pen®, Biojector®, Iject®, J-tip Needle-Free Injector®, Intraject®, Medi-Ject®, e.g., as made or developed by Becton Dickensen (Franklin Lakes, NJ, www.bectondickenson.com), Disetronic (Burgdorf, Switzerland, www.disetronic.com; Bioject, Portland, Oregon (www.bioject.com); National Medical Products, Weston Medical (Peterborough, UK, www.weston-medical.com), Medi-Ject Corp (Minneapolis, MN, www.mediject.com). Recognized devices comprising a dual vial system include those pen-injector systems for reconstituting a lyophilized drug in a cartridge for delivery of the reconstituted solution such as the Humatro-Pen®.

The products presently claimed include packaging material. The packaging material provides, in addition to the information required by the regulatory agencies, the conditions under which the product can be used. The packaging material of the present invention provides instructions to the patient to reconstitute the at least one anti-TNF antibody in the aqueous diluent to form a solution and to use the solution over a period of 2-24 hours or greater for the two vials, wet/dry, product. For the single vial, solution product, the label indicates that such solution can be used over a period of 2-24 hours or greater. The presently claimed products are useful for human pharmaceutical product use.

The formulations of the present invention can be prepared by a process that comprises mixing at least one anti-TNF antibody and a selected buffer, preferably a phosphate buffer containing saline or a chosen salt. Mixing the at least one antibody and buffer in an aqueous diluent is carried out using conventional dissolution and mixing procedures. To prepare a suitable formulation, for example, a measured amount of at least one antibody in water or buffer is combined with the desired buffering agent in water in quantities sufficient to provide the protein and buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed stable or preserved formulations can be provided to patients as clear solutions or as dual vials comprising a vial of lyophilized at least one anti-TNF antibody that is reconstituted with a second vial containing a preservative or buffer and excipients in an aqueous diluent. Either a single solution vial or dual vial requiring reconstitution can be reused multiple times and can suffice for a single or multiple cycles of patient treatment and thus provides a more convenient treatment regimen than currently available.

At least one anti-TNF antibody in either the stable or preserved formulations or solutions described herein, can be administered to a patient in accordance with the present invention via a variety of delivery methods including SC or IM injection; transdermal, pulmonary, transmucosal, implant, osmotic pump, cartridge, micro pump, or other means appreciated by the skilled artisan, as well-known in the art.

Therapeutic Applications. The present invention also provides a method for modulating or treating at least one TNF related disease, in a cell, tissue, organ, animal, or patient, as known in the art or as described herein, using at least one dual integrin antibody of the present invention.

The present invention also provides a method for modulating or treating at least one TNF related disease, in a cell, tissue, organ, animal, or patient including, but not limited to, at least one of obesity, an immune related disease, a cardiovascular disease, an infectious disease, a malignant disease or a neurologic disease.

The present invention also provides a method for modulating or treating at least one immune related disease, in a cell, tissue, organ, animal, or patient including, but not limited to, at least one of rheumatoid arthritis, juvenile, systemic onset juvenile rheumatoid arthritis, Ankylosing Spondylitis, ankylosing spondilitis, gastric ulcer, seronegative arthropathies, osteoarthritis, inflammatory bowel disease, ulcerative colitis, systemic lupus erythematosus, antiphospholipid syndrome, iridocyclitis/uveitis/optic neuritis, idiopathic pulmonary fibrosis, systemic vasculitis/wegener's granulomatosis, sarcoidosis, orchitis/vasectomy reversal procedures, allergic/atopic diseases, asthma, allergic rhinitis, eczema, allergic contact dermatitis, allergic conjunctivitis, hypersensitivity pneumonitis, transplants, organ transplant rejection, graft-versus-host disease, systemic inflammatory response syndrome, sepsis syndrome, gram positive sepsis, gram negative sepsis, culture negative sepsis, fungal sepsis, neutropenic fever, urosepsis, meningococcemia, trauma/hemorrhage, burns, ionizing radiation exposure, acute pancreatitis, adult respiratory distress syndrome, alcohol-induced hepatitis, chronic inflammatory pathologies, sarcoidosis, Crohn's pathology, sickle cell anemia, diabetes, nephrosis, atopic diseases, hypersensitivity reactions, allergic rhinitis, hay fever, perennial rhinitis, conjunctivitis, endometriosis, asthma, urticaria, systemic anaphylaxis, dermatitis, pernicious anemia, hemolytic disease, thrombocytopenia, graft rejection of any organ or tissue, kidney transplant rejection, heart transplant rejection, liver transplant rejection, pancreas transplant rejection, lung transplant rejection, bone marrow transplant (BMT) rejection, skin allograft rejection, cartilage transplant rejection, bone graft rejection, small bowel transplant rejection, fetal thymus implant rejection, parathyroid transplant rejection, xenograft rejection of any organ or tissue, allograft rejection, anti-receptor hypersensitivity reactions, Graves' disease, Raynoud's disease, type B insulin-resistant diabetes, asthma, myasthenia gravis, antibody-meditated cytotoxicity, type III hypersensitivity reactions, systemic lupus erythematosus, POEMS syndrome (polyneuropathy, organomegaly, endocrinopathy, monoclonal gammopathy, and skin changes syndrome), polyneuropathy, organomegaly, endocrinopathy, monoclonal gammopathy, skin changes syndrome, antiphospholipid syndrome, pemphigus, scleroderma, mixed connective tissue disease, idiopathic Addison's disease, diabetes mellitus, chronic active hepatitis, primary billiary cirrhosis, vitiligo, vasculitis, post-MI cardiotomy syndrome, type IV hypersensitivity, contact dermatitis, hypersensitivity pneumonitis, allograft rejection, granulomas due to intracellular organisms, drug sensitivity, metabolic/idiopathic, Wilson's disease, hemachromatosis, alpha-1-antitrypsin deficiency, diabetic retinopathy, hashimoto's thyroiditis, osteoporosis, primary biliary cirrhosis, thyroiditis, encephalomyelitis, cachexia, cystic fibrosis, neonatal chronic lung disease, chronic obstructive pulmonary disease (COPD), familial hematophagocytic lymphohistiocytosis, dermatologic conditions, psoriasis, alopecia, nephrotic syndrome, nephritis, glomerular nephritis, acute renal failure, hemodialysis, uremia, toxicity, preeclampsia, okt3 therapy, anti-cd3 therapy, cytokine therapy, chemotherapy, radiation therapy (e.g., including but not limited to asthenia, anemia, cachexia, and the like), chronic salicylate intoxication, and the like. See, e.g., the Merck Manual, 12th-17th Editions, Merck & Company, Rahway, NJ (1972, 1977, 1982, 1987, 1992, 1999), Pharmacotherapy Handbook, Wells et al., eds., Second Edition, Appleton and Lange, Stamford, Conn. (1998, 2000), each entirely incorporated by reference.

The present invention also provides a method for modulating or treating at least one cardiovascular disease in a cell, tissue, organ, animal, or patient, including, but not limited to, at least one of cardiac stun syndrome, myocardial infarction, congestive heart failure, stroke, ischemic stroke, hemorrhage, arteriosclerosis, atherosclerosis, restenosis, diabetic arteriosclerotic disease, hypertension, arterial hypertension, renovascular hypertension, syncope, shock, syphilis of the cardiovascular system, heart failure, cor pulmonale, primary pulmonary hypertension, cardiac arrhythmias, atrial ectopic beats, atrial flutter, atrial fibrillation (sustained or paroxysmal), post perfusion syndrome, cardiopulmonary bypass inflammation response, chaotic or multifocal atrial tachycardia, regular narrow QRS tachycardia, specific arrhythmias, ventricular fibrillation, His bundle arrhythmias, atrioventricular block, bundle branch block, myocardial ischemic disorders, coronary artery disease, angina pectoris, myocardial infarction, cardiomyopathy, dilated congestive cardiomyopathy, restrictive cardiomyopathy, valvular heart diseases, endocarditis, pericardial disease, cardiac tumors, aortic and peripheral aneurysms, aortic dissection, inflammation of the aorta, occlusion of the abdominal aorta and its branches, peripheral vascular disorders, occlusive arterial disorders, peripheral atherosclerotic disease, thromboangitis obliterans, functional peripheral arterial disorders, Raynaud's phenomenon and disease, acrocyanosis, erythromelalgia, venous diseases, venous thrombosis, varicose veins, arteriovenous fistula, lymphedema, lipedema, unstable angina, reperfusion injury, post pump syndrome, ischemia-reperfusion injury, and the like. Such a method can optionally comprise administering an effective amount of a composition or pharmaceutical composition comprising at least one anti-TNF antibody to a cell, tissue, organ, animal or patient in need of such modulation, treatment or therapy.

The present invention also provides a method for modulating or treating at least one infectious disease in a cell, tissue, organ, animal or patient, including, but not limited to, at least one of: acute or chronic bacterial infection, acute and chronic parasitic or infectious processes, including bacterial, viral and fungal infections, HIV infection/HIV neuropathy, meningitis, hepatitis (A, B or C, or the like), septic arthritis, peritonitis, pneumonia, epiglottitis, e. coli 0157:h7, hemolytic uremic syndrome/thrombolytic thrombocytopenic purpura, malaria, dengue hemorrhagic fever, leishmaniasis, leprosy, toxic shock syndrome, streptococcal myositis, gas gangrene, Mycobacterium tuberculosis, Mycobacterium avium intracellulare, Pneumocystis carinii pneumonia, pelvic inflammatory disease, orchitis/epidydimitis, Legionella, lyme disease, influenza a, epstein-barr virus, viral-associated hemaphagocytic syndrome, vital encephalitis/aseptic meningitis, and the like.

The present invention also provides a method for modulating or treating at least one malignant disease in a cell, tissue, organ, animal or patient, including, but not limited to, at least one of: leukemia, acute leukemia, acute lymphoblastic leukemia (ALL), B-cell, T-cell or FAB ALL, acute myeloid leukemia (AML), chronic myelocytic leukemia (CML), chronic lymphocytic leukemia (CLL), hairy cell leukemia, myelodyplastic syndrome (MDS), a lymphoma, Hodgkin's disease, a malignant lymphoma, non-Hodgkin's lymphoma, Burkitt's lymphoma, multiple myeloma, Kaposi's sarcoma, colorectal carcinoma, pancreatic carcinoma, nasopharyngeal carcinoma, malignant histiocytosis, paraneoplastic syndrome/hypercalcemia of malignancy, solid tumors, adenocarcinomas, sarcomas, malignant melanoma, hemangioma, metastatic disease, cancer related bone resorption, cancer related bone pain, and the like.

The present invention also provides a method for modulating or treating at least one neurologic disease in a cell, tissue, organ, animal or patient, including, but not limited to, at least one of: neurodegenerative diseases, multiple sclerosis, migraine headache, AIDS dementia complex, demyelinating diseases, such as multiple sclerosis and acute transverse myelitis; extrapyramidal and cerebellar disorders' such as lesions of the corticospinal system; disorders of the basal ganglia or cerebellar disorders; hyperkinetic movement disorders such as Huntington's Chorea and senile chorea; drug-induced movement disorders, such as those induced by drugs which block CNS dopamine receptors; hypokinetic movement disorders, such as Parkinson's disease; Progressive supranucleo Palsy; structural lesions of the cerebellum; spinocerebellar degenerations, such as spinal ataxia, Friedreich's ataxia, cerebellar cortical degenerations, multiple systems degenerations (Mencel, Dejerine-Thomas, Shi-Drager, and Machado-Joseph); systemic disorders (Refsum's disease, abetalipoprotemia, ataxia, telangiectasiaa, and mitochondrial multisystem disorder); demyelinating core disorders, such as multiple sclerosis, acute transverse myelitis; and disorders of the motor unit' such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Dementia of Lewy body type; Wernicke-Korsakoff syndrome; chronic alcoholism; Creutzfeldt-Jakob disease; Subacute sclerosing panencephalitis, Hallerrorden-Spatz disease; and Dementia pugilistica, and the like. Such a method can optionally comprise administering an effective amount of a composition or pharmaceutical composition comprising at least one TNF antibody or specified portion or variant to a cell, tissue, organ, animal or patient in need of such modulation, treatment or therapy. See, e.g., the Merck Manual, $_{16th}$ Edition, Merck & Company, Rahway, NJ (1992)

Any method of the present invention can comprise administering an effective amount of a composition or pharmaceutical composition comprising at least one anti-TNF antibody to a cell, tissue, organ, animal or patient in need of such modulation, treatment or therapy. Such a method can optionally further comprise co-administration or combination therapy for treating such immune diseases, wherein the administering of said at least one anti-TNF antibody, specified portion or variant thereof, further comprises administering, before concurrently, and/or after, at least one selected from at least one TNF antagonist (e.g., but not limited to a TNF antibody or fragment, a soluble TNF receptor or fragment, fusion proteins thereof, or a small molecule TNF antagonist), an antirheumatic (e.g., methotrexate, auranofin, aurothioglucose, azathioprine, etanercept, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anethetic, a neuromuscular blocker, an antimicrobial (e.g., aminoglycoside, an antifungal, an antiparasitic, an antiviral, a carbapenem, cephalosporin, a flurorquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropieitin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, domase alpha (Pulmozyme), a cytokine or a cytokine antagonist. Suitable dosages are well known in the art. See, e.g., Wells et al., eds., Pharmacotherapy Handbook, $2^{nd}$ Edition, Appleton and Lange, Stamford, C T (2000); PDR Pharmacopoeia, Tarascon Pocket Pharmacopoeia 2000, Deluxe Edition, Tarascon Publishing, Loma Linda, CA (2000), each of which references are entirely incorporated herein by reference.

TNF antagonists suitable for compositions, combination therapy, co-administration, devices and/or methods of the present invention (further comprising at least one anti body, specified portion and variant thereof, of the present invention), include, but are not limited to, anti-TNF antibodies, antigen-binding fragments thereof, and receptor molecules which bind specifically to TNF; compounds which prevent and/or inhibit TNF synthesis, TNF release or its action on target cells, such as thalidomide, tenidap, phosphodiesterase inhibitors (e.g, pentoxifylline and rolipram), A2b adenosine receptor agonists and A2b adenosine receptor enhancers;

compounds which prevent and/or inhibit TNF receptor signalling, such as mitogen activated protein (MAP) kinase inhibitors; compounds which block and/or inhibit membrane TNF cleavage, such as metalloproteinase inhibitors; compounds which block and/or inhibit TNF activity, such as angiotensin converting enzyme (ACE) inhibitors (e.g., captopril); and compounds which block and/or inhibit TNF production and/or synthesis, such as MAP kinase inhibitors.

As used herein, a "tumor necrosis factor antibody," "TNF antibody," "TNFα antibody," or fragment and the like decreases, blocks, inhibits, abrogates or interferes with TNFα activity in vitro, in situ and/or preferably in vivo. For example, a suitable TNF human antibody of the present invention can bind TNFα and includes anti-TNF antibodies, antigen-binding fragments thereof, and specified mutants or domains thereof that bind specifically to TNFα. A suitable TNF antibody or fragment can also decrease block, abrogate, interfere, prevent and/or inhibit TNF RNA, DNA or protein synthesis, TNF release, TNF receptor signaling, membrane TNF cleavage, TNF activity, TNF production and/or synthesis.

Chimeric antibody cA2 consists of the antigen binding variable region of the high-affinity neutralizing mouse anti-human TNFα IgG1 antibody, designated A2, and the constant regions of a human IgG1, kappa immunoglobulin. The human IgG1 Fc region improves allogeneic antibody effector function, increases the circulating serum half-life and decreases the immunogenicity of the antibody. The avidity and epitope specificity of the chimeric antibody cA2 is derived from the variable region of the murine antibody A2. In a particular embodiment, a preferred source for nucleic acids encoding the variable region of the murine antibody A2 is the A2 hybridoma cell line.

Chimeric A2 (cA2) neutralizes the cytotoxic effect of both natural and recombinant human TNFα in a dose dependent manner. From binding assays of chimeric antibody cA2 and recombinant human TNFα, the affinity constant of chimeric antibody cA2 was calculated to be $1.04 \times 10^{10} M^{-1}$. Preferred methods for determining monoclonal antibody specificity and affinity by competitive inhibition can be found in Harlow, et al., antibodies: A Laboratory Manual, Cold Spring Harbor Laboratory Press, Cold Spring Harbor, New York, 1988; Colligan et al., eds., Current Protocols in Immunology, Greene Publishing Assoc. and Wiley Interscience, New York, (1992-2000); Kozbor et al., Immunol. Today, 4:72-79 (1983); Ausubel et al., eds. Current Protocols in Molecular Biology, Wiley Interscience, New York (1987-2000); and Muller, Meth. Enzymol., 92:589-601 (1983), which references are entirely incorporated herein by reference.

In a particular embodiment, murine monoclonal antibody A2 is produced by a cell line designated c134A. Chimeric antibody cA2 is produced by a cell line designated c168A.

Additional examples of monoclonal anti-TNF antibodies that can be used in the present invention are described in the art (see, e.g., U.S. Pat. No. 5,231,024; Möller, A. et al., Cytokine 2(3):162-169 (1990); U.S. application Ser. No. 07/943,852 (filed Sep. 11, 1992); Rathjen et al., International Publication No. WO 91/02078 (published Feb. 21, 1991); Rubin et al., EPO Patent Publication No. 0 218 868 (published Apr. 22, 1987); Yone et al., EPO Patent Publication No. 0 288 088 (Oct. 26, 1988); Liang, et al., Biochem. Biophys. Res. Comm. 137:847-854 (1986); Meager, et al., Hybridoma 6:305-311 (1987); Fendly et al., Hybridoma 6:359-369 (1987); Bringman, et al., Hybridoma 6:489-507 (1987); and Hirai, et al., J Immunol. Meth. 96:57-62 (1987), which references are entirely incorporated herein by reference).

TNF Receptor Molecules. Preferred TNF receptor molecules useful in the present invention are those that bind TNFα with high affinity (see, e.g., Feldmann et al., International Publication No. WO 92/07076 (published Apr. 30, 1992); Schall et al., Cell 61:361-370 (1990); and Loetscher et al., Cell 61:351-359 (1990), which references are entirely incorporated herein by reference) and optionally possess low immunogenicity. In particular, the 55 kDa (p55 TNF-R) and the 75 kDa (p75 TNF-R) TNF cell surface receptors are useful in the present invention. Truncated forms of these receptors, comprising the extracellular domains (ECD) of the receptors or functional portions thereof (see, e.g., Corcoran et al., Eur. J. Biochem. 223:831-840 (1994)), are also useful in the present invention. Truncated forms of the TNF receptors, comprising the ECD, have been detected in urine and serum as 30 kDa and 40 kDa TNFα inhibitory binding proteins (Engelmann, H. et al., J Biol. Chem. 265:1531-1536 (1990)). TNF receptor multimeric molecules and TNF immunoreceptor fusion molecules, and derivatives and fragments or portions thereof, are additional examples of TNF receptor molecules which are useful in the methods and compositions of the present invention. The TNF receptor molecules which can be used in the invention are characterized by their ability to treat patients for extended periods with good to excellent alleviation of symptoms and low toxicity. Low immunogenicity and/or high affinity, as well as other undefined properties, can contribute to the therapeutic results achieved.

TNF receptor multimeric molecules useful in the present invention comprise all or a functional portion of the ECD of two or more TNF receptors linked via one or more polypeptide linkers or other nonpeptide linkers, such as polyethylene glycol (PEG). The multimeric molecules can further comprise a signal peptide of a secreted protein to direct expression of the multimeric molecule. These multimeric molecules and methods for their production have been described in U.S. application Ser. No. 08/437,533 (filed May 9, 1995), the content of which is entirely incorporated herein by reference.

TNF immunoreceptor fusion molecules useful in the methods and compositions of the present invention comprise at least one portion of one or more immunoglobulin molecules and all or a functional portion of one or more TNF receptors. These immunoreceptor fusion molecules can be assembled as monomers, or hetero- or homo-multimers. The immunoreceptor fusion molecules can also be monovalent or multivalent. An example of such a TNF immunoreceptor fusion molecule is TNF receptor/IgG fusion protein. TNF immunoreceptor fusion molecules and methods for their production have been described in the art (Lesslauer et al., Eur. J. Immunol. 21:2883-2886 (1991); Ashkenazi et al., Proc. Natl. Acad. Sci. USA 88:10535-10539 (1991); Peppel et al., J. Exp. Med. 174:1483-1489 (1991); Kolls et al., Proc. Natl. Acad. Sci. USA 91:215-219 (1994); Butler et al., Cytokine 6(6):616-623 (1994); Baker et al., Eur. J. Immunol. 24:2040-2048 (1994); Beutler et al., U.S. Pat. No. 5,447,851; and U.S. application Ser. No. 08/442,133 (filed May 16, 1995), each of which references are entirely incorporated herein by reference). Methods for producing immunoreceptor fusion molecules can also be found in Capon et al., U.S. Pat. No. 5,116,964; Capon et al., U.S. Pat. No. 5,225,538; and Capon et al., Nature 337:525-531 (1989), which references are entirely incorporated herein by reference.

A functional equivalent, derivative, fragment or region of TNF receptor molecule refers to the portion of the TNF receptor molecule, or the portion of the TNF receptor molecule sequence which encodes TNF receptor molecule, that is of sufficient size and sequences to functionally resemble TNF receptor molecules that can be used in the present invention (e.g., bind TNFα with high affinity and possess low immunogenicity). A functional equivalent of TNF receptor molecule also includes modified TNF receptor molecules that functionally resemble TNF receptor molecules that can be used in the present invention (e.g., bind TNFα with high affinity and possess low immunogenicity). For example, a functional equivalent of TNF receptor molecule can contain a "SILENT" codon or one or more amino acid substitutions, deletions or additions (e.g., substitution of one acidic amino acid for another acidic amino acid; or substitution of one codon encoding the same or different hydrophobic amino acid for another codon encoding a hydrophobic amino acid). See Ausubel et al., *Current Protocols in Molecular Biology*, Greene Publishing Assoc. and Wiley-Interscience, New York (1987-2000).

Cytokines include any known cytokine. See, e.g., CopewithCytokines.com. Cytokine antagonists include, but are not limited to, any antibody, fragment or mimetic, any soluble receptor, fragment or mimetic, any small molecule antagonist, or any combination thereof.

Therapeutic Treatments. Any method of the present invention can comprise a method for treating a TNF mediated disorder, comprising administering an effective amount of a composition or pharmaceutical composition comprising at least one anti-TNF antibody to a cell, tissue, organ, animal or patient in need of such modulation, treatment or therapy. Such a method can optionally further comprise co-administration or combination therapy for treating such immune diseases, wherein the administering of said at least one anti-TNF antibody, specified portion or variant thereof, further comprises administering, before concurrently, and/or after, at least one selected from at least one TNF antagonist (e.g., but not limited to a TNF antibody or fragment, a soluble TNF receptor or fragment, fusion proteins thereof, or a small molecule TNF antagonist), an antirheumatic (e.g., methotrexate, auranofin, aurothioglucose, azathioprine, etanercept, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anethetic, a neuromuscular blocker, an antimicrobial (e.g., aminoglycoside, an antifungal, an antiparasitic, an antiviral, a carbapenem, cephalosporin, a flurorquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropieitin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine or a cytokine antagonist.

Typically, treatment of pathologic conditions is effected by administering an effective amount or dosage of at least one anti-TNF antibody composition that total, on average, a range from at least about 0.01 to 500 milligrams of at least one anti-TNFantibody per kilogram of patient per dose, and preferably from at least about 0.1 to 100 milligrams antibody/kilogram of patient per single or multiple administration, depending upon the specific activity of contained in the composition. Alternatively, the effective serum concentration can comprise 0.1-5000 μg/ml serum concentration per single or multiple administration. Suitable dosages are known to medical practitioners and will, of course, depend upon the particular disease state, specific activity of the composition being administered, and the particular patient undergoing treatment. In some instances, to achieve the desired therapeutic amount, it can be necessary to provide for repeated administration, i.e., repeated individual administrations of a particular monitored or metered dose, where the individual administrations are repeated until the desired daily dose or effect is achieved.

Preferred doses can optionally include 0.1, 0.2, 0.3, 0.4, 0.5, 0.6, 0.7, 0.8, 0.9, 1, 2, 3,4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100-500 mg/kg/administration, or any range, value or fraction thereof, or to achieve a serum concentration of 0.1, 0.5, 0.9, 1.0, 1.1, 1.2, 1.5, 1.9, 2.0, 2.5, 2.9, 3.0, 3.5, 3.9, 4.0, 4.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 20, 12.5, 12.9, 13.0, 13.5, 13.9, 14.0, 14.5, 15, 15.5, 15.9, 16, 16.5, 16.9, 17, 17.5, 17.9, 18, 18.5, 18.9, 19, 19.5, 19.9, 20, 20.5, 20.9, 21, 22, 23, 24, 25, 26, 27, 28, 29, 30, 35, 40, 45, 50, 55, 60, 65, 70, 75, 80, 85, 90, 96, 100, 200, 300, 400, 500, 600, 700, 800, 900, 1000, 1500, 2000, 2500, 3000, 3500, 4000, 4500, and/or 5000 μg/ml serum concentration per single or multiple administration, or any range, value or fraction thereof.

Alternatively, the dosage administered can vary depending upon known factors, such as the pharmacodynamic characteristics of the particular agent, and its mode and route of administration; age, health, and weight of the recipient; nature and extent of symptoms, kind of concurrent treatment, frequency of treatment, and the effect desired. Usually a dosage of active ingredient can be about 0.1 to 100 milligrams per kilogram of body weight. Ordinarily 0.1 to 50, and preferably 0.1 to 10 milligrams per kilogram per administration or in sustained release form is effective to obtain desired results.

As a non-limiting example, treatment of humans or animals can be provided as a one-time or periodic dosage of at least one antibody of the present invention 0.1 to 100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively or additionally, at least one of week 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, or alternatively or additionally, at least one of 1, 2, 3, 4, 5, 6, 7, 8, 9, 10, 11, 12, 13, 14, 15, 16, 17, 18, 19, or 20 years, or any combination thereof, using single, infusion or repeated doses.

Dosage forms (composition) suitable for internal administration generally contain from about 0.1 milligram to about 500 milligrams of active ingredient per unit or container. In these pharmaceutical compositions the active ingredient will ordinarily be present in an amount of about 0.5-99.999% by weight based on the total weight of the composition.

For parenteral administration, the antibody can be formulated as a solution, suspension, emulsion or lyophilized powder in association, or separately provided, with a pharmaceutically acceptable parenteral vehicle. Examples of such vehicles are water, saline, Ringer's solution, dextrose solution, and 1-10% human serum albumin. Liposomes and nonaqueous vehicles such as fixed oils can also be used. The vehicle or lyophilized powder can contain additives that maintain isotonicity (e.g., sodium chloride, mannitol) and chemical stability (e.g., buffers and preservatives). The formulation is sterilized by known or suitable techniques.

Suitable pharmaceutical carriers are described in the most recent edition of Remington's Pharmaceutical Sciences, A. Osol, a standard reference text in this field.

Alternative Administration. Many known and developed modes of administration can be used according to the present invention for administering pharmaceutically effective amounts of at least one anti-TNF antibody according to the present invention. While pulmonary administration is used in the following description, other modes of administration can be used according to the present invention with suitable results.

TNF antibodies of the present invention can be delivered in a carrier, as a solution, emulsion, colloid, or suspension, or as a dry powder, using any of a variety of devices and methods suitable for administration by inhalation or other modes described here within or known in the art.

Parenteral Formulations and Administration. Formulations for parenteral administration can contain as common excipients sterile water or saline, polyalkylene glycols such as polyethylene glycol, oils of vegetable origin, hydrogenated naphthalenes and the like. Aqueous or oily suspensions for injection can be prepared by using an appropriate emulsifier or humidifier and a suspending agent, according to known methods. Agents for injection can be a non-toxic, non-orally administrable diluting agent such as aqueous solution or a sterile injectable solution or suspension in a solvent. As the usable vehicle or solvent, water, Ringer's solution, isotonic saline, etc. are allowed; as an ordinary solvent, or suspending solvent, sterile involatile oil can be used. For these purposes, any kind of involatile oil and fatty acid can be used, including natural or synthetic or semisynthetic fatty oils or fatty acids; natural or synthetic or semi-synthetic mono- or di- or tri-glycerides. Parental administration is known in the art and includes, but is not limited to, conventional means of injections, a gas pressured needleless injection device as described in U.S. Pat. No. 5,851,198, and a laser perforator device as described in U.S. Pat. No. 5,839,446 entirely incorporated herein by reference.

Alternative Delivery. The invention further relates to the administration of at 10 least one anti-TNF antibody by parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal means. At least one anti-TNF antibody composition can be prepared for use for parenteral (subcutaneous, intramuscular or intravenous) or any other administration particularly in the form of liquid solutions or suspensions; for use in vaginal or rectal administration particularly in semi-solid forms such as, but not limited to, creams and suppositories; for buccal, or sublingual administration such as, but not limited to, in the form of tablets or capsules; or intranasally such as, but not limited to, the form of powders, nasal drops or aerosols or certain agents; or transdermally such as not limited to a gel, ointment, lotion, suspension or patch delivery system with chemical enhancers such as dimethyl sulfoxide to either modify the skin structure or to increase the drug concentration in the transdermal patch (Junginger, et al. In "Drug Permeation Enhancement"; Hsieh, D. S., Eds., pp. 59-90 (Marcel Dekker, Inc. New York 1994, entirely incorporated herein by reference), or with oxidizing agents that enable the application of formulations containing proteins and peptides onto the skin (WO 98/53847), or applications of electric fields to create transient transport pathways such as electroporation, or to increase the mobility of charged drugs through the skin such as iontophoresis, or application of ultrasound such as sonophoresis (U.S. Pat. Nos. 4,309,989 and 4,767,402) (the above publications and patents being entirely incorporated herein by reference).

Pulmonary/Nasal Administration. For pulmonary administration, preferably at least one anti-TNF antibody composition is delivered in a particle size effective for reaching the lower airways of the lung or sinuses. According to the invention, at least one anti-TNF antibody can be delivered by any of a variety of inhalation or nasal devices known in the art for administration of a therapeutic agent by inhalation. These devices capable of depositing aerosolized formulations in the sinus cavity or alveoli of a patient include metered dose inhalers, nebulizers, dry powder generators, sprayers, and the like. Other devices suitable for directing the pulmonary or nasal administration of antibodies are also known in the art. All such devices can use of formulations suitable for the administration for the dispensing of antibody in an aerosol. Such aerosols can be comprised of either solution (both aqueous and non-aqueous) or solid particles. Metered dose inhalers like the Ventolin® metered dose inhaler, typically use a propellant gas and require actuation during inspiration (See, e.g., WO 94/16970, WO 98/35888). Dry powder inhalers like Turbuhaler™ (Astra), Rotahaler® (Glaxo), Diskus® (Glaxo), Spiros™ inhaler (Dura), devices marketed by Inhale Therapeutics, and the Spinhaler® powder inhaler (Fisons), use breath-actuation of a mixed powder (U.S. Pat. No. 4,668,218 Astra, EP 237507 Astra, WO 97/25086 Glaxo, WO 94/08552 Dura, U.S. Pat. No. 5,458, 135 Inhale, WO 94/06498 Fisons, entirely incorporated herein by reference). Nebulizers like AERx™ Aradigm, the Ultravent® nebulizer (Mallinckrodt), and the Acorn II® nebulizer (Marquest Medical Products) (U.S. Pat. No. 5,404, 871 Aradigm, WO 97/22376), the above references entirely incorporated herein by reference, produce aerosols from solutions, while metered dose inhalers, dry powder inhalers, etc. generate small particle aerosols. These specific examples of commercially available inhalation devices are intended to be a representative of specific devices suitable for the practice of this invention and are not intended as limiting the scope of the invention. Preferably, a composition comprising at least one anti-TNF antibody is delivered by a dry powder inhaler or a sprayer. There are a several desirable features of an inhalation device for administering at least one antibody of the present invention. For example, delivery by the inhalation device is advantageously reliable, reproducible, and accurate. The inhalation device can optionally deliver small dry particles, e.g. less than about 10 μm, preferably about 1-5 μm, for good respirability.

Administration of TNF antibody Compositions as a Spray. A spray including TNF antibody composition protein can be produced by forcing a suspension or solution of at least one anti-TNF antibody through a nozzle under pressure. The nozzle size and configuration, the applied pressure, and the liquid feed rate can be chosen to achieve the desired output and particle size. An electrospray can be produced, for example, by an electric field in connection with a capillary or nozzle feed. Advantageously, particles of at least one anti-TNF antibody composition protein delivered by a sprayer have a particle size less than about 10 μm, preferably in the range of about 1 μm to about 5 μm, and most preferably about 2 μm to about 3 μm.

Formulations of at least one anti-TNF antibody composition protein suitable for use with a sprayer typically include antibody composition protein in an aqueous solution at a concentration of about 0.1 mg to about 100 mg of at least one anti-TNF antibody composition protein per ml of solution or mg/gm, or any range or value therein, e.g., but not limited to, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/ml or mg/gm. The formulation can include agents such as an excipient, a buffer, an isotonicity agent, a preservative, a surfactant, and, preferably, zinc. The formulation can also include an excipient or agent for stabilization of the antibody composition protein, such as a buffer, a reducing agent, a bulk protein, or a carbohydrate. Bulk proteins useful in formulating antibody composition proteins include albumin, protamine, or the like. Typical carbohydrates useful in formulating antibody composition proteins include sucrose, mannitol, lactose, trehalose, glucose, or the like. The antibody composition protein formulation can also include a surfactant, which can reduce or prevent surface-induced aggregation of the antibody composition protein caused by atomization of the solution in forming an aerosol. Various conventional surfactants can be employed, such as polyoxyethylene fatty acid esters and alcohols, and polyoxyethylene sorbitol fatty acid esters. Amounts will generally range between 0.001 and 14% by weight of the formulation. Especially preferred surfactants for purposes of this invention are polyoxyethylene sorbitan monooleate, polysorbate 80, polysorbate 20, or the like. Additional agents known in the art for formulation of a protein such as TNF antibodies, or specified portions or variants, can also be included in the formulation.

Administration of TNF antibody compositions by a Nebulizer. Antibody composition protein can be administered by a nebulizer, such as jet nebulizer or an ultrasonic nebulizer. Typically, in a jet nebulizer, a compressed air source is used to create a high-velocity air jet through an orifice. As the gas expands beyond the nozzle, a low-pressure region is created, which draws a solution of antibody composition protein through a capillary tube connected to a liquid reservoir. The liquid stream from the capillary tube is sheared into unstable filaments and droplets as it exits the tube, creating the aerosol. A range of configurations, flow rates, and baffle types can be employed to achieve the desired performance characteristics from a given jet nebulizer. In an ultrasonic nebulizer, high-frequency electrical energy is used to create vibrational, mechanical energy, typically employing a piezoelectric transducer. This energy is transmitted to the formulation of antibody composition protein either directly or through a coupling fluid, creating an aerosol including the antibody composition protein. Advantageously, particles of antibody composition protein delivered by a nebulizer have a particle size less than about 10 μm, preferably in the range of about 1 μm to about 5 μm, and most preferably about 2 μm to about 3 μm.

Formulations of at least one anti-TNF antibody suitable for use with a nebulizer, either jet or ultrasonic, typically include a concentration of about 0.1 mg to about 100 mg of at least one anti-TNF antibody protein per ml of solution. The formulation can include agents such as an excipient, a buffer, an isotonicity agent, a preservative, a surfactant, and, preferably, zinc. The formulation can also include an excipient or agent for stabilization of the at least one anti-TNF antibody composition protein, such as a buffer, a reducing agent, a bulk protein, or a carbohydrate. Bulk proteins useful in formulating at least one anti-TNF antibody composition proteins include albumin, protamine, or the like. Typical carbohydrates useful in formulating at least one anti-TNF antibody include sucrose, mannitol, lactose, trehalose, glucose, or the like. The at least one anti-TNF antibody formulation can also include a surfactant, which can reduce or prevent surface-induced aggregation of the at least one anti-TNF antibody caused by atomization of the solution in forming an aerosol. Various conventional surfactants can be employed, such as polyoxyethylene fatty acid esters and alcohols, and polyoxyethylene sorbital fatty acid esters. Amounts will generally range between 0.001 and 4% by weight of the formulation. Especially preferred surfactants for purposes of this invention are polyoxyethylene sorbitan mono-oleate, polysorbate 80, polysorbate 20, or the like. Additional agents known in the art for formulation of a protein such as antibody protein can also be included in the formulation.

Administration of TNF antibody compositions By A Metered Dose Inhaler. In a metered dose inhaler (MDI), a propellant, at least one anti-TNF antibody, and any excipients or other additives are contained in a canister as a mixture including a liquefied compressed gas. Actuation of the metering valve releases the mixture as an aerosol, preferably containing particles in the size range of less than about 10 μm, preferably about 1 μm to about 5 μm, and most preferably about 2 μm to about 3 μm. The desired aerosol particle size can be obtained by employing a formulation of antibody composition protein produced by various methods known to those of skill in the art, including jet-milling, spray drying, critical point condensation, or the like. Preferred metered dose inhalers include those manufactured by 3M or Glaxo and employing a hydrofluorocarbon propellant.

Formulations of at least one anti-TNF antibody for use with a metered-dose inhaler device will generally include a finely divided powder containing at least one anti-TNF antibody as a suspension in a non-aqueous medium, for example, suspended in a propellant with the aid of a surfactant. The propellant can be any conventional material employed for this purpose, such as chlorofluorocarbon, a hydrochlorofluorocarbon, a hydrofluorocarbon, or a hydrocarbon, including trichlorofluoromethane, dichlorodifluoromethane, dichlorotetrafluoroethanol and 1,1,1,2-tetrafluoroethane, HFA-134a (hydrofluroalkane-134a), HFA-227 (hydrofluroalkane-227), or the like. Preferably the propellant is a hydrofluorocarbon. The surfactant can be chosen to stabilize the at least one anti-TNF antibody as a suspension in the propellant, to protect the active agent against chemical degradation, and the like. Suitable surfactants include sorbitan trioleate, soya lecithin, oleic acid, or the like. In some cases, solution aerosols are preferred using solvents such as ethanol. Additional agents known in the art for formulation of a protein can also be included in the formulation.

One of ordinary skill in the art will recognize that the methods of the current invention can be achieved by pulmonary administration of at least one anti-TNF antibody compositions via devices not described herein.

Oral Formulations and Administration. Formulations for oral rely on the co-administration of adjuvants (e.g., resorcinols and nonionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. The active constituent compound of the solid-type dosage form for oral administration can be mixed with at least one additive, including sucrose, lactose, cellulose, mannitol, trehalose, raffinose, maltitol, dextran, starches, agar, arginates, chitins, chitosans, pectins, gum tragacanth, gum arabic, gelatin, collagen, casein, albumin, synthetic or semisynthetic polymer, and glyceride. These dosage forms can also contain other type(s) of additives, e.g., inactive diluting agent, lubricant such as magnesium stearate, paraben, preserving agent such as sorbic acid, ascorbic acid, alpha-tocopherol, antioxidant such as cysteine, disintegrator, binder, thickener, buffering agent, sweetening agent, flavoring agent, perfuming agent, etc.

Tablets and pills can be further processed into enteric-coated preparations. The liquid preparations for oral administration include emulsion, syrup, elixir, suspension and solution preparations allowable for medical use. These preparations can contain inactive diluting agents ordinarily used in said field, e.g., water. Liposomes have also been described as drug delivery systems for insulin and heparin (U.S. Pat. No. 4,239,754). More recently, microspheres of artificial polymers of mixed amino acids (proteinoids) have been used to deliver pharmaceuticals (U.S. Pat. No. 4,925,673). Furthermore, carrier compounds described in U.S. Pat. Nos. 5,879,681 and 5,5,871,753 are used to deliver biologically active agents orally are known in the art.

Mucosal Formulations and Administration. For absorption through mucosal surfaces, compositions and methods of administering at least one anti-TNF antibody include an emulsion comprising a plurality of submicron particles, a mucoadhesive macromolecule, a bioactive peptide, and an aqueous continuous phase, which promotes absorption through mucosal surfaces by achieving mucoadhesion of the emulsion particles (U.S. Pat. No. 5,514,670). Mucous surfaces suitable for application of the emulsions of the present invention can include corneal, conjunctival, buccal, sublingual, nasal, vaginal, pulmonary, stomachic, intestinal, and rectal routes of administration. Formulations for vaginal or rectal administration, e.g. suppositories, can contain as excipients, for example, polyalkyleneglycols, vaseline, cocoa butter, and the like. Formulations for intranasal administration can be solid and contain as excipients, for example, lactose or can be aqueous or oily solutions of nasal drops. For buccal administration excipients include sugars, calcium stearate, magnesium stearate, pregelinatined starch, and the like (U.S. Pat. No. 5,849,695).

Transdermal Formulations and Administration. For transdermal administration, the at least one anti-TNF antibody is encapsulated in a delivery device such as a liposome or polymeric nanoparticles, microparticle, microcapsule, or microspheres (referred to collectively as microparticles unless otherwise stated). A number of suitable devices are known, including microparticles made of synthetic polymers such as polyhydroxy acids such as polylactic acid, polyglycolic acid and copolymers thereof, polyorthoesters, polyanhydrides, and polyphosphazenes, and natural polymers such as collagen, polyamino acids, albumin and other proteins, alginate and other polysaccharides, and combinations thereof (U.S. Pat. No. 5,814,599).

Prolonged Administration and Formulations. It can be sometimes desirable to deliver the compounds of the present invention to the subject over prolonged periods of time, for example, for periods of one week to one year from a single administration. Various slow release, depot or implant dosage forms can be utilized. For example, a dosage form can contain a pharmaceutically acceptable non-toxic salt of the compounds that has a low degree of solubility in body fluids, for example, (a) an acid addition salt with a polybasic acid such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation such as zinc, calcium, bismuth, barium, magnesium, aluminum, copper, cobalt, nickel, cadmium and the like, or with an organic cation formed from e.g., N,N'-dibenzyl-ethylenediamine or ethylenediamine; or (c) combinations of (a) and (b) e.g. a zinc tannate salt. Additionally, the compounds of the present invention or, preferably, a relatively insoluble salt such as those just described, can be formulated in a gel, for example, an aluminum monostearate gel with, e.g. sesame oil, suitable for injection. Particularly preferred salts are zinc salts, zinc tannate salts, pamoate salts, and the like. Another type of slow release depot formulation for injection would contain the compound or salt dispersed for encapsulated in a slow degrading, non-toxic, non-antigenic polymer such as a polylactic acid/polyglycolic acid polymer for example as described in U.S. Pat. No. 3,773,919. The compounds or, preferably, relatively insoluble salts such as those described above can also be formulated in cholesterol matrix silastic pellets, particularly for use in animals. Additional slow release, depot or implant formulations, e.g. gas or liquid liposomes are known in the literature (U.S. Pat. No. 5,770,222 and "Sustained and Controlled Release Drug Delivery Systems", J. R. Robinson ed., Marcel Dekker, Inc., N.Y., 1978).

Having generally described the invention, the same will be more readily understood by reference to the following examples, which are provided by way of illustration and are not intended as limiting.

Example 1: Cloning and Expression of TNF Antibody in Mammalian Cells

A typical mammalian expression vector contains at least one promoter element, which mediates the initiation of transcription of mRNA, the antibody coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRS) from Retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as pIRES1neo, pRetro-Off, pRetro-On, PLXSN, or pLNCX (Clonetech Labs, Palo Alto, CA), pcDNA3.1 (+/−), pcDNA/Zeo (+/−) or pcDNA3.1/Hygro (+/−) (Invitrogen), PSVL and PMSG (Pharmacia, Uppsala, Sweden), pRSVcat (ATCC® 37152), pSV2dhfr (ATCC® 37146) and pBC12MI. Mammalian host cells that could be used include human Hela 293, H9 and Jurkat cells, mouse NIH3T3 and C127 cells, Cos 1, Cos 7 and CV 1, quail QC1-3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, or hygromycin allows the identification and isolation of the transfected cells.

The transfected gene can also be amplified to express large amounts of the encoded antibody. The DHFR (dihydrofolate reductase) marker is useful to develop cell lines that carry several hundred or even several thousand copies of the gene of interest. Another useful selection marker is the enzyme glutamine synthase (GS) (Murphy, et al., Biochem. J. 227:277-279 (1991); Bebbington, et al., Bio/Technology 10:169-175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of antibodies.

The expression vectors pC1 and pC4 contain the strong promoter (LTR) of the Rous Sarcoma Virus (Cullen, et al., Molec. Cell. Biol. 5:438-447 (1985)) plus a fragment of the CMV-enhancer (Boshart, et al., Cell 41:521-530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

Cloning and Expression in CHO Cells

One vector commonly used for expression in CHO cells is pC4. Plasmid pC4 is a derivative of the plasmid pSV2-dhfr (ATCC® 37146). The plasmid contains the mouse DHFR gene under control of the SV40 early promoter. Chinese hamster ovary cells or other cells lacking dihydrofolate activity that are transfected with these plasmids can be selected by growing the cells in a selective medium (e.g., alpha minus MEM, Life Technologies, Gaithersburg, MD) supplemented with the chemotherapeutic agent methotrexate. The amplification of the DHFR genes in cells resistant to methotrexate (MTX) has been well documented (see, e.g., F. W. Alt, et al., J. Biol. Chem. 253:1357-1370 (1978); J. L. Hamlin and C. Ma, Biochem. et Biophys. Acta 1097:107-143 (1990); and M. J. Page and M. A. Sydenham, Biotechnology 9:64-68 (1991)). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach can be used to develop cell lines carrying more than 1,000 copies of the amplified gene(s). Subsequently, when the methotrexate is withdrawn, cell lines are obtained that contain the amplified gene integrated into one or more chromosome(s) of the host cell.

Plasmid pC4 contains for expressing the gene of interest the strong promoter of the long terminal repeat (LTR) of the Rous Sarcoma Virus (Cullen, et al., Molec. Cell. Biol. 5:438-447 (1985)) plus a fragment isolated from the enhancer of the immediate early gene of human cytomegalovirus (CMV) (Boshart, et al., Cell 41:521-530 (1985)). Downstream of the promoter are BamHI, XbaI, and Asp718 restriction enzyme cleavage sites that allow integration of the genes. Behind these cloning sites the plasmid contains the 3' intron and polyadenylation site of the rat preproinsulin gene. Other high efficiency promoters can also be used for the expression, e.g., the human beta-actin promoter, the SV40 early or late promoters or the long terminal repeats from other retroviruses, e.g., HIV and HTLVI. Clontech's Tet-Off and Tet-On gene expression systems and similar systems can be used to express the TNF in a regulated way in mammalian cells (M. Gossen, and H. Bujard, Proc. Nat. Acad. Sci. USA 89: 5547-5551 (1992)). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with restriction enzymes and then dephosphorylated using calf intestinal phosphatase by procedures known in the art. The vector is then isolated from a 1% agarose gel.

The isolated variable and constant region encoding DNA and the dephosphorylated vector are then ligated with T4 DNA ligase. E. coli HB101 or XL-1 Blue cells are then transformed and bacteria are identified that contain the fragment inserted into plasmid pC4 using, for instance, restriction enzyme analysis.

Chinese hamster ovary (CHO) cells lacking an active DHFR gene are used for transfection. 5 μg of the expression plasmid pC4 is cotransfected with 0.5 μg of the plasmid pSV2-neo using lipofectin. The plasmid pSV2neo contains a dominant selectable marker, the neo gene from Tn5 encoding an enzyme that confers resistance to a group of antibiotics including G418. The cells are seeded in alpha minus MEM supplemented with 1 μg/ml G418. After 2 days, the cells are trypsinized and seeded in hybridoma cloning plates (Greiner, Germany) in alpha minus MEM supplemented with 10, 25, or 50 ng/ml of methotrexate plus 1 μg/ml G418. After about 10-14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 mM, 2 mM, 5 mM, 10 mM, 20 mM). The same procedure is repeated until clones are obtained that grow at a concentration of 100-200 mM. Expression of the desired gene product is analyzed, for instance, by SDS-PAGE and Western blot or by reverse phase HPLC analysis.

Example 2: Generation of High Affinity Human IgG Monoclonal Antibodies Reactive with Human TNF Using Transgenic Mice Summary Transgenic mice have been used that contain human heavy and light chain immunoglobulin genes to generate high affinity, completely human, monoclonal antibodies that can be used therapeutically to inhibit the action of TNF for the treatment of one or more TNF-mediated disease. (CBA/J×C57/BL6/J) F2 hybrid mice containing human variable and constant region antibody transgenes for both heavy and light chains are immunized with human recombinant TNF (Taylor et al., Intl. Immunol. 6:579-591 (1993); Lonberg, et al., Nature 368:856-859 (1994); Neuberger, M., Nature Biotech. 14:826 (1996); Fishwild, et al., Nature Biotechnology 14:845-851 (1996)). Several fusions yielded one or more panels of completely human TNF reactive IgG monoclonal antibodies. The completely human anti-TNF antibodies are further characterized. All are IgG1κ. Such antibodies are found to have affinity constants somewhere between $1\times10^9$ and $9\times10^{12}$. The unexpectedly high affinities of these fully human monoclonal antibodies make them suitable candidates for therapeutic applications in TNF related diseases, pathologies or disorders.

Abbreviations. BSA—bovine serum albumin; $CO_2$—carbon dioxide; DMSO—dimethyl sulfoxide; EIA—enzyme immunoassay; FBS—fetal bovine serum; $H_2O_2$-hydrogen peroxide; HRP—horseradish peroxidase; ID—interadermal; Ig—immunoglobulin; TNF—tissue necrosis factor alpha; IP—intraperitoneal; IV—intravenous; Mab or mAb—monoclonal antibody; OD—optical density; OPD—o-Phenylenediamine dihydrochloride; PEG—polyethylene glycol; PSA—penicillin, streptomycin, amphotericin; RT—room temperature; SQ—subcutaneous; v/v—volume per volume; w/v—weight per volume.

Materials and Methods

Animals. Transgenic mice that can express human antibodies are known in the art (and are commercially available (e.g., from GenPharm International, San Jose, CA; Abgenix, Freemont, CA, and others) that express human immunoglobulins but not mouse IgM or Igx. For example, such transgenic mice contain human sequence transgenes that undergo V(D)J joining, heavy-chain class switching, and somatic mutation to generate a repertoire of human sequence immunoglobulins (Lonberg, et al., Nature 368:856-859 (1994)). The light chain transgene can be derived, e.g., in part from a yeast artificial chromosome clone that includes nearly half of the germline human Vκ region. In addition, the heavy-chain transgene can encode both human μ and human γ1 (Fishwild, et al., Nature Biotechnology 14:845-851 (1996)) and/or γ3 constant regions. Mice derived from appropriate genotypic lineages can be used in the immunization and fusion processes to generate fully human monoclonal antibodies to TNF.

Immunization. One or more immunization schedules can be used to generate the anti-TNF human hybridomas. The first several fusions can be performed after the following exemplary immunization protocol, but other similar known protocols can be used. Several 14-20 week old female and/or surgically castrated transgenic male mice are immunized IP and/or ID with 1-1000 μg of recombinant human TNF emulsified with an equal volume of TITERMAX or complete Freund's adjuvant in a final volume of 100-400 μL (e.g., 200). Each mouse can also optionally receive 1-10 μg in 100 μL physiological saline at each of 2 SQ sites. The mice can then be immunized 1-7, 5-12, 10-18, 17-25 and/or 21-34 days later IP (1-400 μg) and SQ (1-400 μg×2) with TNF emulsified with an equal volume of TITERMAX or incomplete Freund's adjuvant. Mice can be bled 12-25 and 25-40 days later by retro-orbital puncture without anticoagulant. The blood is then allowed to clot at RT for one hour and the serum is collected and titered using an TNF EIA assay according to known methods. Fusions are performed when repeated injections do not cause titers to increase. At that time, the mice can be given a final IV booster injection of 1-400 μg TNF diluted in 100 μL physiological saline. Three days later, the mice can be euthanized by cervical dislocation and the spleens removed aseptically and immersed in 10 mL of cold phosphate buffered saline (PBS) containing 100 U/mL penicillin, 100 μg/mL streptomycin, and 0.25 μg/mL amphotericin B (PSA). The splenocytes are harvested by sterilely perfusing the spleen with PSA-PBS. The cells are washed once in cold PSA-PBS, counted using Trypan blue dye exclusion and resuspended in RPMI 1640 media containing 25 mM Hepes.

Cell Fusion. Fusion can be carried out at a 1:1 to 1:10 ratio of murine myeloma cells to viable spleen cells according to known methods, e.g., as known in the art. As a non-limiting example, spleen cells and myeloma cells can be pelleted together. The pellet can then be slowly resuspended, over 30 seconds, in 1 mL of 50% (w/v) PEG/PBS solution (PEG molecular weight 1,450, Sigma) at 37□ C. The fusion can then be stopped by slowly adding 10.5 mL of RPMI 1640 medium containing 25 mM Hepes (37° C.) over 1 minute. The fused cells are centrifuged for 5 minutes at 500-1500 rpm. The cells are then resuspended in HAT medium (RPMI 1640 medium containing 25 mM Hepes, 10% Fetal Clone I serum (Hyclone), 1 mM sodium pyruvate, 4 mM L-glutamine, 10 μg/mL gentamicin, 2.5% Origen culturing supplement (Fisher), 10% 653-conditioned RPMI 1640/Hepes media, 50 μM 2-mercaptoethanol, 100 μM hypoxanthine, 0.4 μM aminopterin, and 16 μM thymidine) and then plated at 200 μL/well in fifteen 96-well flat bottom tissue culture plates. The plates are then placed in a humidified 37 C incubator containing 5% $CO_2$ and 95% air for 7-10 days.

Detection of Human IgG Anti-TNF Antibodies in Mouse Serum. Solid phase EIA's can be used to screen mouse sera for human IgG antibodies specific for human TNF. Briefly, plates can be coated with TNF at 2 μg/mL in PBS overnight. After washing in 0.15M saline containing 0.02% (v/v) Tween 20, the wells can be blocked with 1% (w/v) BSA in PBS, 200 μL/well for 1 hour at RT. Plates are used immediately or frozen at −20° C. for future use. Mouse serum dilutions are incubated on the TNF coated plates at 50 μL/well at RT for 1 hour. The plates are washed and then probed with 50 μL/well HRP-labeled goat anti-human IgG, Fc specific diluted 1:30,000 in 1% BSA-PBS for 1 hour at RT. The plates can again be washed and 100 μL/well of the citrate-phosphate substrate solution (0.1M citric acid and 0.2M sodium phosphate, 0.01% $H_2O_2$ and 1 mg/mL OPD) is added for 15 minutes at RT. Stop solution (4N sulfuric acid) is then added at 25 μL/well and the OD's are read at 490 nm via an automated plate spectrophotometer.

Detection of Completely Human Immunoglobulins in Hybridoma Supernates.

Growth positive hybridomas secreting fully human immunoglobulins can be detected using a suitable EIA. Briefly, 96 well pop-out plates (VWR, 610744) can be coated with 10 μg/mL goat anti-human IgG Fc in sodium carbonate buffer overnight at 4□ C. The plates are washed and blocked with 1% BSA-PBS for one hour at 37° C. and used immediately or frozen at −20□ C. Undiluted hybridoma supernatants are incubated on the plates for one hour at 37° C. The plates are washed and probed with HRP labeled goat anti-human kappa diluted 1:10,000 in 1% BSA-PBS for one hour at 37° C. The plates are then incubated with substrate solution as described above.

Determination of Fully Human Anti-TNF Reactivity. Hybridomas, as above, can be simultaneously assayed for reactivity to TNF using a suitable RIA or other assay. For example, supernatants are incubated on goat anti-human IgG Fc plates as above, washed and then probed with radiolabled TNF with appropriate counts per well for 1 hour at RT. The wells are washed twice with PBS and bound radiolabled TNF is quantitated using a suitable counter.

Human IgG1κ anti-TNF secreting hybridomas can be expanded in cell culture and serially subcloned by limiting dilution. The resulting clonal populations can be expanded and cryopreserved in freezing medium (95% FBS, 5% DMSO) and stored in liquid nitrogen.

Isotyping. Isotype determination of the antibodies can be accomplished using an EIA in a format similar to that used to screen the mouse immune sera for specific titers. TNF can be coated on 96-well plates as described above and purified antibody at 2 µg/mL can be incubated on the plate for one hour at RT. The plate is washed and probed with HRP labeled goat anti-human $IgG_1$ or HRP labeled goat anti-human $IgG_3$ diluted at 1:4000 in 1% BSA-PBS for one hour at RT. The plate is again washed and incubated with substrate solution as described above.

Binding Kinetics of Human Anti-Human TNF Antibodies with Human TNF.

Binding characteristics for antibodies can be suitably assessed using an TNF capture EIA and BIAcore technology, for example. Graded concentrations of purified human TNF antibodies can be assessed for binding to EIA plates coated with 2 µg/mL of TNF in assays as described above. The OD's can be then presented as semi-log plots showing relative binding efficiencies.

Quantitative binding constants can be obtained, e.g., as follows, or by any other known suitable method. A BIAcore CM-5 (carboxymethyl) chip is placed in a BIAcore 2000 unit. HBS buffer (0.01 M HEPES, 0.15 M NaCl, 3 mM EDTA, 0.005% v/v P20 surfactant, pH 7.4) is flowed over a flow cell of the chip at 5 µL/minute until a stable baseline is obtained. A solution (100 µL) of 15 mg of EDC (N-ethyl-N'-(3-dimethyl-aminopropyl)-carbodiimide hydrochloride) in 200 µL water is added to 100 µL of a solution of 2.3 mg of NHS (N-hydroxysuccinimide) in 200 µL water. Forty (40) µL of the resulting solution is injected onto the chip. Six µL of a solution of human TNF (15 µg/mL in 10 mM sodium acetate, pH 4.8) is injected onto the chip, resulting in an increase of ca. 500 RU. The buffer is changed to TBS/Ca/Mg/BSA running buffer (20 mM Tris, 0.15 M sodium chloride, 2 mM calcium chloride, 2 mM magnesium acetate, 0.5% Triton X-100, 25 µg/mL BSA, pH 7.4) and flowed over the chip overnight to equilibrate it and to hydrolyze or cap any unreacted succinimide esters.

Antibodies are dissolved in the running buffer at 33.33, 16.67, 8.33, and 4.17 nM. The flow rate is adjusted to 30 L/min and the instrument temperature to 25° C. Two flow cells are used for the kinetic runs, one on which TNF had been immobilized (sample) and a second, underivatized flow cell (blank). 120 µL of each antibody concentration is injected over the flow cells at 30 L/min (association phase) followed by an uninterrupted 360 seconds of buffer flow (dissociation phase). The surface of the chip is regenerated (tissue necrosis factor alpha/antibody complex dissociated) by two sequential injections of 30 µL each of 2 M guanidine thiocyanate.

Analysis of the data is done using BIA evaluation 3.0 or CLAMP 2.0, as known in the art. For each antibody concentration the blank sensogram is subtracted from the sample sensogram. A global fit is done for both dissociation ($k_d$, $sec^{-1}$) and association ($k_a$, $mol^{-1}$ $sec^{-1}$) and the dissociation constant ($K_D$, mol) calculated ($k_d/k_a$). Where the antibody affinity is high enough that the RUs of antibody captured are >100, additional dilutions of the antibody are run.

Results and Discussion

Generation of Anti-Human TNF Monoclonal Antibodies. Several fusions are performed, and each fusion is seeded in 15 plates (1440 wells/fusion) that yield several dozen antibodies specific for human TNF. Of these, some are found to consist of a combination of human and mouse Ig chains. The remaining hybridomas secret anti-TNF antibodies consisting solely of human heavy and light chains. Of the human hybridomas all are expected to be IgG1κ.

Figure 1:
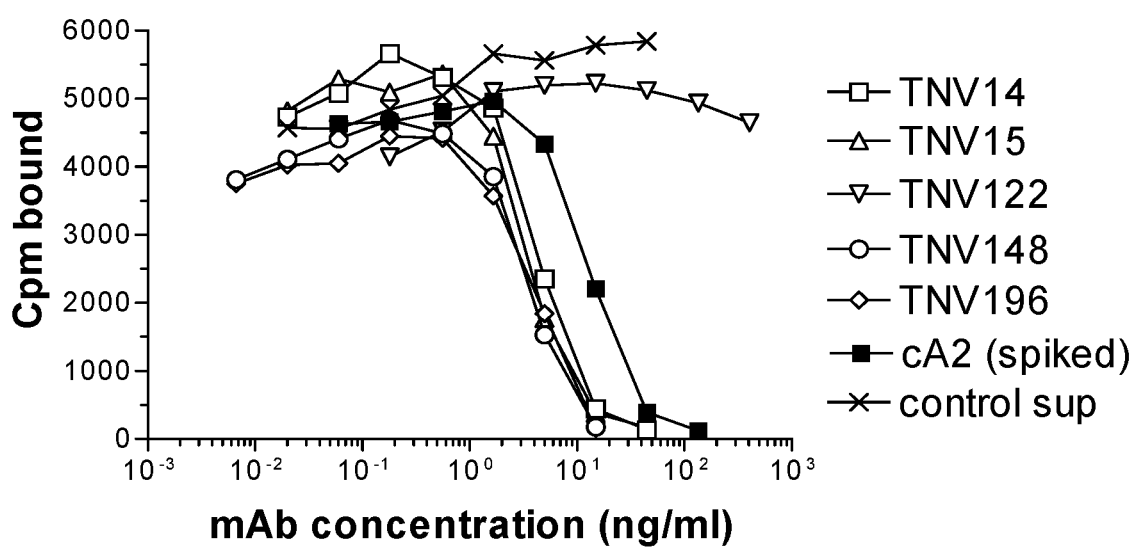
FIG. 1 shows a graphical representation showing an assay for ability of TNV mAbs in hybridoma cell supernatants to inhibit TNFα binding to recombinant TNF receptor. Varying amounts of hybridoma cell supernatants containing known amounts of TNV mAb were preincubated with a fixed concentration (5 ng/ml) of $^{125}$I-labeled TNFα. The mixture was transferred to 96-well Optiplates that had been previously coated with p55-sf2, a recombinant TNF receptor/IgG fusion protein. The amount of TNFα that bound to the p55 receptor in the presence of the mAbs was determined after washing away the unbound material and counting using a gamma counter. Although eight TNV mAb samples were tested in these experiments, for simplicity three of the mAbs that were shown by DNA sequence analyses to be identical to one of the other TNV mAbs (see Section 5.2.2) are not shown here. Each sample was tested in duplicate. The results shown are representative of two independent experiments.
Figure 6:
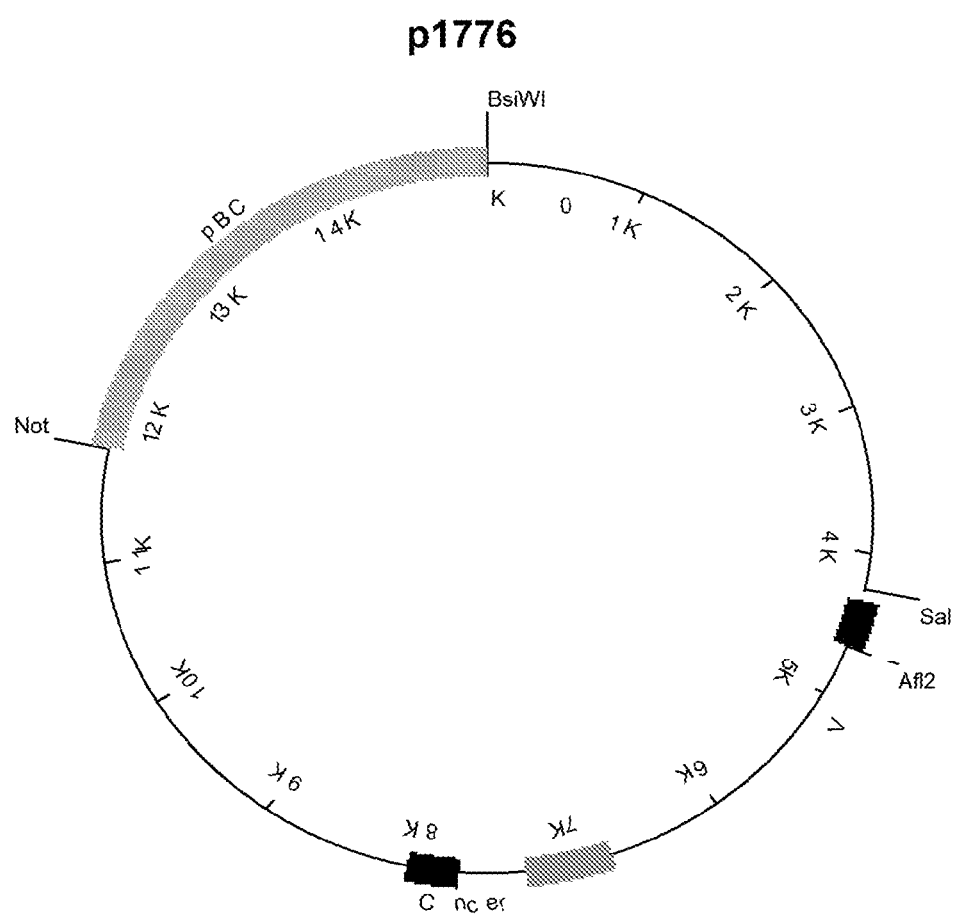

Binding Kinetics of Human Anti-Human TNF Antibodies. ELISA analysis confirms that purified antibody from most or all of these hybridomas bind TNF in a concentration-dependent manner. FIG. 1 and FIG. 2 show the results of the relative binding efficiency of these antibodies. In this case, the avidity of the antibody for its cognate antigen (epitope) is measured. It should be noted that binding TNF directly to the EIA plate can cause denaturation of the protein and the apparent binding affinities cannot be reflective of binding to undenatured protein. Fifty percent binding is found over a range of concentrations.

Quantitative binding constants are obtained using BIAcore analysis of the human antibodies and reveals that several of the human monoclonal antibodies are very high affinity with $K_D$ in the range of $1 \times 10^{-9}$ to $7 \times 10^{-12}$.

Conclusions

Several fusions are performed utilizing splenocytes from hybrid mice containing human variable and constant region antibody transgenes that are immunized with human TNF. A set of several completely human TNF reactive IgG monoclonal antibodies of the IgG1κ isotypes are generated. The completely human anti-TNF antibodies are further characterized. Several of generated antibodies have affinity constants between $1 \times 10^9$ and $9 \times 10^{12}$. The unexpectedly high affinities of these fully human monoclonal antibodies make them suitable for therapeutic applications in TNF-dependent diseases, pathologies or related conditions.

Example 3: Generation of Human IgG Monoclonal Antibodies Reactive to Human TNFα

Summary (CBA/J×C57BL/6J) F2 hybrid mice (1-4) containing human variable and constant region antibody transgenes for both heavy and light chains were immunized with recombinant human TNFα. One fusion, named GenTNV, yielded eight totally human IgG1κ monoclonal antibodies that bind to immobilized recombinant human TNFα. Shortly after identification, the eight cell lines were transferred to Molecular Biology for further characterization. As these Mabs are totally human in sequence, they are expected to be less immunogenic than cA2 (Remicade®) in humans.

Abbreviations. BSA—bovine serum albumin; $CO_2$—carbon dioxide; DMSO—dimethyl sulfoxide; EIA—enzyme immunoassay; FBS—fetal bovine serum; $H_2O_2$—hydrogen peroxide; HC—heavy chain; HRP—horseradish peroxidase; ID—interadermal; Ig—immunoglobulin; TNF—tissue necrosis factor alpha; IP—intraperitoneal; IV—intravenous; Mab—monoclonal antibody; OD—optical density; OPD—o-Phenylenediamine dihydrochloride; PEG—polyethylene glycol; PSA—penicillin, streptomycin, amphotericin; RT—room temperature; SQ—subcutaneous; TNFα—tumor necrosis factor alpha; v/v—volume per volume; w/v—weight per volume.

Introduction. Transgenic mice that contain human heavy and light chain immunoglobulin genes were utilized to generate totally human monoclonal antibodies that are specific to recombinant human TNFα. It is hoped that these unique antibodies can be used, as cA2 (Remicade®) is used to therapeutically inhibit the inflammatory processes involved in TNFα-mediated disease with the benefit of increased serum half-life and decreased side effects relating to immunogenicity.

As defined herein, the term "half-life" indicates that the plasma concentration of a drug (e.g., a therapeutic anti-TNFα antibody) is halved after one elimination half-life. Therefore, in each succeeding half-life, less drug is eliminated. After one half-life the amount of drug remaining in the body is 50% after two half-lives 25%, etc. The half-life of a drug depends on its clearance and volume of distribution. The elimination half-life is considered to be independent of the amount of drug in the body.

Materials and Methods

Animals. Transgenic mice that express human immunoglobulins, but not mouse IgM or Igκ, have been developed by GenPharm International. These mice contain functional human antibody transgenes that undergo V(D)J joining, heavy-chain class switching and somatic mutation to generate a repertoire of antigen-specific human immunoglobulins (1). The light chain transgenes are derived in part from a yeast artificial chromosome clone that includes nearly half of the germline human Vκ locus. In addition to several VH genes, the heavy-chain (HC) transgene encodes both human μ and human γ1 (2) and/or γ3 constant regions. A mouse derived from the HCo12/KCo5 genotypic lineage was used in the immunization and fusion process to generate the monoclonal antibodies described here.

Purification of Human TNFα. Human TNFα was purified from tissue culture supernatant from C237A cells by affinity chromatography using a column packed with the TNFα receptor-Fc fusion protein (p55-sf2) (5) coupled to Sepharose 4B (Pharmacia). The cell supernatant was mixed with one-ninth its volume of 10× Dulbecco's PBS (D-PBS) and passed through the column at 4° C. at 4 m/min. The column was then washed with PBS and the TNFα was eluted with 0.1 M sodium citrate, pH 3.5 and neutralized with 2 M Tris-HCl pH 8.5. The purified TNFα was buffer exchanged into 10 mM Tris, 0.12 M sodium chloride pH 7.5 and filtered through a 0.2 um syringe filter.

Immunizations. A female GenPharm mouse, approximately 16 weeks old, was immunized IP (200 µL) and ID (100 µL at the base of the tail) with a total of 100 µg of TNFα (lot JG102298 or JG102098) emulsified with an equal volume of Titermax adjuvant on days 0, 12 and 28. The mouse was bled on days 21 and 35 by retro-orbital puncture without anti-coagulant. The blood was allowed to clot at RT for one hour and the serum was collected and titered using TNFα solid phase EIA assay. The fusion, named GenTNV, was performed after the mouse was allowed to rest for seven weeks following injection on day 28. The mouse, with a specific human IgG titer of 1:160 against TNFα, was then given a final IV booster injection of 50 µg TNFα diluted in 100 µL physiological saline. Three days later, the mouse was euthanized by cervical dislocation and the spleen was removed aseptically and immersed in 10 mL of cold phosphate-buffered saline (PBS) containing 100 U/mL penicillin, 100 µg/mL streptomycin, and 0.25 µg/mL amphotericin B (PSA). The splenocytes were harvested by sterilely perfusing the spleen with PSA-PBS. The cells were washed once in cold PSA-PBS, counted using a Coulter counter and resuspended in RPMI 1640 media containing 25 mM Hepes.

Cell Lines. The non-secreting mouse myeloma fusion partner, 653 was received into Cell Biology Services (CBS) group on 5-14-97 from Centocor's Product Development group. The cell line was expanded in RPMI medium (JRH Biosciences) supplemented with 10% (v/v) FBS (Cell Culture Labs), 1 mM sodium pyruvate, 0.1 mM NEAA, 2 mM L-glutamine (all from JRH Biosciences) and cryopreserved in 95% FBS and 5% DMSO (Sigma), then stored in a vapor phase liquid nitrogen freezer in CBS. The cell bank was sterile (Quality Control Centocor, Malvern) and free of *mycoplasma* (Bionique Laboratories). Cells were maintained in log phase culture until fusion. They were washed in PBS, counted, and viability determined (>95%) via trypan blue dye exclusion prior to fusion.

Human TNFα was produced by a recombinant cell line, named C237A, generated in Molecular Biology at Centocor. The cell line was expanded in IMDM medium (JRH Biosciences) supplemented with 5% (v/v) FBS (Cell Culture Labs), 2 mM L-glutamine (all from JRH Biosciences), and 0.5:g/mL mycophenolic acid, and cryopreserved in 95% FBS and 5% DMSO (Sigma), then stored in a vapor phase liquid nitrogen freezer in CBS (13). The cell bank was sterile (Quality Control Centocor, Malvern) and free of *mycoplasma* (Bionique Laboratories).

Cell Fusion. The cell fusion was carried out using a 1:1 ratio of 653 murine myeloma cells and viable murine spleen cells. Briefly, spleen cells and myeloma cells were pelleted together. The pellet was slowly resuspended over a 30 second period in 1 mL of 50% (w/v) PEG/PBS solution (PEG molecular weight of 1,450 g/mole, Sigma) at 37° C. The fusion was stopped by slowly adding 10.5 mL of RPMI media (no additives) (JRH) (37° C.) over 1 minute. The fused cells were centrifuged for 5 minutes at 750 rpm.

The cells were then resuspended in HAT medium (RPMI/HEPES medium containing 10% Fetal Bovine Serum (JRH), 1 mM sodium pyruvate, 2 mM L-glutamine, 10 µg/mL gentamicin, 2.5% Origen culturing supplement (Fisher), 50 µM 2-mercaptoethanol, 1% 653-conditioned RPMI media, 100 µM hypoxanthine, 0.4 µM aminopterin, and 16 µM thymidine) and then plated at 200 µL/well in five 96-well flat bottom tissue culture plates. The plates were then placed in a humidified 37° C. incubator containing 5% $CO_2$ and 95% air for 7-10 days.

Detection of Human IgG Anti-TNFα Antibodies in Mouse Serum. Solid phase EIAs were used to screen mouse sera for human IgG antibodies specific for human TNFα. Briefly, plates were coated with TNFα at 1 µg/mL in PBS overnight. After washing in 0.15 M saline containing 0.02% (v/v) Tween 20, the wells were blocked with 1% (w/v) BSA in PBS, 200 µL/well for 1 hour at RT. Plates were either used immediately or frozen at −20° C. for future use. Mouse sera were incubated in two-fold serial dilutions on the human TNFα-coated plates at 50 µL/well at RT for 1 hour. The plates were washed and then probed with 50 µL/well HRP-labeled goat anti-human IgG, Fc specific (Accurate) diluted 1:30,000 in 1% BSA-PBS for 1 hour at RT. The plates were again washed and 100 µL/well of the citrate-phosphate substrate solution (0.1 M citric acid and 0.2 M sodium phosphate, 0.010% $H_2O_2$ and 1 mg/mL OPD) was added for 15 minutes at RT. Stop solution (4N sulfuric acid) was then added at 25 µL/well and the OD's were read at 490 nm using an automated plate spectrophotometer.

Detection of Totally Human Immunoglobulins in Hybridoma Supernatants.

Because the GenPharm mouse is capable of generating both mouse and human immunoglobulin chains, two separate EIA assays were used to test growth-positive hybridoma clones for the presence of both human light chains and human heavy chains. Plates were coated as described above and undiluted hybridoma supernatants were incubated on the plates for one hour at 37° C. The plates were washed and probed with either HRP-conjugated goat anti-human kappa (Southern Biotech) antibody diluted 1:10,000 in 1% BSA-HBSS or HRP-conjugated goat anti-human IgG Fc specific antibody diluted to 1:30,000 in 1% BSA-HBSS for one hour at 37° C. The plates were then incubated with substrate solution as described above. Hybridoma clones that did not give a positive signal in both the anti-human kappa and anti-human IgG Fc EIA formats were discarded.

Isotyping. Isotype determination of the antibodies was accomplished using an EIA in a format similar to that used to screen the mouse immune sera for specific titers. EIA plates were coated with goat anti-human IgG (H+L) at 10:g/mL in sodium carbonate buffer overnight at 4EC and blocked as described above. Neat supernatants from 24 well cultures were incubated on the plate for one hour at RT. The plate was washed and probed with HRP-labeled goat anti-human $IgG_1$, $IgG_2$, $IgG_3$ or $IgG_4$ (Binding Site) diluted at 1:4000 in 1% BSA-PBS for one hour at RT. The plate was again washed and incubated with substrate solution as described above.

Results and Discussion. Generation of Totally Human Anti-Human TNFα Monoclonal Antibodies. One fusion, named GenTNV, was performed from a GenPharm mouse immunized with recombinant human TNFα protein. From this fusion, 196 growth-positive hybrids were screened. Eight hybridoma cell lines were identified that secreted totally human IgG antibodies reactive with human TNFα. These eight cell lines each secreted immunoglobulin of the human IgG1κ isotype and all were subcloned twice by limiting dilution to obtain stable cell lines (>90% homogeneous). Cell line names and respective C code designations are listed in Table 1. Each of the cell lines was frozen in 12-vial research cell banks stored in liquid nitrogen.

Parental cells collected from wells of a 24-well culture dish for each of the eight cell lines were handed over to Molecular Biology group on 2-18-99 for transfection and further characterization.

TABLE 1

GenTNV Cell Line Designations

| Name | C Code Designation |
|---|---|
| GenTNV14.17.12 | C414A |
| GenTNV15.28.11 | C415A |
| GenTNV32.2.16 | C416A |
| GenTNV86.14.34 | C417A |
| GenTNV118.3.36 | C418A |
| GenTNV122.23.2 | C419A |
| GenTNV148.26.12 | C420A |
| GenTNV196.9.1 | C421A |

Conclusion.

The GenTNV fusion was performed utilizing splenocytes from a hybrid mouse containing human variable and constant region antibody transgenes that was immunized with recombinant human TNFα prepared at Centocor. Eight totally human, TNFα-reactive IgG monoclonal antibodies of the IgG1κ isotype were generated. Parental cell lines were transferred to Molecular Biology group for further characterization and development. One of these new human antibodies may prove useful in anti-inflammatory with the potential benefit of decreased immunogenicity and allergic-type complications as compared with Remicade®.

REFERENCES

Taylor, et al., *International Immunology* 6:579-591 (1993).
Lonberg, et al., *Nature* 368:856-859 (1994).
Neuberger, M. *Nature Biotechnology* 14:826 (1996).
Fishwild, et al., *Nature Biotechnology* 14:845-851 (1996).
Scallon, et al., *Cytokine* 7:759-770 (1995).

Example 4: Cloning and Preparation of Cell Lines Expressing Human Anti-Tnfα Antibody Summary A panel of eight human monoclonal antibodies (mAbs) with a TNV designation were found to bind immobilized human TNFα with apparently high avidity. Seven of the eight mAbs were shown to efficiently block huTNFα binding to a recombinant TNF receptor. Sequence analysis of the DNA encoding the seven mAbs confirmed that all the mAbs had human V regions. The DNA sequences also revealed that three pairs of the mAbs were identical to each other, such that the original panel of eight mAbs contained only four distinct mAbs, represented by TNV14, TNV15, TNV148, and TNV196. Based on analyses of the deduced amino acid sequences of the mAbs and results of in vitro TNFα neutralization data, mAb TNV148 and TNV14 were selected for further study.

Because the proline residue at position 75 (framework 3) in the TNV148 heavy chain was not found at that position in other human antibodies of the same subgroup during a database search, site-directed DNA mutagenesis was performed to encode a serine residue at that position in order to have it conform to known germline framework e sequences. The serine modified mAb was designated TNV148B. PCR-amplified DNA encoding the heavy and light chain variable regions of TNV148B and TNV14 was cloned into newly prepared expression vectors that were based on the recently cloned heavy and light chain genes of another human mAb (12B75), disclosed in U.S. patent application No. 60/236, 827, filed Oct. 7, 2000, entitled IL-12 Antibodies, Compositions, Methods and Uses, published as WO 02/12500 which is entirely incorporated herein by reference.

P3X63Ag8.653 (653) cells or Sp2/0-Ag14 (Sp2/0) mouse myeloma cells were transfected with the respective heavy and light chain expression plasmids and screened through two rounds of subcloning for cell lines producing high levels of recombinant TNV148B and TNV14 (rTNV148B and rTNV14) mAbs. Evaluations of growth curves and stability of mAb production over time indicated that 653-transfectant clones C466D and C466C stably produced approximately 125:g/ml of rTNV148B mAb in spent cultures whereas Sp2/0 transfectant 1.73-12-122 (C467A) stably produced approximately 25:g/ml of rTNV148B mAb in spent cultures. Similar analyses indicated that Sp2/0-transfectant clone C476A produced 18:g/ml of rTNV14 in spent cultures.

Introduction. A panel of eight mAbs derived from human TNFα-immunized GenPharm/Medarex mice (HCol2/KCo5 genotype) were previously shown to bind human TNFα and to have a totally human IgG1, kappa isotype. A simple binding assay was used to determine whether the exemplary mAbs of the invention were likely to have TNFα-neutralizing activity by evaluating their ability to block TNFα from binding to recombinant TNF receptor. Based on those results, DNA sequence results, and in vitro characterizations of several of the mAbs, TNV148 was selected as the mAb to be further characterized.

DNA sequences encoding the TNV148 mAb were cloned, modified to fit into gene expression vectors that encode suitable constant regions, introduced into the well-characterized 653 and Sp2/0 mouse myeloma cells, and resulting transfected cell lines screened until subclones were identified that produced 40-fold more mAb than the original hybridoma cell line.

Materials and Methods.

Reagents and Cells. TRIZOL reagent was purchased from Gibco BRL. Proteinase K was obtained from Sigma Chemical Company. Reverse Transcriptase was obtained from Life Sciences, Inc. Taq DNA Polymerase was obtained from either Perkin Elmer Cetus or Gibco BRL. Restriction enzymes were purchased from New England Biolabs. QIAquick PCR Purification Kit was from Qiagen. A QuikChange Site-Directed Mutagenesis Kit was purchased from Stratagene. Wizard plasmid miniprep kits and RNasin were from Promega. Optiplates were obtained from Packard. $^{125}$Iodine was purchased from Amersham. Custom oligonucleotides were purchased from Keystone/Biosource International. The names, identification numbers, and sequences of the oligonucleotides used in this work are shown in Table 2.

TABLE 2

Oligonucleotides used to clone, engineer, or sequence the TNV mAb genes. The amino acids encoded by oligonucleotide 5'14s and HuH-J6 are shown above the sequence. The 'M' amino acid residue represents the translation start codon. The underlined sequences in oligonucleotides 5'14s and HuH-J6 mark the BsiWI and BstBI restriction sites, respectively. The slash in HuH-J6 corresponds to the exon/intron boundary. Note that oligonucleotides whose sequence corresponds to the minus strand are written in a 3'-5' orientation.

| Name | ID | Sequence |
| --- | --- | --- |
| HG1-4b | 119 | 3'-TTGGTCCAGTCGGACTGG-5' (SEQ ID NO: 10) |
| HG1-5b | 354 | 3'-CACCTGCACTCGGTGCTT-5' (SEQ ID NO: 11) |
| HG1hg | 360 | 3'-CACTGTTTTGAGTGTGTACG GGCTTAAGTT-5' (SEQ ID NO: 12) |
| HG1-6 | 35 | 3'-GCCGCACGTGTGGAAGGG-5' (SEQ ID NO: 13) |
| HCK1-3E | 117 | 3'-AGTCAAGGTCGGACTGGCTT AAGTT-5' (SEQ ID NO: 14) |
| HuK-3'Hd | 208 | 3'-GTTGTCCCCTCTCACAATCT TCGAATTT-5' (SEQ ID NO: 15) |
| HVKRNAseq | 34 | 3'-GGCGGTAGACTACTCGTC-5' (SEQ ID NO: 16) |
| | | BsiWI M D W T W S I (SEQ ID NO: 17) |
| 5'14s | 366 | 5-TTTCGTACGCCACCATGGACT GGACCTGGAGCATC-3' (SEQ ID NO: 18) |
| 5'46s | 367 | 5'-TTTCGTACGCCACCATGGGG TTTGGGCTGAGCTG-3' (SEQ ID NO: 19) |
| 5'47s | 368 | 5'-TTTCGTACGCCACCATGGAG TTTGGGCTGAGCATG-3' (SEQ ID NO: 20) |

TABLE 2-continued

Oligonucleotides used to clone, engineer, or sequence the TNV mAb genes. The amino acids encoded by oligonucleotide 5'14s and HuH-J6 are shown above the sequence. The 'M' amino acid residue represents the translation start codon. The underlined sequences in oligonucleotides 5'14s and HuH-J6 mark the BsiWI and BstBI restriction sites, respectively. The slash in HuH-J6 corresponds to the exon/intron boundary. Note that oligonucleotides whose sequence corresponds to the minus strand are written in a 3'-5' orientation.

| Name | ID | Sequence |
| --- | --- | --- |
| 5'63s | 369 | 5'-TTTCGTACGCCACCATGAAA CACCTGTGGTTCTTC-3' (SEQ ID NO: 21) |
| 5'73s | 370 | 5'-TTTCGTACGCCACCATGGGG TCAACCGCCATCCTC-3' (SEQ ID NO: 22) |
| | | T V T V S S BstBI (SEQ ID NO: 23) |
| HuH-J6 | 388 | 3'GTGCCAGTGGCAGAGGAGTCC ATTCAAGCTTAAGTT-5' (SEQ ID NO: 24) |
| | | SalI M D M R V (SEQ ID NO: 25) |
| LK7s | 362 | 5'-TTTGTCGACACCATGGACAT GAGGGTCC(TC)C-3' (SEQ ID NO: 26) |
| LVgs | 363 | 5'-TTT GTCGAC ACCATGGAAGC CCCAGCTC-3' (SEQ ID NO: 27) T K V D I K (SEQ ID NO: 28) Afl2 |
| HuL-J3 | 380 | 3'-CTGGTTTCACCTATAGTTTG/ CATTCAGAATTCGGCGCCTTT (SEQ ID NO: 29) |
| V148-QC1 | 399 | 5'-CATCTCCAGAGACAATtCCAA GAACACGCTGTATC-3' (SEQ ID NO: 30) |
| V148-QC2 | 400 | 3'-GTAGAGGTCTCTGTTAaGGTT CTTGTGCGACATAG-5' (SEQ ID NO: 31) |

A single frozen vial of 653 mouse myeloma cells was obtained. The vial was thawed that day and expanded in T flasks in IMDM, 5% FBS, 2 mM glutamine (media). These cells were maintained in continuous culture until they were transfected 2 to 3 weeks later with the anti-TNF DNA described here. Some of the cultures were harvested 5 days after the thaw date, pelleted by centrifugation, and resuspended in 95% FBS, 5% DMSO, aliquoted into 30 vials, frozen, and stored for future use. Similarly, a single frozen vial of Sp2/0 mouse myeloma cells was obtained. The vial was thawed, a new freeze-down prepared as described above, and the frozen vials stored in CBC freezer boxes AA and AB. These cells were thawed and used for all Sp2/0 transfections described here.

Assay for Inhibition of TNF Binding to Receptor. Hybridoma cell supernatants containing the TNV mAbs were used to assay for the ability of the mAbs to block binding of $^{125}$I-labeled TNFα to the recombinant TNF receptor fusion protein, p55-sf2 (Scallon et al. (1995) Cytokine 7:759-770). 50:1 of p55-sf2 at 0.5:g/ml in PBS was added to Optiplates to coat the wells during a one-hour incubation at 37° C. Serial dilutions of the eight TNV cell supernatants were prepared in 96-well round-bottom plates using PBS/0.1% BSA as diluent. Cell supernatant containing anti-IL-18 mAb was included as a negative control and the same anti-IL-18 supernatant spiked with cA2 (anti-TNF chimeric antibody, Remicade®, U.S. Pat. No. 5,770,198, entirely incorporated herein by reference) was included as a positive control. $^{125}$I-labeled TNFα (58:Ci/:g, D. Shealy) was added to 100:1 of cell supernatants to have a final TNFα concentration of 5 ng/ml. The mixture was preincubated for one hour at RT. The coated Optiplates were washed to remove unbound p55-sf2 and 50:1 of the $^{125}$I-TNFα/cell supernatant mixture was transferred to the Optiplates. After 2 hrs at RT, Optiplates were washed three times with PBS-Tween. 100:1 of Microscint-20 was added and the cpm bound determined using the TopCount gamma counter.

Amplification of V Genes and DNA Sequence Analysis. Hybridoma cells were washed once in PBS before addition of TRIZOL reagent for RNA preparation. Between 7×10$^6$ and 1.7×10$^7$ cells were resuspended in 1 ml TRIZOL. Tubes were shaken vigorously after addition of 200 μl of chloroform. Samples were centrifuged at 4° C. for 10 minutes. The aqueous phase was transferred to a fresh microfuge tube and an equal volume of isopropanol was added. Tubes were shaken vigorously and allowed to incubate at room temperature for 10 minutes. Samples were then centrifuged at 4° C. for 10 minutes. The pellets were washed once with 1 ml of 70% ethanol and dried briefly in a vacuum dryer. The RNA pellets were resuspended with 40 μl of DEPC-treated water. The quality of the RNA preparations was determined by fractionating 0.5 μl in a 1% agarose gel. The RNA was stored in a −80° C. freezer until used.

To prepare heavy and light chain cDNAs, mixtures were prepared that included 3 μl of RNA and 1 μg of either oligonucleotide 119 (heavy chain) or oligonucleotide 117 (light chain) (see Table 1) in a volume of 11.5 μl. The mixture was incubated at 70° C. for 10 minutes in a water bath and then chilled on ice for 10 minutes. A separate mixture was prepared that was made up of 2.5 μl of 10× reverse transcriptase buffer, 10 μl of 2.5 mM dNTPs, 1 μl of reverse transcriptase (20 units), and 0.4 μl of ribonuclease inhibitor RNasin (1 unit). 13.5 μl of this mixture was added to the 11.5 μl of the chilled RNA/oligonucleotide mixture and the reaction incubated for 40 minutes at 42° C. The cDNA synthesis reaction was then stored in a −20° C. freezer until used.

The unpurified heavy and light chain cDNAs were used as templates to PCR-amplify the variable region coding sequences. Five oligonucleotide pairs (366/354, 367/354, 368/354, 369/354, and 370/354, Table 1) were simultaneously tested for their ability to prime amplification of the heavy chain DNA. Two oligonucleotide pairs (362/208 and 363/208) were simultaneously tested for their ability to prime amplification of the light chain DNA. PCR reactions were carried out using 2 units of PLATINUM™ high fidelity (HIFI) Taq DNA polymerase in a total volume of 50 μl. Each reaction included 2 μl of a cDNA reaction, 10 pmoles of each oligonucleotide, 0.2 mM dNTPs, 5 μl of 10×HIFI Buffer, and 2 mM magnesium sulfate. The thermal cycler program was 95° C. for 5 minutes followed by 30 cycles of (94° C. for 30 seconds, 62° C. for 30 seconds, 68° C. for 1.5 minutes). There was then a final incubation at 68° C. for 10 minutes.

To prepare the PCR products for direct DNA sequencing, they were purified using the QIAquick™ PCR Purification Kit according to the manufacturer's protocol. The DNA was eluted from the spin column using 50 μl of sterile water and then dried down to a volume of 10 μl using a vacuum dryer. DNA sequencing reactions were then set up with 1 μl of purified PCR product, 10 μM oligonucleotide primer, 4 μl BigDye Terminator™ ready reaction mix, and 14 μl sterile water for a total volume of 20 μl. Heavy chain PCR products made with oligonucleotide pair 367/354 were sequenced with oligonucleotide primers 159 and 360. Light chain PCR products made with oligonucleotide pair 363/208 were sequenced with oligonucleotides 34 and 163. The thermal cycler program for sequencing was 25 cycles of (96° C. for 30 seconds, 50° C. for 15 seconds, 60° C. for 4 minutes) followed by overnight at 4° C. The reaction products were fractionated through a polyacrylamide gel and detected using an ABI 377 DNA Sequencer.

Site-directed Mutagenesis to Change an Amino Acid. A single nucleotide in the TNV148 heavy chain variable region DNA sequence was changed in order to replace Pro$^{75}$ with a Serine residue in the TNV148 mAb. Complimentary oligonucleotides, 399 and 400 (Table 1), were designed and ordered to make this change using the QuikChange™ site-directed mutagenesis method as described by the manufacturer. The two oligonucleotides were first fractionated through a 15% polyacrylamide gel and the major bands purified. Mutagenesis reactions were prepared using either 10 ng or 50 ng of TNV148 heavy chain plasmid template (p1753), 5 μl of 10× reaction buffer, 1 μl of dNTP mix, 125 ng of primer 399, 125 ng of primer 400, and 1 μl of Pfu DNA Polymerase. Sterile water was added to bring the total volume to 50 μl. The reaction mix was then incubated in a thermal cycler programmed to incubate at 95° C. for 30 seconds, and then cycle 14 times with sequential incubations of 95° C. for 30 seconds, 55° C. for 1 minute, 64° C. for 1 minute, and 68° C. for 7 minutes, followed by 30° C. for 2 minutes (1 cycle). These reactions were designed to incorporate the mutagenic oligonucleotides into otherwise identical, newly synthesized plasmids. To rid of the original TNV148 plasmids, samples were incubated at 37° C. for 1 hour after addition of 1 μl of DpnI endonuclease, which cleaves only the original methylated plasmid. One p1 of the reaction was then used to transform Epicurian Coli XL1-Blue supercompetent E. coli by standard heat-shock methods and transformed bacteria identified after plating on LB-ampicillin agar plates. Plasmid minipreps were prepared using the Wizard™ kits as described by the manufacturer. After elution of sample from the Wizard™ column, plasmid DNA was precipitated with ethanol to further purify the plasmid DNA and then resuspended in 20 μl of sterile water. DNA sequence analysis was then performed to identify plasmid clones that had the desired base change and to confirm that no other base changes were inadvertently introduced into the TNV148 coding sequence. One p1 of plasmid was subjected to a cycle sequencing reaction prepared with 3 μl of BigDye mix, 1 μl of pUC19 Forward primer, and 10 μl of sterile water using the same parameters described in Section 4.3.

Construction of Expression Vectors from 12B75 Genes. Several recombinant DNA steps were performed to prepare a new human IgG1 expression vector and a new human kappa expression vector from the previously-cloned genomic copies of the 12B75-encoding heavy and light chain genes, respectively, disclosed in U.S. patent application No. 60/236,827, filed Oct. 7, 2000, entitled IL-12 Antibodies, Compositions, Methods and Uses, published as WO 02/12500, which is entirely incorporated herein by reference. The final vectors were designed to permit simple, one-step replacement of the existing variable region sequences with any appropriately-designed, PCR-amplified, variable region.

To modify the 12B75 heavy chain gene in plasmid p1560, a 6.85 kb BamHI/HindIII fragment containing the promoter and variable region was transferred from p1560 to pUC19 to make p1743. The smaller size of this plasmid compared to p1560 enabled use of QuikChange™ mutagenesis (using oligonucleotides BsiWI-1 and BsiWI-2) to introduce a unique BsiWI cloning site just upstream of the translation initiation site, following the manufacturer's protocol. The resulting plasmid was termed p1747. To introduce a BstBI site at the 3' end of the variable region, a 5' oligonucleotide primer was designed with SalI and BstBI sites. This primer was used with the pUC reverse primer to amplify a 2.75 kb fragment from p1747. This fragment was then cloned back into the naturally-occurring SalI site in the 12B75 variable region and a HindIII site, thereby introducing the unique BstB1 site. The resulting intermediate vector, designated p1750, could accept variable region fragments with BsiWI and BstBI ends. To prepare a version of heavy chain vector in which the constant region also derived from the 12B75 gene, the BamHI-HindIII insert in p1750 was transferred to pBR322 in order to have an EcoRI site downstream of the HindIII site. The resulting plasmid, p1768, was then digested with HindIII and EcoRI and ligated to a 5.7 kb HindIII-EcoRI fragment from p1744, a subclone derived by cloning the large BamHI-BamHI fragment from p1560 into pBC. The resulting plasmid, p1784, was then used as vector for the TNV Ab cDNA fragments with BsiWI and BstBI ends. Additional work was done to prepare expression vectors, p1788 and p1798, which include the IgG1 constant region from the 12B75 gene and differ from each other by how much of the 12B75 heavy chain J-C intron they contain.

To modify the 12B75 light chain gene in plasmid p1558, a 5.7 kb SalI/AflII fragment containing the 12B75 promoter and variable region was transferred from p1558 into the XhoI/AflII sites of plasmid L28. This new plasmid, p1745, provided a smaller template for the mutagenesis step. Oligonucleotides (C340sal1 and C340sal2) were used to introduce a unique SalI restriction site at the 5' end of the variable region by QuikChange™ mutagenesis. The resulting intermediate vector, p1746, had unique SalI and AflII restriction sites into which variable region fragments could be cloned. Any variable region fragment cloned into p1746 would preferably be joined with the 3' half of the light chain gene. To prepare a restriction fragment from the 3' half of the 12B75 light chain gene that could be used for this purpose, oligonucleotides BAHN-1 and BAHN-2 were annealed to each other to form a double-stranded linker containing the restriction sites BsiW1, AflII, HindII, and NotI and which contained ends that could be ligated into KpnI and SacI sites. This linker was cloned between the KpnI and SacI sites of pBC to give plasmid p1757. A 7.1 kb fragment containing the 12B75 light chain constant region, generated by digesting p1558 with AflII, then partially digesting with HindIII, was cloned between the AflII and HindII sites of p1757 to yield p1762. This new plasmid contained unique sites for BsiWI and AflII into which the BsiWI/AflII fragment containing the promoter and variable regions could be transferred uniting the two halves of the gene.

cDNA Cloning and Assembly of Expression Plasmids. All RT-PCR reactions (see above) were treated with Klenow enzyme to further fill in the DNA ends. Heavy chain PCR fragments were digested with restriction enzymes BsiWI and BstBI and then cloned between the BsiWI and BstBI sites of plasmid L28 (L28 used because the 12B75-based intermediate vector p1750 had not been prepared yet). DNA sequence analysis of the cloned inserts showed that the resulting constructs were correct and that there were no errors introduced during PCR amplifications. The assigned identification numbers for these L28 plasmid constructs (for TNV14, TNV15, TNV148, TNV148B, and TNV196) are shown in Table 3.

The BsiWI/BstBI inserts for TNV14, TNV148, and TNV148B heavy chains were transferred from the L28 vector to the newly prepared intermediate vector, p1750. The assigned identification numbers for these intermediate plasmids are shown in Table 2. This cloning step and subsequent steps were not done for TNV15 and TNV196. The variable regions were then transferred into two different human IgG1 expression vectors. Restriction enzymes EcoRI and HindIII were used to transfer the variable regions into Centocor's previously-used IgG1 vector, p104. The resulting expression plasmids, which encode an IgG1 of the Gm(f+) allotype, were designated p1781 (TNV14), p1782 (TNV148), and p1783 (TNV148B) (see Table 2). The variable regions were also cloned upstream of the IgG1 constant region derived from the 12B75 (GenPharm) gene. Those expression plasmids, which encode an IgG1 of the G1m(z) allotype, are also listed in Table 3.

TABLE 3

Plasmid identification numbers for various heavy and light chain plasmids. The L28 vector or pBC vector represents the initial Ab cDNA clone. The inserts in those plasmids were transferred to an incomplete 12B75-based vector to make the intermediate plasmids. One additional transfer step resulted in the final expression plasmids that were either introduced into cells after being linearized or used to purify the mAb gene inserts prior to cell transfection. (ND) = not done.

| | Gm(f+) | | G1m(z) | |
|---|---|---|---|---|
| Mab | L28 vector Plasmid ID | Intermediate Plasmid ID | Expression Plasmid ID | Expression Plasmid ID |
| Heavy Chains | | | | |
| TNV14 | p1751 | p1777 | p1781 | p1786 |
| TNV15 | p1752 | (ND) | (ND) | (ND) |
| TNV148 | p1753 | p1778 | p1782 | p1787 |
| TNV148B | p1760 | p1779 | p1783 | p1788 |
| TNV196 | p1754 | (ND) | (ND) | (ND) |
| | pBC vector Plasmid ID | Intermediate Plasmid ID | Expression Plasmid ID | |
| Light Chains | | | | |
| TNV 14 | p1748 | p1755 | p1775 | |
| TNV 15 | p1748 | p1755 | p1775 | |
| TNV 148 | p1749 | p1756 | p1776 | |
| TNV 196 | p1749 | p1756 | p1776 | |

Light chain PCR products were digested with restriction enzymes SalI and SacII and then cloned between the SalI and SacII sites of plasmid pBC. The two different light chain versions, which differed by one amino acid, were designated p1748 and p1749 (Table 2). DNA sequence analysis confirmed that these constructs had the correct sequences. The SalI/AflII fragments in p1748 and p1749 were then cloned between the SalI and AflII sites of intermediate vector p1746 to make p1755 and p1756, respectively. These 5' halves of the light chain genes were then joined to the 3' halves of the gene by transferring the BsiWI/AflII fragments from p1755 and p1756 to the newly prepared construct p1762 to make the final expression plasmids p1775 and p1776, respectively (Table 2).

Cell Transfections, Screening, and Subcloning. A total of 15 transfections of mouse myeloma cells were performed with the various TNV expression plasmids (see Table 3 in the Results and Discussion section). These transfections were distinguished by whether (1) the host cells were Sp2/0 or 653; (2) the heavy chain constant region was encoded by Centocor's previous IgG1 vector or the 12B75 heavy chain constant region; (3) the mAb was TNV148B, TNV148, TNV14, or a new HC/LC combination; (4) whether the DNA was linearized plasmid or purified Ab gene insert; and (5) the presence or absence of the complete J-C intron sequence in the heavy chain gene. In addition, several of the transfections were repeated to increase the likelihood that a large number of clones could be screened.

Sp2/0 cells and 653 cells were each transfected with a mixture of heavy and light chain DNA (8-12:g each) by electroporation under standard conditions as previously described (Knight D M et al. (1993) *Molecular Immunology* 30:1443-1453). For transfection numbers 1, 2, 3, and 16, the appropriate expression plasmids were linearized by digestion with a restriction enzyme prior to transfection. For example, SalI and NotI restriction enzymes were used to linearize TNV148B heavy chain plasmid p1783 and light chain plasmid p1776, respectively. For the remaining transfections, DNA inserts that contained only the mAb gene were separated from the plasmid vector by digesting heavy chain plasmids with BamHI and light chain plasmids with BsiWI and NotI. The mAb gene inserts were then purified by agarose gel electrophoresis and Qiex purification resins. Cells transfected with purified gene inserts were simultaneously transfected with 3-5:g of PstI-linearized pSV2gpt plasmid (p13) as a source of selectable marker. Following electroporation, cells were seeded in 96-well tissue culture dishes in IMDM, 15% FBS, 2 mM glutamine and incubated at 37° C. in a 5% $CO_2$ incubator. Two days later, an equal volume of IMDM, 5% FBS, 2 mM glutamine, 2×MHX selection (1×MHX=0.5:g/ml mycophenolic acid, 2.5:g/ml hypoxanthine, 50:g/ml xanthine) was added and the plates incubated for an additional 2 to 3 weeks while colonies formed.

Cell supernatants collected from wells with colonies were assayed for human IgG by ELISA as described. In brief, varying dilutions of the cell supernatants were incubated in 96-well EIA plates coated with polyclonal goat anti-human IgG Fc fragment and then bound human IgG was detected by using Alkaline Phosphatase-conjugated goat anti-human IgG(H+L) and the appropriate color substrates. Standard curves, which used as standard the same purified mAb that was being measured in the cell supernatants, were included on each EIA plate to enable quantitation of the human IgG in the supernatants. Cells in those colonies that appeared to be producing the most human IgG were passaged into 24-well plates for additional production determinations in spent cultures and the highest-producing parental clones were subsequently identified.

The highest-producing parental clones were subcloned to identify higher-producing subclones and to prepare a more homogenous cell line. 96-well tissue culture plates were seeded with one cell per well or four cells per well in of IMDM, 5% FBS, 2 mM glutamine, 1×MHX and incubated at 37° C. in a 5% $CO_2$ incubator for 12 to 20 days until colonies were apparent. Cell supernatants were collected from wells that contained one colony per well and analyzed by ELISA as described above. Selected colonies were passaged to 24-well plates and the cultures allowed to go spent before identifying the highest-producing subclones by quantitating the human IgG levels in their supernatants. This process was repeated when selected first-round subclones were subjected to a second round of subcloning. The best second-round subclones were selected as the cell lines for development.

Characterization of Cell Subclones. The best second-round subclones were chosen and growth curves performed to evaluate mAb production levels and cell growth characteristics. T75 flasks were seeded with $1\times10^5$ cells/ml in 30 ml IMDM, 5% FBS, 2 mM glutamine, and 1×MHX (or serum-free media). Aliquots of 300 μl were taken at 24 hr intervals and live cell density determined. The analyses continued until the number of live cells was less than $1\times10^5$ cells/ml. The collected aliquots of cell supernatants were assayed for the concentration of antibody present. ELISA assays were performed using as standard rTNV148B or rTNV14 JG92399. Samples were incubated for 1 hour on ELISA plates coated with polyclonal goat anti-human IgG Fc and bound mAb detected with Alkaline Phosphatase-conjugated goat anti-human IgG(H+L) at a 1:1000 dilution.

A different growth curve analysis was also done for two cell lines for the purpose of comparing growth rates in the presence of varying amounts of MHX selection. Cell lines C466A and C466B were thawed into MHX-free media (IMDM, 5% FBS, 2 mM glutamine) and cultured for two additional days. Both cell cultures were then divided into three cultures that contained either no MHX, 0.2×MHX, or 1×MHX (1×MHX=0.5:g/ml mycophenolic acid, 2.5:g/ml hypoxanthine, 50:g/ml xanthine). One day later, fresh T75 flasks were seeded with the cultures at a starting density of $1\times10^5$ cells/ml and cells counted at 24 hour intervals for one week. Aliquots for mAb production were not collected. Doubling times were calculated for these samples using the formula provided in SOP PD32.025.

Additional studies were performed to evaluate stability of mAb production over time. Cultures were grown in 24-well plates in IMDM, 5% FBS, 2 mM glutamine, either with or without MHX selection. Cultures were split into fresh cultures whenever they became confluent and the older culture was then allowed to go spent. At this time, an aliquot of supernatant was taken and stored at 4° C. Aliquots were taken over a 55-78 day period. At the end of this period, supernatants were tested for amount of antibody present by the anti-human IgG Fc ELISA as outlined above.

Results and Discussion

Inhibition of TNF Binding to Recombinant Receptor.

A simple binding assay was done to determine whether the eight TNV mAbs contained in hybridoma cell supernatant were capable of blocking TNFα binding to receptor. The concentrations of the TNV mAbs in their respective cell supernatants were first determined by standard ELISA analysis for human IgG. A recombinant p55 TNF receptor/IgG fusion protein, p55-sf2, was then coated on EIA plates and $^{125}$I-labeled TNFα allowed to bind to the p55 receptor in the presence of varying amounts of TNV mAbs. As shown in FIG. 1, all but one (TNV122) of the eight TNV mAbs efficiently blocked TNFα binding to p55 receptor. In fact, the TNV mAbs appeared to be more effective at inhibiting TNFα binding than cA2 positive control mAb that had been spiked into negative control hybridoma supernatant. These results were interpreted as indicating that it was highly likely that the TNV mAbs would block TNFα bioactivity in cell-based assays and in vivo and therefore additional analyses were warranted.

DNA Sequence Analysis.
Confirmation that the RNAs Encode Human mAbs.

As a first step in characterizing the seven TNV mAbs (TNV14, TNV15, TNV32, TNV86, TNV 118, TNV148, and TNV196) that showed TNFα-blocking activity in the receptor binding assay, total RNA was isolated from the seven hybridoma cell lines that produce these mAbs. Each RNA sample was then used to prepare human antibody heavy or light chain cDNA that included the complete signal sequence, the complete variable region sequence, and part of the constant region sequence for each mAb. These cDNA products were then amplified in PCR reactions and the PCR-amplified DNA was directly sequenced without first cloning the fragments. The heavy chain cDNAs sequenced were >90% identical to one of the five human germline genes present in the mice, DP-46 (FIG. 2). Similarly, the light chain cDNAs sequenced were either 100% or 98% identical to one of the human germline genes present in the mice (FIG. 3). These sequence results confirmed that the RNA molecules that were transcribed into cDNA and sequenced encoded human antibody heavy chains and human antibody light chains. It should be noted that, because the variable regions were PCR-amplified using oligonucleotides that map to the 5' end of the signal sequence coding sequence, the first few amino acids of the signal sequence may not be the actual sequence of the original TNV translation products, but they do represent the actual sequences of the recombinant TNV mAbs.

Unique Neutralizing mAbs.

Analyses of the cDNA sequences for the entire variable regions of both heavy and light chains for each mAb revealed that TNV32 is identical to TNV15, TNV118 is identical to TNV14, and TNV86 is identical to TNV148. The results of the receptor binding assay were consistent with the DNA sequence analyses, i.e. both TNV86 and TNV148 were approximately 4-fold better than both TNV 118 and TNV14 at blocking TNF binding. Subsequent work was therefore focused on only the four unique TNV mAbs, TNV14, TNV15, TNV148, and TNV196.

Relatedness of the Four mAbs

The DNA sequence results revealed that the genes encoding the heavy chains of the four TNV mAbs were all highly homologous to each other and appear to have all derived from the same germline gene, DP-46 (FIG. 2). In addition, because each of the heavy chain CDR3 sequences are so similar and of the same length, and because they all use the J6 exon, they apparently arose from a single VDJ gene rearrangement event that was then followed by somatic changes that made each mAb unique. DNA sequence analyses revealed that there were only two distinct light chain genes among the four mAbs (FIG. 3). The light chain variable region coding sequences in TNV14 and TNV15 are identical to each other and to a representative germline sequence of the Vg/38K family of human kappa chains. The TNV148 and TNV196 light chain coding sequences are identical to each other but differ from the germline sequence at two nucleotide positions (FIG. 3).

The deduced amino acid sequences of the four mAbs revealed the relatedness of the actual mAbs. The four mAbs contain four distinct heavy chains (FIG. 4) but only two distinct light chains (FIG. 5). Differences between the TNV mAb sequences and the germline sequences were mostly confined to CDR domains but three of the mAb heavy chains also differed from the germline sequence in the framework regions (FIG. 4). Compared to the DP-46 germline-encoded Ab framework regions, TNV14 was identical, TNV15 differed by one amino acid, TNV148 differed by two amino acids, and TNV196 differed by three amino acids.

Cloning of cDNAs, Site-specific Mutagenesis, and Assembly of Final Expression Plasmids. Cloning of cDNAs. Based on the DNA sequence of the PCR-amplified variable regions, new oligonucleotides were ordered to perform another round of PCR amplification for the purpose of adapting the coding sequence to be cloned into expression vectors. In the case of the heavy chains, the products of this second round of PCR were digested with restriction enzymes BsiWI and BstBI and cloned into plasmid vector L28 (plasmid identification numbers shown in Table 2). In the case of the light chains, the second-round PCR products were digested with SalI and AflII and cloned into plasmid vector pBC. Individual clones were then sequenced to confirm that their sequences were identical to the previous sequence obtained from direct sequencing of PCR products, which reveals the most abundant nucleotide at each position in a potentially heterogeneous population of molecules.

Site-specific Mutagenesis to Change TNV148. mAbs TNV148 and TNV196 were being consistently observed to be four-fold more potent than the next best mAb (TNV14) at neutralizing TNFα bioactivity. However, as described above, the TNV148 and TNV196 heavy chain framework sequences differed from the germline framework sequences. A comparison of the TNV148 heavy chain sequence to other human antibodies indicated that numerous other human mAbs contained an Ile residue at position 28 in framework 1 (counting mature sequence only) whereas the Pro residue at position 75 in framework 3 was an unusual amino acid at that position.

A similar comparison of the TNV196 heavy chain suggested that the three amino acids by which it differs from the germline sequence in framework 3 may be rare in human mAbs. There was a possibility that these differences may render TNV148 and TNV196 immunogenic if administered to humans. Because TNV148 had only one amino acid residue of concern and this residue was believed to be unimportant for TNFα binding, a site-specific mutagenesis technique was used to change a single nucleotide in the TNV148 heavy chain coding sequence (in plasmid p1753) so that a germline Ser residue would be encoded in place of the Pro residue at position 75. The resulting plasmid was termed p1760 (see Table 2). The resulting gene and mAb were termed TNV148B to distinguish it from the original TNV148 gene and mAb (see FIG. 5).

Assembly of Final Expression Plasmids. New antibody expression vectors were prepared that were based on the 12B75 heavy chain and light chain genes previously cloned as genomic fragments. Although different TNV expression plasmids were prepared (see Table 2), in each case the 5' flanking sequences, promoter, and intron enhancer derived from the respective 12B75 genes. For the light chain expression plasmids, the complete J-C intron, constant region coding sequence and 3' flanking sequence were also derived from the 12B75 light chain gene. For the heavy chain expression plasmids that resulted in the final production cell lines (p1781 and p1783, see below), the human IgG1 constant region coding sequences derived from Centocor's previously-used expression vector (p104). Importantly, the final production cell lines reported here express a different allotype (Gm(f+)) of the TNV mAbs than the original, hybridoma-derived TNV mAbs (G1m(z)). This is because the 12B75 heavy chain gene derived from the GenPharm mice encodes an Arg residue at the C-terminal end of the CH1 domain whereas Centocor's IgG1 expression vector p104 encodes a Lys residue at that position. Other heavy chain expression plasmids (e.g. p1786 and p1788) were prepared in which the J-C intron, complete constant region coding sequence and 3' flanking sequence were derived from the 12B75 heavy chain gene, but cell lines transfected with those genes were not selected as the production cell lines. Vectors were carefully designed to permit one-step cloning of future PCR-amplified V regions that would result in final expression plasmids.

PCR-amplified variable region cDNAs were transferred from L28 or pBC vectors to intermediate-stage, 12B75-based vectors that provided the promoter region and part of the J-C intron (see Table 2 for plasmid identification numbers). Restriction fragments that contained the 5' half of the antibody genes were then transferred from these intermediate-stage vectors to the final expression vectors that provided the 3' half of the respective genes to form the final expression plasmids (see Table 2 for plasmid identification numbers).

Cell Transfections and Subcloning. Expression plasmids were either linearized by restriction digest or the antibody gene inserts in each plasmid were purified away from the plasmid backbones. Sp2/0 and 653 mouse myeloma cells were transfected with the heavy and light chain DNA by electroporation. Fifteen different transfections were done, most of which were unique as defined by the Ab, specific characteristics of the Ab genes, whether the genes were on linearized whole plasmids or purified gene inserts, and the host cell line (summarized in Table 4). Cell supernatants from clones resistant to mycophenolic acid were assayed for the presence of human IgG by ELISA and quantitated using purified rTNV148B as a reference standard curve.

Highest-Producing rTNV148B Cell Lines

Figure 8:
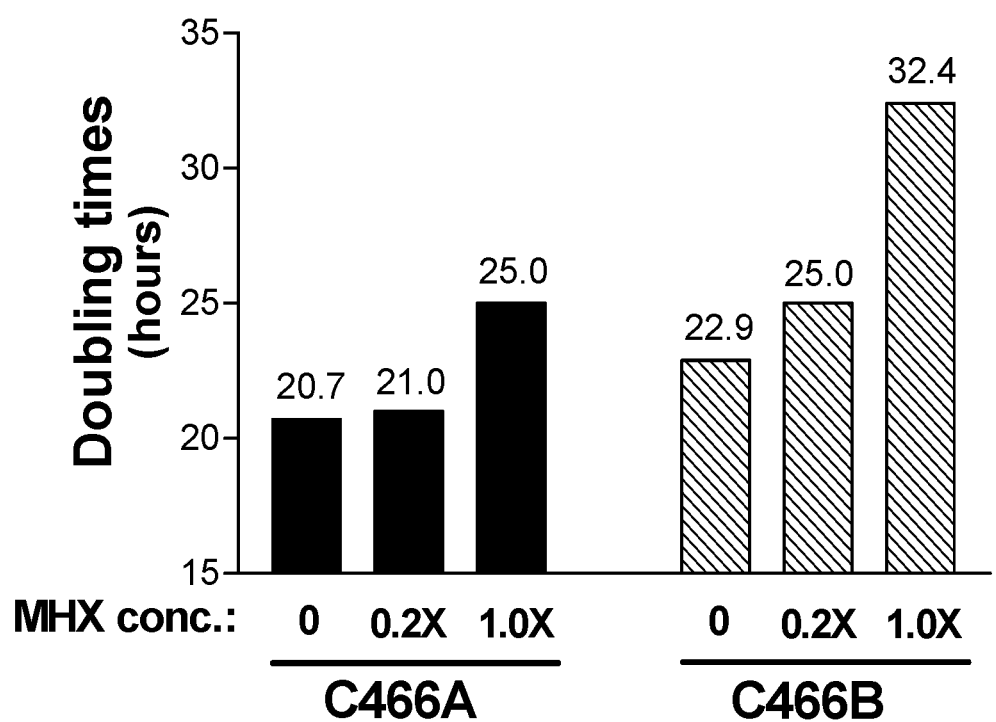

Ten of the best-producing 653 parental lines from rTNV148B transfection 2 (produced 5-10:g/ml in spent 24-well cultures) were subcloned to screen for higher-producing cell lines and to prepare a more homogeneous cell population. Two of the subclones of the parental line 2.320, 2.320-17 and 2.320-20, produced approximately 50:g/ml in spent 24-well cultures, which was a 5-fold increase over their parental line. A second round of subcloning of subcloned lines 2.320-17 and 2.320-20 led The identification numbers of the heavy and light chain plasmids that encode each mAb are shown. In the case of transfections done with purified mAb gene inserts, plasmid p13 (pSV2gpt) was included as a source of the gpt selectable marker. The heavy chain constant regions were encoded either by the same human IgG1 expression vector used to encode Remicade® ('old') or by the constant regions contained within the 12B75 (GenPharm/Medarex) heavy chain gene ('new'). H1/L2 refers to a "novel" mAb made up of the TNV14 heavy chain and the TNV148 light chain. Plasmids p1783 and p1801 differ only by how much of the J-C intron their heavy chain genes contain. The transfection numbers, which define the first number of the generic names for cell clones, are shown on the right. The rTNV148B-producing cell lines C466 (A, B, C, D) and C467A described here derived from transfection number 2 and 1, respectively. The rTNV14-producing cell line C476A derived from transfection number 3.

TABLE 4

Summary of Cell Transfections.

| Transfection no. | Plasmids | HC | | DNA | |
|---|---|---|---|---|---|
| mAb | HC/LC/gpt | vector | format | Sp2/0 | 653 |
| rTNV148B | 1783/1776 | old | linear | 1 | 2 |
| rTNV14 | 1781/1775 | old | linear | 3 | — |
| rTNV148B | 1788/1776/13 | new | insert | 4, 6 | 5, 7 |
| rTNV14 | 1786/1775/13 | new | insert | 8, 10 | 9, 11 |
| rTNV148 | 1787/1776/13 | new | insert | 12 | 17 |
| rH1/L2 | 1786/1776/13 | new | insert | 13 | 14 |
| rTNV148B | 1801/1776 | old | linear | 16 | |

ELISA assays on spent 24-well culture supernatants indicated that these second-round subclones all produced between 98 and 124:g/ml, which was at least a 2-fold increase over the first-round subclones. These 653 cell lines were assigned C code designations as shown in Table 5.

Three of the best-producing Sp2/0 parental lines from rTNV148B transfection 1 were subcloned. Two rounds of subcloning of parental line 1.73 led to the identification of a clone that produced 25:g/ml in spent 24-well cultures. This Sp2/0 cell line was designated C467A (Table 5).

Highest-Producing rTNV14 Cell Lines

Three of the best-producing Sp2/0 parental lines from rTNV14 transfection 3 were subcloned once. Subclone 3.27-1 was found to be the highest-producer in spent 24-well cultures with a production of 19:g/ml. This cell line was designated C476A (Table 5).

TABLE 5

Summary of Selected Production Cell Lines and their C codes. The first digit of the original clone names indicates which transfection the cell line derived from. All of the C-coded cell lines reported here were derived from transfections with heavy and light chain whole plasmids that had been linearized with restriction enzymes.

| mAb | Original Clone Name | C code | Spent 24-well Host Cell | Production |
|---|---|---|---|---|
| rTNV148B | 2.320-17-36 | C466A | 653 | 103:g/ml |
| | 2.320-20-111 | C466B | 653 | 102:g/ml |
| | 2.320-17-4 | C466C | 653 | 98:g/ml |
| | 2.320-20-99 | C466D | 653 | 124:g/ml |
| | 1.73-12-122 | C467A | Sp2/0 | 25:g/ml |
| rTNV14 | 3.27-1 | C476A | Sp2/0 | 19:g/ml |

Characterization of Subcloned Cell Lines

To more carefully characterize cell line growth characteristics and determine mAb-production levels on a larger scale, growth curves analyses were performed using T75 cultures. The results showed that each of the four C466 series of cell lines reached peak cell density between $1.0\times10^6$ and $1.25\times10^6$ cells/ml and maximal mAb accumulation levels of between 110 and 140:g/ml (FIG. 7). In contrast, the best-producing Sp2/0 subclone, C467A, reached peak cell density of $2.0\times10^6$ cells/ml and maximal mAb accumulation levels of 25:g/ml (FIG. 7). A growth curve analysis was not done on the rTNV14-producing cell line, C476A.

An additional growth curve analysis was done to compare the growth rates in different concentrations of MHX selection. This comparison was prompted by recent observations that C466 cells cultured in the absence of MHX seemed to be growing faster than the same cells cultured in the normal amount of MHX (1×). Because the cytotoxic concentrations of compounds such as mycophenolic acid tend to be measured over orders of magnitude, it was considered possible that the use of a lower concentration of MHX might result in significantly faster cell doubling times without sacrificing stability of mAb production. Cell lines C466A and C466B were cultured either in: no MHX, 0.2×MHX, or 1×MHX. Live cell counts were taken at 24-hour intervals for 7 days. The results did reveal an MHX concentration-dependent rate of cell growth (FIG. 8). Cell line C466A showed a doubling time of 25.0 hours in 1×MHX but only 20.7 hours in no MHX. Similarly, cell line C466B showed a doubling time of 32.4 hours in 1×MHX but only 22.9 hours in no MHX. Importantly, the doubling times for both cell lines in 0.2× MHX were more similar to what was observed in no MHX than in 1×MHX (FIG. 8). This observation raises the possibility than enhanced cell performance in bioreactors, for which doubling times are an important parameter, could be realized by using less MHX. However, although stability test results (see below) suggest that cell line C466D is capable of stably producing rTNV148B for at least 60 days even with no MHX present, the stability test also showed higher mAb production levels when the cells were cultured in the presence of MHX compared to the absence of MHX.

To evaluate mAb production from the various cell lines over a period of approximately 60 days, stability tests were performed on cultures that either contained, or did not contain, MHX selection. Not all of the cell lines maintained high mAb production. After just two weeks of culture, clone C466A was producing approximately 45% less than at the beginning of the study. Production from clone C466B also appeared to drop significantly. However, clones C466C and C466D maintained fairly stable production, with C466D showing the highest absolute production levels (FIG. 9).

Conclusion

From an initial panel of eight human mAbs against human TNFα, TNV148B was selected as preferred based on several criteria that included protein sequence and TNF neutralization potency, as well as TNV14. Cell lines were prepared that produce greater than 100:g/ml of rTNV148B and 19:g/ml rTNV14.

Example 5: Arthritic Mice Study Using Anti-TNF Antibodies and Controls Using Single Bolus Injection At approximately 4 weeks of age the Tg197 study mice were assigned, based on gender and body weight, to one of 9 treatment groups and treated with a single intraperitoneal bolus dose of Dulbecco's PBS (D-PBS) or an anti-TNF antibody of the present invention (TNV14, TNV148 or TNV196) at either 1 mg/kg or 10 mg/kg.

RESULTS: When the weights were analyzed as a change from pre-dose, the animals treated with 10 mg/kg cA2 showed consistently higher weight gain than the D-PBS-treated animals throughout the study. This weight gain was significant at weeks 3-7. The animals treated with 10 mg/kg TNV148 also achieved significant weight gain at week 7 of the study. (See FIG. 10).

FIG. 11A-C represent the progression of disease severity based on the arthritic index. The 10 mg/kg cA2-treated group's arthritic index was lower than the D-PBS control group starting at week 3 and continuing throughout the remainder of the study (week 7). The animals treated with 1 mg/kg TNV14 and the animals treated with 1 mg/kg cA2 failed to show significant reduction in AI after week 3 when compared to the D-PBS-treated Group. There were no significant differences between the 10 mg/kg treatment groups when each was compared to the others of similar dose (10 mg/kg cA2 compared to 10 mg/kg TNV14, 148 and 196). When the 1 mg/kg treatment groups were compared, the 1 mg/kg TNV148 showed a significantly lower AI than 1 mg/kg cA2 at 3, 4 and 7 weeks. The 1 mg/kg TNV148 was also significantly lower than the 1 mg/kg TNV14-treated Group at 3 and 4 weeks. Although TNV196 showed significant reduction in AI up to week 6 of the study (when compared to the D-PBS-treated Group), TNV148 was the only 1 mg/kg treatment that remained significant at the conclusion of the study.

Example 6: Arthritic Mice Study Using Anti-TNF Antibodies and Controls as Multiple Bolus Doses At approximately 4 weeks of age the Tg197 study mice were assigned, based on body weight, to one of 8 treatment groups and treated with a intraperitoneal bolus dose of control article (D-PBS) or antibody (TNV14, TNV148) at 3 mg/kg (week 0). Injections were repeated in all animals at weeks 1, 2, 3, and 4. Groups 1-6 were evaluated for test article efficacy. Serum samples, obtained from animals in Groups 7 and 8 were evaluated for immune response induction and pharmacokinetic clearance of TNV14 or TNV148 at weeks 2, 3 and 4.

RESULTS: No significant differences were noted when the weights were analyzed as a change from pre-dose. The animals treated with 10 mg/kg cA2 showed consistently higher weight gain than the D-PBS-treated animals throughout the study. (See FIG. 12).

FIG. 13A-C represent the progression of disease severity based on the arthritic index. The 10 mg/kg cA2-treated group's arthritic index was significantly lower than the D-PBS control group starting at week 2 and continuing throughout the remainder of the study (week 5). The animals treated with 1 mg/kg or 3 mg/kg of cA2 and the animals treated with 3 mg/kg TNV14 failed to achieve any significant reduction in AI at any time throughout the study when compared to the d-PBS control group. The animals treated with 3 mg/kg TNV148 showed a significant reduction when compared to the d-PBS-treated group starting at week 3 and continuing through week 5. The 10 mg/kg cA2-treated animals showed a significant reduction in AI when compared to both the lower doses (1 mg/kg and 3 mg/kg) of cA2 at weeks 4 and 5 of the study and was also significantly lower than the TNV14-treated animals at weeks 3-5. Although there appeared to be no significant differences between any of the 3 mg/kg treatment groups, the AI for the animals treated with 3 mg/kg TNV14 were significantly higher at some time points than the 10 mg/kg whereas the animals treated with TNV148 were not significantly different from the animals treated with 10 mg/kg of cA2.

Example 7: Arthritic Mice Study Using Anti-TNF Antibodies and Controls as Single Intraperitoneal Bolus Dose At approximately 4 weeks of age the Tg197 study mice were assigned, based on gender and body weight, to one of 6 treatment groups and treated with a single intraperitoneal bolus dose of antibody (cA2, or TNV148) at either 3 mg/kg or 5 mg/kg. This study utilized the D-PBS and 10 mg/kg cA2 control Groups.

When the weights were analyzed as a change from pre-dose, all treatments achieved similar weight gains. The animals treated with either 3 or 5 mg/kg TNV148 or 5 mg/kg cA2 gained a significant amount of weight early in the study (at weeks 2 and 3). Only the animals treated with TNV148 maintained significant weight gain in the later time points.

Both the 3 and 5 mg/kg TNV148-treated animals showed significance at 7 weeks and the 3 mg/kg TNV148 animals were still significantly elevated at 8 weeks post injection. (See FIG. 14).

FIG. 15 represents the progression of disease severity based on the arthritic index. All treatment groups showed some protection at the earlier time points, with the 5 mg/kg cA2 and the 5 mg/kg TNV148 showing significant reductions in AI at weeks 1-3 and all treatment groups showing a significant reduction at week 2. Later in the study the animals treated with 5 mg/kg cA2 showed some protection, with significant reductions at weeks 4, 6 and 7. The low dose (3 mg/kg) of both the cA2 and the TNV148 showed significant reductions at 6 and all treatment groups showed significant reductions at week 7. None of the treatment groups were able to maintain a significant reduction at the conclusion of the study (week 8). There were no significant differences between any of the treatment groups (excluding the saline control group) at any time point.

Example 8: Arthritic Mice Study Using Anti-TNF Antibodies and Controls as Single Intraperitoneal Bolus Dose Between Anti-TNF Antibody and Modified Anti-TNF Antibody To compare the efficacy of a single intraperitoneal dose of TNV148 (derived from hybridoma cells) and rTNV148B (derived from transfected cells). At approximately 4 weeks of age the Tg197 study mice were assigned, based on gender and body weight, to one of 9 treatment groups and treated with a single intraperitoneal bolus dose of Dulbecco=S PBS (D-PBS) or antibody (TNV148, rTNV148B) at 1 mg/kg.

When the weights were analyzed as a change from pre-dose, the animals treated with 10 mg/kg cA2 showed a consistently higher weight gain than the D-PBS-treated animals throughout the study. This weight gain was significant at weeks 1 and weeks 3-8. The animals treated with 1 mg/kg TNV148 also achieved significant weight gain at weeks 5, 6 and 8 of the study. (See FIG. 16).

FIG. 17 represents the progression of disease severity based on the arthritic index. The 10 mg/kg cA2-treated group's arthritic index was lower than the D-PBS control group starting at week 4 and continuing throughout the remainder of the study (week 8). Both of the TNV148-treated Groups and the 1 mg/kg cA2-treated Group showed a significant reduction in AI at week 4. Although a previous study (P-099-017) showed that TNV148 was slightly more effective at reducing the Arthritic Index following a single 1 mg/kg intraperitoneal bolus, this study showed that the AI from both versions of the TNV antibody-treated groups was slightly higher. Although (with the exception of week 6) the 1 mg/kg cA2-treated Group was not significantly increased when compared to the 10 mg/kg cA2 group and the TNV148-treated Groups were significantly higher at weeks 7 and 8, there were no significant differences in AI between the 1 mg/kg cA2, 1 mg/kg TNV148 and 1 mg/kg TNV148B at any point in the study.

Example 9: Manufacturing Processes to Produce SIMPONI® (Golimumab) Background for Golimumab Therapies with anti-TNFα agents have been used successfully in the treatment of inflammatory arthritides, but the early anti-TNFα agents had limitations with respect to safety, dosing regimen, cost, and/or immunogenicity. To address some of the limitations, a fully human anti-TNFα mAb was developed, designated SIMPONI® (golimumab). Golimumab (also known as CNTO 148 and rTNV148B) is a fully human monoclonal antibody with an Immunoglobulin G 1 (IgG1) heavy chain isotype (G1m[z] allotype) and a kappa light chain isotype. Golimumab has a heavy chain (HC) comprising SEQ ID NO:36 and a light chain (LC) comprising SEQ ID NO:37. The molecular weight of golimumab ranges from 149,802 to 151,064 Daltons.

Golimumab forms high affinity, stable complexes with both the soluble and transmembrane bioactive forms of human tumor necrosis factor alpha (TNFα) with high affinity and specificity which prevents the binding of TNFα to its receptors and neutralizes TNFα bioactivity. No binding to other TNFα superfamily ligands was observed; in particular, golimumab does not bind or neutralize human lymphotoxin. TNFα is synthesized primarily by activated monocytes, macrophages and T cells as a transmembrane protein that self-associates to form a bioactive homotrimer that is rapidly released from the cell surface by proteolysis. The binding of TNFα to either the p55 or p75 TNF receptors leads to clustering of the receptor cytoplasmic domains and initiates signaling. Tumor necrosis factor α has been identified as a key sentinel cytokine that is produced in response to various stimuli and subsequently promotes the inflammatory response through activation of the caspase-dependent apoptosis pathway and the transcription factors nuclear factor (NF)-κB and activator protein-1 (AP-1). Tumor necrosis factor α also modulates the immune response through its role in the organization of immune cells in germinal centers. Elevated expression of TNFα has been linked to chronic inflammatory diseases such as rheumatoid arthritis (RA), as well as spondyloarthropathies such as psoriatic arthritis (PsA) and ankylosing spondylitis (AS) and is an important mediator of the articular inflammation and structural damage that are characteristic of these diseases.

Clinical Trials with Golimumab

In a global, randomized, double-blind, placebo-controlled Phase 3 study of subcutaneously (SC) administered golimumab in subjects with Ankylosing Spondylitis (AS) (Study C0524T09), golimumab was demonstrated to be efficacious in improving the signs and symptoms, physical function, and health-related quality of life (HRQOL) in subjects affected by Ankylosing Spondylitis (AS). Furthermore, safety analyses showed that SC golimumab was generally well tolerated and demonstrated a safety profile similar to that observed with other anti-TNFα agents.

Given the known safety and efficacy of SC golimumab, it was anticipated that IV golimumab would also prove efficacious with an acceptable safety profile consistent with other anti-TNFα agents in rheumatologic diseases such as RA, PsA, and AS. Intravenous golimumab has been definitively studied in a Phase 3 study (CNT0148ART3001) that formed the basis of approval for the treatment of RA. The CNT0148ART3001 study was a randomized, double-blind, placebo-controlled, multicenter, 2-arm study of the efficacy and safety of IV administration of golimumab 2 mg/kg infusions administered over a period of 30±10 minutes at Weeks 0, 4, and every 8 weeks (q8w) thereafter in subjects with active RA despite concurrent methotrexate (MTX) therapy. Subjects with active RA despite MTX were randomized to receive either placebo infusions or IV golimumab administered 2 mg/kg at Weeks 0, 4, and every 8 weeks through Week 24. Starting at Week 24, all subjects were treated with IV golimumab through Week 100. It was demonstrated that IV golimumab provided substantial benefits in improving RA signs and symptoms, physical function, and health related quality of life, as well as inhibiting the progression of structural damage. Golimumab administered intravenously in the treatment of RA (CNT0148ART3001) demonstrated robust efficacy and an acceptable safety profile with a low incidence of infusion reactions.

More recently, two Phase 3 studies were designed to evaluate the efficacy and safety of intravenous (IV) golimumab in the treatment of subjects with active Ankylosing Spondylitis (AS) and active Psoriatric Arthritis (PsA). The IV route of administration in subjects is being evaluated since currently available IV anti-TNFα agents have limitations with respect to immunogenicity and infusion reactions and have longer infusion times (60 to 120 minutes) compared with the 30±10 minute infusions with IV golimumab. Patients may also prefer the maintenance dosage schedule IV golimumab rather than more frequent administrations compared with SC agents.

Manufacturing Process Overview

SIMPONI® (golimumab) is manufactured in a 9-stage process that includes continuous perfusion cell culture followed by purification. An overview of the manufacturing process is provided in FIG. 18.

Preculture, cell expansion, and cell production are performed in Stages 1 and 2. In Stage 1, preculture is initiated from a single working cell bank vial of transfected Sp2/0 cells expressing the HC and LC sequences of golimumab and the cells are expanded in culture flasks, disposable culture bags, and either a 50-L perfusion seed bioreactor equipped with an internal spin filter or a 200-L perfusion seed bioreactor equipped with an alternating tangential flow hollow-fiber filter (ATF) cell retention system. The cells are cultured until the cell density and volume required for inoculation of a 500-L or a 1000-L production bioreactor are obtained. In Stage 2, the cell culture is continuously perfused in a 500-L or a 1000-L production bioreactor using an ATF system. Cell culture permeate (harvest) is collected from the ATF system while cells are returned to the bioreactor, and the culture is replenished with fresh medium. Biomass removed from the bioreactor may be combined with harvest withdrawn from the ATF system and then may be clarified to create a pooled harvest for further processing.

Purification of golimumab from the cell culture harvest is performed in Stages 3 through 8 by a combination of affinity and ion exchange chromatography steps and steps to inactivate or remove potential virus contamination (solvent/ detergent treatment and virus removal filtration). In Stage 3, harvest and/or pooled harvest is clarified and purified using Protein A affinity chromatography. The resultant direct product capture (DPC) eluate is frozen until further processing. DPC eluates are filtered and pooled in Stage 4 following thaw, and subsequently treated in Stage 5 with tri-n-butyl phosphate (TNBP) and polysorbate 80 (PS 80) to inactivate any lipid-enveloped viruses potentially present.

In Stage 6, TNBP and PS 80 reagents and impurities are removed from the golimumab product using cation exchange chromatography. The golimumab product is further purified using anion exchange chromatography in Stage 7 to remove DNA, potentially present viruses, and impurities. In Stage 8, the purified golimumab product is diluted and filtered through a virus retentive filter.

Final preparation of golimumab is performed in Stage 9. The ultrafiltration step concentrates the golimumab product, and the diafiltration step adds the formulation excipients and removes the in-process buffer salts. PS 80 is added, and the bulk intermediate is filtered into polycarbonate containers for frozen storage as formulated bulk (FB) to be used for drug substance (DS) and drug product (DP).

As used herein, the terms "drug substance" (abbreviated as "DS") and "drug product" (abbreviated as "DP") refer to compositions for use as commercial drugs, for example in clinical trials or as marketed drugs. A DS is an active ingredient that is intended to furnish pharmacological activity or other direct effect in the diagnosis, cure, mitigation, treatment, or prevention of disease or to affect the structure or any function of the human body. A DP (also referred to as a medicinal product, medicine, medication, or medicament) is a drug used in the diagnosis, cure, mitigation, treatment, or prevention of disease or to affect the structure or any function of the human body. The formulated bulk (FB) produced in the manufacturing process is the drug substance (DS). The DP is the DS that has been prepared as the medicinal product for sale and/or administration to the patient.

Description of Cell Culture in large-scale Manufacturing Process with Sp2/0 cells Stage 1

Preculture and Expansion

The first stage in the production of Simponi (golimumab) is the initiation of preculture from a Working Cell Bank (WCB) vial of transfected Sp2/0 cells expressing the HC and LC sequences of golimumab and subsequent expansion of the cell culture in culture flasks, disposable culture bags, and 50- or 200-L seed bioreactor. The cells are cultured until the cell density and volume required for inoculation of the 500- or 1000-L production bioreactor are obtained. A flow diagram of Stage 1 depicting the preculture and expansion steps with in-process controls and process monitoring tests are provided in FIG. 19.

Manufacturing Procedure

A cryovial from the WCB is thawed and diluted to a seeding density of $0.2$-$0.4 \times 10^6$ viable cells (VC)/mL with chemically defined medium supplemented with 6 mM L-glutamine, 0.5 mg/L mycophenolic acid, 2.5 mg/L hypoxanthine, an d 50 mg/L xanthine (CD-A medium). Culture viability at thaw must be ≥50%. The initial passage is maintained in culture flask(s) in a humidified $CO_2$ incubator with temperature and $CO_2$ controlled. The culture is incubated for 2-3 days until a minimum cell density of $0.6 \times 10^6$ VC/mL is obtained.

Scale-up is accomplished by sequentially expanding the culture in culture flasks and disposable culture bags. Each passage is started at a cell density of $0.2$-$0.4 \times 10^6$ VC/mL by dilution with CD-A medium. Passages are incubated for 2-3 days at each expansion step until a minimum cell density of $0.6 \times 10^6$ VC/mL is obtained. Once sufficient culture volume is achieved in a disposable culture bag at $\geq 0.8 \times 10^6$ VC/mL and ≥80% culture viability, the culture may be inoculated into the 50- or 200-L seed bioreactor.

Each preculture passage is sampled for viable cell density (VCD), culture viability, and microscopic examination. Prior to inoculation of the 50- or 200-L seed bioreactor, the preculture is sampled for bioburden. Preculture may be maintained for a maximum of 30 days post-thaw. Preculture is terminated if microbial contamination is detected or the maximum duration is exceeded. A back-up preculture may be retained upon inoculation of the seed bioreactor or may be started with a new WCB vial thaw. The back-up preculture is expanded as described above and is subject to the same in-process controls and operating parameters as the primary cultures. A back-up preculture may be maintained and used to inoculate a 50- or 200-L seed bioreactor as needed.

When the preculture meets inoculation criteria, the contents of the disposable culture bag(s) are transferred to the 50- or 200-L seed bioreactor to achieve a seeding density of ≥0.3×10$^6$ VC/mL. The 50- or 200-L seed bioreactor is fed with CD-A culture medium and, at full working volume, is operated in perfusion mode. The culture is controlled for pH, temperature, and dissolved oxygen concentration to support cell growth. The 50- or 200-L seed bioreactor culture is expanded until a cell density of ≥2.0×10$^6$ VC/mL, at ≥80% culture viability, is obtained. The 50- or 200-L seed bioreactor culture is sampled throughout the process for VCD, culture viability, and microscopic examination. Prior to inoculation of the 500- or 1000-L production bioreactor, the 50- or 200-L seed bioreactor is sampled for bioburden. If the VCD of the 50- or 200-L seed bioreactor reaches≥2.0×10$^6$ VC/mL and the 500- or 1000-L production bioreactor is not ready for inoculation, the culture may be continued in perfusion mode up to the maximum culture duration of 6 days post inoculation of the 50-L seed bioreactor and 7 days post inoculation of the 200-L seed bioreactor. The 50- or 200-L seed bioreactor operation is terminated if microbial contamination is detected or the maximum duration is exceeded.

Stage 2
Bioreactor Production

The second stage in the manufacturing process is perfusion cell culture in a 500- or 1000-L production bioreactor. Cell culture permeate (harvest) is collected from the production bioreactor while cells are retained via an alternating tangential flow (ATF) hollow fiber cell-retention device, and the culture is replenished with fresh media. A flow diagram depicting the 500- or 1000-L production bioreactor process is provided in FIG. 20.

Manufacturing Procedure

The inoculation of the 500-L or 1000-L production bioreactor is performed by transferring the contents of the 50- or 200-L seed bioreactor into the 500- or 1000-L production bioreactor containing chemically defined medium supplemented with 6 mM L-glutamine, 0.5 mg/L mycophenolic acid, 2.5 mg/L hypoxanthine, and 50 mg/L xanthine (CD-A medium). The volume transferred must be sufficient to yield a seeding density of ≥0.3×10$^6$ viable cells (VC)/mL. The cultures are maintained at a temperature of 34.0-38.0° C., a pH of 6.80-7.40, and dissolved oxygen concentration of 10-80%. Sampling is performed throughout the 500- or 1000-L production process for viable cell density (VCD), culture viability, bioburden, and immunoglobulin G (IgG) concentration.

After inoculation, the medium feed rate to the culture is increased according to a predetermined schedule until the maximum feed rate is reached. The maximum feed rate is controlled to 0.80-1.50 reactor volumes per day. When the full working volume of the bioreactor is reached, perfusion is initiated using the ATF system to separate cells from the permeate. Permeate is continuously withdrawn through the ATF filter, while cell culture is cycled between the ATF system and the bioreactor. The ATF permeate is collected in bioprocess containers (BPCs).

The medium feed to the bioreactor is switched from CD-A to chemically defined medium supplemented with 6 mM L-glutamine, 0.5 mg/L mycophenolic acid, 2.5 mg/L hypoxanthine, 50 mg/L xanthine, and 10 mM sodium acetate (CD-B medium) when the VCD reaches 8.5×10$^6$ VC/mL, but no later than Day 15 post inoculation of the 500- or 1000-L production bioreactor. The viable cell density in the bioreactor is controlled to a target of at least 12.0×10$^6$VC/mL by means of a variable biomass removal flow from the culture.

Biomass removed from the bioreactor may be discarded or combined with the ATF permeate and clarified by filtration.

The ATF permeate is designated as the harvest stream. Ethylenediaminetetraacetic acid (EDTA) is added to the harvest stream to a concentration of 5-20 mM. The harvest is stored in bioprocess containers (BPCs) in a 2-8° C. environment for a maximum period of 21 days after disconnection from the bioreactor. Each harvest BPC is sampled for IgG concentration, endotoxin, and bioburden prior to direct product capture (Stage 3).

Perfusion cell culture operation in the 500- or 1000-L production bioreactor continues for up to 60 days post inoculation. On the final day of the 500- or 1000-L production bioreactor operation, the culture is sampled for *mycoplasma* and adventitious virus testing. The bioreactor IgG concentration is monitored and reported for information only.

Methods
Methods for Determining Viable Cell Density (VCD) and % Viability

Total cells per/ml, viable cells/ml (VCD), and % viability are typically determined with a Beckman Coulter Vi-CELL-XR cell viability analyzer using manufacturer provided protocols, software and reagents. Alternatively, a CEDEX automated cell counting system has also been used. It should also be noted, however, that other methods for determining VCD and % viability are well known by those skilled in the art, e.g., using a hemocytometer and trypan blue exclusion.

Bioactivity (Potency) Assay

Measurement of bioactivity (potency) of golimumab is performed with an in vitro assay based on the ability of golimumab to protect WEHI 164 cells (Mouse BALB/c fibrosarcoma cells, obtained from Walter and Eliza Hall Institute, Melbourne, Australia) from TNFα induced cytotoxicity. Each assay plate contains 100-µL serial dilutions of 500 ng/mL (6 replicates) of golimumab test article and golimumab Reference Standard. TNFα is then added and the plates are incubated. After neutralization and incubation, WEHI 164 cells are added to the microtiter plate followed by another incubation step. Afterwards, a metabolic substrate (which is an indicator of live cells) is added and the converted substrate is measured spectrophotometrically.

The test article and Reference Standard neutralization curves are fit using a 4-parameter logistic analysis. The potency is calculated by comparing the 50% effective dose ($ED_{50}$) of the golimumab Reference Standard and the golimumab test article.

The following system suitability acceptance criteria are applied during the performance of the bioactivity procedure in order to yield a valid result:

Reference Standard:
  Each of the neutralization curves must be an S-shape curve with a lower plateau within 40% of the average OD value of the Cells+TNFα controls of the 3 assay plates, a higher plateau within 25% of the average OD value of the Cells Only controls of the 3 assay plates, and a linear part between the plateaus.
  The slope of each curve must be ≥0.7 and ≤3.5.
  The $r^2$ value for each curve must be ≥0.97.
  All replicate $ED_{50}$ values must be ≥2 ng/mL and ≤20 ng/mL.
  The RSD of the average $ED_{50}$ values (n=6) must be ≤20%.

TNFα Cytotoxicity Curve:
  The TNFα cytotoxicity curve must show an S-shape curve with a lower plateau, upper plateau and a linear part between the plateaus.
  The slope must be ≤2.0 for each fitted curve.
  The $r^2$ values for the TNFα cytotoxicity curves must be ≥0.97.
  The OD value at a TNFα concentration of 1.68 ng/mL should fall between 0.1 and 0.4.
Controls:
  The OD range (difference between the mean OD values of the Cells+TNF Control and Cells Only Control) for each plate must be ≥0.68.
  The average OD value (n=6) of the Cells Only controls must be ≥0.75 for each plate. The RSD of the Cells Only controls must be ≤20%.
  The average OD value (n=6) of the Cells+TNFα controls must be ≤0.50 for each plate. And the RSD of the TNFα controls must be ≤20%.
Test Articles:
  Each of the neutralization curves must be an S-shape curve with a lower plateau within 40% of the average OD value of the Cells+TNFα controls of the 3 assay plates, a higher plateau within 25% of the average OD value of the Cells only controls of the 3 assay plates, and a linear part between the plateaus.
  The slope of each curve must be 0.7 and 3.5.
  The $r^2$ value for each curve must be 0.97.
  The RSD of the average $ED_{50}$ ratio values (n=6) must be 25%.
  The mean slope ratio between the test article and reference standard curves is ≥0.8 and ≤1.2, which assures that the slope values of the test article and reference standard curves are comparable (with no more than a 20% difference).
  The mean upper asymptote value of the test article neutralization curves does not differ from that of reference standard by more than 10% (difference in mean upper asymptote values≤10%).
  The mean lower asymptote value of the test article neutralization curves does not differ from that of reference standard by more than 15% (difference in mean lower asymptote values≤15%).

Methods for Determining Oligosaccharide Composition
Oligosaccharide Profile of Golimumab Golimumab is N-glycosylated at a single site on each heavy chain, on asparagine 306. These N-linked oligosaccharide structures can be any in a group of biantennary oligosaccharide structures linked to the protein through the primary amine of the asparagine residue, but on golimumab they consist primarily of biantennal core-fucosylated species, with galactose and sialic acid heterogeneity. Individual oligosaccharide species include "G0F", an asialo, agalacto core-fucosylated biantennary glycan, "G1F", an asialo, mono-galacto core-fucosylated biantennary glycan, and "G2F", an asialo, di-galacto core-fucosylated biantennary glycan. Golimumab glycosylation is monitored as an in-process control during Stage 9 of manufacturing, with specifications in place for total neutral oligosaccharides, total charged oligosaccharides, and individual neutral oligosaccharide species G0F, G1F, and G2F. A diagrammatic overview of some of the primary N-linked oligosaccharide species in golimumab IgG is shown in FIG. 21. The role of some of the enzymes in the glycosylation maturation process, including roles of some divalent cations (e.g. $Mn^{2+}$ and $Cu^{2+}$) in these enzymatic processes are also shown.

Oligosaccharide Composition by HPLC

The N-linked oligosaccharide composition of golimumab is determined with a normal phase anion exchange HPLC method with fluorescent detection using an Agilent 1100/1200 Series HPLC System with Chemstation/Chemstore software. To quantitate the relative amounts of glycans, the N-linked oligosaccharides are first cleaved from the reduced and denatured test article with N-glycanase (PNGase F). The released glycans are labeled using anthranilic acid, purified by filtration using 0.45-μm nylon filters, and analyzed by normal phase anion exchange HPLC with fluorescence detection. The HPLC chromatogram serves as a map that can be used to identify and quantitate the relative amounts of N-linked oligosaccharides present in the sample. Glycans are identified by co-elution with oligosaccharide standards and by retention time in accordance with historical results from extensive characterizations. A representative HPLC chromatogram for a golimumab reference standard is shown FIG. 22.

The amount of each glycan is quantitated by peak area integration and expressed as a percentage of total glycan peak area (peak area %). Results can be reported for G0F, G1F, G2F, total neutrals and total charged glycans. Other neutrals are the sum of all integrated peaks between 17 and 35 minutes, excluding the peaks corresponding to G0F, G1F and G2F. Total neutral glycans is the sum of G0F, G1F, G2F and the other neutrals. Total charged glycans is the sum of all mono-sialylated glycan peaks eluting between 42 and 55 minutes and all di-sialylated glycan peaks eluting between 78 and 90 minutes.

A mixture of oligosaccharide standards (G0F, G2F, G2F+N-acetylneuraminic acid (NANA) and G2F+2NANA) is analyzed in parallel as a positive control for the labeling reaction, as standards for peak identification, and as a measure of system suitability. Reconstituted oligosaccharides from Prozyme, G0F (Cat. No. GKC-004301), G2F (Cat. No. GKC-024301), SA1F (Cat. No. GKC-124301), and SA2F (Cat. No. GKC-224301), or equivalent, are used as reference standards. A method blank negative control and pre-labeled G0F standard are also run for system suitability purposes. The following system suitability and assay (test article) acceptance criteria are applied during the performance of the oligosaccharide mapping procedure in order to yield a valid result:

System Suitability Criteria:
  1. Resolution (USP) between the G0F and G2F peaks in the oligosaccharide standard must be ≥3.0.
  2. Theoretical plate count (tangent method) of the G0F peak in the oligosaccharide standards must be ≥5000.
  3. The total glycan peak area for the golimumab reference standard must be ≥1.5 times of the major glycan peak area of the pre-labeled G0F.
  4. If any reference standard glycan peak is off-scale, the reference standard is re-injected with less injection volume
  5. The retention time of G0F peak in the golimumab reference standard must be within 0.4 min of the G0F retention time in the oligosaccharide standards.

Assay Acceptance Criteria:
  The method blank must have no detectable peaks that co-elute with assigned oligosaccharide peaks in golimumab.
  The total glycan peak area of each test article must be ≥1.5 times the major glycan peak area of the pre-labeled G0F standard.
  If any sample glycan peak is off-scale, that sample is re-injected with less injection volume, together with pre-labeled G0F, the oligosaccharide standards, Method Blank and reference standard with normal volume.

The retention time for the G0F peak in each test article must be within 0.4 min of the retention time for the G0F peak in the oligosaccharide standards.

If the assay fails to meet any acceptance criteria, the assay is invalidated

Oligosaccharide Composition by IRMA

The IdeS-RMA (IRMA) method allows differentiation between major glycoforms by Reduced Mass Analysis (RMA) after the enzymatic treatment of immunoglobulin G (IgG) with FabRICATOR®, an IgG degrading enzyme of *Streptococcus pyogenes* (IdeS) available from Genovis AB (SKU: A0-FR1-050). See also, for example, U.S. Pat. No. 7,666,582. Reduced Mass Analysis (RMA) involves disulfide bond reduction of antibodies followed by the intact mass analysis of the heavy chain of the antibody and its attached glycan moieties. Some antibodies show a large degree of heterogeneity due to the presence of N-terminal modifications such as pyroglutamate formation and carboxylation. Consequently, disulfide reduction and heavy chain mass measurement results in a complex pattern of deconvoluted peaks. Therefore, in some applications, proteolytic generation of antibody fragments is desired over generation of light and heavy chains using reduction agents such as dithiothreitol (DTT). Traditionally papain and pepsin are used to generate antibody fragments all of which are laborious processes. Cleavage of IgG with pepsin requires extensive optimization and it is done at low acidic pH. Papain needs an activator and both F(ab')2 and Fab can be obtained depending on the reaction conditions resulting in a heterogeneous pool of fragments. These drawbacks can be circumvented by using the novel enzyme, FabRICATOR®. The cleavage procedure is very fast, simple, and importantly no optimization is needed. It is performed at neutral pH generating precise F(ab')2 and Fc fragments. No further degradation or over-digestion is observed as is commonly associated with other proteolytic enzymes like pepsin or papain. Importantly, as FabRICATOR® cleaves just C-terminally of the disulfide bridges in the heavy chain, no reduction step is required and an intact F(ab')2 and two residual Fc fragments are obtained.

Definitions

H: hexose (mannose, glucose, and galactose)
Man5: mannose 5
N: N-acetylhexosamine (N-acetylglucosamine and N-acetylgalactosamine)
F: fucose
S: sialic acid (N-acetylneuraminic acid (NANA) and N-glycolylneuraminic acid (NGNA))
G0: asialo-agalacto-afucosylated biantennary oligosaccharide
G0F: asialo-agalacto-fucosylated biantennary oligosaccharide
G1: asialo-monogalactosylated-afucosylated biantennary oligosaccharide
G1F: asialo-monogalactosylated-fucosylated biantennary oligosaccharide
G2: asialo-digalactosylated-afucosylated biantennary oligosaccharide
G2F: asialo-digalactosylated-fucosylated biantennary oligosaccharide
GlcNAc: N-Acetyl-D-Glucosamine
Lys: Lysine
−Lys: Truncated heavy chain (no C-terminal Lysine residue present)
+Lys: Heavy chain containing C-terminal Lysine
ppm: parts per million Equipment
Thermo Scientific Q Exactive (Plus) mass spectrometer
Agilent 1200 HPLC system
Applied Biosystems POROS R2/10 2.1 mmD×100 mmL column
Thermo Scientific Q Exactive Tune software
Thermo Scientific Protein Deconvolution software
Analytical balance capable of weighing 0.01 mg
Vortex mixer, any suitable model
Water bath or heating block, any suitable model
Calibrated Thermometer—10 to 110° C., any suitable model
Calibrated Pipettes
Microcentrifuge, any suitable model Procedure IdeS Digestion of Samples
samples (equal to 50 µg IgG).
add 1 µl (50 units) of IdeS enzyme to 50 µg of IgG, vortex briefly, spin down, and incubate at 37° C. for 30 minutes (stock enzyme @ 5000 units per 100 µl. 1 unit of enzyme fully digests 1 µg of IgG in 30 minutes at 37° C.)
spin down samples and transfer to LC-MS vials, and load sample vials into Agilent 1200 autosampler LC-MS Method Solution Preparation
Mobile phase A (0.1% Formic Acid (FA) in ultrapure water)—Add 999 mL of ultrapure water to a 1 L HPLC Mobile phase bottle, add 1 mL FA and stir. This solution can be stored at RT for 2 months.
Mobile phase B (0.1% FA, 99.9% acetonitrile)—Add 999 mL of acetonitrile to a 1 L HPLC Mobile phase bottle, add 1 mL FA and stir. This solution can be stored at RT for 2 months.

LC Method
Column: Applied Biosystems POROS R2/10 2.1 mmD× 100 mmL
Column temperature: 60° C.
Auto sampler temperature: 4° C.
Flow rate: 300 µL/min
Injection volume: 5 µL
Mobile phase A: 0.10% FA in ultrapure water
Mobile phase B: 0.1% FA in acetonitrile

TABLE 6

LC Gradient Table

| Time (min) | % Mobile phase B |
|---|---|
| 0.0 | 10 |
| 6.0 | 30 |
| 11.9 | 42 |
| 12.0 | 95 |
| 15.9 | 95 |
| 16.0 | 10 |
| 21.0 | 10 |

MS Method
Scan Parameters:
Scan type: Full MS
Scan range: 700 to 3500 m/z
Fragmentation: In-source CID 35.0 eV
Resolution: 17500
Polarity: Positive Lock masses: On, m/z 445.12002
AGC target: 3e6
Maximum injection time: 250
Hesi Source:
Sheath gas flow rate: 32
Aux gas flow rate: 7
Sweep gas flow rate: 0
Spray voltage (|kV|): 4.20
Capillary temp. (° C.): 280
S-lens RF level: 55.0
Heater temp. (° C.): 80

Data Analysis

The relative content of each detected glycan species is recorded based on analysis of deconvoluted mass spectra. FIG. 23 shows a representative deconvoluted mass spectrum for IRMA analysis of golimumab produced in Sp2/0 cells. The major structures determined by IRMA analysis include, e.g., Man 5 (H5N2), G0 (H3N4), G0F (H3N4F1), G1F-GlcNAc (H4N3F1), H5N3 G1 (H4N4), H5N3F1, G1F (H4N4F1), G2 (H5N4), G2F (H5N4F1), G1FS (H4N4F1S1), H6N4F1, G2FS (H5N4F1S1), H7N4F1, H6N4F1S1, G2FS2 (H5N4F1S2). The percentage of each of these structures is monitored. The measured peak intensity represents the percentage of each structure after normalization (% of Total Assigned). Glycans of which the observed mass is outside the 100 ppm mass deviation threshold are not included in the calculations, e.g., *G1F-GlcNAc-Lys, *H5N3-Lys, *G1-Lys, *H5N3F1-Lys, and *G2-Lys. As noted, these are indicated with an asterisk ("*"). Also, Man5-Lys is not always detected in the spectra since it has a very low intensity, nevertheless it is considered and included into the calculations when present. The percentage of a glycan is calculated as detected on both isoforms of the Fc fragment with and without terminal Lysine, e.g., percentage G0F is (% G0F−Lys+% G0F+Lys). Structures detected on only one of the heavy chain isoforms are indicated with a double asterisk (""), e.g., G1F−GlcNAc+Lys, H5N3+Lys, G1+Lys, H5N3F1+Lys, G2+Lys, G2FS−Lys, H6N4F1S1−Lys, G2FS2−Lys, H6N4F1−Lys, **H7N4F1−Lys. Most of these structures are low abundant and cannot be resolved from adjacent peaks with higher intensities or are below the detection capabilities of the method.

Note: Differences between the HPLC and IRMA methods (e.g., see Table 7 below) may result from co-elution of species in HPLC and possibly underestimation of some sialylated species by IRMA because some of the intensities are very close to the detection capabilities of the IRMA method.

TABLE 7

Glycan abundance comparison for IRMA and HPLC for a representative golimumab sample produced in Sp2/0 cells

| Glycan Group | IRMA % | HPLC % |
| --- | --- | --- |
| G0F | 28.7 | 32.5 |
| G1F | 31.7 | 36.4 |
| G2F | 10.5 | 9.9 |
| Other neutral oligosaccharides | 15.2 | 6.8 |
| Total neutral oligosaccharides | 86.1 | 85.7 |
| Monosialylated | 12.6 | 13.8 |
| Disialylated | 1.3 | 0.6 |
| Total charged oligosaccharides | 13.9 | 14.3 |

Deamidation and Deamidation Assay

Deamidation

Cyclic imide mediated reactions, including deamidation, isomerization, and cyclization, constitute a common degradation pathway in proteins. The reactions occur primarily at asparagine in the protein chain but are also observed for glutamine, aspartic acid, and glutamic acid (Aswad, D. W. (1995). Deamidation and isoaspartate formation in peptides and proteins. Boca Raton, CRC Press). Commonly observed byproducts include aspartic acid, iso-aspartic acid, glutamic acid, and stable cyclic imides.

Cyclic imide formation at asparagine residues usually involves nucleophilic attack from the amino group of the carboxyl amino acid residue on the carbonyl carbon of asparagine, leading to deamidation (FIG. 24) (Voorter, C. E., et al. (1988). "Spontaneous peptide bond cleavage in aging alpha-crystallin through a succinimide intermediate." J Biol Chem 263(35): 19020-19023). Alternately, the asparagine amide nitrogen can attack the peptide bond carbonyl, leading to chain cleavage (FIG. 24). The rate of reaction is affected by primary structure (Asn-Gly reacts fastest, followed by Asn-Ser, Asn-His, and Asn-Thr), tertiary structure (residues in flexible, exposed regions react faster than non-exposed residues), pH (elevated pH can accelerate the reaction), and buffer (bicarbonate and especially phosphate anions accelerate reaction).

Forced deamidation of golimumab was examined in order to ensure that analytical procedures employed for release and stability testing were capable of detecting the degradants formed. The information also helped in establishing specified limits for common degradant species as part of an overall strategy to control the manufacturing process. The results of the forced degradation studies showed that the most prevalent degradation pathway observed for golimumab involved cyclic imide mediated reactions, in particular significant deamidation of heavy chain (HC) asparagine 43 (HC Asn43) and to a lesser extent also the formation of a cyclic succinimide at light chain (LC) Asn93 (designated LC cycAsn93). The cyclic imide mediated reactions are monitored during the manufacturing process and during storage using a deamidation assay, but the primary assay to monitor deamidation of golimumab is the capillary isoelectric focusing procedure (cIEF). Both assays are described below.

Deamidation Assay

The deamidation method uses Lys C peptide mapping to resolve and quantitate native and deamidated peptides related to deamidation at HC Asn43 and LC Asn93. The method employs desalting of 200 μg of protein on a reversed-phase HPLC column to remove the sample matrix. A single sample of the test article is subsequently reduced (dithiothrietol), alkylated (iodoacetamide), and digested for four hours at 37° C. using endoproteinase Lys C. After digestion, the Lys C enzyme is inactivated using trifluoroacetic acid, and the resulting peptides are separated on a C18 reversed-phase HPLC column (2.1 mm×250 mm, ~20 μg injection) with a gradient of water and acetonitrile containing 0.10% trifluoroacetic acid.

The method is able to resolve the native LC40-104 peptide having Asn93, from the deamidated peptides, LC40-104 (LC isoAsp93 and LC Asp93), and LC40-104 (LC cycAsn93). Two native peptides having Asn43 (HC1-58 and HC1-59) are separated from the deamidated peptides having the deamidated forms (isoAsp43 and Asp43). UV absorbance at 214 nm is used to detect and quantitate the eluting peptides. The native and deamidated peptide peaks are integrated, and the peak areas are used to calculate the relative amounts (%) of native LC Asn93 and HC Asn43, total deamidated forms of HC Asn43 (HC isoAsp43+HC Asp43) and LC Asn93 (LC isoAsp93+LC Asp93+LC cycAsn93) and relative amounts of HC isoAsp43. A representative Lys C peptide mapping chromatogram for golimumab is shown in FIG. 25. In addition, peptide map chromatograms from a time course of forced deamidation of golimumab are shown in FIG. 26. The chromatograms are from the region with the HC 1-58 and HC 1-59 peptides and show the two Asp43 peptides increasing while the native Asn43 peptides and isoAsp43 peptides are decreasing.

System Suitability:

System suitability is evaluated prior to test article analysis through injection of a golimumab reference standard (RS) to ensure proper sample preparation, operation, and column separation efficiency (resolution).

The chromatogram of the RS injection must be visually similar to a representative chromatogram for reference material of golimumab. If the chromatogram is not visually similar, then the HPLC analysis, the enzyme digest or both failed, and the assay must be repeated.

The resolution of the HC 1-59 Asp43 and HC 1-58 Asp43 peptide peaks must be greater than or equal to 1.1 (identified in a representative chromatogram in the SOP). If the resolution is not ≥1.1, the cause of the resolution failure must be corrected, and the run must be repeated.

Golimumab test article samples must be bracketed by the RS at the beginning and the end of the procedure.

Golimumab test article samples must be bracketed by the RS.

The LC Asn93 deamidation results at the beginning and the end of the run must be ≤5.8% (the current specification), and their difference must be ≤0.9%.

The HC isoAsp43 result at the beginning and the end of the run must be between ≤30%, and their difference must be ≤2.0%.

Capillary Isoelectric Focusing

Capillary isoelectric focusing (cIEF) separates proteins on the basis of overall charge or isoelectric point (pI). The method is used to monitor the distribution of charge-based isoforms in golimumab. Unlike the gel-based IEF procedures, cIEF provides a quantitative measure of the charged species present. In addition, cIEF shows increased resolution, sensitivity, and reproducibility compared to the gel-based method. The cIEF procedure separates 4 to 6 charge-based isoforms of golimumab with nearly baseline resolution, while IEF gel analysis separates only 4 to 5 species with partial resolution. A representative cIEF electropherogram of golimumab expressed in Sp2/0 cells is shown in FIG. 27, with the four major peaks labeled as C, 1, 2, and 3 and minor peak labeled B. A graphic representing the general relationship between cIEF peaks and decreasing negative charge/degree of sialylation is also shown.

The cIEF assay is performed on a commercially available imaging cIEF analyzer equipped with an autosampler able to maintain sample temperature<10.5° C. in an ambient environment of <30° C., such as the Alcott autosampler (GP Instruments, Inc.). The analysis employs an inner wall-coated silica capillary without an outer wall polyimide coating to allow for whole column detection. In addition, an anolyte solution of dilute phosphoric acid and methylcellulose, a catholyte solution of sodium hydroxide and methylcellulose, and a defined mixture of broad range (pH 3-10) and narrow range (pH 8-10.5) ampholytes are used. The assay employs a pre-treatment of both test articles and Reference Standard (RS) with carboxypeptidase B (CPB) which removes the heavy chain C-terminal lysine and eliminates ambiguities introduced by the presence of multiple C-terminal variants.

Before each analysis, the autosampler temperature setpoint is set to 4° C. and the autosampler is pre-cooled for at least 30 minutes and the ambient room temperature of the lab is maintained 30° C. The pre-treated test article and RS, sample vials, vial inserts, the reagents used in the assay including purified water, the parent solution containing N,N,N',N'-Tetramethylethylenediamine (TEMED) (which optimizes focusing within the capillary), ampholytes, pI 7.6 and 9.5 markers for internal standards and methylcellulose (MC) are kept on ice for at least 30 minutes before starting sample preparation. The samples are prepared on ice and the time of addition of the parent solution is recorded and exposure to TEMED is controlled. The assay must be completed within 180 minutes after this addition. System suitability controls are injected once, and test articles and RS are injected twice following the sequence table below (Table 8):

TABLE 8

Sample Running Sequence

| Sample Name | Sample Vial Position | Number of Injections |
| --- | --- | --- |
| System Suitability | 1 | 1 |
| Blank | 2 | 1 |
| CPB Control | 3 | 1 |
| CPB Treated RS | 4 | 2 |
| CPB Treated Sample 1 | 5 | 2 |
| CPB Treated RS | 6 | 2 |

After the samples are injected into the capillary by a syringe pump, an electric field (3 kV) is applied across the capillary for 8 min, forming a pH gradient, and charge-based isoforms of golimumab are separated according to their isoelectric point (pI). The protein isoforms in the capillary are detected by imaging the entire capillary at 280 nm, and the data are presented in the form of an electropherogram as a function of pI value vs A280. Values for pI are assigned by comparison to the internal pI standards (pI 7.6 and 9.5) using the instrument software, and peak areas are determined from the electropherogram using standard data acquisition software. The average pI and average peak area percentage from duplicate injections of all peaks≥LOQ, the ΔpI value compared to Reference Standard, and the sum of percent area of peaks C, 1, 2, and 3 are reported.

System Suitability Criteria:

The following system suitability and assay acceptance criteria are applied during the performance of the cIEF procedure in order to yield a valid result:

1. For the System Suitability Standard, four pI marker peaks must be clearly visible. The middle two peaks (pI 8.7 and pI 9.0 markers) must be baseline resolved, with Resolution Factor (R)≥5.0 by USP method.
2. The two pI marker peaks (pI 7.6 and pI 9.5) must be observed in the Blank, CPB Control, CPB treated RS, and CPB treated samples.
3. There must be no peaks between pI 7.6 and pI 9.5 marker peaks in the region of analysis in the Blank.
4. There must be no peaks between pI 7.6 and pI 9.5 marker peaks in the region of analysis in CPB Control.
5. The tray temperature of the autosampler must be maintained≤8° C. for all injections. This criterion is specific for the Alcott autosampler and must be reestablished for any new type of autosampler as part of instrument qualification to maintain sample temperature≤10.5° C.

6. The ambient room temperature of the lab must be maintained≤30° C. throughout the assay.

7. The electropherograms of the duplicate injections must look similar to each other (as defined in criteria 8 and 9). If the electropherograms of the duplicates do not look similar, the data for that sample is considered invalid.

8. For CPB treated RS, Peaks C, 1, 2, and 3 must be observed. The pI range of peaks 1, 2, and 3 must be between 8.6 and 9.4. The sum of the peak heights of the peaks 1, 2, and 3 must be 15,000.

9. For CPB treated sample, Peaks C, 1, 2, and 3 must be observed. The pI range of peaks 1, 2, and 3 must be between 8.6 and 9.4. The sum of the peak heights of the peaks 1, 2, and 3 peaks must be ≥15,000.

10. Test article samples must be bracketed by RS at the beginning and end of the assay.

11. The last injection of CPB treated RS must be completed within 3 hours of addition of the parent solution.

12. The percent area of Peak 3 for RS at the beginning of the run must be between 16.1 and 19.5%. These values are specific for RS Lot 08G31AA and a new range will be established for each new lot of RS as part of its qualification procedure.

13. The percent area of Peak 3 for RS at the end of the run must be between 15.4 and 19.2%. These values are specific for RS Lot 08G31AA and a new range will be established for each new lot of RS as part of its qualification procedure.

14. The difference in percent area of Peak 3 result for RS at the beginning of the run and the RS result at the end of the run must be <0.5%

Characterization of Golimumab cIEF Isoforms

The reference cIEF profile of golimumab produced on Sp2/0 cells contains four major peaks labeled as C, 1, 2, and 3 and minor peak B as shown in the representative electropherogram (FIG. 27). A minor peak A is also sometimes observed. For golimumab, the major source of variability in the cIEF profile is the deamidation and isomerization of heavy chain asparagine 43 (HC Asn43). Basic Peak 3 in cIEF represents non-deamidated HC Asn43 as well as deamidated heavy chain isoaspartic acid 43 (HC isoAsp43), while the more acidic peaks represent deamidated HC Asp43 and degree of sialylation. The predicted identities of the different cIEF peaks are listed in Table 9.

TABLE 9

Identities for Peaks Observed in cIEF Electropherogram of Golimumab

| cIEF Peak | Identity of Major Species | Identity of Minor Species |
| --- | --- | --- |
| B | 2 HC Asp43, 2 SA | HC Asp43, HC isoAsp43, 3 SA 2 HC isoAsp43, 4 SA |
| C | 2 HC Asp43, 1 SA | HC Asp43, HC isoAsp43, 2 SA 2 HC isoAsp43, 3 SA |
| 1 | 2 HC Asp43 | HC Asp43, HC isoAsp43, 1 SA 2 HC isoAsp43, 2 SA |
| 2 | HC Asp43, HC isoAsp43 | 2 HC isoAsp43, 1 SA HC Asp43, HC Asn43 |
| 3 | 2 HC isoAsp43 | HC isoAsp43, HC Asn43 |

$^a$SA is sialic acid; variants containing HC Asn43 in place of Asp43 or isoAsp43 are also present at low levels but are not included in the table.

Effect of LC Asn93 Deamidation on Golimumab Potency

As noted above, another site for deamidation of golimumab is LC Asn93. Considering that LC Asn93 is located in a CDR of golimumab, it is important to understand if modifications at the site affect antigen binding and activity of the anti-TNF antibody. Deamidation of LC Asn93 results in the formation of a cyclized intermediate that is relatively stable and is detected as cycAsn93 with the deamidation assay. To understand how deamidation of LC Asn93 affects potency, a correlation analysis was performed by plotting % LC cycAsn93 versus potency for a number of different batches of golimumab with varying % LC cycAsn93 (FIG. 28). The results showed a statistically significant correlation with a Pearson bivariate correlation coefficient of −0.782 ($p<0.0001$). Although evidence of correlation does not prove a causal relationship, when coupled with the location of LC Asn93 in a CDR the results suggest that cyclization of LC Asn93 affects potency. Based on the correlation analysis (FIG. 28) and data qualified in clinical studies, deamidation acceptance criteria for total LC Asn93 deamidation were established. Those data are presented in U.S. Prov. App. No. 62/695,859, filed Jul. 10 2018. Alternatively, results for potency (bioactivity assay) may also serve as a surrogate measure for LC Asn93 deamidation, i.e., significantly high potency suggests that there is only limited LC Asn93 deamidation.

Introduction to Manufacturing Control Strategies

During large-scale commercial production, manufacturing control strategies are developed to maintain consistent drug substance (DS) and drug product (DP) characteristics of therapeutic proteins with regard to bioactivity (potency), oligosaccharide profile, deamidation, and/or other characteristics of the DS and DP. For example, glycosylation, total % HC Asn43 deamidation, and total % LC Asn93 deamidation are monitored as in-process controls for formulated bulk (FB) at Stage 9 of the manufacturing process of the therapeutic antibody golimumab. For golimumab glycosylation, there are upper and lower specifications in place for mean % total neutral oligosaccharides, % total charged oligosaccharides, and % individual neutral oligosaccharide species, G0F, G1F, and G2F. These control measures are necessary, because regulatory agencies require adherence to certain lot release specifications to ensure a consistent, safe and effective product.

Heavy Chain N43D Mutant (HC N43D)

After recognizing that the major source of variability in the cIEF profile of golimumab is the deamidation of heavy chain asparagine 43 (HC Asn43), work was initiated to eliminate that variability. One aspect of that work was to establish a manufacturing operating range (MOR) for processes during manufacturing of golimumab to ensure that DP remained within a limit for total deamidation of ≤79% for HC Asn43 that was qualified in previous clinical studies. The established MOR also considered the impact of HC Asn43 deamidation on the cIEF profile for golimumab and ensured that DS and DP batches released within the cIEF specifications would remain within specification during the 22-month shelf life. Those data are presented in U.S. Prov. App. No. 62/695,859, filed Jul. 10, 2018. A second strategy was to eliminate the variation at the source, by introducing an aspartic acid residue (Asp, D) in place of the asparagine residue (Asn, N) at amino acid 43 of the heavy chain (HC) of golimumab. That mutant is referred to herein as golimumab HC N43D (HC N43D). The sequence comparison is included below for golimumab and golimumab HC N43D.

Sequences:

Golimumab

Heavy chain asparagine (Asn, N) 43 (HC N43) is shown underlined and in bold text in SEQ ID NO:36 below. Heavy chain CDRs (HCDRs) and light chain CDRs (LCDRs) are underlined in the heavy chain and light chain of golimumab (defined by Kabat). Note that HC N43 is located in heavy chain framework region 2 (HFR2), between HCDR1 and HCDR2. Framework regions are highly conserved regions of the variable region of an antibody that provide for proper protein folding during expression and stabilization of the CDR regions of the mature antibody, and mutations may affect the binding properties of the antibody (Ovchinnikov et al. Role of framework mutations and antibody flexibility in the evolution of broadly neutralizing antibodies. *eLife.* 2018; 7: e33038).

Controlling Oligosaccharide Profile

In addition to controlling deamidation, controlling the oligosaccharide profile of therapeutic antibodies is also critical because changes in the oligosaccharide profile of a recombinant monoclonal antibody can significantly affect antibody biological functions. For example, biological studies have shown that the distribution of different glycoforms on the Fc region can significantly impact antibody efficacy, stability, and effector function (*J. Biosci. Bioeng.* 2014 117(5):639-644; *Bio-Process Int.* 2011, 9(6):48-53; *Nat. Rev. Immunol.* 2010, 10(5):345-352). In particular, afucosylation (*J. Mol. Biol.* 368:767-779) and galactosylation (*Biotechnol. Prog.* 21:1644-1652) can play a huge role in the

```
                    Heavy Chain (HC) - SEQ ID NO: 36

1 QVQLVESGGG VVQPGRSLRL SCAASGFIFS SYAMHWVRQA PGNGLEWVAF MSYDGSNKKY

61 ADSVKGRFTI SRDNSKNTLY LQMNSLRAED TAVYYCARDR GIAAGGNYYY YGMDVWGQGT

121 TVTVSSASTK GPSVFPLAPS SKSTSGGTAA LGCLVKDYFP EPVTVSWNSG ALTSGVHTFP

181 AVLQSSGLYS LSSVVTVPSS SLGTQTYICN VNHKPSNTKV DKKVEPKSCD KTHTCPPCPA

241 PELLGGPSVF LFPPKPKDTL MISRTPEVTC VVVDVSHEDP EVKFNWYVDG VEVHNAKTKP

301 REEQYNSTYR VVSVLTVLHQ DWLNGKEYKC KVSNKALPAP IEKTISKAKG QPREPQVYTL

361 PPSRDELTKN QVSLTCLVKG FYPSDIAVEW ESNGQPENNY KTTPPVLDSD GSFFLYSKLT

421 VDKSRWQQGN VFSCSVMHEA LHNHYTQKSL SLSPGK 456

Light chain (LC) - SEQ ID NO: 37

1 EIVLTQSPAT LSLSPGERAT LSCRASQSVY SYLAWYQQKP GQAPRLLIYD ASNRATGIPA

61 RFSGSGSGTD FTLTISSLEP EDFAVYYCQQ RSNWPPFTFG PGTKVDIKRT VAAPSVFIFP

121 PSDEQLKSGT ASVVCLLNNF YPREAKVQWK VDNALQSGNS QESVTEQDSK DSTYSLSSTL

181 TLSKADYEKH KVYACEVTHQ GLSSPVTKSF NRGEC
```

Golimumab HC N43D

Heavy chain aspartic acid (Asp, D) 43 (HC N43D) is shown underlined and in bold text in SEQ ID NO:38 below antibody-dependent cell-mediated cytotoxicity (ADCC) and complement-dependent cytotoxicity (CDC), two important mechanisms by which antibodies mediate killing target cells

```
                    Heavy Chain (HC) - SEQ ID NO: 38

1 QVQLVESGGG VVQPGRSLRL SCAASGFIFS SYAMHWVRQA PGDGLEWVAF MSYDGSNKKY

61 ADSVKGRFTI SRDNSKNTLY LQMNSLRAED TAVYYCARDR GIAAGGNYYY YGMDVWGQGT

121 TVTVSSASTK GPSVFPLAPS SKSTSGGTAA LGCLVKDYFP EPVTVSWNSG ALTSGVHTFP

181 AVLQSSGLYS LSSVVTVPSS SLGTQTYICN VNHKPSNTKV DKKVEPKSCD KTHTCPPCPA

241 PELLGGPSVF LFPPKPKDTL MISRTPEVTC VVVDVSHEDP EVKFNWYVDG VEVHNAKTKP

301 REEQYNSTYR VVSVLTVLHQ DWLNGKEYKC KVSNKALPAP IEKTISKAKG QPREPQVYTL

361 PPSRDELTKN QVSLTCLVKG FYPSDIAVEW ESNGQPENNY KTTPPVLDSD GSFFLYSKLT

421 VDKSRWQQGN VFSCSVMHEA LHNHYTQKSL SLSPGK 456

Light chain (LC) - SEQ ID NO: 37 LC

1 EIVLTQSPAT LSLSPGERAT LSCRASQSVY SYLAWYQQKP GQAPRLLIYD ASNRATGIPA

61 RFSGSGSGTD FTLTISSLEP EDFAVYYCQQ RSNWPPFTFG PGTKVDIKRT VAAPSVFIFP

121 PSDEQLKSGT ASVVCLLNNF YPREAKVQWK VDNALQSGNS QESVTEQDSK DSTYSLSSTL

181 TLSKADYEKH KVYACEVTHQ GLSSPVTKSF NRGEC
``` through the immune function. In addition, high mannose levels have been shown to adversely affect efficacy by increasing clearance of the antibody (*Glycobiology*. 2011, 21(7):949-959) and sialic acid content can affect anti-inflammatory activity (*Antibodies*. 2013 2(3):392-414). As a result of these biological consequences from changes in the oligosaccharide profile, certain regulatory agencies require control of the antibody glycosylation pattern to ensure adherence to lot release specifications.

Oligosaccharide Profile—Effects from Expression in Different Cells

Two commonly used host cell lines for the recombinant expression of antibodies are Chinese hamster ovary cells (CHO) and mouse myeloma cells (e.g., Sp2/0 cells). CHO cells express recombinant antibodies which can be virtually devoid of sialic acid glycan and the glycans can be up to 99% fucosylated. In contrast, mouse myeloma cells express recombinant antibodies that can contain up to 50% sialic acid and generally have less fucose. These differences can have significant effects on antibody activity in vivo, e.g., it has been shown that such differences can affect the structure of the Fc-portion of the molecule and thereby alter antibody effector functions such as antibody-dependent cellular cytotoxicity (ADCC) and complement-dependent cytotoxicity (CDC) (see, e.g., U.S. Pat. No. 8,975,040). For example, reduced ADCC activity has been noted with increased sialylated (charged) Fc glycans (Scallon et al. *Mol Immunol* 2007; 44:1524-34).

The effects on ADCC activity may be particularly important for anti-TNF antibodies because it has been suggested that for some approved indications a crucial mode of action (MOA) for anti-TNF antibodies may be destruction of TNF-α producing cells through ADCC, e.g., for treating inflammatory bowel disease (IBD), such as Crohn's disease (CD) and/or ulcerative colitis (UC). It has also been shown that Flixabi®, a CHO derived biosimilar of Remicade® (infliximab), has a higher mean ADCC activity in a NK92-CD16a cell line. Infliximab is produced in Sp2/0 cells and has an oligosaccharide profile that has a higher percentage of charged glycan than Flixabi® that is produced in CHO cells (Lee et al. *MAbs*. 2017 August; 9(6): 968-977). Accordingly, it may be desirable to reduce sialylation and thus the percentage of charged glycans associated with anti-TNF antibodies.

In addition, antibodies produced in CHO and Sp2/0 cells can have significant differences in the levels of two glycan epitopes, galactose-α-1,3-galactose (α-gal) and the sialylated N-glycan Neu5Gc-α-2-6-galactose (Neu5Gc). For example, it has been shown that CHO cells can express antibodies with undetectable or only trace levels of α-Gal and Neu5Gc, while Sp2/0 cells can express much higher levels of the two glycan structures (Yu et al., *Sci Rep*. 2016 Jan. 29; 7:20029). In contrast, humans are genetically deficient in the gene for biosynthesizing α-gal and the gene responsible for production of Neu5Gc is irreversibly mutated in all humans. As a result, α-Gal and Neu5Gc are not produced in humans. Furthermore, the presence of these non-human glycan epitopes on therapeutic antibodies can cause undesirable immune reactions in certain human populations because of higher levels of pre-existing antibodies to α-Gal and Neu5Gc. For example, anti-α-gal IgE mediated anaphylactic responses have been reported for cetuximab (Chung, C. H. et al., *N Engl J Med*. 2008 Mar. 13; 358(11): 1109-17) and the presence of circulating anti-Neu5Gc antibodies has been reported to promote clearance of cetuximab (Ghaderi et al., *Nat Biotechnol*. 2010 August; 28(8):863-7).

Description for small-scale production of golimumab HC N43D in CHO cells Cloning The CHO cell line was originally created by T. T. Puck from the ovary of an adult Chinese hamster. CHO-K1 (ATCC® CCL-61) is a subclone of the parental CHO cell line that lacks the proline synthesis gene. CHO-K1 was also deposited at the European Collection of Cell Cultures, CHO-K1 (ECACC 85051005). A master cell bank (MCB) of CHO-K1, 024 M, was established at Celltech Biologics (now Lonza Biologics) and used for adaptation of CHO-K1 to suspension culture and serum-free medium. The adapted cell line was named CHOK1SV. The CHOK1SV cell line was further adapted in protein-free medium to create a MCB of cells referred to as 269-M. Cells derived from the 269-M MCB were transfected as described below to create the CHO cell lines expressing golimumab HC N43D.

Cell lines were generated, expanded, and maintained in a humidified incubator at 37° C. and 5% $CO_2$ using cell culture plates and shake flasks. Routine seeding density in shake flasks was $3 \times 10^5$ viable cells per mL (vc/mL). All shake flask cultures were maintained at 130 revolutions per minute (rpm) with a 25 mm orbit and 96-deepwell (DW, Thermo Scientific, Waltham, MA, Cat. #278743) cultures were maintained at 800 rpm with a 3 mm orbit.

CHO clones expressing golimumab HC N43D were created using media identified as MACH-1, an in-house developed, chemically-defined medium for CHO cell culture. The basal medium for the routine passage of the CHO host cell line was MACH-1 supplemented with 6 mM L-glutamine (Invitrogen, Carlsbad, CA, Cat. #25030-081). CHO cells transfected with the glutamine synthetase (GS) gene were grown in MACH-1+MSX unless otherwise noted, which is MACH-1 supplemented with 25 µM L-methionine sulfoximine (MSX, Sigma, St. Louis, MO, Cat. #M5379-1G) to inhibit glutamine synthetase function. For bolus fed-batch shake flask and bioreactor experiments, cells were cultured in MACH-1+F8, which is MACH-1 supplemented with 8 g/kg F8 (a supplement of proprietary growth enhancers) to further support cell growth and antibody production. Proprietary feed media were used in shake flask and bioreactor experiments.

The DNA encoding the genes of interest were cloned into a glutamine-synthetase (GS) double gene expression plasmid (Lonza Biologics). Expression of the heavy chain (HC) and light chain (LC) genes were driven by separate human cytomegalovirus (hCMV-MIE) promoters. The GS gene selection marker, driven by the Simian Virus SV40 promoter, allows for the selection of transfected cells in glutamine-free media in the presence of MSX.

Prior to each transfection, 1 aliquot of plasmid DNA, containing both the HC and LC coding regions of golimumab HC N43D, was linearized by restriction enzyme digestion. A linearized 15 µg DNA aliquot was transfected into a $1 \times 10^7$ cell aliquot using the BTX ECM 830 Electro Cell Manipulator (Harvard Apparatus, Holliston, MA). Cells were electroporated 3 times at 250 volts with 15 millisecond pulse lengths and 5 second pulse intervals in a 4 mm gap cuvette. Transfected cells were transferred to MACH-1+L-glutamine in a shake flask and incubated for 1 day. Transfections were centrifuged, then resuspended in MACH-1+25 uM MSX for selection and transferred to shake flasks to incubate for 6 days.

Following chemical selection, cells were plated in a single cell suspension in custom glutamine-free Methocult™ medium containing 2.5% (w/v) methylcellulose in a Dulbecco's Modified Eagle's Medium (DMEM) base media (Methocult™, StemCell Technologies, Inc., Vancouver, BC, Cat. #03899). The working solution also contained 30% (v/v) gamma-irradiated dialyzed fetal bovine serum (dFBS.IR, Hyclone, Logan, UT, Cat. #SH30079.03), 1× GS Supplement (SAFC, St. Louis, MO, Cat. #58672-100M), 1.5 mg animal component-free Protein G Alexa Fluor™ 488 (immunofluorescent stain) conjugate (Protein G, Invitrogen, Carlsbad, CA, Cat. #C47010), 25 µM MSX, Dulbecco's Modified Eagle's Medium with F12 (DMEM/F12, Gibco/Invitrogen, Carlsbad, CA, Cat. #21331-020), and cell suspension.

Protein G recognizes human monoclonal antibodies and binds to the IgG that is secreted by the cells. The Protein G is conjugated to the fluorescent label Alexa Fluor™ 488 (immunofluorescent stain), so that cell colonies secreting the most antibodies will show the highest levels of fluorescence. After incubation for 12 to 18 days, colonies with the highest fluorescence levels were picked into 100 µL phenol red-containing MACH-1+MSX in 96-well plates using a ClonePix FL colony picking instrument (Molecular Devices, Sunnyvale, CA) and incubated without shaking for 5-7 days. After 5-7 days, cells from the 96-well plate were expanded by adding to 50-100 µL phenol red-containing MACH-1+MSX in a 96DW plate (Thermo Scientific, Waltham, MA, Cat. #278743) and shaken at 800 rpm with a 3 mm orbit. The 96DW plates were fed and at 7 days post 96DW seeding were titered via Octet (ForteBio, Menlo Park, CA). The top 10 cultures corresponding to the highest batch 96DW overgrow titers were expanded to shake flasks in MACH-1+MSX, and frozen cell banks were created with cells suspended in in MACH-1+MSX medium containing 10% DMSO.

Cell Culture for Small-Scale Production

As in large-scale production of golimumab, preculture, cell expansion, and cell production of golimumab HC N43D are performed in Stages 1 and 2 for small-scale production. In Stage 1, preculture is initiated from a single cell bank vial of transfected CHO cells expressing the HC and LC sequences of golimumab HC N43D (SEQ ID NO:38 and SEQ ID NO:37, respectively) and the cells are expanded in culture flasks. The cells are cultured until the cell density and volume required for inoculation of a 10-L production bioreactor are obtained. In Stage 2, the cell culture is run in fed-batch mode in a 10-L production bioreactor. For the duration of the 15-day bioreactor run the culture is fed as required with concentrated glucose-based and amino acid-based feeds. At the completion of the production bioreactor run cell culture harvest is clarified to remove biomass and filtered for further processing.

Purification

The purification steps for small-scale production of golimumab HC N43D were identical to the large-scale manufacturing process, except the Stage 8 virus filtration step was omitted for small-scale production. In brief, for small-scale production, purification of golimumab HC N43D from the cell culture harvest is performed in Stages 3 through 7 by a combination of affinity and ion exchange chromatography steps and steps to inactivate or remove potential virus contamination (solvent/detergent treatment and virus removal). In Stage 3, harvest and/or pooled harvest is clarified and purified using Protein A affinity chromatography. The resultant direct product capture (DPC) eluate is frozen until further processing. DPC eluates are filtered and pooled in Stage 4 following thaw, and subsequently treated in Stage 5 with tri-n-butyl phosphate (TNBP) and polysorbate 80 (PS 80) to inactivate any lipid-enveloped viruses potentially present.

In Stage 6, TNBP and PS 80 reagents and impurities are removed from the golimumab HC N43D product using cation exchange chromatography. The golimumab HC N43D product is further purified using anion exchange chromatography in Stage 7 to remove DNA, potentially present viruses, and impurities. As noted above, Stage 8 filtering through a virus retentive filter was omitted from the small-scale product purification process.

Final preparation of golimumab HC N43D is performed in Stage 9 (reference to large-scale stages). The ultrafiltration step concentrates the golimumab HC N43D product, and the diafiltration step adds the formulation excipients and removes the in-process buffer salts. PS 80 is added, and the bulk intermediate is filtered into polycarbonate containers for frozen storage as formulated bulk.

Characterization of Golimumab HC N43D Expressed in CHO Cells

As shown in Table 10, except for shifts in cIEF peak percentages that are consistent with replacing HC Asn43 (HC N43) with HC Asp43 (HC N43D) and the elimination of deamidation at HC N43, there are only minor differences for golimumab and the golimumab HC N43D mutant expressed in CHO cells. Most importantly, the difference in bioactivity is within the acceptance criteria for large-scale commercial production of golimumab. Furthermore, the observed difference was likely caused by differences in processing (i.e., large-scale commercial production vs. small-scale production). Thus, it was concluded that there were no ill effects caused by the HC N43D mutation and that golimumab HC N43D is comparable to golimumab.

TABLE 10

Representative comparison of selected characteristics of golimumab expressed in Sp20 cells and golimumab with Heavy Chain N43D mutant (HC N43D) expressed in CHO cells

| Test | Parameter | Golimumab Sp2/0 | HC N43D CHO |
|---|---|---|---|
| DW-SE-HPLC | % Purity | 99.88% | 99.68% |
| | % Aggregate | 0.11% | 0.31% |
| | % Fragment | <LOD | <LOD |
| cSDS Reduced | % Purity | 98.7% | 98.3% |
| cSDS Non-Reduced | % Purity | 98.9% | 97.9% |
| Bioactivity | % Bioactivity | NA | 85%[a] |
| cIEF | peak 1 | 22.5% | 55.0% |
| | peak 2 | 37.1% | 27.5% |
| | peak 3 | 27.9% | 5.1% |
| | peak C | 8.4% | 9.6% |
| | peak B | 2.6% | 2.9% |
| | Peak A | 0.8% | <LOD |
| | Sum of major peaks: C, 1, 2, and 3 | 95.8% | 97.1% |
| Peptide mapping | HC N43 deamidation | 65% | NA |
| | C-terminal Lysine | 8.5% | 0.9% |
| IMW | Mass | NA | all within 42 Da* |

[a]Compared to golimumab reference material
<LOD—below limit of detection
NA—Not Applicable for bioactivity and mass of golimumab reference material and HC N43 deamidation for HC N43D mutant
*No SA detected in CHO HC N43D by IRMA Oligosaccharide of Golimumab Expressed in Sp2/0 Cells and Golimumab HC N43D expressed in CHO Cells Compiled HPLC data from multiple commercial production runs of golimumab showed that DS or DP produced in Sp2/0 cells comprises anti-TNF antibodies comprising total neutral oligosaccharide species≥82.0% to ≤94.4%, total charged oligosaccharide species≥5.6% to ≤18.0%, and individual neutral oligosaccharide species G0F>25.6% to ≤42.2%, G1F≥31.2% to ≤43.6%, and G2F≥5.6% to ≤14.2%. As shown in Table 11, the oligosaccharide profile of a golimumab HC N43D expressed in CHO cells is dramatically different from golimumab expressed in Sp2/0 cells. Compared to golimumab produced in Sp2/0 cells, the oligosaccharide profile for golimumab HC N43D produced in CHO cells is shifted toward very low levels of charged glycans and higher levels of neutral glycans that are predominantly G0F. The oligosaccharide profile for golimumab produced in CHO cells comprises total neutral oligosaccharide species>99.0%, total charged oligosaccharide species<1.0%, and individual neutral oligosaccharide species G0F>60.0%, G1F<20.0%, and G2F<5.0%. Furthermore, no disialylated glycan species were detected by IRMA or by HPLC for golimumab produced in CHO cells and monosialylated glycan species were at very low levels based on HPLC analysis and undetectable by IRMA analysis.

TABLE 11

Representative results for IRMA and HPLC analysis of total neutral, total charged, and other selected oligosaccharide species for golimumab produced in Sp2/0 cells and golimumab HC N43D expressed in CHO cells

| Glycans | IRMA | | HPLC | |
|---|---|---|---|---|
| | Golimumab Sp2/0 | HC N43D CHO | Golimumab Sp2/0 | HC N43D CHO |
| G0F | 29.2 | 75.9 | 32.0 | 86.9 |
| G1F | 31.6 | 9.1 | 36.0 | 9.6 |
| G2F | 9.5 | <LOD | 10.0 | 2.4 |
| Other neutral | 17.3 | 15.0 | 7.4 | 0.8 |
| Total neutral | 87.6 | 100.0% | 85.4 | 99.7 |
| Monosialylated | 11.6 | <LOD | 13.9 | 0.3 |
| Disialylated | 0.7 | <LOD | 0.7 | <LOD |
| Total charged | 12.3 | <LOD | 14.6 | 0.3 |

<LOD—below limit of detection
Numbers are % of totals

TABLE 12

Representative results for IRMA analysis of individual oligosaccharide species for golimumab produced in Sp2/0 cells and golimumab HC N43D expressed in CHO cells

| Glycan | Golimumab Sp2/0 | HC N43D CHO |
|---|---|---|
| G0F | 29.2 | 75.9 |
| G1F | 31.6 | 9.1 |
| G2F | 9.5 | <LOD |
| Man5 | 1.6 | 1.1 |
| G0 | 3.0 | 7.4 |
| G1FS | 4.7 | <LOD |
| *G1F-GlcNAc + Lys | 0.8 | <LOD |
| *H5N3 + Lys | 1.8 | 0.3 |
| *G1 + Lys | 2.2 | 0.5 |
| *H5N3F1 + Lys | 0.5 | <LOD |
| *G2 + Lys | 0.7 | <LOD |
| *G2FS − Lys | 3.9 | <LOD |
| *H6N4F1S1 − Lys | 3.0 | <LOD |
| *G2FS2 − Lys | 0.7 | <LOD |
| *H6N4F1 − Lys | 2.4 | <LOD |
| *H7N4F1 − Lys | 1.4 | <LOD |
| **G1F-GlcNAc − Lys | 0.0 | <LOD |
| **H5N3 − Lys | 0.0 | <LOD |
| **G1 − Lys | 1.7 | 5.0 |
| **H5N3F1 − Lys | 0.0 | <LOD |
| **H5N4 − Lys | 1.0 | 0.7 |

<LOD—below limit of detection
Numbers are % of totals

Conclusion

Thus, as described supra, a successful strategy was implemented to eliminate the variation in golimumab caused by deamidation of HC Asn43. The strategy was to introduce an aspartic acid residue (Asp, D) in place of the asparagine residue (Asn, N) at amino acid 43 of the heavy chain (HC) of golimumab. Golimumab HC N43D was cloned, expressed in CHO cells and purified, and characterization of golimumab HC N43D expressed in CHO cells showed that it had bioactivity and other characteristics that were comparable to golimumab. The recombinant anti-TNF antibody, golimumab HC N43D, comprises a heavy chain (HC) comprising amino acid sequence SEQ ID NO:38 and a light chain (LC) comprising amino acid sequence SEQ ID NO:37.

Furthermore, it was determined that golimumab HC N43D expressed in CHO cells comprises mammalian anti-TNF antibodies having a heavy chain (HC) comprising an amino acid sequence of SEQ ID NO:38 and a light chain (LC) comprising an amino acid sequence of SEQ ID NO:37, wherein the oligosaccharide profile of the anti-TNF antibodies comprises total neutral oligosaccharide species>99.0%, total charged oligosaccharide species<1.0%, and individual neutral oligosaccharide species G0F>60.0%, G1F<20.0%, and G2F<5.0%. In addition, no disialylated glycan species were detected by IRMA or by HPLC for golimumab produced in CHO cells and monosialylated glycan species were at very low levels based on HPLC analysis and undetectable by IRMA analysis. In contrast, golimumab expressed in Sp2/0 cells comprises anti-TNF antibodies having a heavy chain (HC) comprising an amino acid sequence of SEQ ID NO:36 and a light chain (LC) comprising an amino acid sequence of SEQ ID NO:37, wherein the oligosaccharide profile of the anti-TNF antibodies comprises total neutral oligosaccharide species≥82.0% to ≤94.4%, total charged oligosaccharide species≥5.6% to ≤18.0%, and individual neutral oligosaccharide species G0F≥25.6% to ≤42.2%, G1F≥31.2% to ≤43.6%, and G2F≥5.6% to ≤14.2%.

Compared to golimumab, the changes in the oligosaccharide profile for golimumab HC N43D expressed in CHO cells may provide a variety of benefits in different therapeutic indications and in different patient populations. For example, reduced sialylated (charged) Fc glycans on the anti-TNF antibodies may increase ADCC activity in vivo, such that efficacy is enhanced in the treatment of certain diseases, e.g., inflammatory bowel disease (IBD), such as Crohn's disease (CD) and/or ulcerative colitis (UC). In addition, the reduction in sialylated species generally and the reduction of Neu5Gc specifically for anti-TNF antibodies produced in CHO cells may provide a benefit by reducing undesirable immunogenic responses when administered to humans. For example, reduced levels of Neu5Gc could reduce clearance so that anti-TNF antibodies produced in CHO cells would have a longer half-life compared to anti-TNF antibodies expressed in Sp2/0 cells, especially for patient populations with higher levels of anti-Neu5Gc antibodies.

What is claimed is:

1. Anti-TNF antibodies comprising: (i) a heavy chain comprising an amino acid sequence of SEQ ID NO:38; and (ii) a light chain comprising an amino acid sequence of SEQ ID NO:37, wherein the oligosaccharide profile of the anti-TNF antibodies comprises total neutral oligosaccharide species>99.0% and total charged oligosaccharide species<1.0%.

2. The anti-TNF antibodies of claim 1, wherein the oligosaccharide profile of the anti-TNF antibodies further comprises individual neutral oligosaccharide species G0F>60.0%, G1F<20.0%, and G2F<5.0%.

3. The anti-TNF antibodies of claim 1, wherein the anti-TNF antibodies have no disialylated glycan species as determined by High Performance Liquid Chromatography (HPLC) or Reduced Mass Analysis (RMA).

4. The anti-TNF antibodies of claim 1, wherein the anti-TNF antibodies have a longer half-life or increased antibody-dependent cell-mediated cytotoxicity (ADCC) compared to anti-TNF antibodies expressed in Sp2/0 cells.

5. The anti-TNF antibodies of claim 4, wherein the anti-TNF antibodies are a follow-on biologic.

6. The recombinant anti-TNF antibody of claim 4, wherein the anti-TNF antibody inhibits the activity of TNF alpha (TNFα).

7. A pharmaceutical composition comprising the recombinant anti-TNF antibody of claim 4.

8. A method of manufacture for producing anti-TNF antibodies comprising: (i) a heavy chain comprising an amino acid sequence of SEQ ID NO:38; and (ii) a light chain comprising an amino acid sequence of SEQ ID NO:37, wherein the anti-TNF antibodies are produced by a method of manufacture comprising:
   a. culturing Chinese Hamster Ovary cells (CHO cells) with nucleotides encoding the anti-TNF antibodies;
   b. expressing the anti-TNF antibodies in the CHO cells; and,
   c. purifying the anti-TNF antibodies, wherein the oligosaccharide profile of the anti-TNF antibodies comprises total neutral oligosaccharide species>99.0% and total charged oligosaccharide species<1.0%.

9. The method of manufacture of claim 8, wherein the oligosaccharide profile of the anti-TNF antibodies further comprises individual neutral oligosaccharide species G0F>60.0%, G1F<20.0%, and G2F<5.0%.

10. The method of manufacture of claim 8, wherein the anti-TNF antibodies have no disialylated glycan species as determined by High Performance Liquid Chromatography (HPLC) or Reduced Mass Analysis (RMA).

11. The method of manufacture of claim 8, wherein the anti-TNF antibodies have a longer half-life or increased antibody-dependent cell-mediated cytotoxicity (ADCC) compared to anti-TNF antibodies expressed in Sp2/0 cells.

12. The method of manufacture of claim 9, wherein the anti-TNF antibodies are a follow-on biologic.

13. A composition comprising anti-TNF antibodies: (i) a heavy chain comprising an amino acid sequence of SEQ ID NO:38; and (ii) a light chain comprising an amino acid sequence of SEQ ID NO:37, wherein the oligosaccharide profile of the anti-TNF antibodies comprises total neutral oligosaccharide species>99.0% and total charged oligosaccharide species<1.0%.

14. The composition of claim 13, wherein the oligosaccharide profile of the anti-TNF antibodies further comprises individual neutral oligosaccharide species G0F>60.0%, G1F<20.0%, and G2F<5.0%.

15. The composition of claim 13, wherein the anti-TNF antibodies have no disialylated glycan species as determined by High Performance Liquid Chromatography (HPLC).

16. The composition of claim 13, wherein the anti-TNF antibodies have a longer half-life or increased antibody-dependent cell-mediated cytotoxicity (ADCC) compared to anti-TNF antibodies expressed in Sp2/0 cells.

17. The composition of claim 14, wherein the anti-TNF antibodies are a follow-on biologic.

* * * * *